(12) United States Patent
Zhang et al.

(10) Patent No.: US 10,077,241 B2
(45) Date of Patent: Sep. 18, 2018

(54) TETRAHYDRO-BENZOIMIDAZOLYL MODULATORS OF TGR5

(71) Applicant: Janssen Pharmaceutica NV, Beerse (BE)

(72) Inventors: Xuqing Zhang, Audubon, PA (US); Mark J. Wall, Lansdale, PA (US); Zhihua Sui, Norristown, PA (US)

(73) Assignee: Jansen Pharmaceutica NV, Beerse (BE)

(*) Notice: Subject to any disclaimer, the term of this patent is extended or adjusted under 35 U.S.C. 154(b) by 0 days.

(21) Appl. No.: 15/303,746

(22) PCT Filed: Apr. 14, 2015

(86) PCT No.: PCT/US2015/025702
§ 371 (c)(1),
(2) Date: Oct. 13, 2016

(87) PCT Pub. No.: WO2015/160772
PCT Pub. Date: Oct. 22, 2015

(65) Prior Publication Data
US 2017/0029381 A1    Feb. 2, 2017

Related U.S. Application Data

(60) Provisional application No. 61/979,577, filed on Apr. 15, 2014.

(51) Int. Cl.
| | | |
|---|---|---|
| C07D 405/04 | (2006.01) |
| C07D 413/04 | (2006.01) |
| C07D 235/02 | (2006.01) |
| C07D 403/12 | (2006.01) |
| A61K 31/12 | (2006.01) |
| A61K 31/4184 | (2006.01) |
| A61K 31/4188 | (2006.01) |
| A61K 31/423 | (2006.01) |
| A61K 31/427 | (2006.01) |
| A61K 31/5377 | (2006.01) |
| C07D 407/12 | (2006.01) |
| C07D 409/12 | (2006.01) |
| C07D 413/12 | (2006.01) |
| C07D 417/12 | (2006.01) |
| C07D 491/052 | (2006.01) |
| A61K 45/06 | (2006.01) |
| C07D 401/12 | (2006.01) |

(52) U.S. Cl.
CPC ............ *C07D 235/02* (2013.01); *A61K 31/12* (2013.01); *A61K 31/4184* (2013.01); *A61K 31/4188* (2013.01); *A61K 31/423* (2013.01); *A61K 31/427* (2013.01); *A61K 31/5377* (2013.01); *A61K 45/06* (2013.01); *C07D 401/12* (2013.01); *C07D 403/12* (2013.01); *C07D 405/04* (2013.01); *C07D 407/12* (2013.01); *C07D 409/12* (2013.01); *C07D 413/12* (2013.01); *C07D 417/12* (2013.01); *C07D 491/052* (2013.01)

(58) Field of Classification Search
None
See application file for complete search history.

(56) References Cited

U.S. PATENT DOCUMENTS

| | | |
|---|---|---|
| 5,883,110 A | 3/1999 | Tang et al. |
| 2006/0199795 A1 | 9/2006 | Itoh et al. |

FOREIGN PATENT DOCUMENTS

| | | |
|---|---|---|
| EP | 1167366 A1 | 1/2002 |
| EP | 1179343 A1 | 2/2002 |
| EP | 1666067 A1 | 6/2006 |
| WO | WO 2004/043468 A1 | 5/2004 |
| WO | WO 2004/067008 A1 | 8/2004 |
| WO | WO 2011/106273 A1 | 9/2011 |
| WO | WO 2014/055647 A1 | 4/2014 |

OTHER PUBLICATIONS

Duboc et al., The bile acid TGR5 membrane receptor: From basic research to clinical application, 2014, Digestive and Liver Disease, vol. 46, pp. 302-312.*
International Search Report for corresponding International Patent Application No. PCT/US2015/025702; dated Jul. 10, 2015.
Written Opinion of the International Searching Authority for corresponding International Patent Application No. PCT/US2015/025702; dated Jul. 10, 2015.
Brubaker et al., "Regulation of Glucagon-Like Peptide-1 Synthesis and Secretion in the GLUTag Enteroendocrine Cell Line.", Endocrinology, 1998, pp. 4108-4114, vol. 139(10).

(Continued)

*Primary Examiner* — James D Anderson
*Assistant Examiner* — Meghan R Finn

(57) ABSTRACT

The present invention comprises compounds of Formula (I).

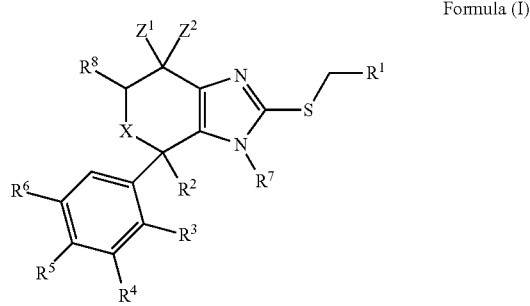

Formula (I)

wherein:
$R^1$, $R^2$, $R^3$, $R^4$, $R^5$, $R^6$, $R^7$, $R^8$, X, $Z^1$ and $Z^2$ are defined in the specification.

11 Claims, No Drawings

(56) References Cited

OTHER PUBLICATIONS

Chang et al., "Pituitary adenylate cyclase-activating polypeptide stimulates cholecystokinin secretion in STC-1 cells.", Am J Physiol. 1996, 271:G516-G523.
Grundy et al., "Diagnosis and Management of the Metabolic Syndrome.", Circulation, 2005, pp. e285-e290, vol. 112.
Katsuma et al., "Bile acids promote glucagon-like peptide-1 secretion through TGR5 in a murine enteroendocrine cell line STC-1.", Biochem. Biophys. Res. Commun., 2005, pp. 386-390, vol. 329.
Kawamata et al., "A G Protein-coupled Receptor Responsive to Bile Acids.", J. Biol. Chem., 2003, pp. 9435-9440, vol. 278.
Kreymann et al., "Glucagon-Like Peptide-1 7-36: A Physiological Incretin in Man.", Lancet, 1987, pp. 1300-1304, vol. 2.
Maruyama et al., "Identification of membrane-type receptor for bile acids (M-BAR).", Biochem. Biophs. Res. Commun., 2002, pp. 714-719, vol. 298.
Pols et al., "TGR5 Activation Inhibits Atherosclerosis by Reducing Macrophage Inflammation and Lipid Loading.", Cell Metabolism, 2011, pp. 747-757, vol. 14.
Reimer et al., "A Human Cellular Model for Studying the Regulation of Glucagon-Like Peptide-1 Secretion.", Endocrinology, 2001, pp. 4522-4528, vol. 142.
Thomas et al., "TGR5-Mediated Bile Acid Sensing Controls Glucose Homeostasis.", Cell Metabolism , 2009, pp. 167-177, vol. 10.
Watanabe et al., "Bile acids induce energy expenditure by promoting intracellular thyroid hormone activation.", Nature, 2006, pp. 484-489, vol. 439.

\* cited by examiner

TETRAHYDRO-BENZOIMIDAZOLYL MODULATORS OF TGR5

CROSS REFERENCE TO RELATED APPLICATIONS

This application is a national stage of Application No. PCT/US202015/025702, filed Apr. 14, 2015, which claims the benefit of U.S. Provisional Application 61/979,577, filed on Apr. 15, 2014, which is incorporated by reference herein in its entirety.

FIELD OF THE INVENTION

Disclosed herein are heterocyclic compounds and compositions and their application as pharmaceuticals for the treatment of disease. Methods of modulation of TGR5 activity in a human or animal subject are also provided for the treatment of diseases mediated by TGR5.

BACKGROUND OF THE INVENTION

The G-protein coupled receptor (GPCR), TGR5 (aka M-BAR) was independently discovered by two groups [Kawamata Y. et al, J. Biol. Chem., 278:9435-9440, 2003; Maruyama T. et al. Biochem. Biophs. Res. Commun. 298, 714-719, 2002]. TGR5 is a seven transmembrane Gs-coupled GPCR and stimulation by ligand binding causes activation of adenylyl cyclase which leads to the elevation of intracellular cAMP and subsequent activation of downstream signaling pathways. Maruyama et al. [Maruyama T. et al. Biochem. Biophs. Res. Commun. 298, 714-719, 2002] showed that TGR5 is expressed in intestinal enteroendocrine cell lines from human (NCI-H716) and murine (STC-I, GLUTag) origin, but not in the intestinal epithelial cells (CaCo-2 and HT-29). Stimulation of TGR5 by bile acids (BA) in NCI-H716 cells stimulated cAMP production. This suggested that bile acids may induce the secretion of glucagon-like peptide-1 (GLP-I) or cholecystokinin (CCK) from the enteroendocrine cells through TGR5 stimulation, since cAMP stimulated the secretion of GLP-I and CCK from these cells [Reimer R. A. et al. Endocrinology 142, 4522-4528, 2001; Chang C H. et al. Am. J. Physiol. 271, G516-G523, 1996; Brubaker P X. et al, Endocrinology 139, 4108-4114, 1998]. Additional work by Katsuma S. et al. has demonstrated that activation of TGR5 by BA promoted release of GLP-I in STC-I cells [Katsuma S. et al. Biochem. Biophys. Res. Commun. 329, 386-390, 2005]. RNA interference experiments revealed that reduced expression of TGR5 resulted in reduced secretion of GLP-I. GLP-I has been shown to stimulate insulin release in a glucose dependent manner in humans [Kreymann et al. Lancet 2 (8571) 1300-1304, 1987], and studies in experimental animals demonstrated that this incretin hormone is necessary for normal glucose homeostasis. In addition, GLP-I can exert several beneficial effects in diabetes and obesity, including 1) increased glucose disposal, 2) suppression in glucose production, 3) reduced gastric emptying, 4) reduction in food intake and 5) weight loss.

Recently published data suggested that activation of TGR5 might be beneficial for the treatment of obesity and diabetes. Watanabe et al. (Nature, 439, 484-489, 2006) reported that mice fed high fat diet (HFD) containing 0.5% cholic acid gained less weight than control mice on HFD alone. There was no difference between the two groups in terms of food intake. These effects were independent of FXR-alpha, and instead stem from the binding of bile acids to TGR5 and the subsequent induction of the cAMP-dependent thyroid hormone activating enzyme type 2 (D2) which converts the inactive T3 into active T4, leading to stimulation of the thyroid hormone receptor and promoting energy expenditure. Mice lacking the D2 gene (D2$^{--}$) were resistant to cholic acid-induced weight loss. In both rodents and humans, the most thermogenically important tissues (the brown adipose and skeletal muscle) are specifically targeted by this mechanism because they co-express D2 and TGR5. The BA-TGR5-cAMP-D2 signaling pathway is therefore a crucial mechanism for fine-tuning energy homeostasis that can be targeted to improve metabolic control. Taken together, a small molecule TGR5 modulator could be used for the treatment of obesity, diabetes and a wide range of acute and chronic inflammatory diseases. Thomas et al. Cell Metabolism 10, 167-177 2009.

In addition, certain substituted heterocyclic compounds have been described as agonists of TGR5 for the treatment of metabolic, cardiovascular, and inflammatory diseases. (EP01/591120A1, WO04/043468A1, WO04/067008A1, and JP24346059A2).

Obesity is associated with a number of diseases including insulin resistance, glucose intolerance, dyslipidemia, and hypertension, collectively known as the metabolic syndrome or syndrome X. Patients with metabolic syndrome have a higher risk for coronary artery disease and stroke [Grundy S. M. et al. Circulation 112:e285-e290, 2005]. Epidemiologic studies have shown that treating diabetes/insulin resistance in these patients can reduce the risk of coronary artery disease. Indeed, in mouse models of atherosclerosis, TGR5 agonism was shown to reduce macrophage mediated atherosclerosis via reduction of lipid loading. Pois, et al. Cell Metabolism 14, 747-757 2011. Current strategies for reducing the risk of coronary artery disease and stroke in obese patients include treatment of diabetes and insulin resistance. Marketed drugs to treat diabetes and insulin resistance include biguanides (such as metformin), peroxisome proliferator activated receptor gamma (PPARγ) agonists (such as rosiglitazone and pioglitazone), sulphonylureas, and most recently GLP-I mimetics such as Exenatide (Byetta®). However, there remains a need for additional agents that can treat the root cause(s) of metabolic syndrome by treating obesity and diabetes. TGR5 modulators described in this invention represent such an opportunity.

Compounds and pharmaceutical compositions, certain of which have been found to modulate TGR5 are included herein, together with methods of synthesizing and using the compounds including methods for the treatment of TGR5-mediated diseases in a patient by administering the compounds.

SUMMARY OF THE INVENTION

The present invention is directed in part to compounds of Formula (I).

Formula (I)

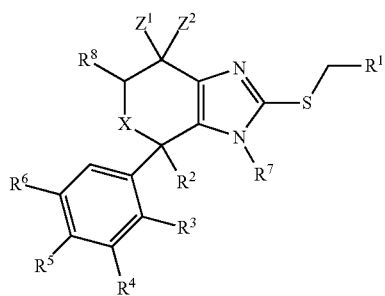

wherein:
R¹ is

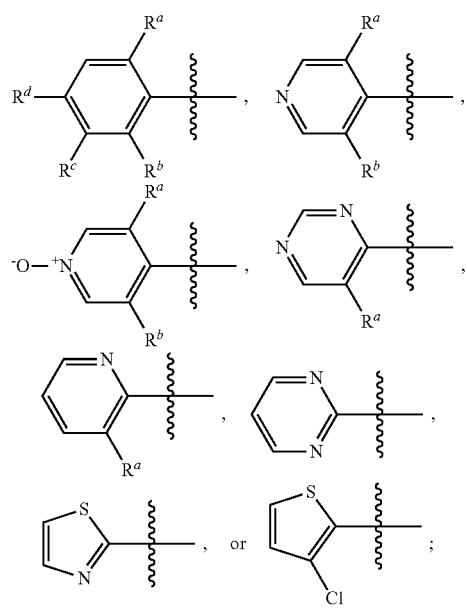

$R^a$ is H, F, Br, or Cl;
$R^b$ is H, F, Cl, Br, CF₃, OCH₃, —CN, or NO₂;
$R^c$ is H, F, OH, or $(OCH_2CH_2)_nN(CH_3)_2$;
$R^d$ is H, —CN, Br, SO₂NH₂, SO₂NHSO₂CH₃, $C_{(2-3)}$alkylOH, $C_{(2-3)}$alkylN(CH₃)₂, CH₂CH₂-tetrazolyl, CH₂CH₂CO₂CH₂CH₃, CH₂CH₂CO₂H, OCH₂CN, OCH₂CO₂H, OCH₂-tetrazolyl, $(OCH_2CH_2)_nN(CH_3)_2$, $(OCH_2CH_2)_n$-pyrrolidinyl, $(OCH_2CH_2)_n$Cl, $(OCH_2CH_2)_n$OH, $(OCH_2CH_2)_n$OCH₃, CO₂H, C(O)NH₂, C(O)NHCH₃, C(O)N(CH₃)₂, C(O)NHCH₂CH₂N(CH₃)₃⁺(CF₃CO₂)⁻, SO₂NH(CH₂)₃N(CH₃)₃⁺(CF₃CO₂)⁻, C(O)NHCH₂CH₂$(OCH_2CH_2)_n$OH, C(O)NHCH₂CH₂$(OCH_2CH_2)_n$OCH₃, C(O)-morpholinyl, CH₂CH₂-morpholinyl, CH₂CH₂CN, CH₂CH₂C(O)NH₂,

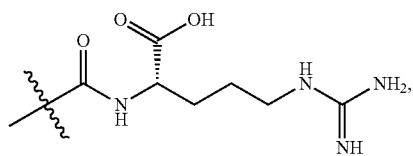

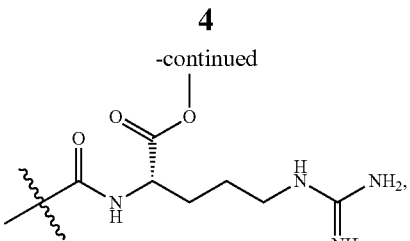

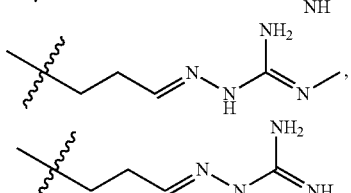

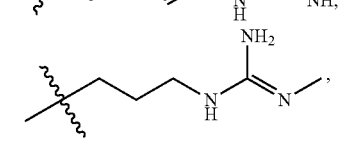

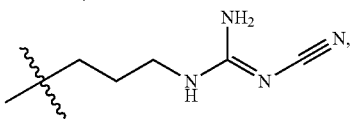


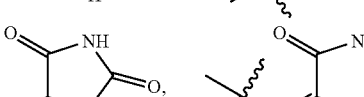

or tetrazolyl;
n is 0, 1, 2, 3, or 4;
R² is H, CH₃, CH₂CH₃, CH₂OH, CH₂F, or CH=O;
R³ is H or Br;
R⁴ is H or Br;
R⁵ is Cl, H, F, or OCH₃;
R⁶ is OCH₃, or Cl, or R⁶ and R⁵ may be taken together with their attached phenyl to form the fused ring system

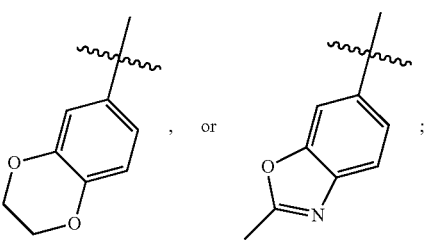 [SMILES: *c1ccc2c(c1)OCCO2 ; *c1ccc2nc(C)oc2c1]

R⁷ is phenyl, wherein said phenyl is optionally substituted with one substituent selected from the group consisting of F, CH₃, Cl, CF₃, and OCH₃, and further optionally substituted with up to two additional fluorine atoms;
R⁸ is H or CH₃;
X is O or CH₂; and
Z¹ and Z² are H, or Z¹ and Z² may be taken together with their attached carbon to form a

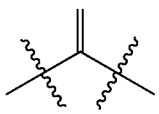

group;
and pharmaceutically acceptable salts thereof.

In certain embodiments, the present invention is further directed to processes for the preparation of the compounds of Formula (I). In certain embodiments, the present invention is further directed to a product prepared according to the process described herein.

In certain embodiments, the present invention is directed to a pharmaceutical composition comprising a pharmaceutically acceptable carrier and a compound of Formula (I) described herein. An illustration of an embodiment of the invention is a pharmaceutical composition made by mixing a compound of Formula (I) described herein and a pharmaceutically acceptable carrier.

In an embodiment, the present invention is directed to a compound of Formula (I) for use as a medicament.

In certain embodiments, the present invention is directed to a method of treating a TGR5 mediate syndrome, disease or disorder comprising administering to a subject in need thereof an effective amount of any of the compounds or pharmaceutical compositions described herein.

In another embodiment, the present invention is directed to a method of treating a syndrome, disease or disorder such as diabetes (type I and type II) and conditions which may be associated with diabetic diseases which include, but are not limited to, Syndrome X (also known as metabolic syndrome), hyperglycemia, hyperlipidemia, hyperinsulinemia, insulin resistance, inadequate glucose tolerance, impaired glucose metabolism, diabetic nephropathy, glomerulosclerosis, diabetic neuropathy, erectile dysfunction, macular degeneration, diabetic retinopathy, chronic microvascular complications, peripheral vascular disease, cataracts, stroke, foot ulcerations, renal failure, kidney disease, ketosis, metabolic acidosis, and related disorders, obesity, myocardial infarction, angina pectoris, coronary artery disease, atherosclerosis, cardiac hypertrophy, allergic diseases, fatty liver disease, nonalcoholic steatohepatitis, liver fibrosis, kidney fibrosis, anorexia nervosa, bulimia vervosa, autoimmune diseases, inflammatory diseases including rheumatoid arthritis, asthma, chronic obstructive pulmonary disease (COPD), psoriasis, ulcerative colitis, proliferative disorders, infectious diseases, angiogenic disorders, reperfusion/ischemia in stroke, vascular hyperplasia, organ hypoxia, cardiac hypertrophy, thrombin-induced platelet aggregation, and conditions associated with prostaglandin endoperoxidase synthetase-2 (COX-2) comprising administering to a subject in need thereof an effective amount of any of the compounds or pharmaceutical compositions described herein.

In an embodiment, the present invention is directed to a method of treating a syndrome, disease or disorder selected from the group consisting of: (a) obesity, (b) type-II diabetes, (c) Syndrome X (also known as metabolic syndrome), (d) hypertriglyceridemia, (e) dyslipidemia, (f) hypercholesterolemia, (g) hyperlipidemia, and (h) mixed dyslipidemia, comprising administering to a subject in need thereof an effective amount of any of the compounds or pharmaceutical compositions described herein.

DETAILED DESCRIPTION OF THE INVENTION

In certain embodiments, the present invention is directed to compounds of Formula (I).

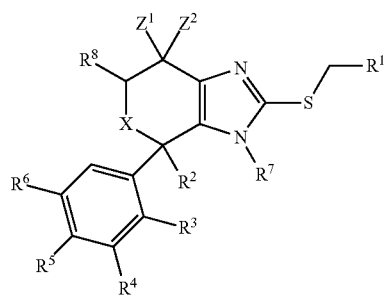

Formula (I)

wherein:

$R^1$ is

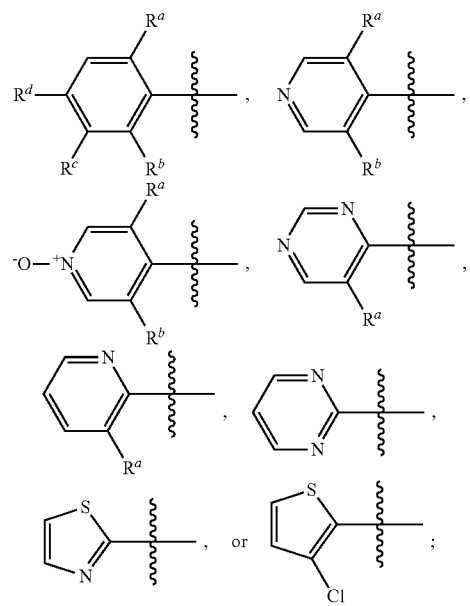

$R^a$ is H, F, Br, or Cl;

$R^b$ is H, F, Cl, Br, $CF_3$, $OCH_3$, —CN, or $NO_2$;

$R^c$ is H, F, OH, or $(OCH_2CH_2)_n N(CH_3)_2$;

$R^d$ is H, —CN, Br, $SO_2NH_2$, $SO_2NHSO_2CH_3$, $C_{(2-3)}$alkylOH, $C_{(2-3)}$alkylN(CH_3)_2$, $CH_2CH_2$-tetrazolyl, $CH_2CH_2CO_2CH_2CH_3$, $CH_2CH_2CO_2H$, $OCH_2CN$, $OCH_2CO_2H$, $OCH_2$-tetrazolyl, $(OCH_2CH_2)_n N(CH_3)_2$, $(OCH_2CH_2)_n$-pyrrolidinyl, $(OCH_2CH_2)_n Cl$, $(OCH_2CH_2)_n OH$, $(OCH_2CH_2)_n OCH_3$, $CO_2H$, $C(O)NH_2$, $C(O)NHCH_3$, $C(O)N(CH_3)_2$, $C(O)NHCH_2CH_2N(CH_3)_3^+(CF_3CO_2)^-$, $SO_2NH(CH_2)_3N(CH_3)_3^+(CF_3CO_2)^-$, $C(O)NHCH_2CH_2(OCH_2CH_2)_n OH$, $C(O)NHCH_2CH_2(OCH_2CH_2)_n OCH_3$, $C(O)$-morpholinyl, $CH_2CH_2$-morpholinyl, $CH_2CH_2CN$, $CH_2CH_2C(O)NH_2$,

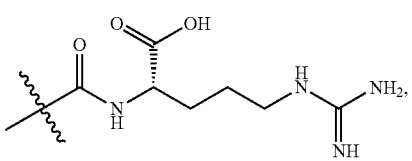

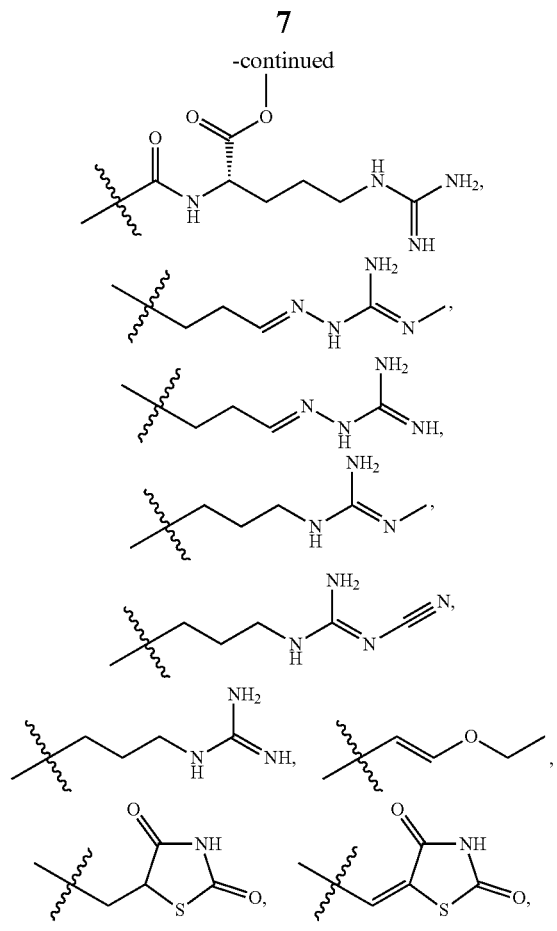

or tetrazolyl;

n is 0, 1, 2, 3, or 4;

$R^2$ is H, $CH_3$, $CH_2CH_3$, $CH_2OH$, $CH_2F$, or $CH=O$;

$R^3$ is H or Br;

$R^4$ is H or Br;

$R^5$ is Cl, H, F, or $OCH_3$;

$R^6$ is $OCH_3$, or Cl, or $R^6$ and $R^5$ may be taken together with their attached phenyl to form the fused ring system

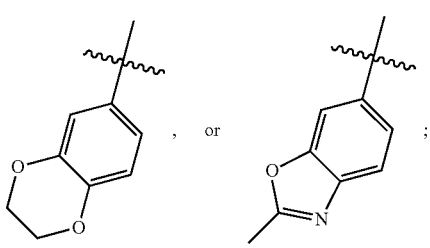 [SMILES: *c1ccc2c(c1)OCCO2 ; *c1ccc2nc(C)oc2c1]

$R^7$ is phenyl, wherein said phenyl is optionally substituted with one substituent selected from the group consisting of F, $CH_3$, Cl, $CF_3$, and $OCH_3$, and further optionally substituted with up to two additional fluorine atoms;

$R^8$ is H or $CH_3$;

X is O or $CH_2$; and $Z^1$ and $Z^2$ are H, or $Z^1$ and $Z^2$ may be taken together with their attached carbon to form a group;

and pharmaceutically acceptable salts thereof.

In another embodiment the present invention is directed to compounds of Formula (I) wherein:

$R^1$ is

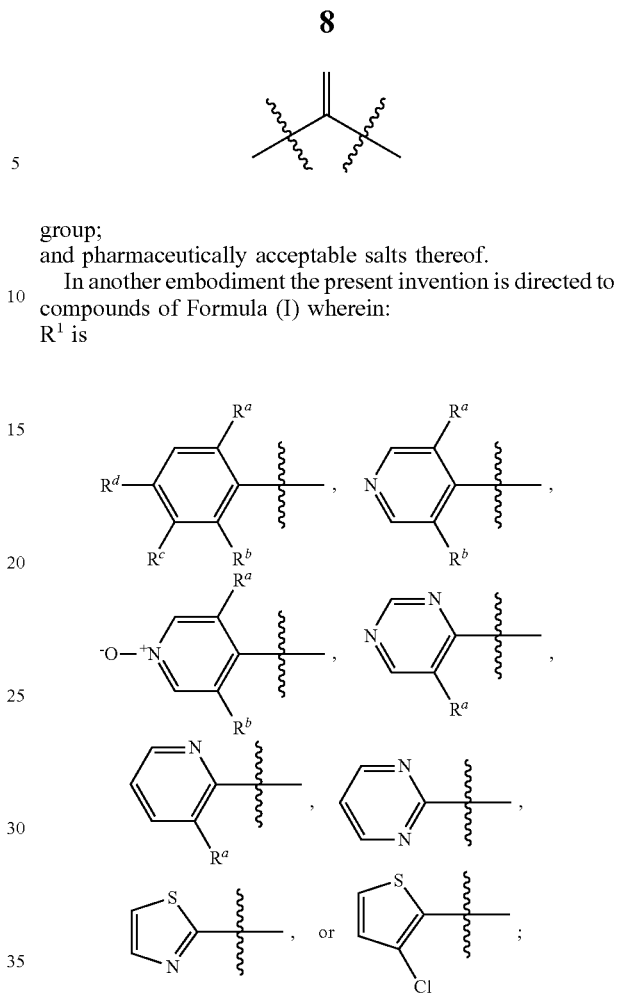

$R^a$ is H, F, Br, or Cl;

$R^b$ is H, F, Cl, Br, $CF_3$, $OCH_3$, —CN, or $NO_2$;

$R^c$ is H, F, OH, or $(OCH_2CH_2)_nN(CH_3)_2$;

$R^d$ is H, —CN, Br, $SO_2NH_2$, $SO_2NHSO_2CH_3$, $C_{(2-3)}$alkylOH, $C_{(2-3)}$alkylN$(CH_3)_2$, $CH_2CH_2$-tetrazolyl, $CH_2CH_2CO_2CH_2CH_3$, $CH_2CH_2CO_2H$, $OCH_2CN$, $OCH_2CO_2H$, $OCH_2$-tetrazolyl, $(OCH_2CH_2)_nN(CH_3)_2$, $(OCH_2CH_2)_n$-pyrrolidinyl, $(OCH_2CH_2)_nCl$, $(OCH_2CH_2)_n$OH, $(OCH_2CH_2)_nOCH_3$, $CO_2H$, $C(O)NH_2$, $C(O)NHCH_3$, $C(O)N(CH_3)_2$, $C(O)NHCH_2CH_2N(CH_3)_3^+(CF_3CO_2)^-$, $SO_2NH(CH_2)_3N(CH_3)_3^+(CF_3CO_2)^-$, $C(O)NHCH_2(OCH_2CH_2)_nOH$, $C(O)NHCH_2CH_2(OCH_2CH_2)_nOCH_3$, C(O)-morpholinyl, $CH_2CH_2$-morpholinyl, $CH_2CH_2CN$, $CH_2CH_2C(O)NH_2$, NH

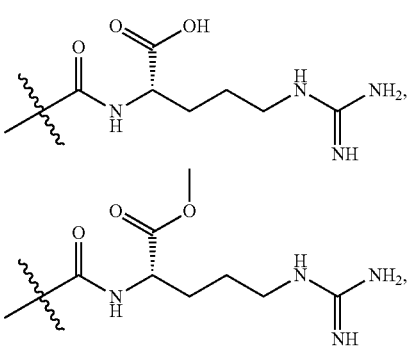

-continued

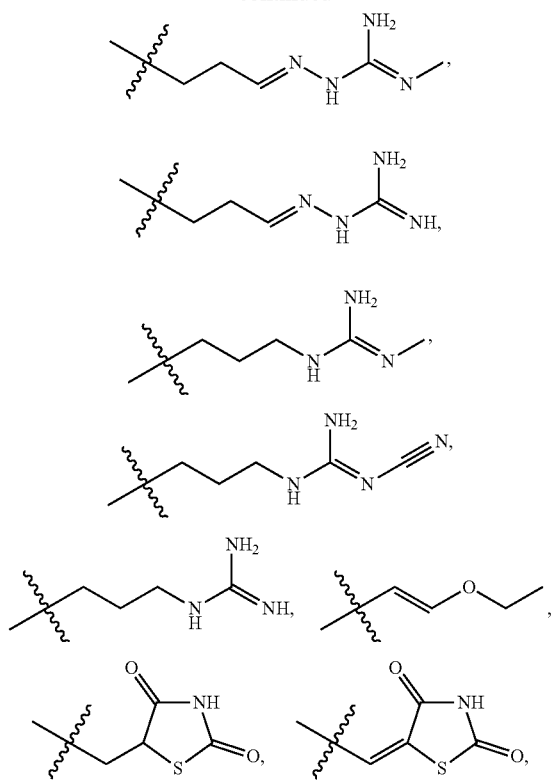

or tetrazolyl;

n is 0, 1, 2, 3, or 4;

$R^2$ is H, $CH_3$, $CH_2CH_3$, $CH_2OH$, $CH_2F$, or CH=O;

$R^3$ is H or Br;

$R^4$ is H or Br;

$R^5$ is Cl, H, F, or $OCH_3$;

$R^6$ is $OCH_3$, or Cl, or $R^6$ and $R^5$ may be taken together with their attached phenyl to form the fused ring system

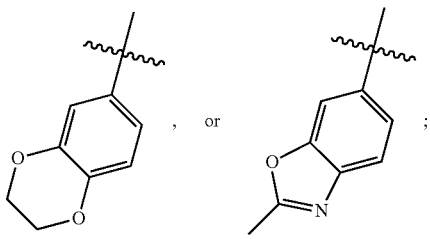 [SMILES: *c1ccc2c(c1)OCCO2 ; *c1ccc2nc(C)oc2c1]

$R^7$ is phenyl, wherein said phenyl is optionally substituted with one substituent selected from the group consisting of F, $CH_3$, Cl, $CF_3$, and $OCH_3$, and further optionally substituted with up to two additional fluorine atoms;

$R^8$ is H or $CH_3$;

X is $CH_2$;

$Z^1$ and $Z^2$ are H;

and pharmaceutically acceptable salts thereof.

In another embodiment the present invention is directed to compounds of Formula (I) wherein:

$R^1$ is

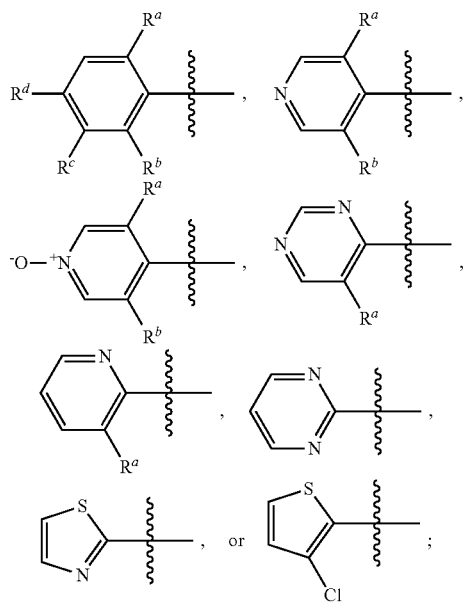

$R^a$ is H, F, Br, or Cl;
$R^b$ is H, F, Cl, Br, $CF_3$, $OCH_3$, —CN, or $NO_2$;
$R^c$ is H, F, OH, or $(OCH_2CH_2)_nN(CH_3)_2$;
$R^d$ is H, —CN, Br, $SO_2NH_2$, $SO_2NHSO_2CH_3$, $C_{(2-3)}$alkylOH, $C_{(2-3)}$alkylN$(CH_3)_2$, $CH_2CH_2$-tetrazolyl, $CH_2CH_2CO_2CH_2CH_3$, $CH_2CH_2CO_2H$, $OCH_2CN$, $OCH_2CO_2H$, $OCH_2$-tetrazolyl, $(OCH_2CH_2)_nN(CH_3)_2$, $(OCH_2CH_2)_n$-pyrrolidinyl, $(OCH_2CH_2)_nCl$, $(OCH_2CH_2)_nOH$, $(OCH_2CH_2)_nOCH_3$, $CO_2H$, $C(O)NH_2$, $C(O)NHCH_3$, $C(O)N(CH_3)_2$, $C(O)NHCH_2CH_2N(CH_3)_3{}^+(CF_3CO_2)^-$, $SO_2NH(CH_2)_3N(CH_3)_3{}^+(CF_3CO_2)^-$, $C(O)NHCH_2CH_2(OCH_2CH_2)_nOH$, $C(O)NHCH_2CH_2(OCH_2CH_2)_nOCH_3$, $C(O)$-morpholinyl, $CH_2CH_2$-morpholinyl, $CH_2CH_2CN$, $CH_2CH_2C(O)NH_2$,

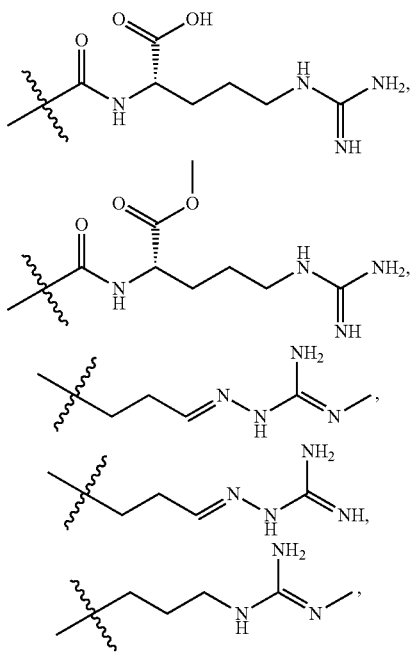

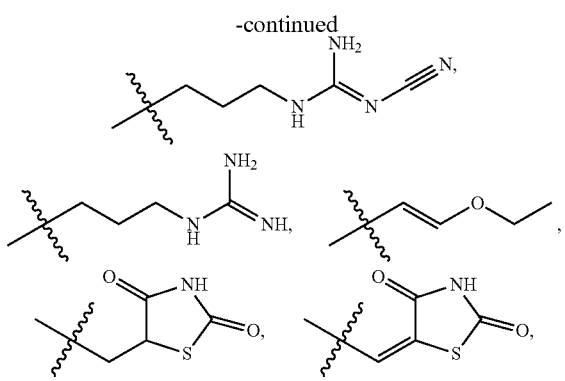

or tetrazolyl;
n is 0, 1, 2, 3, or 4;
$R^2$ is H, $CH_3$, $CH_2CH_3$, $CH_2OH$, $CH_2F$, or $CH=O$;
$R^3$ is H or Br;
$R^4$ is H or Br;
$R^5$ is Cl;
$R^6$ is $OCH_3$;
$R^7$ is phenyl, wherein said phenyl is optionally substituted with one substituent selected from the group consisting of F, $CH_3$, Cl, $CF_3$, and $OCH_3$, and further optionally substituted with up to two additional fluorine atoms;
$R^8$ is H or $CH_3$;
X is $CH_2$;
$Z^1$ and $Z^2$ are H;
and pharmaceutically acceptable salts thereof.

In another embodiment the present invention is directed to compounds of Formula (I) wherein:
$R^1$ is

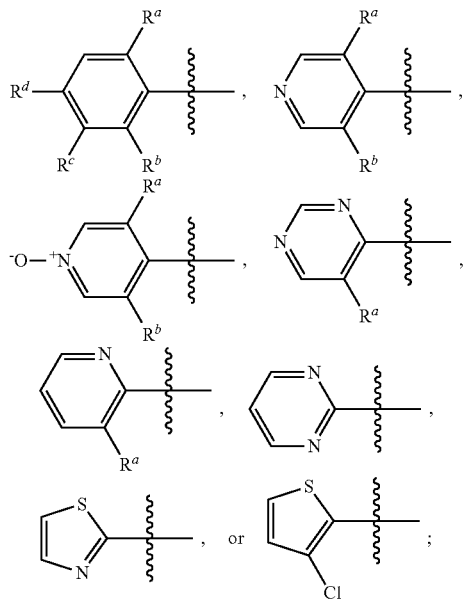

$R^a$ is H, F, Br, or Cl;
$R^b$ is H, F, Cl, Br, $CF_3$, $OCH_3$, —CN, or $NO_2$;
$R^c$ is H, F, OH, or $(OCH_2CH_2)_nN(CH_3)_2$;
$R^d$ is H, —CN, Br, $SO_2NH_2$, $SO_2NHSO_2CH_3$, $C_{(2-3)}$alkylOH, $C_{(2-3)}$alkylN$(CH_3)_2$, $CH_2CH_2$-tetrazolyl, $CH_2CH_2CO_2CH_2CH_3$, $CH_2CH_2CO_2H$, $OCH_2CN$, $OCH_2CO_2H$, $OCH_2$-tetrazolyl, $(OCH_2CH_2)_nN(CH_3)_2$, $(OCH_2CH_2)_n$-pyrrolidinyl, $(OCH_2CH_2)_nCl$, $(OCH_2CH_2)_nOH$, $(OCH_2CH_2)_nOCH_3$, $CO_2H$, $C(O)NH_2$, $C(O)NHCH_3$, $C(O)N(CH_3)_2$, $C(O)NHCH_2CH_2N(CH_3)_3^+(CF_3CO_2)^-$, $SO_2NH(CH_2)_3N(CH_3)_3^+(CF_3CO_2)^-$, $C(O)NHCH_2(OCH_2CH_2)_nOH$, $C(O)NHCH_2CH_2(OCH_2CH_2)_nOCH_3$, C(O)-morpholinyl, $CH_2CH_2$-morpholinyl, $CH_2CH_2CN$, $CH_2CH_2C(O)NH_2$,

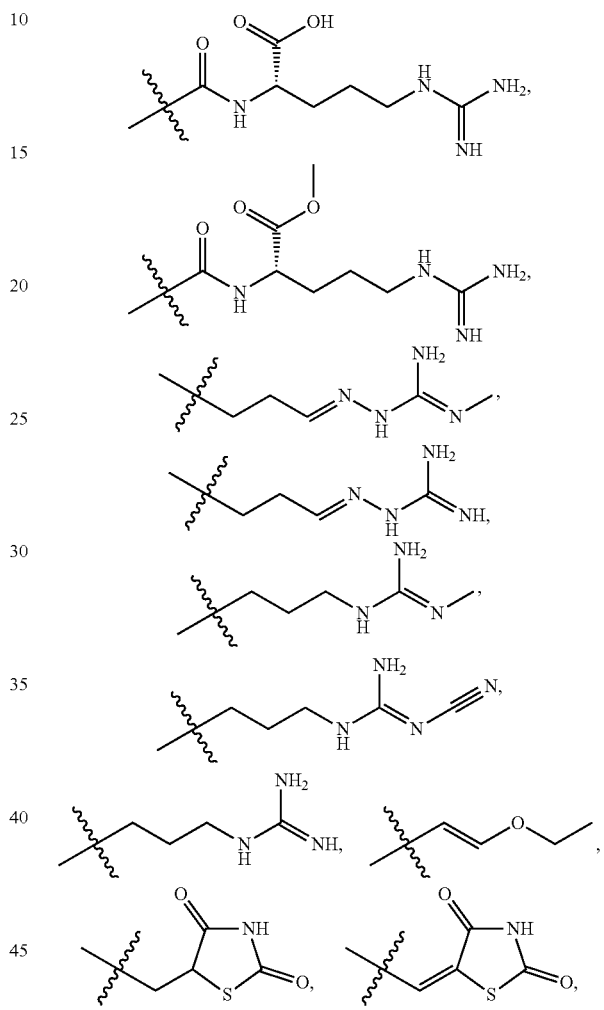

or tetrazolyl;
n is 0, 1, 2, 3, or 4;
$R^2$ is H, $CH_3$, $CH_2CH_3$, $CH_2OH$, $CH_2F$, or $CH=O$;
$R^3$ is H or Br;
$R^4$ is H or Br;
$R^5$ is Cl;
$R^6$ is $OCH_3$;
$R^7$ is

$R^8$ is H or $CH_3$;
X is $CH_2$;
$Z^1$ and $Z^2$ are H;
and pharmaceutically acceptable salts thereof.

In another embodiment the present invention is directed to a compound selected from the group consisting of:
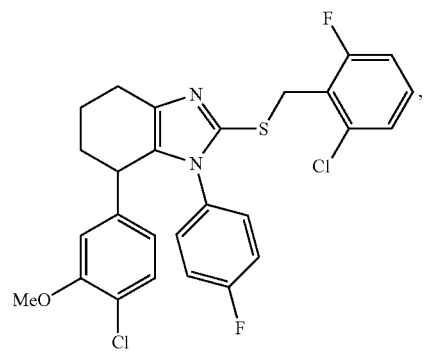
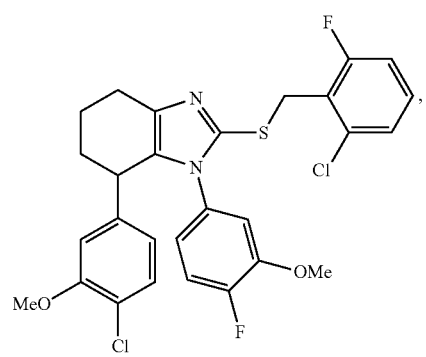
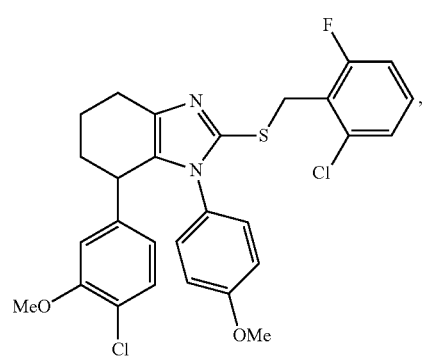
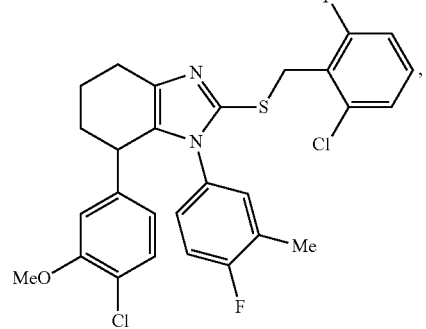
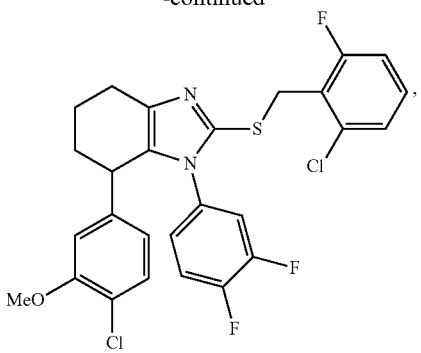
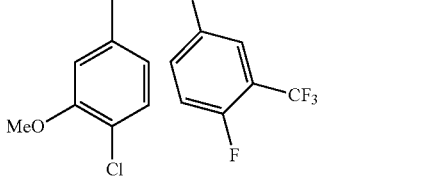
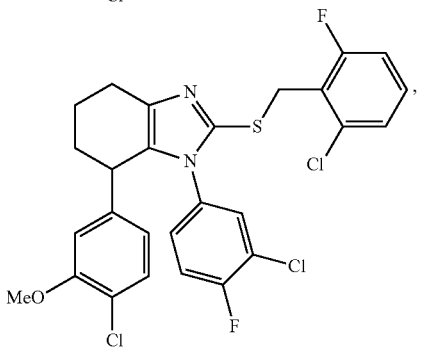
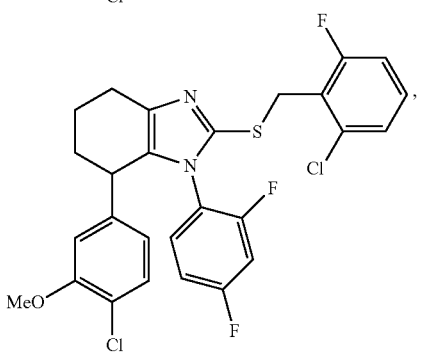

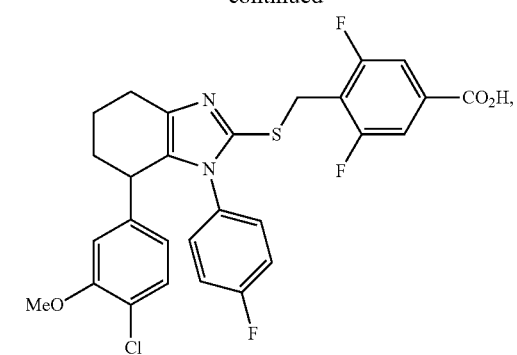
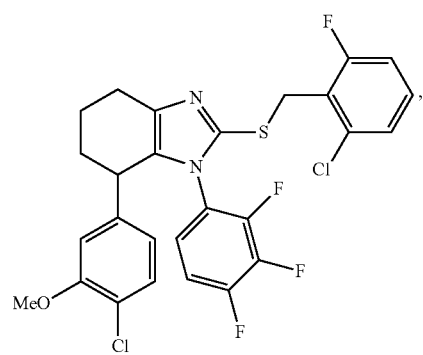
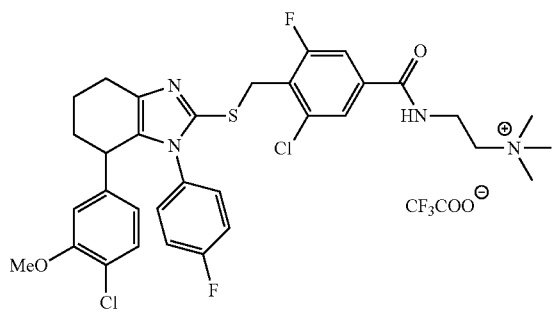
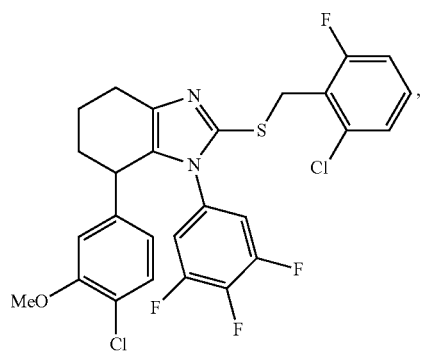
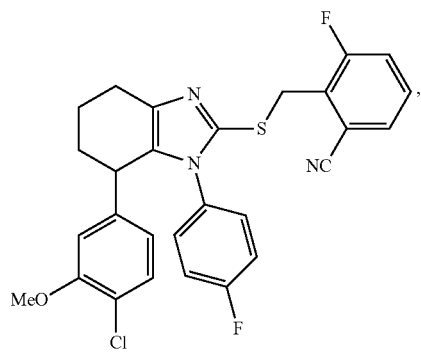
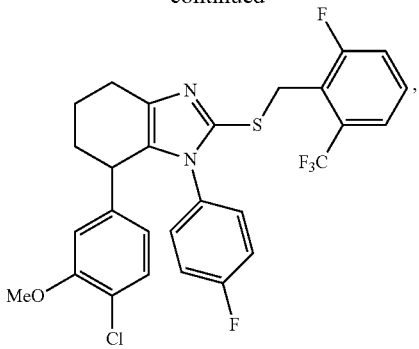
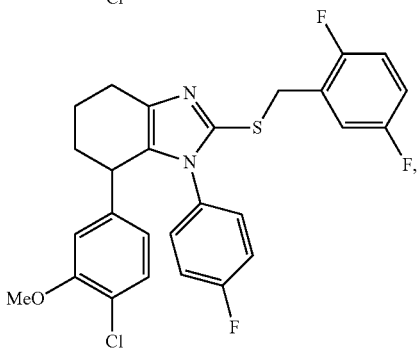
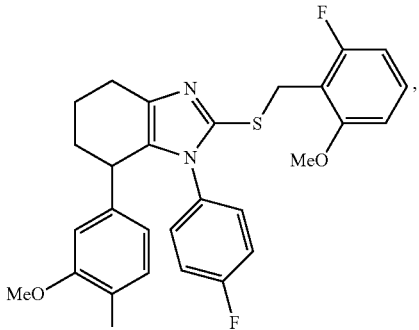
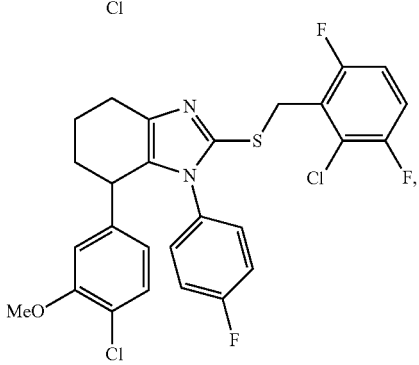
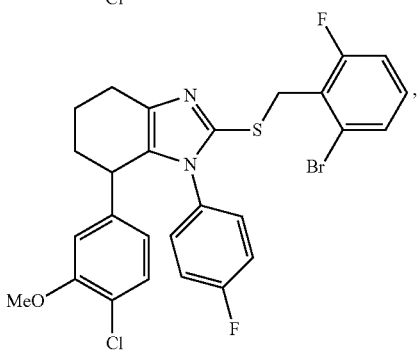

17
-continued
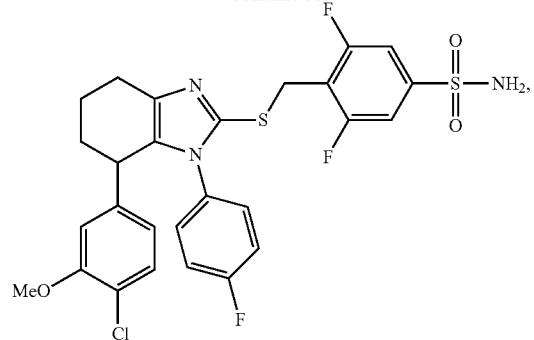
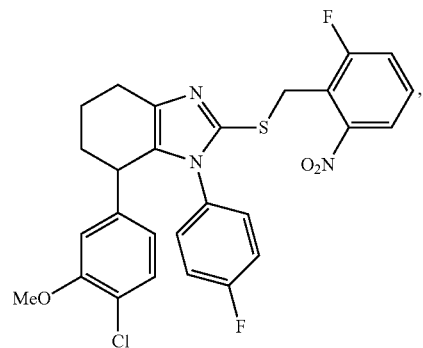
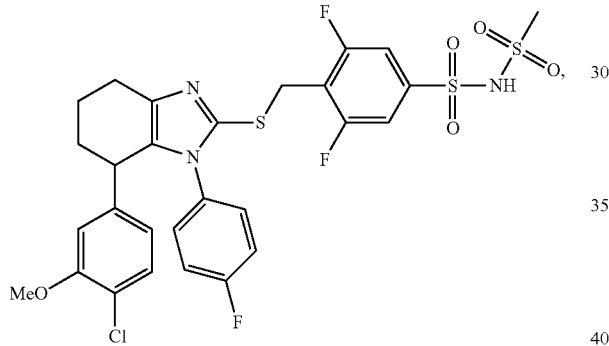
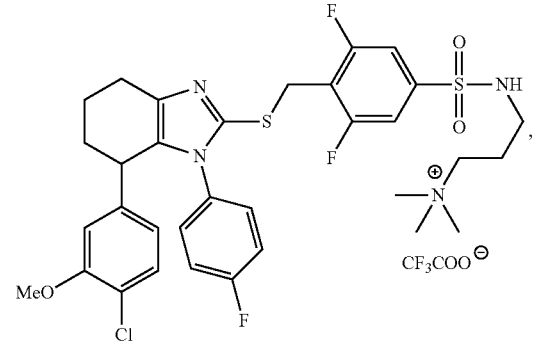
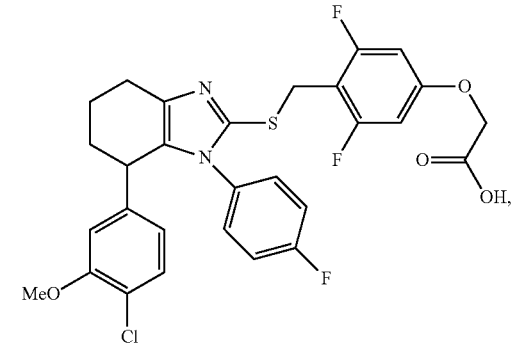
18
-continued
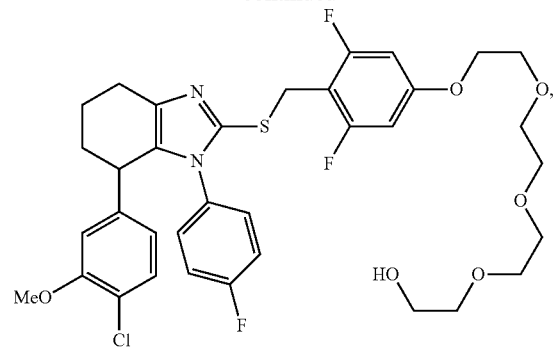
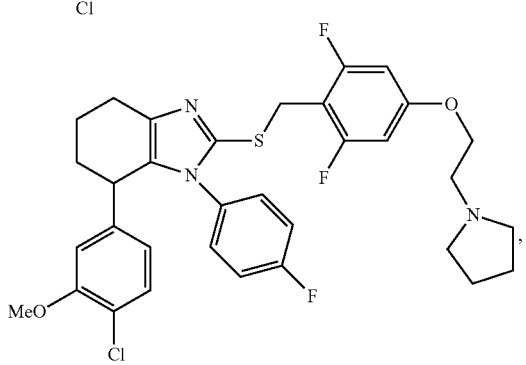
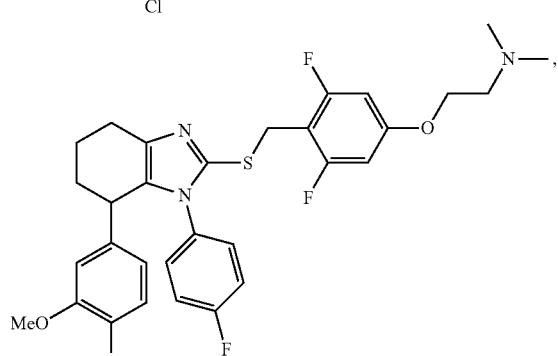
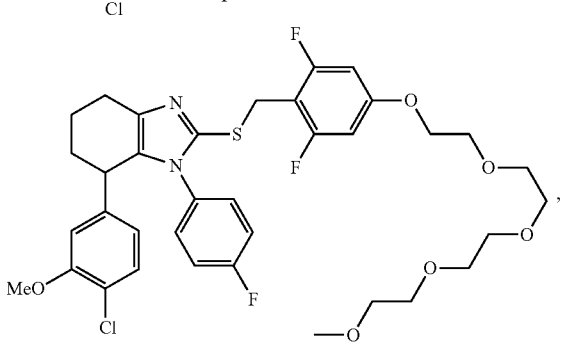
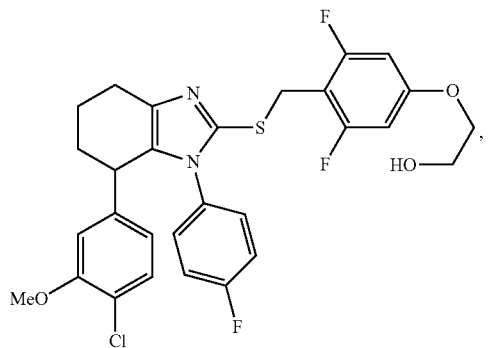

-continued
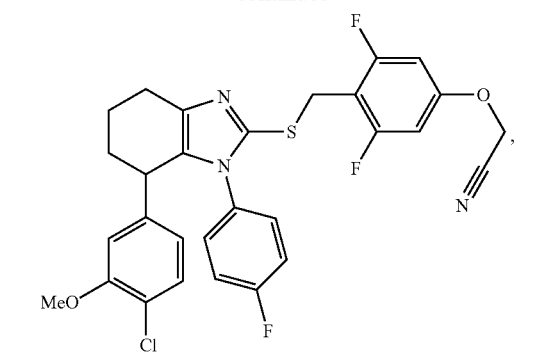
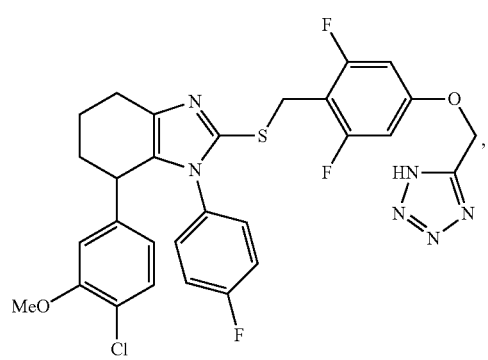
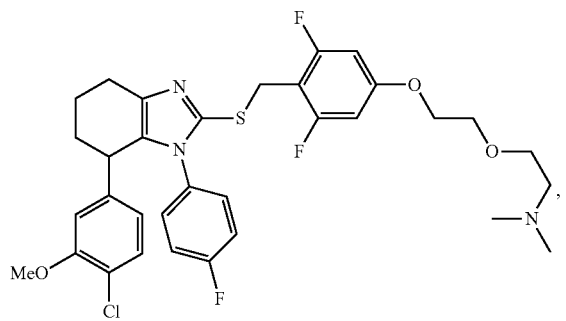
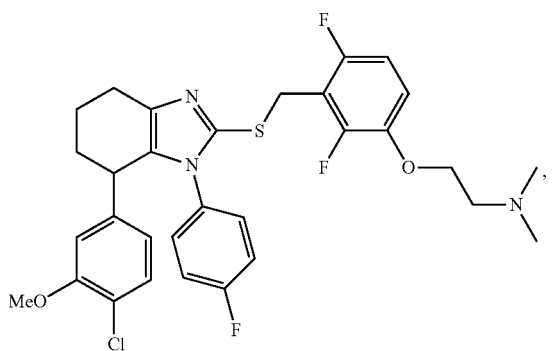
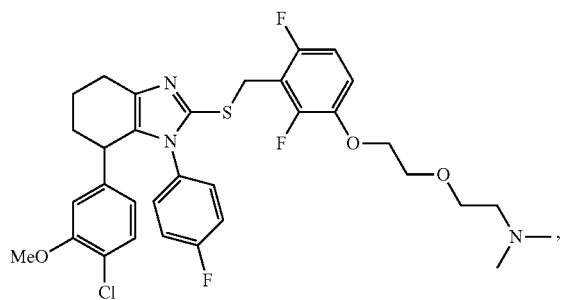
-continued
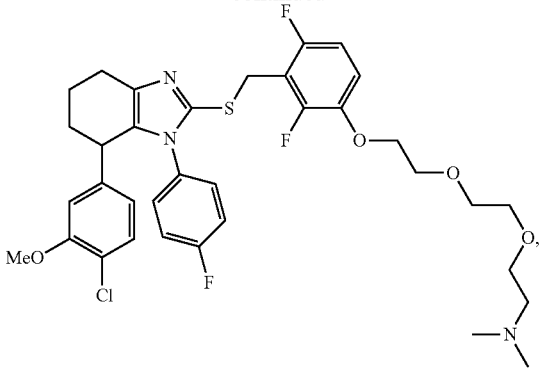
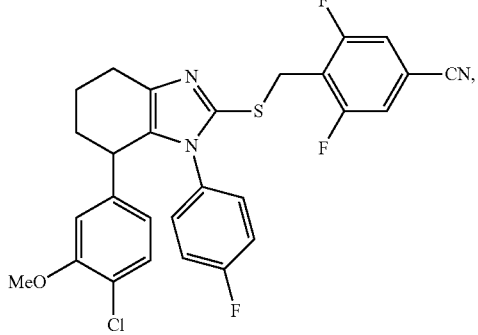
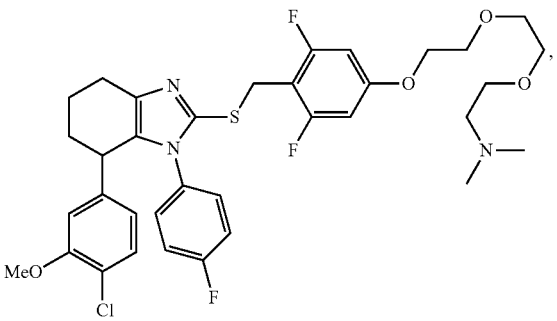
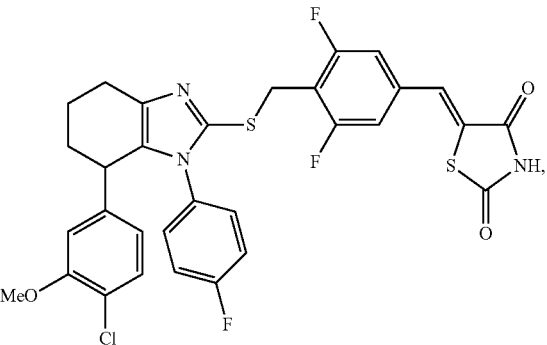
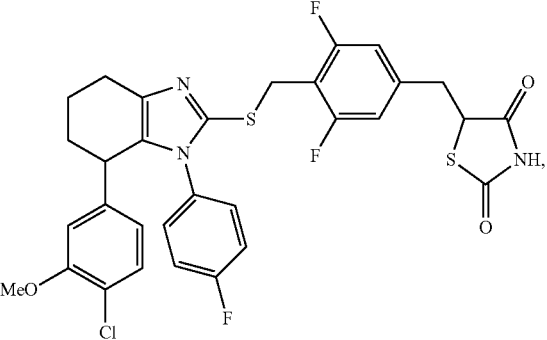

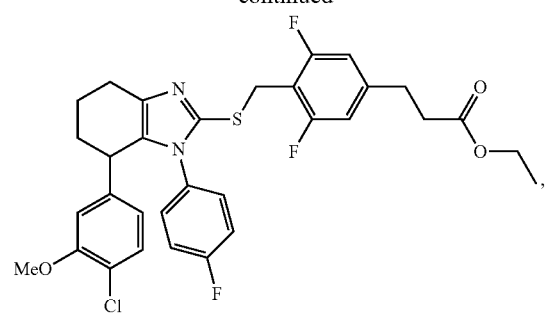
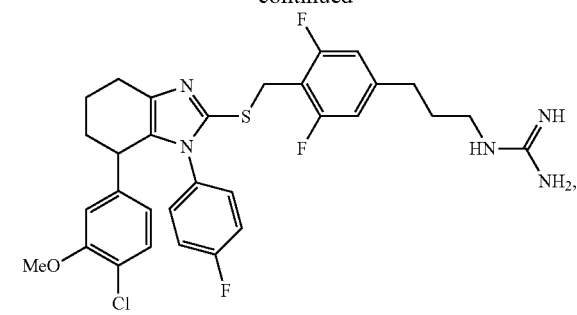
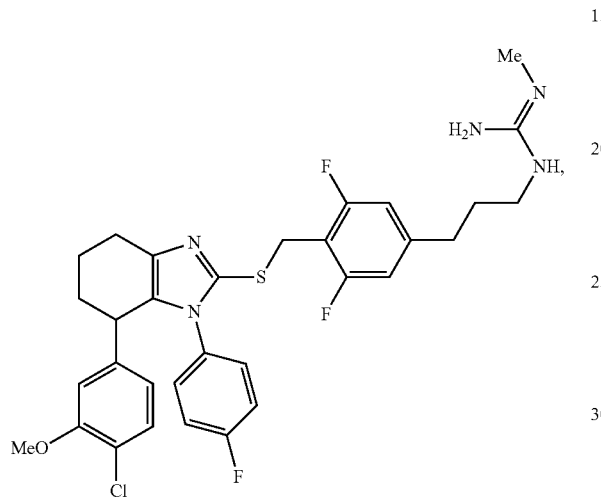
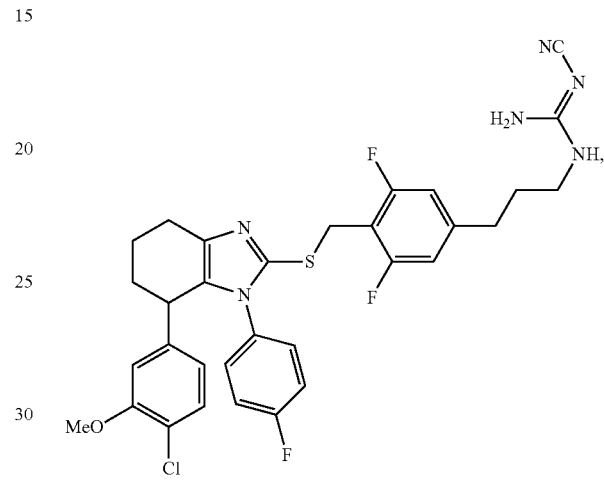
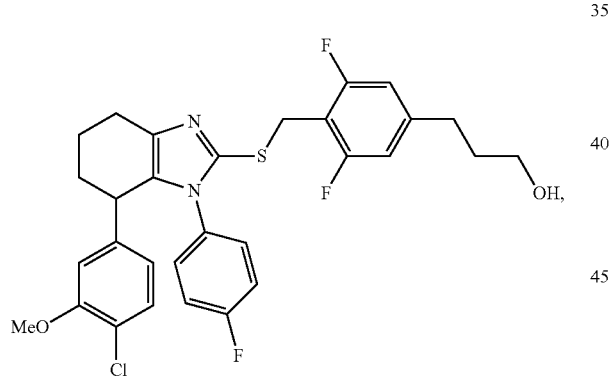
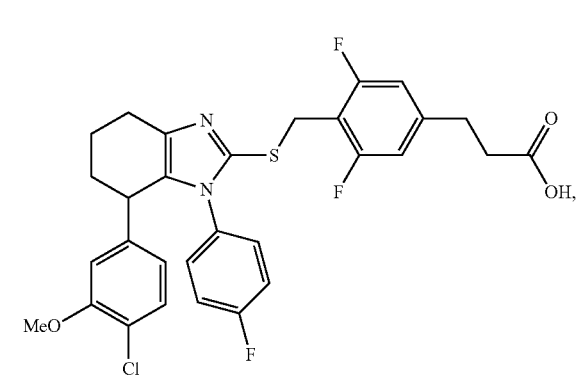
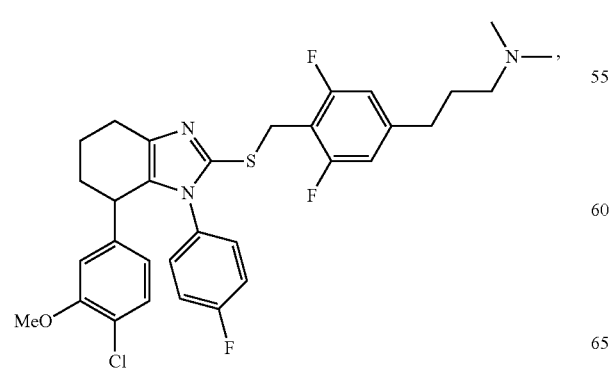
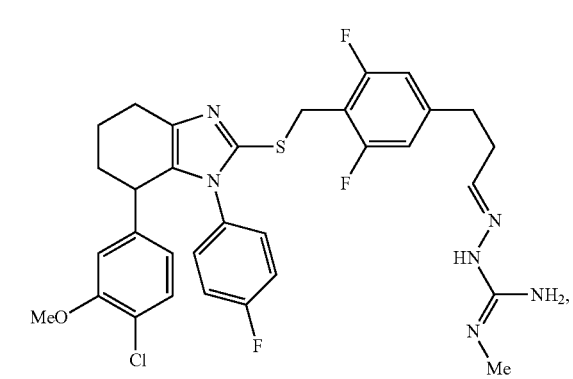

-continued
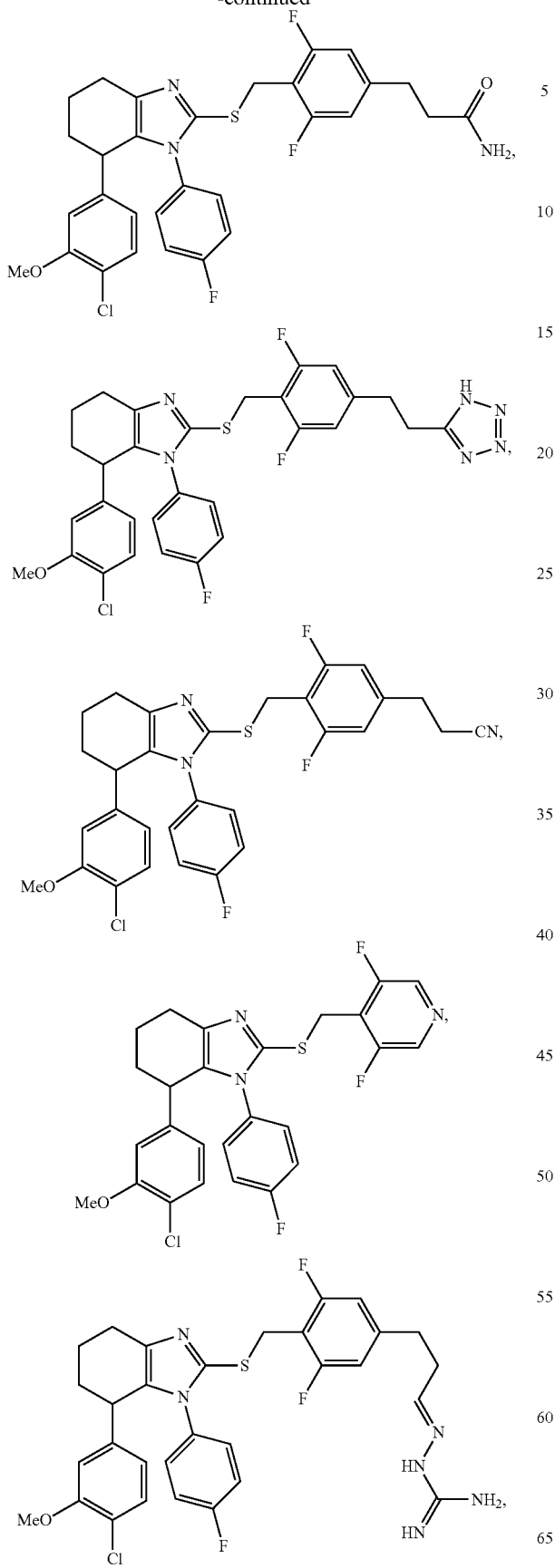
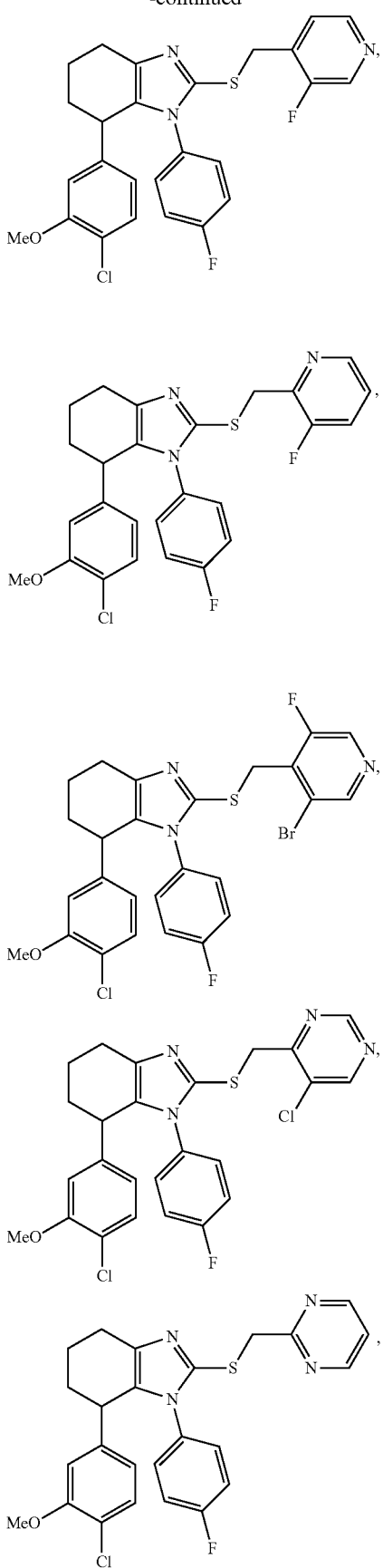

25
-continued
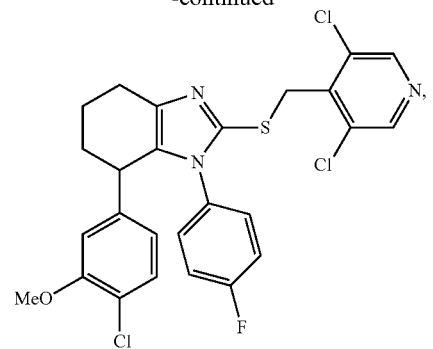
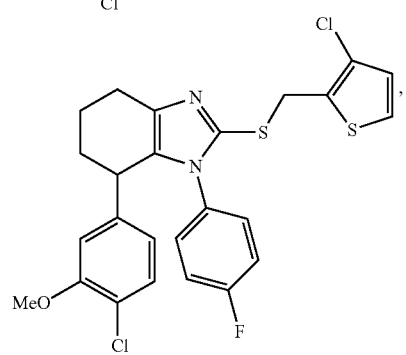
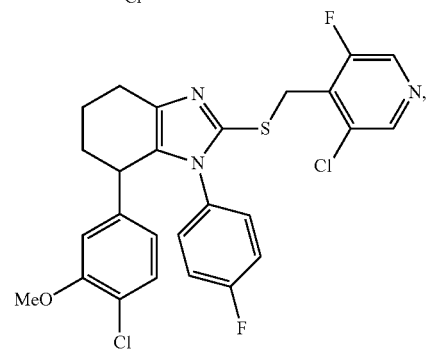
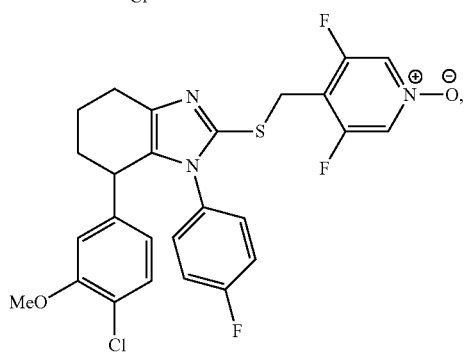
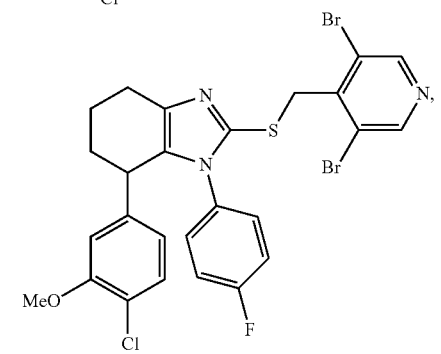
26
-continued
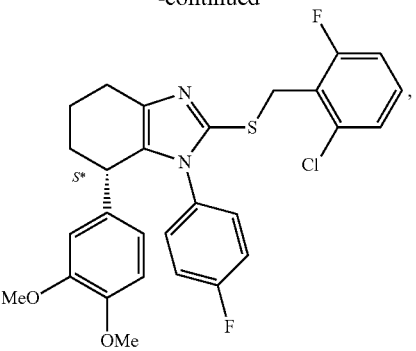
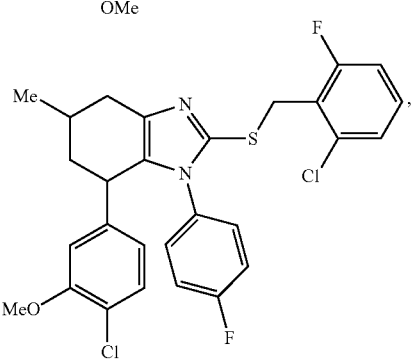
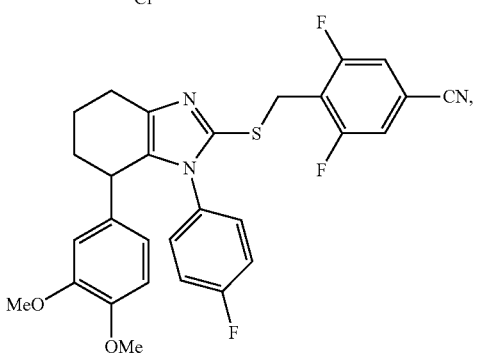
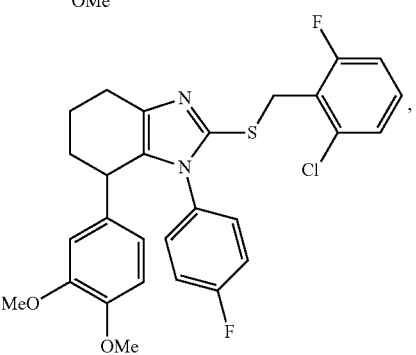
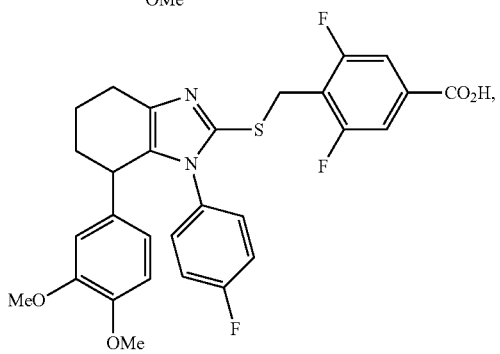

27
-continued
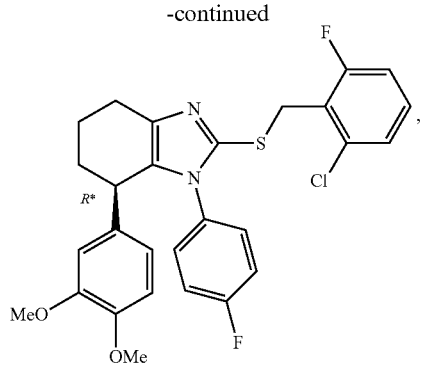
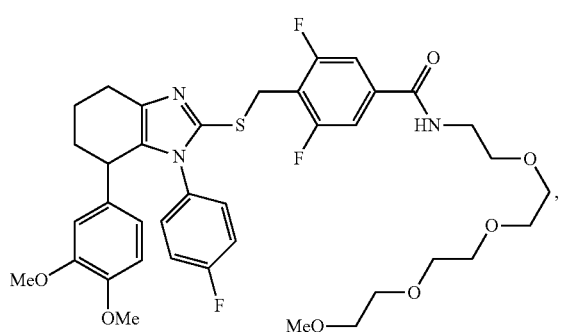
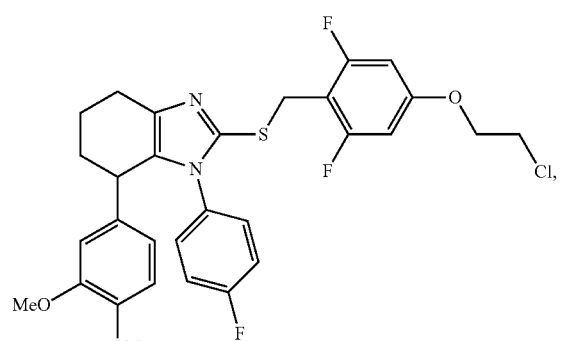
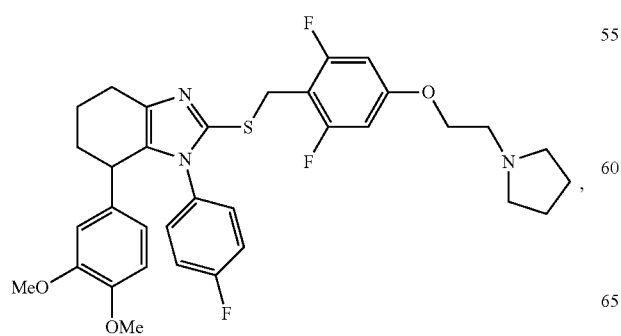
28
-continued
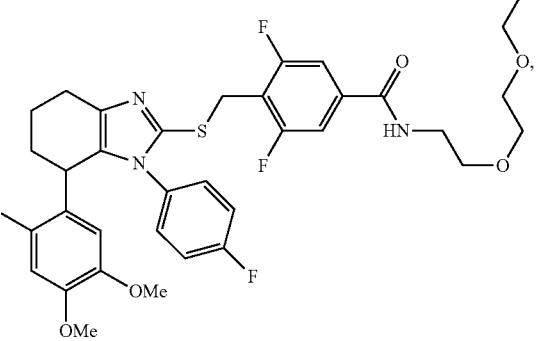
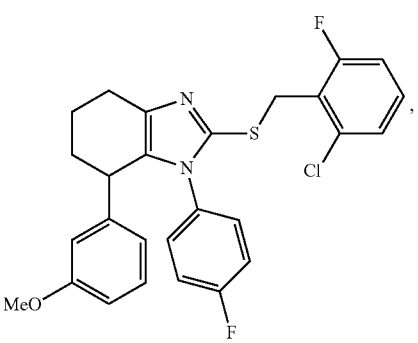
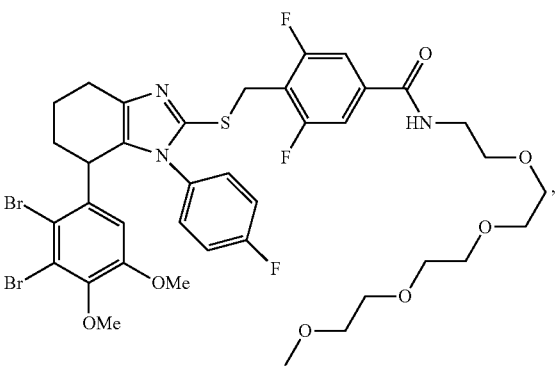
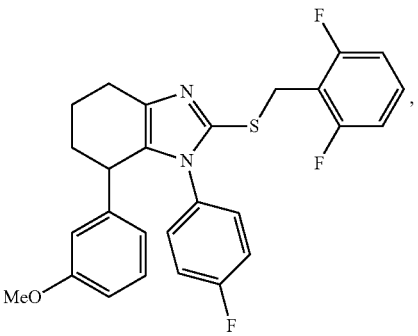

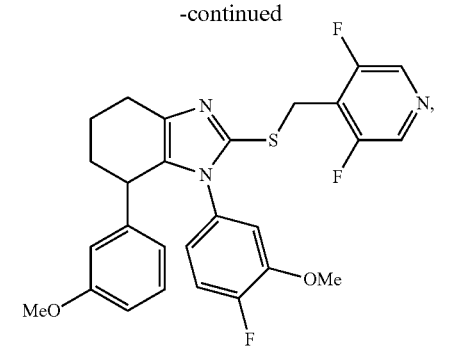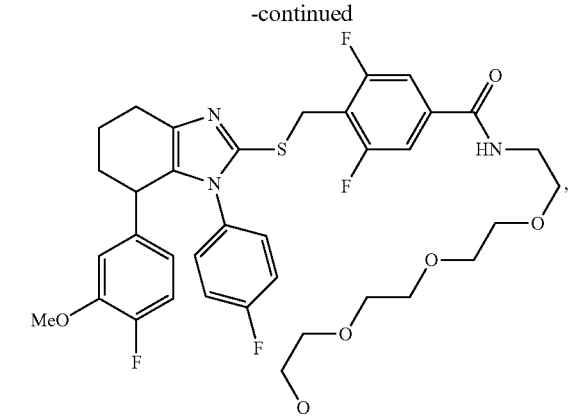

-continued
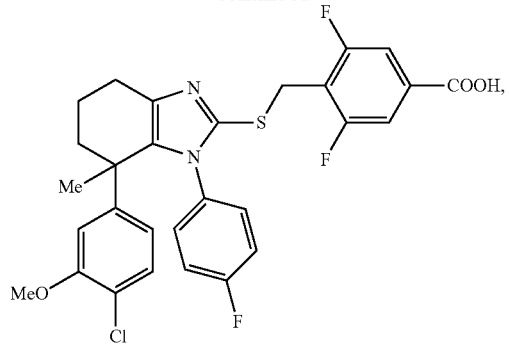
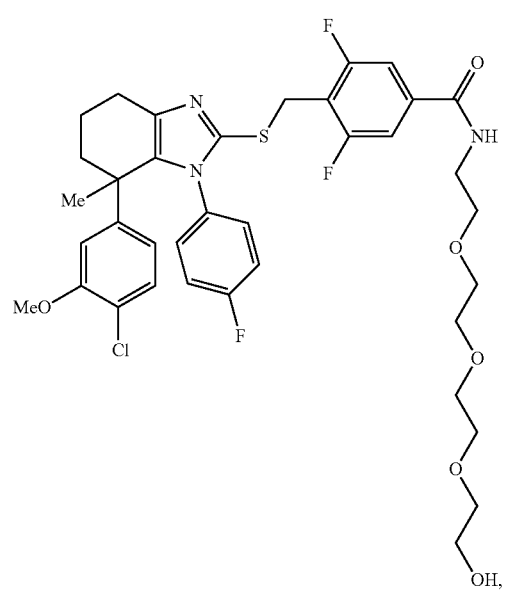
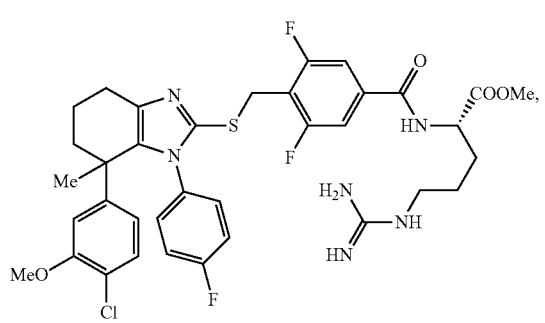
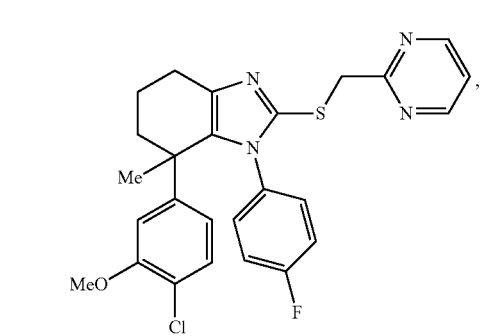
-continued
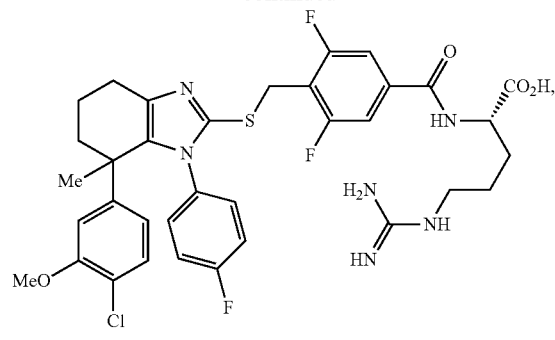
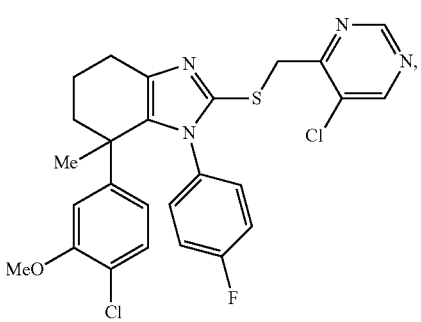
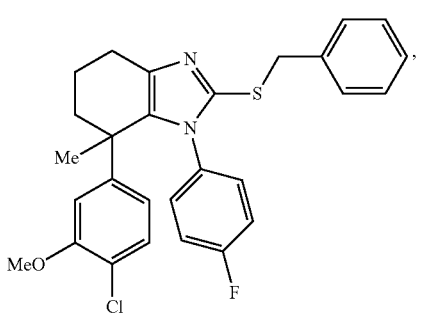
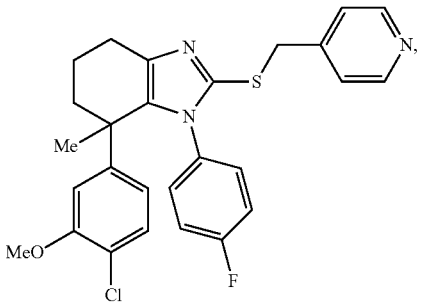
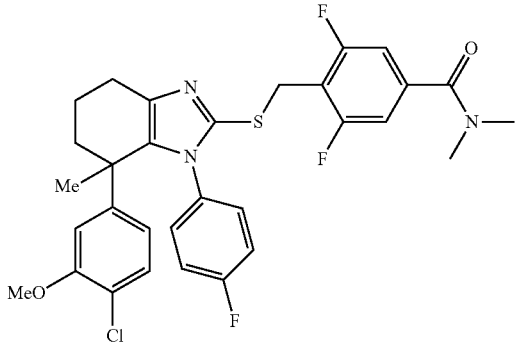

-continued
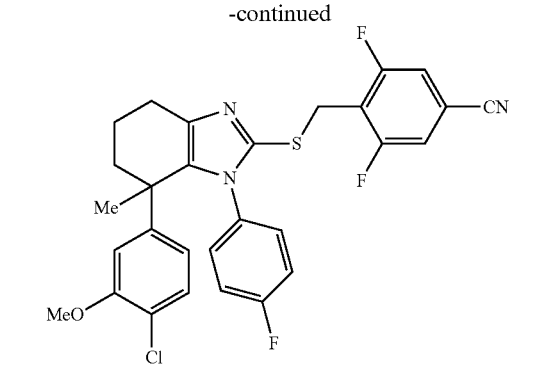
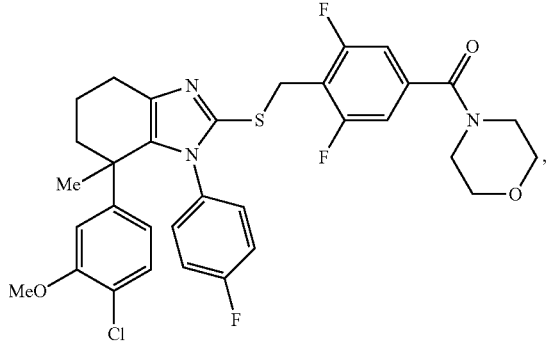
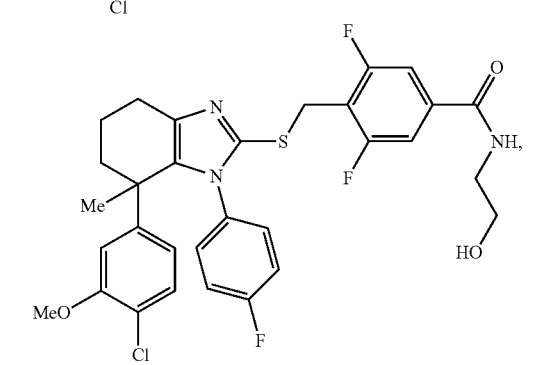

-continued
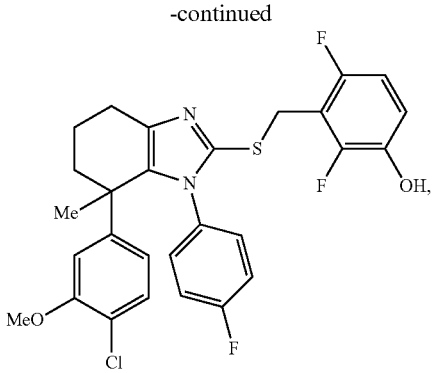
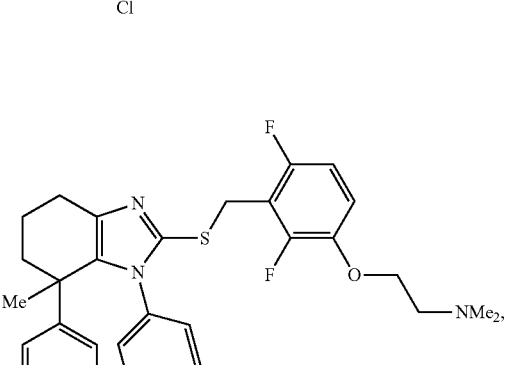
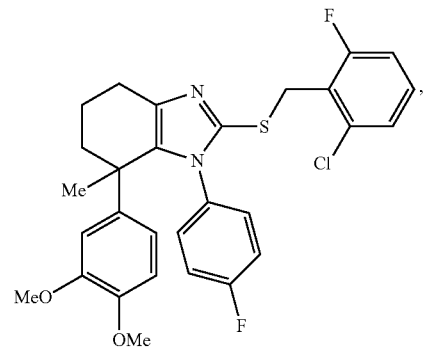
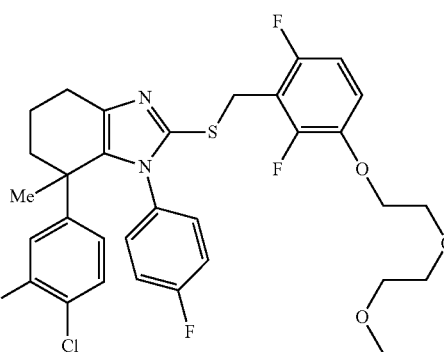

-continued
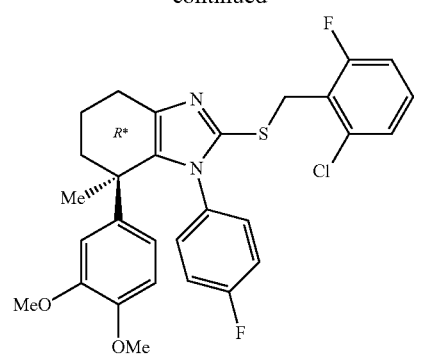
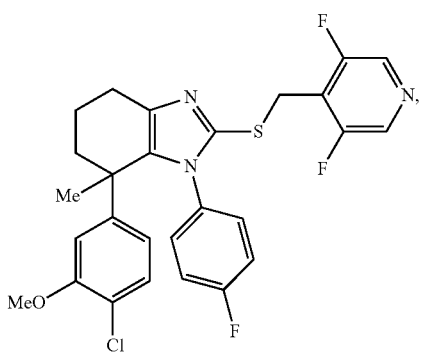
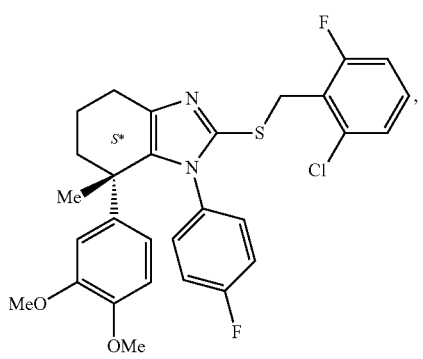
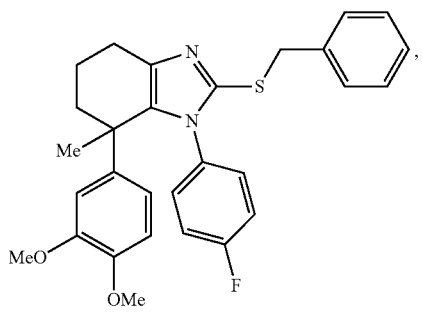
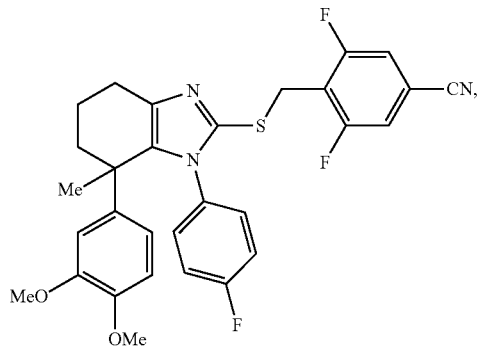
-continued
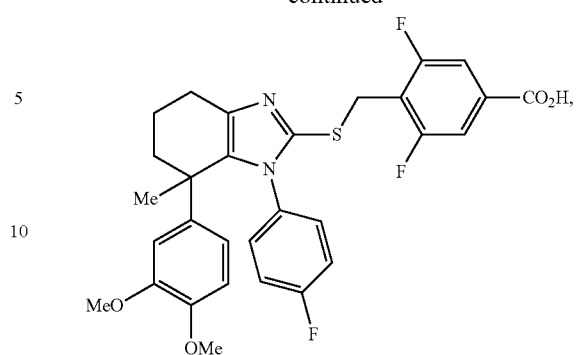
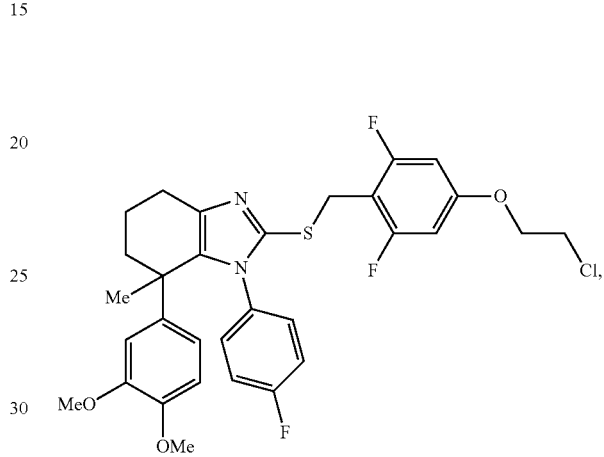
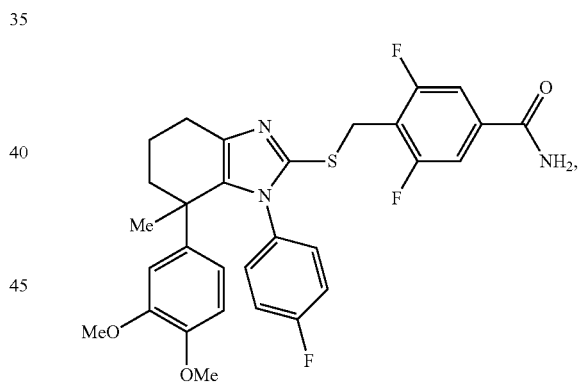
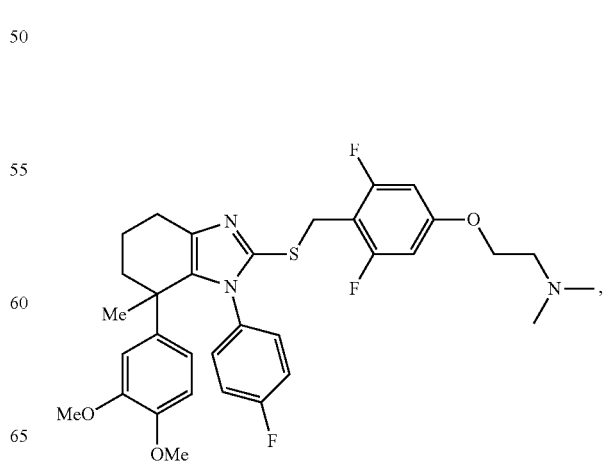

37
-continued
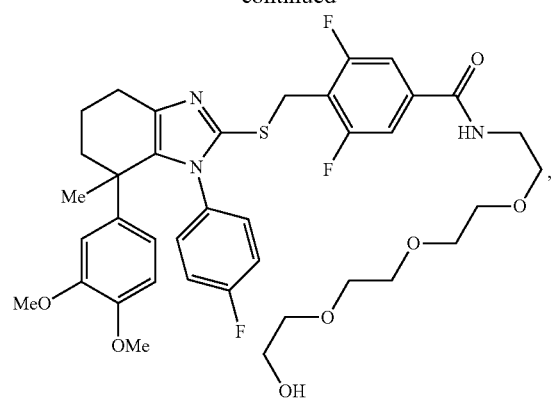
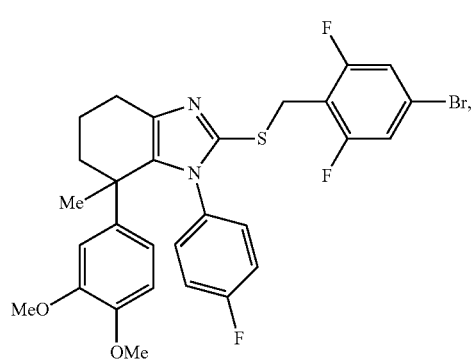
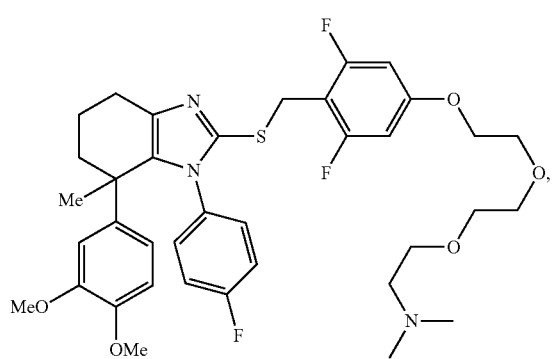
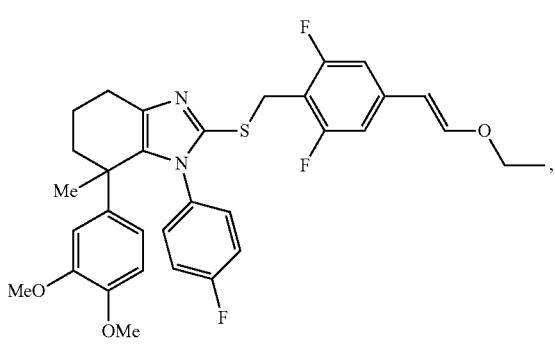
38
-continued
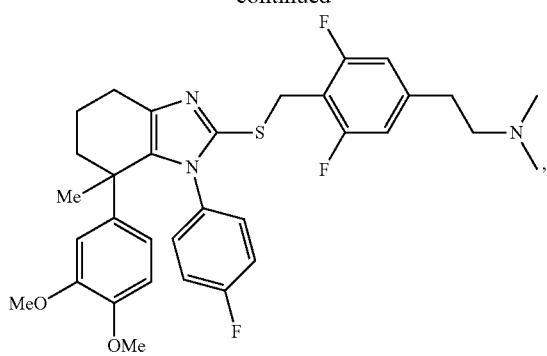
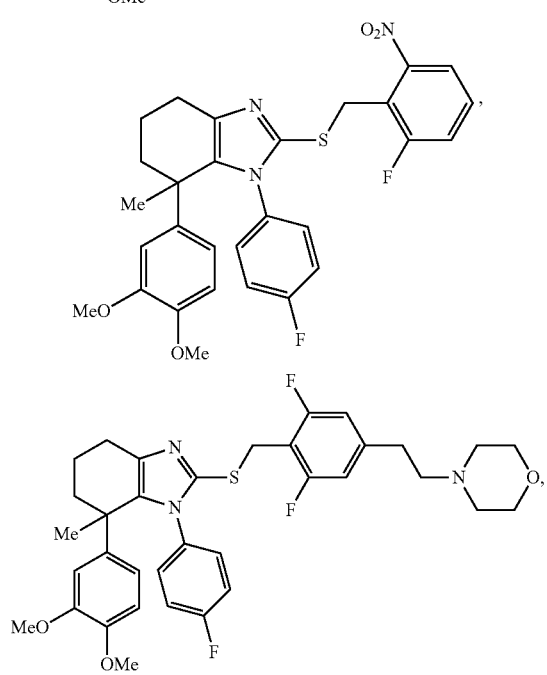
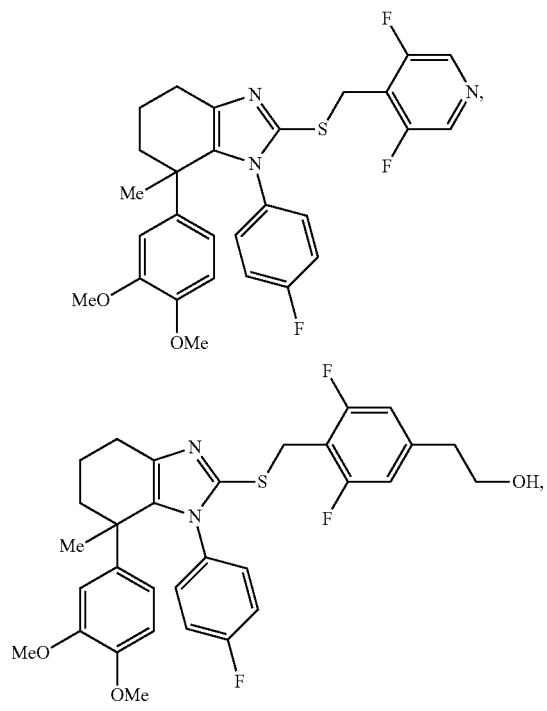

39
-continued
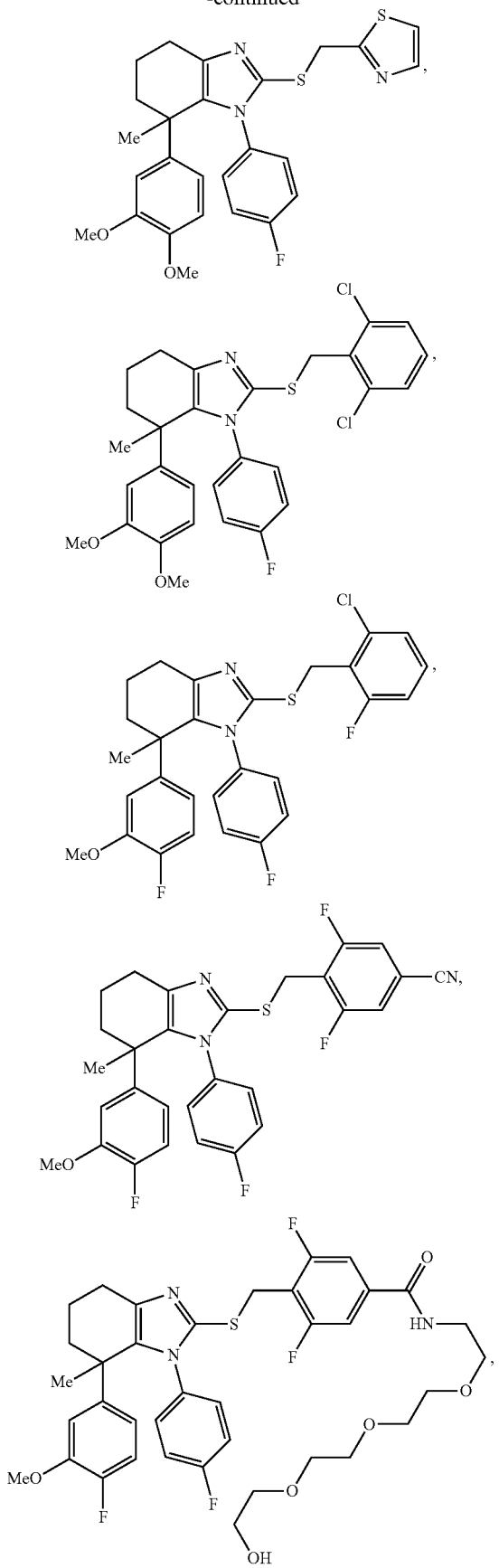
40
-continued
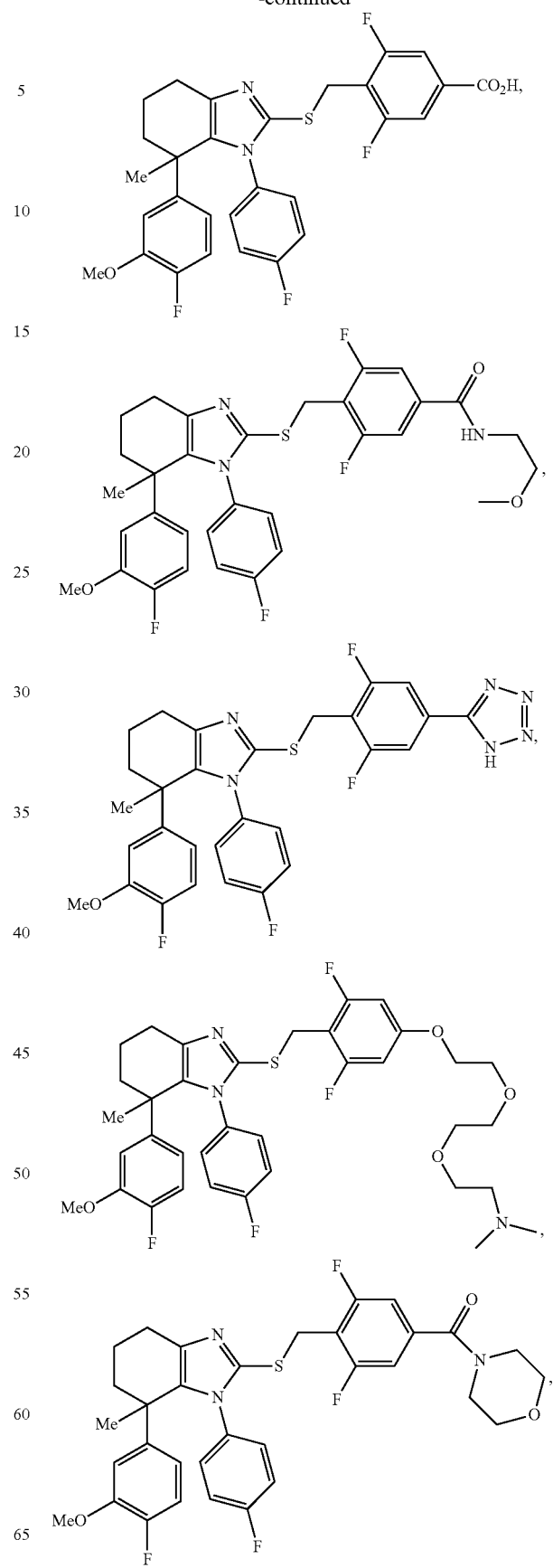

41
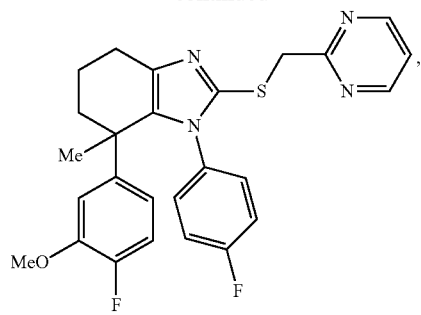
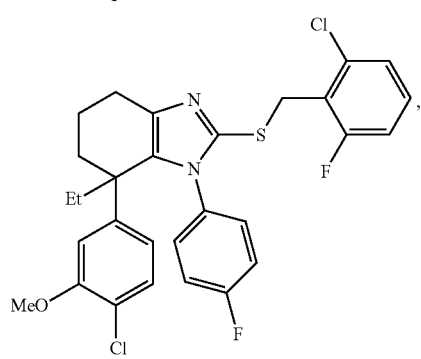
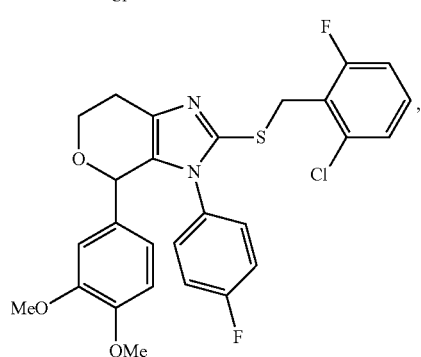
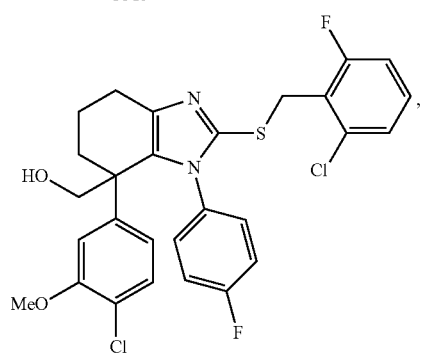
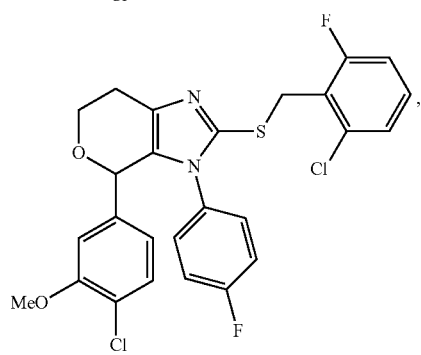
42
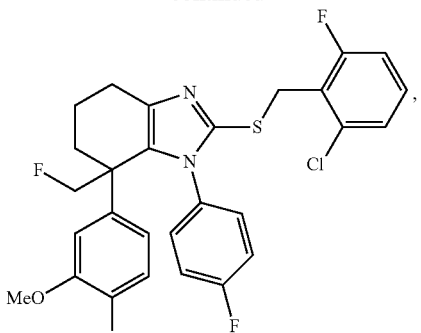
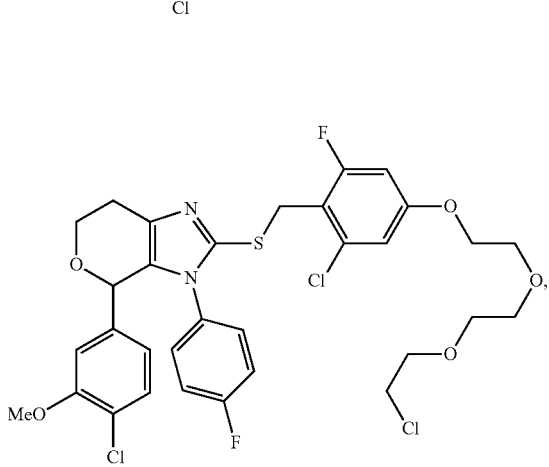
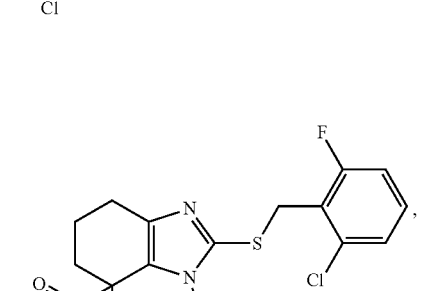
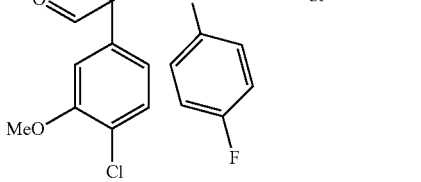
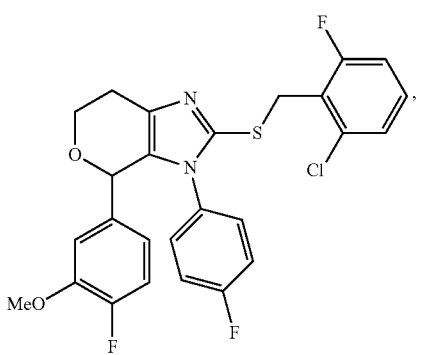

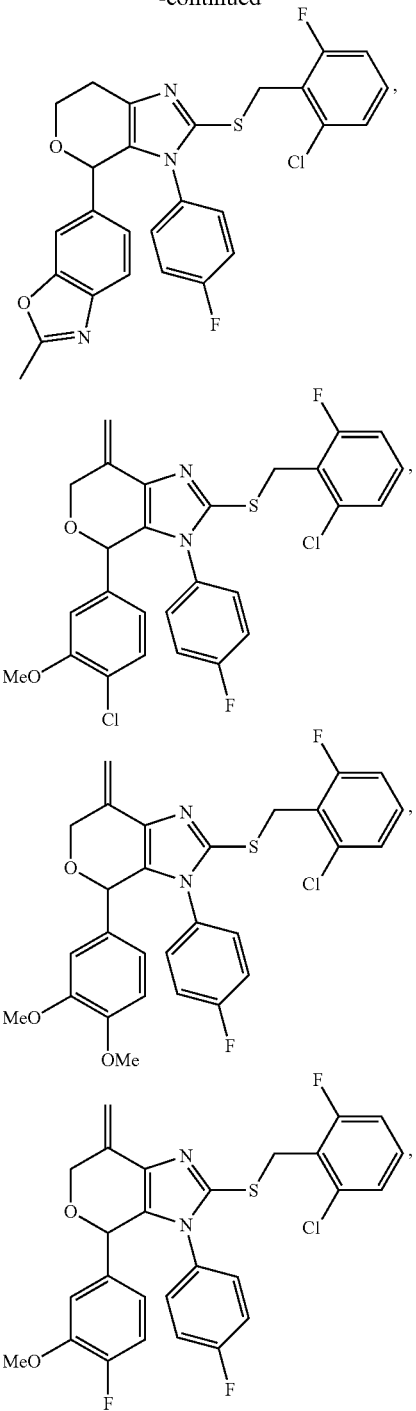

and pharmaceutically acceptable salts thereof.

Additional embodiments of the present invention, include those wherein the substituents selected for one or more of the variables defined herein (i.e. $R^1$, $R^2$, $R^3$, $R^4$, $R^5$, $R^6$, etc.) are independently selected to be any individual substituent or any subset of substituents selected from the complete list as defined herein.

In another embodiment the present invention is directed to a pharmaceutical composition comprising a compound of Formula (I) and a pharmaceutically acceptable carrier.

In another embodiment, the present invention is directed to a method for preventing or treating a TGR5 mediated syndrome, disorder or disease comprising administering to a subject in need thereof an effective amount of a compound of Formula (I) or a form, pharmaceutical composition or medicament thereof.

In another embodiment, the present invention is directed to a method of treating a disorder or condition such as diabetes (type I and type II), Syndrome X, hyperglycemia, hyperlipidemia, hyperinsulinemia, insulin resistance, inadequate glucose tolerance, impaired glucose metabolism, diabetic nephropathy, glomerulosclerosis, diabetic neuropathy, erectile dysfunction, macular degeneration, diabetic retinopathy, chronic microvascular complications, peripheral vascular disease, cataracts, stroke, foot ulcerations, renal failure, kidney disease, ketosis, metabolic acidosis, and related disorders, obesity, myocardial infarction, angina pectoris, coronary artery disease, atherosclerosis, cardiac hypertrophy, allergic diseases, fatty liver disease, nonalcoholic steatohepatitis, liver fibrosis, kidney fibrosis, anorexia nervosa, bulimia vervosa, autoimmune diseases, inflammatory diseases including rheumatoid arthritis, asthma, chronic obstructive pulmonary disease (COPD), psoriasis, ulcerative colitis, proliferative disorders, infectious diseases, angiogenic disorders, reperfusion/ischemia in stroke, vascular hyperplasia, organ hypoxia, cardiac hypertrophy, thrombin-induced platelet aggregation, and conditions associated with prostaglandin endoperoxidase synthetase-2 (COX-2) comprising administering to a subject in need thereof an effective amount of a compound of Formula (I) or a form, pharmaceutical composition or medicament thereof.

In another embodiment, the present invention is directed to a method of preventing or treating a syndrome, disorder or disease, wherein said syndrome, disorder or disease is selected from the group comprising: obesity, diabetes (type I or type II), metabolic diseases, cardiovascular diseases, inflammatory diseases, coronary artery disease, and atherosclerosis comprising administering to a subject in need thereof an effective amount of a compound of Formula (I) or a form, pharmaceutical composition or medicament thereof.

In another embodiment, the present invention is directed to a method of treating a syndrome, disorder or disease, wherein said syndrome, disorder or disease is selected from the group consisting of: obesity and type II diabetes.

In another embodiment, the present invention is directed to a method of treating a syndrome, disorder or disease, wherein said syndrome, disorder or disease is obesity comprising administering to a subject in need thereof an effective amount of a compound of Formula (I) or a form, pharmaceutical composition or medicament thereof.

In another embodiment, the present invention is directed to a method of treating a syndrome, disorder or disease, wherein said syndrome, disorder or disease is type II diabetes comprising administering to a subject in need thereof an effective amount of a compound of Formula (I) or a form, pharmaceutical composition or medicament thereof.

In another embodiment, the present invention is directed to a method of modulating TGR5 activity in a mammal by administration of an effective amount of at least one compound of Formula (I) to said mammal.

The term "subject" refers to a patient, which may be animal, typically a mammal, typically a human, which has been the object of treatment, observation or experiment and is at risk of (or susceptible to) developing a syndrome, disorder or disease that is associated with aberrant TGR5 expression or TGR5 underexpression, or a patient with a condition that accompanies syndromes, disorders or diseases associated with aberrant TGR5 expression or TGR5 underexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing or treating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, tert-butyl, pentyl and the like. Similarly, the term "$C_{X-Y}$alkyl", wherein X and Y are each integers shall include straight and branched chains containing between X and Y carbon atoms. For example, "$C_{1-4}$alkyl" shall mean straight and branched chains between 1 and 4 carbon atoms and include methyl, ethyl, propyl, isopropyl, butyl, isobutyl, sec-butyl and t-butyl. One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" or "preventing" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Pharmaceutically acceptable acidic/anionic salts suitable for use in accordance with the present invention may include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts for use in accordance with the present invention may include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

The pharmaceutically-acceptable salts of the compounds of Formula (I) may also include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

When employed as TGR5 modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating or preventing a syndrome, disorder or disease described herein with the compounds of the present invention or a polymorph or solvate thereof, which would be included within the scope of the invention albeit not specifically disclosed.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of the present invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

Preferably the pharmaceutical compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Preferably the pharmaceutical compositions are administered orally.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of TGR5 disorders is required.

ABBREVIATIONS

Herein and throughout the application, the following abbreviations may be used.
Ac acetyl
ACN acetonitrile
ADDP 1,1'-(azodicarbonyl)dipiperidine
BAST bis-(2-methoxyethyl)aminosulfur trifluoride
BINAP 2,2'-bis(diphenylphosphino)-1,1'-binaphthyl
Boc tert-butyloxycarbonyl
br broad
Bu butyl
n-BuLi n-butyl lithium
d doublet
dba dibenzylideneacetone
DCM dichloromethane
Dess-Martin periodinane 1,1,1-tris(acetyloxy)-1,1-dihydro-1,2-benziodoxol-3-(1H)-one
DIAD diisopropyl azodicarboxylate
DIBAL-H or DIBAL diisobutyl aluminum hydride
DIPEA or DIEA diisopropyl ethyl amine
DMA dimethylacetamide
DMF N,N-dimethylformamide
DMSO dimethyl sulfoxide
dppf (diphenylphosphino)ferrocene
EA ethyl acetate
EDCI N-(3-dimethylaminopropyl)-N'-ethylcarbodiimide hydrochloride
ESI electrospray ionization
Et ethyl
EtOH ethyl alcohol
HATU O-(7-azabenzotriazol-1-yl)-N,N,N',N'-tetramethyluronium hexafluorophosphate
HOBt hydroxybenzotriazole
HPLC high pressure liquid chromatography
Hz hertz
iPr, i-Pr, iPr, or i-Pr isopropyl
i-PrOH isopropyl alcohol
LiHMDS lithium hexamethyldisilazane
LDA lithium diisopropyl amine
m multiplet
M molar (moles/liter)
mCPBA meta-chloroperoxybenzoic acid
Me methyl
MeOH methanol
MHz megahertz
min minutes
mL milliliters
MsCl mesyl chloride
nBu, n-Bu, nBu, or n-Bu normal butyl
nm nanometers
NBS N-bromosuccinimide
NIS N-iodosuccinimide
NMR nuclear magnetic resonance
OTf triflate
$Pd_2(dba)_3$ tris(dibenzylideneacetone)dipalladium(0)
PE petroleum ether
Ph phenyl
PMB para-methoxybenzyl or 4-methoxybenzyl
ppm parts per million Pr propyl
pTSA para-toluene sulfonic acid
q quartet
s singlet
SEMCl 2-(trimethylsilyl)ethoxymethyl chloride
TBAF tetra butyl ammonium fluoride
TBS tert-butyl dimethyl silyl
TEA triethylamine
TES triethylsilyl
TFA trifluoroacetic acid
THF tetrahydrofuran
TIPS triisopropylsilyl
TLC thin layer chromatography
TMS trimethylsilyl
UV ultra-violet
Xantphos 4,5-bis(diphenylphosphino)-9,9-dimethylxanthene The compounds of the present invention can be synthesized using the methods described below, together with synthetic methods known in the art of synthetic organic chemistry, or variations thereof as appreciated by those skilled in the art. The following reaction schemes are only meant to represent examples of the invention and are in no way meant to be a limit of the invention.

General Synthetic Schemes

Compounds of Formula (I) where X is $CH_2$ and $Z^1$ and $Z^2$ are H, may be prepared according to the process described in Scheme 1.

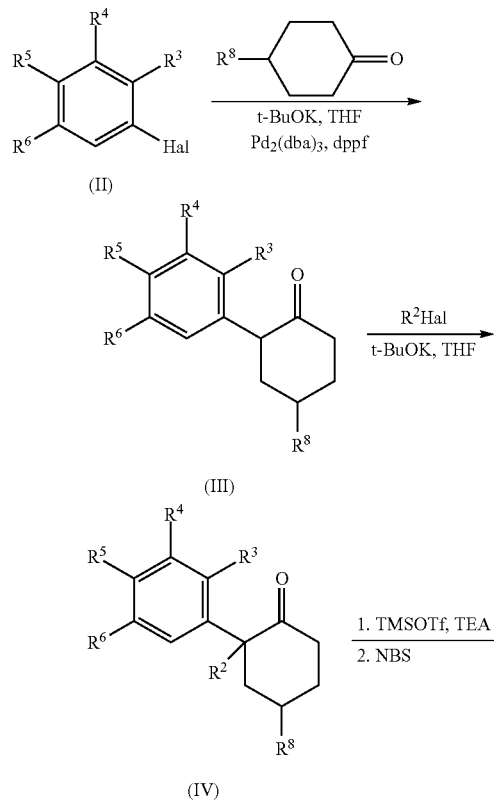

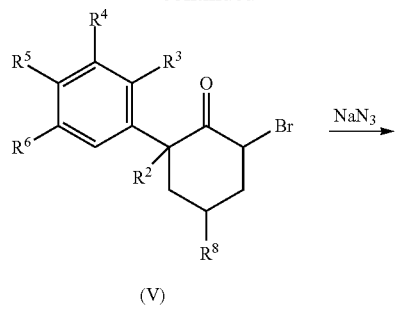

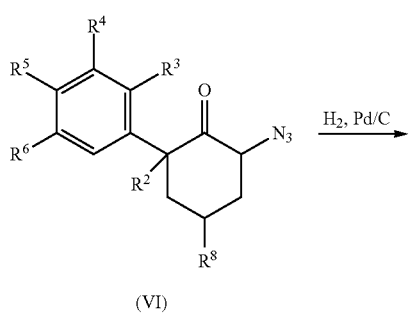

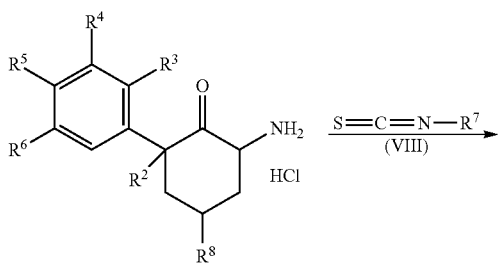

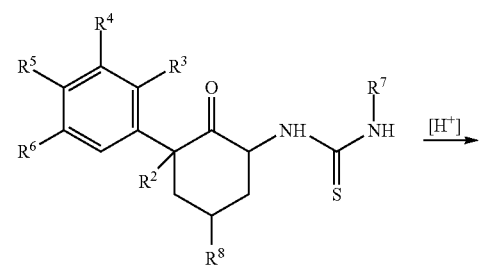

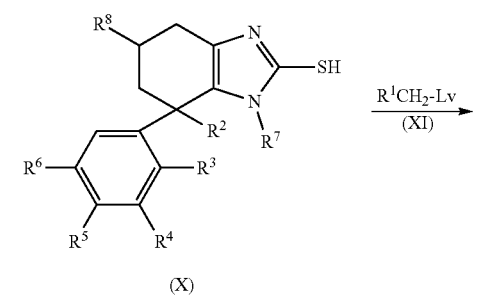

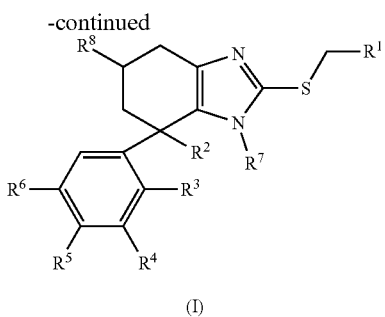

(I)

A suitably substituted compound of Formula (II) wherein Hal is Br or I, a commercially available compound or compound prepared by known methods, is reacted with cyclohexanone (or 4-methyl cyclohexanone), in the presence of an inorganic base such as t-BuOK, t-BuONa, $Cs_2CO_3$, and the like, in the presence of a suitably selected Pd containing reagent such $Pd(OAc)_2$, $Pd(Ph_3P)_4$, $Pd_2(dba)_3$, and the like, in the presence of a suitably selected ligand such as $Ph_3P$, BINAP, dppf, and the like, in a suitably selected organic solvent such as THF, 1,4-dioxane, toluene and the like at a temperature in the range from 25° C. to about 80° C., to yield the corresponding compound of formula (III).

A suitably substituted compound of Formula (III) is reacted with a suitably substituted commercially available compound $R^2$Hal wherein Hal is Br or I, and the like, in an inorganic base such as t-BuOK, t-BuONa, NaH, and the like, in an organic solvent such as toluene, THF, dioxane and the like, at a temperature in the range from 25° C. to about 60° C., to yield the corresponding compound of formula (IV).

A suitably substituted compound of Formula (IV) is reacted with commercially available reagent such as TMSOTf, TESOTf, TIPSOTf, and the like, in an organic base such as TEA, DIPEA, pyridine and the like, in an organic solvent such as DCM, THF, ether and the like, at a temperature in the range from −78° C. to −40° C., to yield the corresponding enol ether intermediate, which is then reacted with commercially available reagent NBS, $Br_2$ and the like, in an organic solvent such as DCM, THF, ether and the like, at a temperature in the range from −78° C. to 0° C., to yield the corresponding bromide (V).

Bromide (V) is reacted with commercially available $NaN_3$, in an organic solvent such as DMF, DMSO, DMA and the like, at a temperature in the range from 25° C. to 70° C., to yield the corresponding azide (VI).

Azide (VI) is reduced under 20~50 psi of hydrogen gas in the presence of a commercially available catalyst, such as 5% Pd/C, $PtO_2$ and the like, in an organic solvent such as MeOH, EtOH, AcOH and the like, in the presence of concentrated HCl and the like, at a temperature in the range from 25° C. to 70° C., to yield the corresponding amine (VII).

Amine (VII) is reacted with compound (VIII), an isothiocyanate prepared by known methods or commercially available, in the presence of an organic base such as TEA, DIPEA, pyridine and the like, in an organic solvent such as DCM, THF and the like, at a temperature in the range from 0° C. to 25° C., to yield the corresponding thiourea (IX).

Thiourea (IX) is heated in an acidic solvent such as AcOH, trifluoroacetic acid and the like, at a temperature in the range from 25° C. to 80° C., to yield the corresponding imidazole (X).

Imidazole (X) is reacted with a commercially available compound or compound prepared by known methods of formula (XI), where Lv is a leaving group, in the presence of an inorganic base such as $Cs_2CO_3$, $K_2CO_3$, NaH and the like, in an organic solvent such as DMF, DMSO, acetone and the like, at a temperature in the range from 25° C. to 80° C., to yield the corresponding compound of Formula (I) where X is $CH_2$ and $Z^1$ and $Z^2$ are H.

Compounds of Formula (I) where X is O and $Z^1$ and $Z^2$ are H, may be prepared as described in Scheme 2, below.

Scheme 2

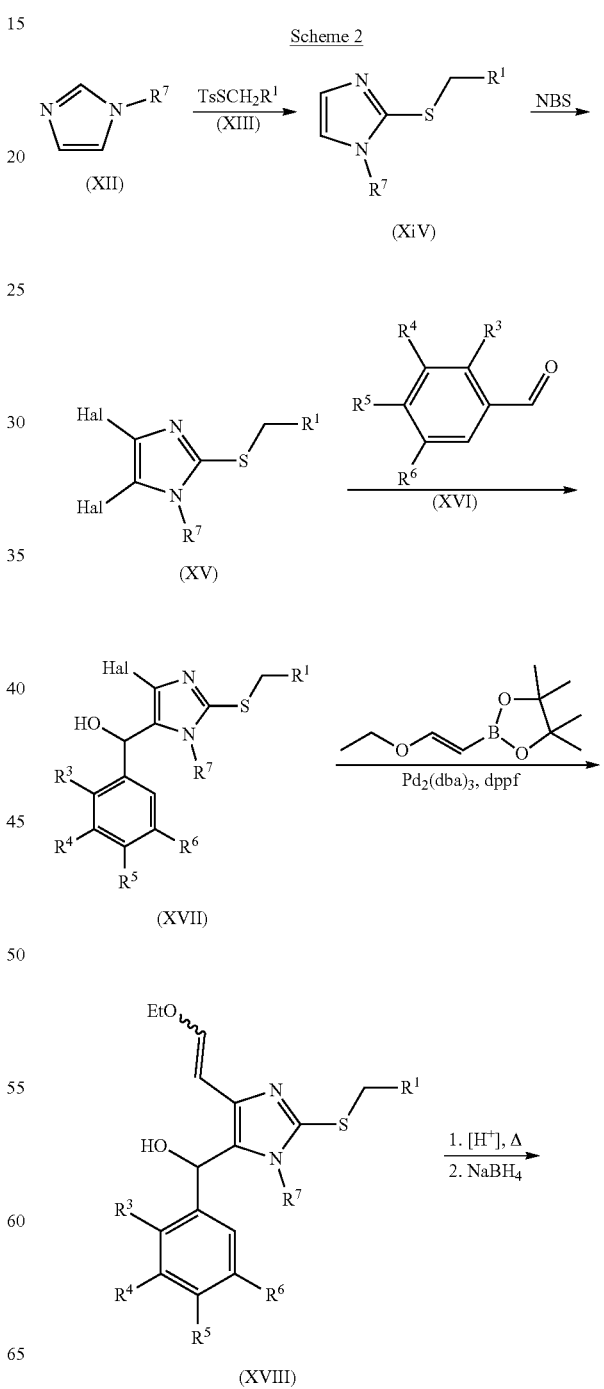

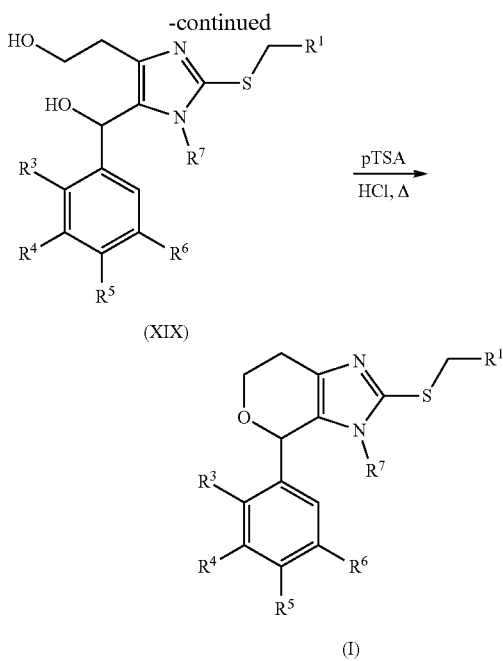

(XIX)

(I)

An imidadole of Formula (XII) (generated by reaction of $R^7$—$B(OH)_2$ with imidazole in the presence of $Cu_2O$, $Cu(OAc)_2$ or other appropriate catalyst, in a suitably selected organic solvent such as THF, 1,4-dioxane, MeOH and the like, at a temperature in the range from 25° C. to about 80° C.), is reacted with a suitably substituted commercially available compound of formula $TsSCH_2R^1$ (XIII), a compound prepared by known methods, in an organic base such as n-BuLi, LDA, LiHMDS and the like, in an organic solvent such as THF, dioxane, ether and the like, at a temperature in the range from −78° C. to −40° C., to yield the corresponding compound of Formula (XIV).

A suitably substituted compound of formula (XIV) is reacted with a commercially available reagent such as NIS or NBS in an organic solvent such as DCM, THF, MeOH and the like, at a temperature in the range from 25° C. to 60° C., to yield the corresponding compound of Formula (XV) wherein Hal is Br or I.

A suitably substituted compound of formula (XV) wherein Hal is Br or I is reacted with a suitably substituted commercially available aldehyde of formula (XVI), in an organic base such as n-BuLi, i-Pr—MgBr and the like, in an organic solvent such as THF, dioxane, ether and the like, at a temperature in the range from −78° C. to 0° C., to yield the corresponding compound of Formula (XVII).

A suitably substituted compound of formula (XVII) is reacted with a commercially available reagent such as 2-(2-ethoxyvinyl)-4,4,5,5-tetramethyl-1,3,2-dioxaborolane or tributyl(2-ethoxyvinyl)stannane, in the presence or in the absence of an inorganic base such as $t-Na_2CO_3$, $K_2CO_3$, $K_3PO_4$, and the like, in the presence of a suitably selected Pd containing reagent such $Pd(OAc)_2$, $Pd(Ph_3P)_4$, $Pd_2(dba)_3$, and the like, in the presence of a suitably selected ligand such as $Ph_3P$, BINAP, dppf, and the like, in a mixed solvent of a suitably selected organic solvent such as THF, 1,4-dioxane, toluene and the like, and water at a temperature in the range from 50° C. to about 100° C., to yield the corresponding compound of formula (XVIII).

A suitably substituted compound of formula (XVIII) is reacted in an acidic solution of HCl, in a mixed solvent of a suitably selected organic solvent such as THF, 1,4-dioxane, MeOH and the like, and water at a temperature in the range from room temperature to about 50° C., to yield the corresponding intermediates, which is then reacted with a commercially available reducing reagent such as $NaBH_4$, $LiBH_4$ and the like in a suitably selected organic solvent such as THF, MeOH and the like, at a temperature in the range from 0° C. to room temperature, to yield the corresponding compound of Formula (XIX).

A suitably substituted compound of Formula (XIX) is reacted in an acidic solution of HCl, pTSA and the like in a mixed solvent of a suitably selected organic solvent such as THF, 1,4-dioxane, MeOH and the like, and water or a suitably selected organic solvent such as benzene, toluene and the like at a temperature in the range from room temperature to about 80° C., to yield the corresponding compound of Formula (I).

Alternatively, compounds of Formula (I) where X is O and $Z^1$ and $Z^2$ are H may be prepared according to the process as described in the Scheme 3, below.

Scheme 3

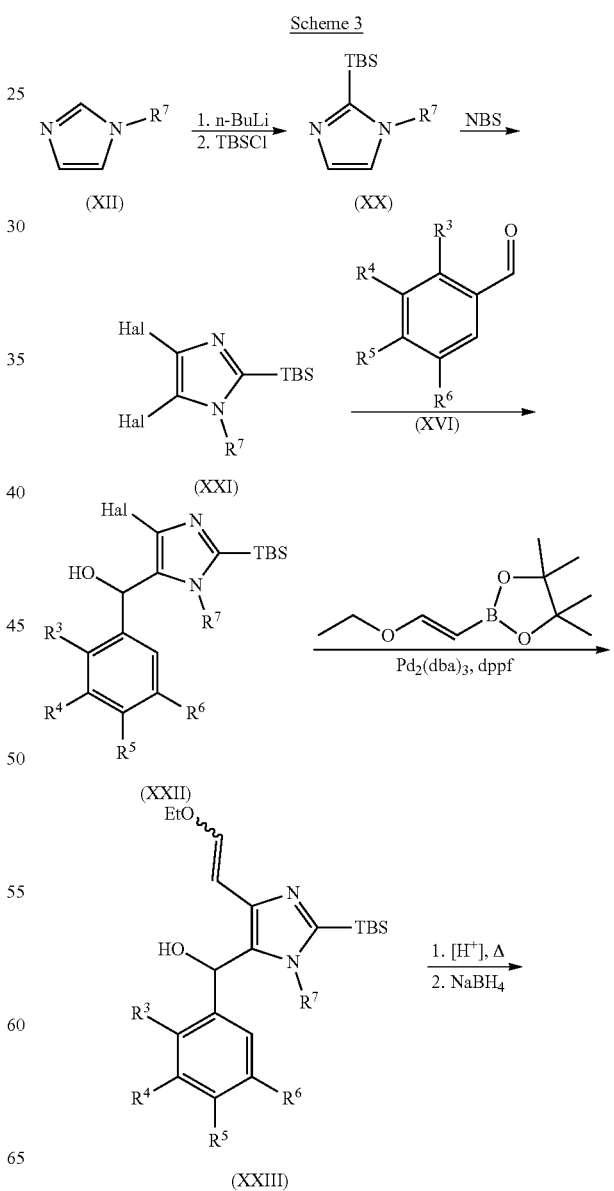

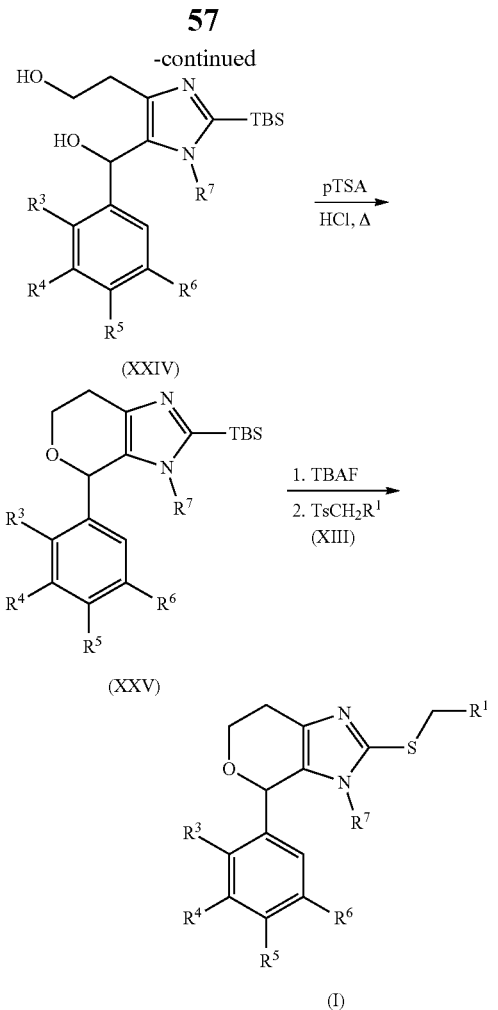

A suitably substituted compound of Formula (XII) is reacted with a commercially available reagent such as TBSCl or TBSOTf in an organic base such as n-BuLi, LiHMDS and the like, in an organic solvent such as THF, dioxane, ether and the like, at a temperature in the range from −78° C. to 0° C., to yield the corresponding compound of Formula (XX).

Imidazole (XX) is reacted with a commercially available reagent such as NIS or NBS in an organic solvent such as DCM, THF, MeOH and the like, in the presence of catalytic amount of an acid such as pTSA, CSA and the like, at a temperature in the range from 25° C. to 60° C., to yield the corresponding compound of Formula (XXI) wherein Hal=Br or I.

A suitably substituted compound of Formula (XXI) wherein Hal=Br or I is reacted with a suitably substituted commercially available aldehyde (XVI), in the presence of an organic base such as n-BuLi, i-Pr—MgBr and the like, in an organic solvent such as THF, dioxane, ether and the like, at a temperature in the range from −78° C. to 0° C., to yield the corresponding compound of Formula (XXII).

A suitably substituted compound of formula (XXII) is reacted with a commercially available reagent such as 2-(2-ethoxyvinyl)-4,4,5,5-tetramethyl-1,3,2-dioxaborolane or tributyl(2-ethoxyvinyl)stannane, in the presence or in the absence of an inorganic base such as t-Na$_2$CO$_3$, K$_2$CO$_3$, K$_3$PO$_4$, and the like, in the presence of a suitably selected Pd containing reagent such Pd(OAc)$_2$, Pd(Ph$_3$P)$_4$, Pd$_2$(dba)$_3$, and the like, in the presence of a suitably selected ligand such as Ph$_3$P, BINAP, dppf, and the like, in a mixed solvent of a suitably selected organic solvent such as THF, 1,4-dioxane, toluene and the like, and water at a temperature in the range from 50° C. to about 100° C., to yield the corresponding compound of Formula (XXIII).

A suitably substituted compound of formula (XXIII) is reacted in an acidic solution of HCl, in a mixed solvent of a suitably selected organic solvent such as THF, 1,4-dioxane, MeOH and the like, and water at a temperature in the range from room temperature to about 50° C., to yield the corresponding intermediates, which is then reacted with a commercially available reducing reagent such as NaBH$_4$, LiBH$_4$ and the like in a suitably selected organic solvent such as THF, MeOH and the like, at a temperature in the range from 0° C. to room temperature, to yield the corresponding compound of Formula (XXIV).

A suitably substituted compound of Formula (XXIV) is reacted in an acidic solution of HCl, pTSA and the like in a mixed solvent of a suitably selected organic solvent such as THF, 1,4-dioxane, MeOH and the like, and water or a suitably selected organic solvent such as benzene, toluene and the like at a temperature in the range from room temperature to about 80° C., to yield the corresponding compound of Formula (XXV).

A suitably substituted compound of Formula (XXV) is reacted with a commercially available reagent such as TBAF, KF and the like, in an organic solvent such as THF, dioxane, ether and the like, at a temperature in the range from 0° C. to room temperature, followed by reaction with a suitably substituted commercially available compound of formula TsSCH$_2$R$^1$ (XV), a compound prepared by known methods, in an organic base such as n-BuLi, LDA, LiHMDS and the like, in an organic solvent such as THF, dioxane, ether and the like, at a temperature in the range from −78° C. to −40° C., to yield the corresponding compound of Formula (I).

Compounds of Formula (I) where X is O and Z$^1$ and Z$^2$ are taken together with their attached carbon to form a

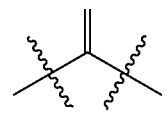 [SMILES: *C(*)=C]

group may be prepared according to the process as described in the Scheme 4, below.

Scheme 4

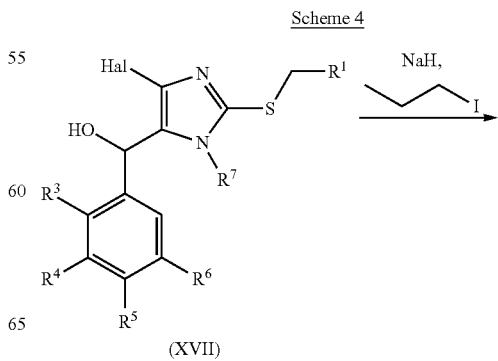

(XVII)

-continued

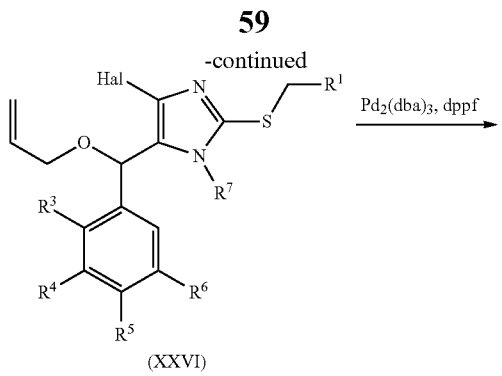

(XXVI)

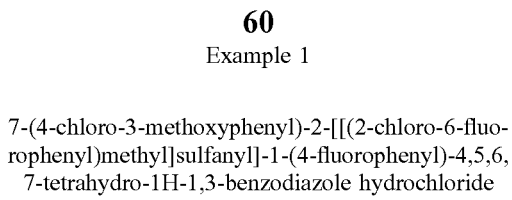

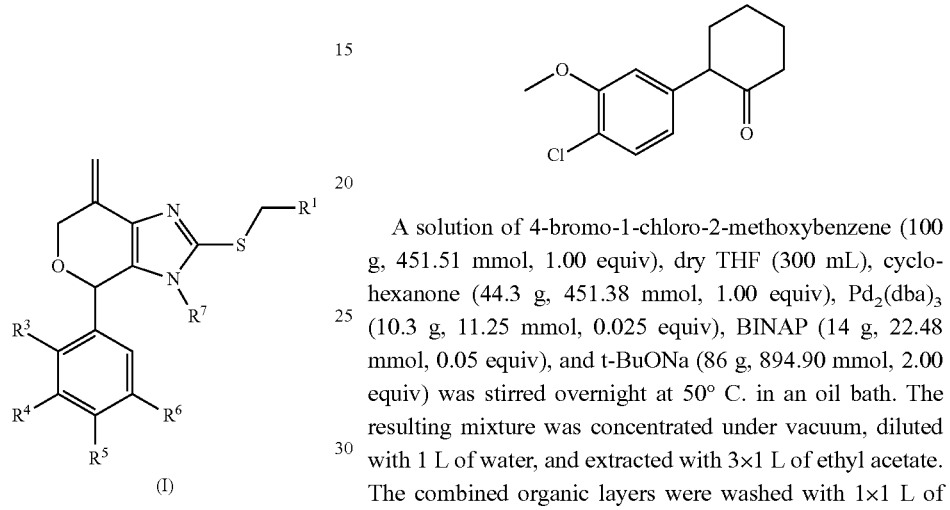

(I)

A suitably substituted compound of formula (XVII) is reacted with a commercially available reagent such as 3-iodoprop-1-ene or 3-bromoprop-1-ene, in the presence or in the absence of an inorganic base such as $Cs_2CO_3$, NaH, and the like, in a suitably selected organic solvent such as THF, DMF and the like, at a temperature in the range from 0° C. to room temperature, to yield the corresponding compound of formula (XXVI).

A suitably substituted compound of formula (XXVI) is reacted in the presence of a suitably selected Pd containing reagent such $Pd(OAc)_2$, $Pd(Ph_3P)_4$, $Pd_2(dba)_3$, and the like, in the presence of a suitably selected ligand such as $Ph_3P$, BINAP, dppf, and the like, in a suitably selected organic solvent such as THF, 1,4-dioxane, toluene and the like, at a temperature in the range from 80° C. to about 100° C., to yield the corresponding compound of Formula (I).

EXAMPLES

Compounds of the present invention can be prepared by methods known to those who are skilled in the art. The following examples are only meant to represent examples of the invention and are in no way meant to be a limit of the invention.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

7-(4-chloro-3-methoxyphenyl)-2-[[(2-chloro-6-fluorophenyl)methyl]sulfanyl]-1-(4-fluorophenyl)-4,5,6,7-tetrahydro-1H-1,3-benzodiazole hydrochloride Step 1:
2-(4-chloro-3-methoxyphenyl)cyclohexan-1-one

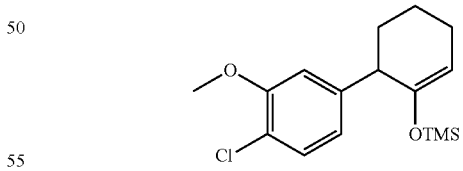

A solution of 4-bromo-1-chloro-2-methoxybenzene (100 g, 451.51 mmol, 1.00 equiv), dry THF (300 mL), cyclohexanone (44.3 g, 451.38 mmol, 1.00 equiv), $Pd_2(dba)_3$ (10.3 g, 11.25 mmol, 0.025 equiv), BINAP (14 g, 22.48 mmol, 0.05 equiv), and t-BuONa (86 g, 894.90 mmol, 2.00 equiv) was stirred overnight at 50° C. in an oil bath. The resulting mixture was concentrated under vacuum, diluted with 1 L of water, and extracted with 3×1 L of ethyl acetate. The combined organic layers were washed with 1×1 L of brine, dried over anhydrous sodium sulfate, filtered, and concentrated. The residue was applied onto a silica gel column with ethyl acetate/petroleum ether (1:5). The crude product was applied onto a reverse phase column and eluted with $MeCN/H_2O$ (1:19 to 4:1 in 1 h) to give 2-(4-chloro-3-methoxyphenyl)cyclohexan-1-one as a light yellow solid. Mass spectrum (ESI, m/z): Calcd. for: $C_{13}H_{15}ClO_2$: 239.1 (M+H). found 239.1.

Step 2: [[6-(4-chloro-3-methoxyphenyl)cyclohex-1-en-1-yl]oxy]trimethylsilane

A solution of 2-(4-chloro-3-methoxyphenyl) cyclohexan-1-one (10 g, 41.89 mmol, 1.00 equiv), TEA (8.84 g, 87.36 mmol, 2.09 equiv), and dry dichloromethane (20 mL) was treated with TMSOTf (11.19 g, 50.4 mmol, 1.20 equiv) dropwise at 0° C. with stirring. The resulting solution was stirred for 30 min at 0° C. The solution was concentrated under vacuum to give [[6-(4-chloro-3-methoxyphenyl)cyclohex-1-en-1-yl]oxy]trimethylsilane as yellow oil.

Step 3: 2-bromo-6-(4-chloro-3-methoxyphenyl)cy-clohexan-1-one

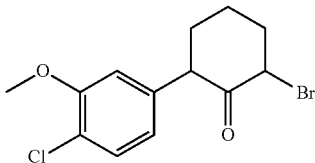 [SMILES: COc1cc(C2CCCC(Br)C2=O)ccc1Cl]

A solution of [[6-(4-chloro-3-methoxyphenyl)cyclohex-1-en-1-yl]oxy]trimethylsilane (13.05 g, 41.98 mmol, 1.00 equiv), and dry THF (100 mL) was treated with NBS (7.47 g, 41.97 mmol, 1.00 equiv), added in several batches at 0° C. The resulting solution was stirred for 30 min at 0° C. in a water/ice bath. The solution was concentrated under vacuum to give 2-bromo-6-(4-chloro-3-methoxyphenyl)cyclohexan-1-one as yellow oil.

Step 4: 2-azido-6-(4-chloro-3-methoxyphenyl)cyclo-hexan-1-one

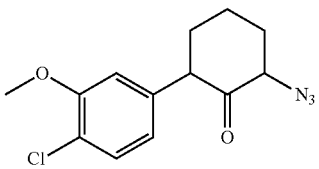 [SMILES: COc1cc(C2CCCC(N=[N+]=[N-])C2=O)ccc1Cl]

A solution of 2-bromo-6-(4-chloro-3-methoxyphenyl)cyclohexan-1-one (13.3 g, 41.88 mmol, 1.00 equiv), and N,N-dimethylformamide (50 mL) was treated with $NaN_3$ (13.6 g, 209.20 mmol, 5.00 equiv) in several batches at 0° C. The resulting solution was stirred for 1 h at 0° C. The reaction was quenched by the addition of 100 mL of water, extracted with 3×200 mL of ethyl acetate, and the combined organic layers were concentrated under vacuum. Chromatography (silica gel column with ethyl acetate/petroleum ether (1:10)) gave 2-azido-6-(4-chloro-3-methoxyphenyl)cyclohexan-1-one as yellow oil. Mass spectrum (ESI, m/z): Calcd. for: $C_{13}H_{14}ClN_3O_2$:279.1 (M+H). found 279.1.

Step 5: 2-amino-6-(4-chloro-3-methoxyphenyl)cy-clohexan-1-one hydrochloride

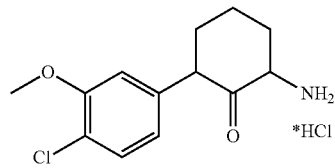 [SMILES: COc1cc(C2CCCC(N)C2=O)ccc1Cl]

A room temperature suspension of 2-azido-6-(4-chloro-3-methoxyphenyl) cyclohexan-1-one (8.9 g, 31.9 mmol, 1.00 equiv), Pd/C (10%, 8.9 g), methanol (60 mL), and concentrated hydrochloric acid (4 mL) under hydrogen atmosphere was stirred for 1 h, filtered, and concentrated under vacuum to give 2-amino-6-(4-chloro-3-methoxyphenyl)cyclohexan-1-one hydrochloride as a yellow solid. Mass spectrum (ESI, m/z): Calcd. for $C_{13}H_{16}ClNO_2$, 254.1 (M−HCl+H). found 254.1.

Step 6: 1-(3-(4-chloro-3-methoxyphenyl)-2-oxocy-clohexyl)-3-(4-fluorophenyl)thiourea

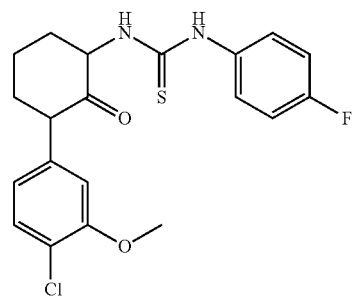 [SMILES: COc1cc(C2CCCC(NC(=S)Nc3ccc(F)cc3)C2=O)ccc1Cl]

A solution of 2-amino-6-(4-chloro-3-methoxyphenyl) cyclohexan-1-one hydrochloride (8.0 g, 27.7 mmol, 1.00 equiv), dichloromethane (30 mL), and 1-fluoro-4-isothiocyanatobenzene (8.5 g, 55.4 mmol, 2.00 equiv) was treated with TEA (8.4 g, 83.1 mmol, 3.00 equiv) dropwise at 0° C. The reaction was stirred for 1 h at r.t and concentrated under vacuum to give 1-(3-(4-chloro-3-methoxy phenyl)-2-oxocyclohexyl)-3-(4-fluorophenyl)thiourea (crude) as a yellow solid. Mass spectrum (ESI, m/z): Calcd. for $C_{20}H_{20}ClFN_2O_2S$, 407.1 (M+H). found 407.1.

Step 7: 7-(4-chloro-3-methoxyphenyl)-1-(4-fluoro-phenyl)-4,5,6,7-tetrahydro-1H-benzo[d]imidazole-2-thiol

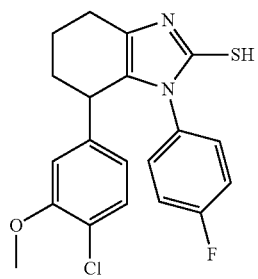 [SMILES: COc1cc(C2CCCc3nc(S)n(-c4ccc(F)cc4)c32)ccc1Cl]

A solution of 3-[3-(4-chloro-3-methoxyphenyl)-2-oxocyclohexyl]-1-(4-fluorophenyl)thiourea (11.2 g, 27.7 mmol, 1.00 equiv), and AcOH (80 mL) was stirred at r.t. overnight. The resulting mixture was concentrated under vacuum. Silica gel column chromatography (ethyl acetate/petroleum ether (1:1)) gave 7-(4-chloro-3-methoxyphenyl)-1-(4-fluorophenyl)-4,5,6,7-tetrahydro-1H-benzo[d]imidazole-2-thiol as a yellow solid. Mass spectrum (ESI, m/z): Calcd. for $C_{20}H_{18}ClFN_2OS$, 389.1 (M+H). found 389.1.

Step 8: 7-(4-chloro-3-methoxyphenyl)-2-(2-chloro-6-fluorobenzylthio)-1-(4-fluorophenyl)-4,5,6,7-tetrahydro-1H-benzo[d]imidazole trifluoroacetic acid

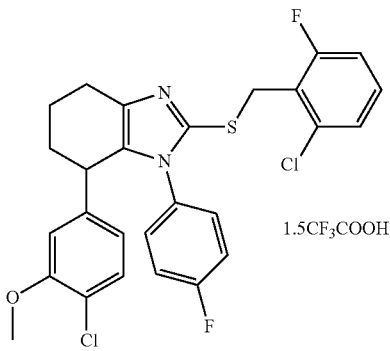 [SMILES: COc1cc(C2CCCc3nc(SCc4c(F)cccc4Cl)n(-c4ccc(F)cc4)c32)ccc1Cl]

1.5CF$_3$COOH

A solution of 7-(4-chloro-3-methoxyphenyl)-1-(4-fluorophenyl)-4,5,6,7-tetrahydro-1H-benzo[d]imidazole-2-thiol (80 mg, 0.21 mmol, 1.00 equiv), propan-2-one (5 mL), and Cs$_2$CO$_3$ (134 mg, 0.41 mmol, 2.00 equiv) was treated dropwise with a 2-(bromomethyl)-1-chloro-3-fluorobenzene (55 mg, 0.25 mmol, 1.20 equiv). The resulting solution was stirred for 3 h at 25° C. The reaction was quenched by the addition of 20 mL of water, extracted with 2×20 mL of ethyl acetate, and the combined organic layers were washed with 50 mL brine, dried over anhydrous sodium sulfate, and concentrated under vacuum. Silica gel chromatography (ethyl acetate/petroleum ether (1:3)) gave 7-(4-chloro-3-methoxyphenyl)-2-(2-chloro-6-fluorobenzylthio)-1-(4-fluorophenyl)-4,5,6,7-tetrahydro-1H-benzo[d]imidazole trifluoroacetic acid as a off-white solid. $^1$H NMR (400 MHz, CDCl$_3$) δ 7.22-7.26 (m, 1H), 7.17-7.19 (m, 2H), 6.71-7.10 (m, 4H), 6.34-6.35 (m, 2H), 4.52 (d, J=13.2 Hz, 1H), 4.38 (d, J=13.2 Hz, 1H), 3.76-3.78 (m, 4H), 2.91-3.07 (m, 2H), 2.22-2.22 (m, 1H), 1.86-2.18 (m, 3H). $^{19}$F NMR (400 MHz, CDCl$_3$) δ −75.77, −108.49, −112.46. Mass spectrum (ESI, m/z): Calcd. for C$_{30.024}$H$_{23.512}$Cl$_2$F$_{6.536}$N$_2$O$_{4.024}$S, 531.1 (M−1.5CF$_3$COOH+H). found 531.1.

Step 9: 7-(4-chloro-3-methoxyphenyl)-2-[[(2-chloro-6-fluorophenyl)methyl]sulfanyl]-1-(4-fluorophenyl)-4,5,6,7-tetrahydro-1H-1,3-benzodiazole hydrochloride

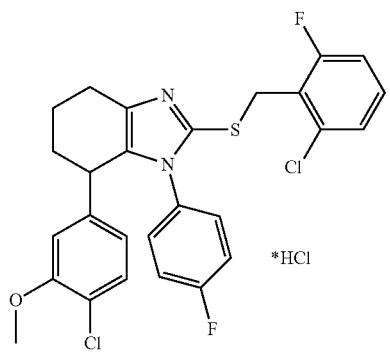 [SMILES: COc1cc(C2CCCc3nc(SCc4c(F)cccc4Cl)n(-c4ccc(F)cc4)c32)ccc1Cl]

*HCl

A solution of 7-(4-chloro-3-methoxyphenyl)-1-(4-fluorophenyl)-4,5,6,7-tetrahydro-1H-benzo[d]imidazole-2-thiol (100 mg, 0.26 mmol, 1.00 equiv), acetone (2 mL), potassium carbonate (107 mg, 0.77 mmol, 3.00 equiv), and 1-chloro-2-(chloromethyl)-3-fluorobenzene (303 mg, 1.69 mmol, 1.20 equiv) was stirred for 4 h at room temperature. The reaction was quenched by the addition of 20 mL of water, extracted with 3×20 mL of dichloromethane, and the combined organic layers were washed with 20 mL of brine, dried over anhydrous sodium sulfate, filtered and concentrated. The crude product was purified by Prep-HPLC (1#Water 2767-1): Column, Sun Fire Prep HPLC C18*5 µm, 19*100 mm; mobile phase, water with 0.05% TFA (25% CH$_3$CN up to 40 in 8 min, up to 100% in 2 min, down to 25% in 2 min); Detector, 254 nm. The purified material was treated with 4.0 mL H$_2$O and 4 drops of con.HCl was added, followed by evaporation of the water. The acidification and evaporation procedure was repeated twice, followed by lyophilization to give 7-(4-chloro-3-methoxyphenyl)-2-[[(2-chloro-6-fluorophenyl)methyl]sulfanyl]-1-(4-fluoro phenyl)-4,5,6,7-tetrahydro-1H-1,3-benzodiazole hydrochloride as a white solid. $^1$H NMR (400 MHz, CD$_3$OD): δ 7.40-7.46 (m, 1H), 7.30-7.35 (m, 1H), 7.14-7.18 (m, 3H), 6.90 (br, 2H), 6.52 (s, 1H), 6.41-6.43 (m, 1H), 6.30 (br, 1H), 4.31 (s, 2H), 4.05-4.07 (m, 1H), 3.33 (s, 3H), 2.80-2.96 (m, 2H), 2.29-2.34 (m, 1H), 2.04-2.11 (m, 1H), 1.80-2.0 (m, 2H). $^{19}$F NMR (400 MHz, CD$_3$OD): δ −111.29, −115.30. Mass spectrum (ESI, m/z): Calcd. for C$_{27}$H$_{23}$Cl$_3$F$_2$N$_2$OS, 531.1 (M−HCl+H). found 531.1.

Example 2

7-(4-chloro-3-methoxyphenyl)-2-[[(2-chloro-6-fluorophenyl)methyl]sulfanyl]-1-(4-methoxyphenyl)-4,5,6,7-tetrahydro-1H-1,3-benzodiazole Step 1: 1-(3-(4-Chloro-3-methoxyphenyl)-2-oxocyclohexyl)-3-(4-methoxyphenyl)thiourea

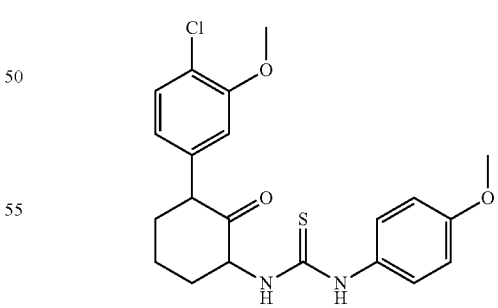

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1-methoxy-4-isothiocyanatobenzene to afford the desired product as a yellow solid. Mass spectrum (ESI, m/z): Calcd. for C$_{21}$H$_{23}$ClN$_2$O$_3$S, 419.1 (M+H). found 419.1.

Step 2: 7-(4-chloro-3-methoxyphenyl)-1-(4-methoxyphenyl)-4,5,6,7-tetrahydro-1H-1,3-benzodiazole-2-thiol

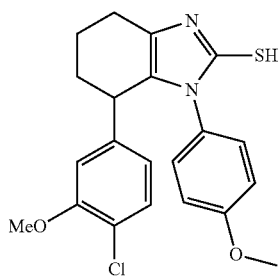 [SMILES: COc1ccc(-n2c(S)nc3c2C(c2ccc(Cl)c(OC)c2)CCC3)cc1]

The title compound was prepared according to the procedure described in Example 1 step 7 by heating 3-[3-(4-chloro-3-methoxyphenyl)-2-oxocyclohexyl]-1-(4-methoxyphenyl) thiourea in acetic acid to afford the desired product as a white solid. Mass spectrum (ESI, m/z): Calcd. for $C_{21}H_{21}ClN_2O_2S$, 401.1 (M+Na). found 401.1.

Step 3: 7-(4-chloro-3-methoxyphenyl)-2-[[(2-chloro-6-fluorophenyl)methyl]sulfanyl]-1-(4-methoxyphenyl)-4,5,6,7-tetrahydro-1H-1,3-benzodiazole

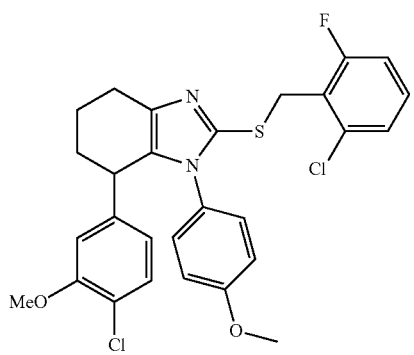 [SMILES: COc1ccc(-n2c(SCc3c(F)cccc3Cl)nc3c2C(c2ccc(Cl)c(OC)c2)CCC3)cc1]

The title compound was prepared according to the procedure described in Example 1 step 8 by coupling 7-(4-chloro-3-methoxyphenyl)-1-(4-methoxyphenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1$H NMR (300 MHz, $CD_3OD$): δ 7.14-7.31 (m, 3H), 7.03 (t, J=8.1 Hz, 1H), 6.90-7.00 (m, 1H), 5.90-6.53 (m, 3H), 4.04-4.18 (m, 2H), 3.87-3.90 (m, 1H), 3.73 (s, 3H), 3.31-3.49 (m, 3H), 2.61-2.81 (m, 2H), 2.15-2.23 (m, 1H), 1.70-2.02 (m, 3H). Mass spectrum (ESI, m/z): Calcd. for $C_{28}H_{25}Cl_2FN_2O_2S$, 543.1 (M+H). found 543.1.

Example 3

7-(4-chloro-3-methoxyphenyl)-2-[[(2-chloro-6-fluorophenyl)methyl]sulfanyl]-1-(3,4-difluorophenyl)-4,5,6,7-tetrahydro-1H-1,3-benzodiazole Step 1: 1-(3-(4-Chloro-3-methoxyphenyl)-2-oxocyclohexyl)-3-(3,4-difluorophenyl)thiourea

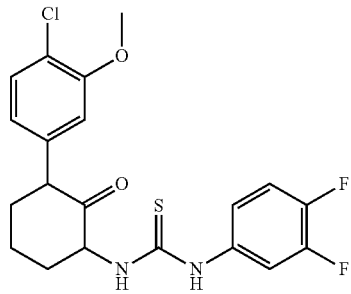 [SMILES: COc1cc(C2CCCC(NC(=S)Nc3ccc(F)c(F)c3)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1,2-difluoro-4-isothiocyanatobenzene to afford the desired product as a yellow solid. Mass spectrum (ESI, m/z): Calcd. for $C_{20}H_{19}ClF_2N_2O_2S_5$, 425.1 (M+H). found 425.1.

Step 2: 7-(4-chloro-3-methoxyphenyl)-1-(3,4-difluorophenyl)-4,5,6,7-tetrahydro-1H-1,3-benzodiazole-2-thiol

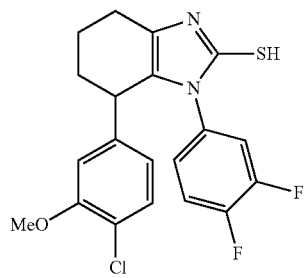 [SMILES: COc1cc(C2CCCc3nc(S)n(-c4ccc(F)c(F)c4)c32)ccc1Cl]

The title compound was prepared according to the procedure described in Example 1 step 7 by heating 3-[3-(4-chloro-3-methoxyphenyl)-2-oxocyclohexyl]-1-(3,4-difluorophenyl) thiourea in acetic acid to afford the desired product as a white solid. Mass spectrum (ESI, m/z): Calcd. for $C_{20}H_{17}ClF_2N_2OS$, 407.1 (M+H). found 407.1.

Step 3: 7-(4-chloro-3-methoxyphenyl)-2-[[(2-chloro-6-fluorophenyl)methyl]sulfanyl]-1-(3,4-difluorophenyl)-4,5,6,7-tetrahydro-1H-1,3-benzodiazole

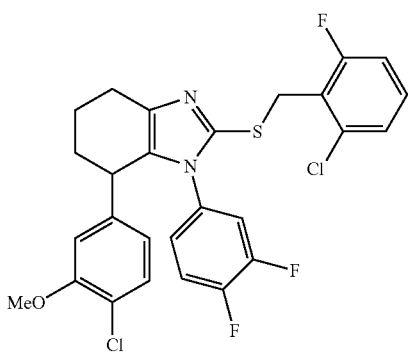 [SMILES: COc1cc(C2CCCc3nc(SCc4c(F)cccc4Cl)n(-c4ccc(F)c(F)c4)c32)ccc1Cl]

The title compound was prepared according to the procedure described in Example 1 step 8 by coupling 7-(4-chloro-3-methoxyphenyl)-1-(3,4-difluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1$H NMR (300 MHz, $CD_3OD$): δ 6.99-7.32 (m, 5H), 6.20-6.70 (m, 3H), 4.03-4.17 (m, 2H), 3.89-3.92 (m, 1H), 3.73 (s, 3H), 2.26-2.79 (m, 2H), 2.16-2.25 (m, 1H), 1.83-2.01 (m, 3H). Mass spectrum (ESI, m/z): Calcd. for $C_{27}H_{21}Cl_2F_3N_2OS$, 549.1 (M+H). found 549.1.

Example 4

7-(4-chloro-3-methoxyphenyl)-2-[[(2-chloro-6-fluorophenyl)methyl]sulfanyl]-1-(4-fluoro-3-methoxyphenyl)-4,5,6,7-tetrahydro-1H-1,3-benzodiazole Step 1: 1-(3-(4-Chloro-3-methoxyphenyl)-2-oxocyclohexyl)-3-(4-fluoro-3-methoxyphenyl)thiourea

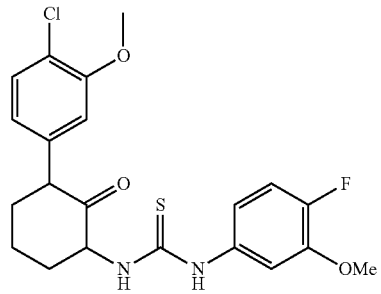 [SMILES: COc1cc(NC(=S)NC2CCCC(c3ccc(Cl)c(OC)c3)C2=O)ccc1F]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1-fluoro-2-methoxy-4-isothiocyanatobenzene to afford the desired product as a yellow solid. Mass spectrum (ESI, m/z): Calcd. for $C_{21}H_{22}ClFN_2O_3S$, 437.1 (M+H). found 437.1.

Step 2: 7-(4-chloro-3-methoxyphenyl)-1-(4-fluoro-3-methoxyphenyl)-4,5,6,7-tetrahydro-1H-1,3-benzodiazole-2-thiol

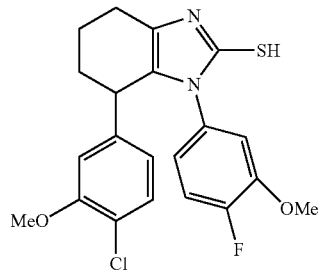 [SMILES: COc1cc(-n2c(S)nc3c2C(c2ccc(Cl)c(OC)c2)CCC3)ccc1F]

The title compound was prepared according to the procedure described in Example 1 step 7 by heating 3-[3-(4-chloro-3-methoxyphenyl)-2-oxocyclohexyl]-1-(3-methoxy-4-fluorophenyl) thiourea in acetic acid to afford the desired product as a white solid. Mass spectrum (ESI, m/z): Calcd. for $C_{21}H_{20}ClFN_2O_2S$, 419.1 (M+H). found 419.1.

Step 3: 7-(4-chloro-3-methoxyphenyl)-2-[[(2-chloro-6-fluorophenyl)methyl]sulfanyl]-1-(4-fluoro-3-methoxyphenyl)-4,5,6,7-tetrahydro-1H-1,3-benzodiazole

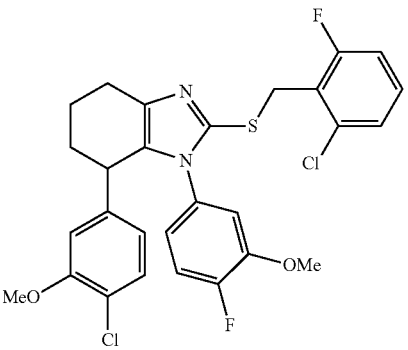 [SMILES: COc1cc(-n2c(SCc3c(F)cccc3Cl)nc3c2C(c2ccc(Cl)c(OC)c2)CCC3)ccc1F]

The title compound was prepared according to the procedure described in Example 1 step 8 by coupling 7-(4-chloro-3-methoxyphenyl)-1-(3-methoxy-4-fluorophenyl)-4,5,6,7-tetrahydro-1H-1,3-benzo diazole-2-thiol with 1-chloro-2-(chloromethyl)-3-fluorobenzene under $Cs_2CO_3$ to afford the desired product as a white solid. $^1$H NMR (300 MHz, $CD_3OD$): δ 7.22-7.31 (m, 2H), 7.16 (d, J=20.1 Hz, 1H), 7.04 (t, J=14.1 Hz, 1H), 6.25-6.85 (m, 5H), 4.00-4.15 (m, 2H), 3.83-3.85 (m, 1H), 3.70-3.72 (m, 6H), 2.50-2.85 (m, 2H), 2.04-2.22 (m, 1H), 1.7-1.99 (m, 3H). Mass spectrum (ESI, m/z): Calcd. for $C_{28}H_{24}Cl_2F_2N_2O_2S$, 561.1 (M+H). found 561.1.

Example 5

2-(2-chloro-6-fluorobenzylthio)-7-(4-chloro-3-methoxyphenyl)-1-(4-fluoro-3-methylphenyl)-4,5,6,7-tetrahydro-1H-benzo[d]imidazole trifluoroacetic acid Step 1: 3-[3-(4-chloro-3-methoxyphenyl)-2-oxocyclohexyl]-1-(4-fluoro-3-methylphenyl)thiourea

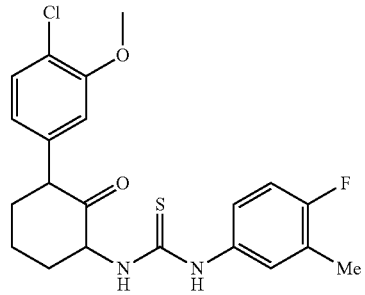 [SMILES: COc1cc(C2CCCC(NC(=S)Nc3ccc(F)c(C)c3)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1-fluoro-2-methyl-4-isothiocyanatobenzene to afford the desired product as a yellow solid. Mass spectrum (ESI, m/z): Calcd. for $C_{21}H_{22}ClFN_2O_2S$, 421.1 (M+H). found 421.1.

Step 2: 7-(4-chloro-3-methoxyphenyl)-1-(4-fluoro-3-methylphenyl)-4,5,6,7-tetrahydro-1H-1,3-benzodiazole-2-thiol

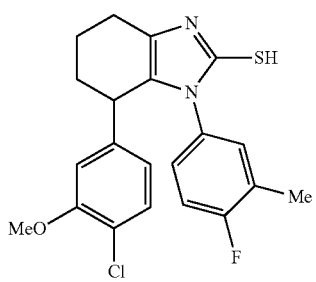 [SMILES: COc1cc(C2CCCc3nc(S)n(-c4ccc(F)c(C)c4)c32)ccc1Cl]

The title compound was prepared according to the procedure described in Example 1 step 7 by heating 3-[3-(4-chloro-3-methoxyphenyl)-2-oxocyclohexyl]-1-(3-methyl-4-fluorophenyl) thiourea in acetic acid to afford the desired product as a white solid. Mass spectrum (ESI, m/z): Calcd. for $C_{21}H_{20}ClFN_2OS$, 403.1 (M+H). found 403.1.

Step 3: 2-(2-chloro-6-fluorobenzylthio)-7-(4-chloro-3-methoxyphenyl)-1-(4-fluoro-3-methylphenyl)-4,5,6,7-tetrahydro-1H-benzo[d]imidazole trifluoroacetic acid

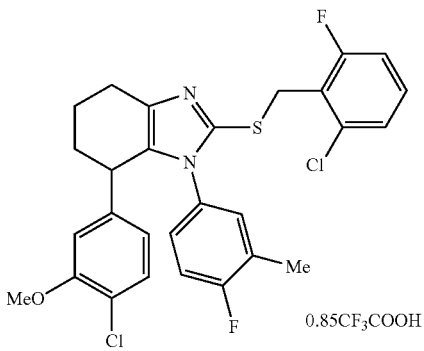 [SMILES: COc1cc(C2CCCc3nc(SCc4c(F)cccc4Cl)n(-c4ccc(F)c(C)c4)c32)ccc1Cl]

The title compound was prepared according to the procedure described in Example 1 step 8 by coupling 7-(4-chloro-3-methoxyphenyl)-1-(3-methyl-4-fluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1$H NMR (400 MHz, $CD_3OD$): δ 7.30-7.43 (m, 2H), 7.11-7.19 (m, 2H), 6.97 (br, 1H), 6.41-6.46 (m, 2H), 4.18-4.30 (m, 2H), 4.06 (s, 1H), 3.73 (s, H), 2.78-2.92 (m, 2H), 1.92-2.29 (m, 7H), 4.15 (br, 4H), 2.71-2.87 (m, 2H). $^{19}$F NMR (400 MHz, $CD_3OD$): −77.07, −115.21, −116.15. Mass spectrum (ESI, m/z): Calcd. for $C_{29.7}H_{24.85}Cl_2F_{4.55}N_2O_{2.7}S$, 545.1 (M−0.85$CF_3COOH$+H). found 545.1.

Example 6

7-(4-chloro-3-methoxyphenyl)-2-[[(2-chloro-6-fluorophenyl)methyl]sulfanyl]-1-[4-fluoro-3-(trifluoromethyl)phenyl]-4,5,6,7-tetrahydro-1H-1,3-benzodiazole Step 1: 3-[3-(4-chloro-3-methoxyphenyl)-2-oxocyclohexyl]-1-[4-fluoro-3-(trifluoromethyl)phenyl]thiourea

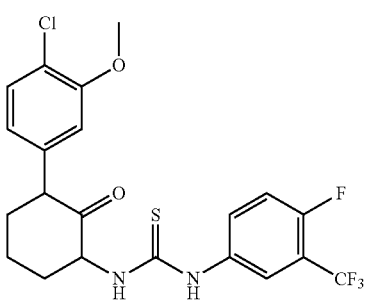 [SMILES: COc1cc(C2CCCC(NC(=S)Nc3ccc(F)c(C(F)(F)F)c3)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1-fluoro-2-trifluoromethyl-4-isothiocyanatobenzene to afford the desired product as a yellow solid. Mass spectrum (ESI, m/z): Calcd. for $C_{21}H_{19}ClF_4N_2O_2S$, 475.1 (M+H). found 475.1.

Step 2: 7-(4-chloro-3-methoxyphenyl)-1-[4-fluoro-3-(trifluoromethyl)phenyl]-4,5,6,7-tetrahydro-1H-1,3-benzodiazole-2-thiol

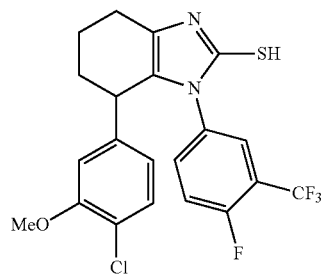 [SMILES: COc1cc(C2CCCc3nc(S)n(-c4ccc(F)c(C(F)(F)F)c4)c32)ccc1Cl]

The title compound was prepared according to the procedure described in Example 1 step 7 by heating 3-[3-(4-chloro-3-methoxyphenyl)-2-oxocyclohexyl]-1-(3-trifluoromethyl-4-fluorophenyl) thiourea in acetic acid to afford the desired product as a white solid. Mass spectrum (ESI, m/z): Calcd. for $C_{21}H_{17}ClF_4N_2OS$, 457.1 (M+H). found 457.1.

Step 3: 7-(4-chloro-3-methoxyphenyl)-2-[[(2-chloro-6-fluorophenyl)methyl]sulfanyl]-1-[4-fluoro-3-(trifluoromethyl)phenyl]-4,5,6,7-tetrahydro-1H-1,3-benzodiazole

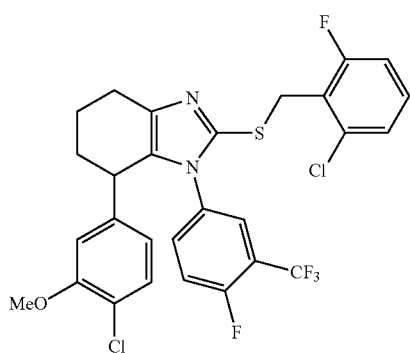 [SMILES: COc1cc(C2CCCc3nc(SCc4c(F)cccc4Cl)n(-c4ccc(F)c(C(F)(F)F)c4)c32)ccc1Cl]

The title compound was prepared according to the procedure described in Example 1 step 8 by coupling 7-(4-chloro-3-methoxyphenyl)-1-(3-trifluoromethyl-4-fluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1$H NMR (400 MHz, $CD_3OD$): δ 7.23-7.29 (m, 1H), 6.98-7.18 (m, 5H), 6.51 (s, 1H), 6.38-6.50 (m, 1H), 4.167 (d, J=13.2 Hz, 1H), 4.05 (d, J=13.2 Hz, 1H), 3.72-3.87 (m, 1H), 3.72 (s, 3H), 2.69-2.82 (m, 2H), 2.15-2.24 (m, 1H), 1.99-2.04 (m, 1H), 1.78-1.87 (m, 2H). Mass spectrum (ESI, m/z): Calcd. for $C_{28}H_{21}Cl_2F_5N_2OS$, 599.1 (M+H). found 598.9.

Example 7

2-(2-chloro-6-fluorobenzylthio)-7-(4-chloro-3-methoxyphenyl)-1-(3-chloro-4-fluorophenyl)-4,5,6,7-tetrahydro-1H-benzo[d]imidazole trifluoroacetic acid Step 1: 3-[3-(4-chloro-3-methoxyphenyl)-2-oxocyclohexyl]-1-(3-chloro-4-fluorophenyl)thiourea

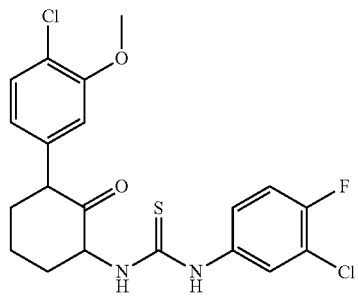 [SMILES: COc1cc(C2CCCC(NC(=S)Nc3ccc(F)c(Cl)c3)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1-fluoro-2-chloro-4-isothiocyanatobenzene to afford the desired product as a yellow solid. Mass spectrum (ESI, m/z): Calcd. for $C_{20}H_{19}Cl_2FN_2O_2S$, 441.1 (M+H). found 441.1.

Step 2: 7-(4-chloro-3-methoxyphenyl)-1-(3-chloro-4-fluorophenyl)-4,5,6,7-tetrahydro-1H-1,3-benzodiazole-2-thiol

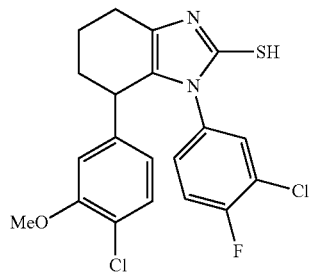 [SMILES: COc1cc(C2CCCc3nc(S)n(-c4ccc(F)c(Cl)c4)c32)ccc1Cl]

The title compound was prepared according to the procedure described in Example 1 step 7 by heating 3-[3-(4-chloro-3-methoxyphenyl)-2-oxocyclohexyl]-1-(3-chloro-4-fluorophenyl) thiourea in acetic acid to afford the desired product as a white solid. Mass spectrum (ESI, m/z): Calcd. for $C_{20}H_{17}Cl_2FN_2OS$, 423.0 (M+H). found 423.0.

Step 3: 2-(2-chloro-6-fluorobenzylthio)-7-(4-chloro-3-methoxyphenyl)-1-(3-chloro-4-fluorophenyl)-4,5,6,7-tetrahydro-1H-benzo[d]imidazole trifluoroacetic acid

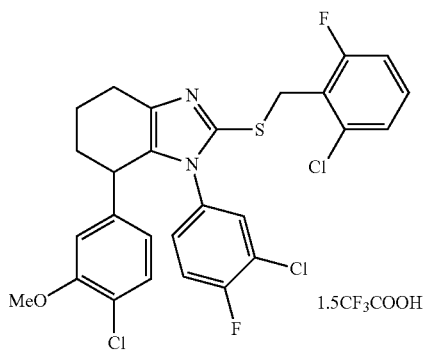 [SMILES: COc1cc(C2CCCc3nc(SCc4c(F)cccc4Cl)n(-c4ccc(F)c(Cl)c4)c32)ccc1Cl]

1.5CF₃COOH

The title compound was prepared according to the procedure described in Example 1 step 8 by coupling 7-(4-chloro-3-methoxyphenyl)-1-(3-chloro-4-fluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1H$ NMR (400 MHz, $CD_3OD$): δ 7.40-7.45 (m, 1H), 7.31-7.33 (m, 1H), 7.13-7.20 (m, 3H), 6.52 (s, 1H), 6.41-6.43 (m, 1H), 4.27-4.29 (m, 2H), 4.02 (s, 1H), 3.74 (s, 3H), 2.80-2.96 (m, 2H), 2.27-2.33 (m, 1H), 2.05-2.14 (m, 1H), 1.91-1.99 (m, 2H). $^{19}F$ NMR (400 MHz, $CD_3OD$): −77.27, −114.00, −115.25. Mass spectrum (ESI, m/z): Calcd. for $C_{30}H_{22.5}Cl_3F_{6.5}N_2O_4S$, 565.0 (M−1.5CF₃COOH+H). found 565.1.

Example 8

2-(2-chloro-6-fluorobenzylthio)-7-(4-chloro-3-methoxyphenyl)-1-(2,4-difluorophenyl)-4,5,6,7-tetrahydro-1H-benzo[d]imidazole trifluoroacetic acid Step 1: 3-[3-(4-chloro-3-methoxyphenyl)-2-oxocyclohexyl]-1-(2,4-difluorophenyl)thiourea

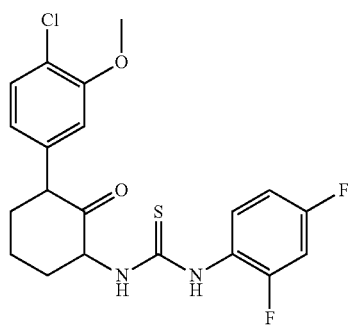 [SMILES: COc1cc(C2CCCC(NC(=S)Nc3ccc(F)cc3F)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1,3-difluoro-4-isothiocyanatobenzene to afford the desired product as a yellow solid. Mass spectrum (ESI, m/z): Calcd. for $C_{20}H_{19}ClF_2N_2O_2S$, 425.1 (M+H). found 425.1.

Step 2: 7-(4-chloro-3-methoxyphenyl)-1-(2,4-difluorophenyl)-4,5,6,7-tetrahydro-1H-1,3-benzodiazole-2-thiol

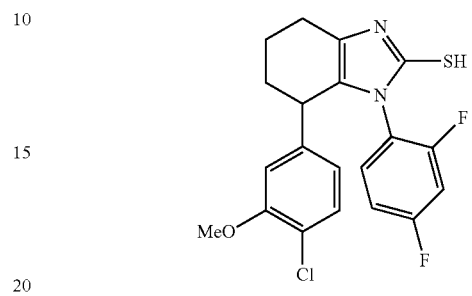

The title compound was prepared according to the procedure described in Example 1 step 7 by heating 3-[3-(4-chloro-3-methoxyphenyl)-2-oxocyclohexyl]-1-(2,4-difluorophenyl) thiourea in acetic acid to afford the desired product as a white solid. Mass spectrum (ESI, m/z): Calcd. for $C_{20}H_{17}ClF_2N_2OS$, 407.1 (M+H). found 407.1.

Step 3: 2-(2-chloro-6-fluorobenzylthio)-7-(4-chloro-3-methoxyphenyl)-1-(2,4-difluorophenyl)-4,5,6,7-tetrahydro-1H-benzo[d]imidazole trifluoroacetic acid

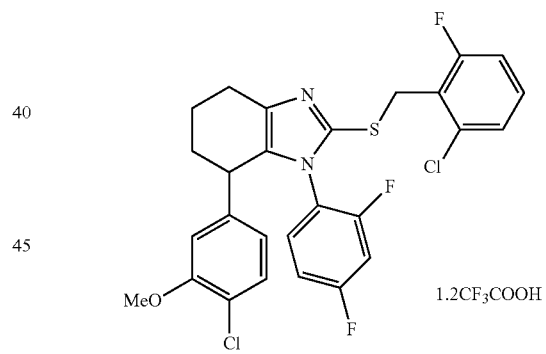

1.2CF₃COOH

The title compound was prepared according to the procedure described in Example 1 step 8 by coupling 7-(4-chloro-3-methoxyphenyl)-1-(2,4-difluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1H$ NMR (400 MHz, $CD_3OD$): δ 7.27-7.39 (m, 2H), 7.10-7.19 (m, 3H), 6.39-7.07 (m, 4H), 4.16-4.35 (m, 2H), 3.93-4.08 (m, 1H), 3.74 (d, J=14.8 Hz, 1H), 2.82-2.88 (m, 2H), 2.07-2.08 (m, 1H), 1.90-1.91 (m, 1H), 1.87-1.88 (m, 2H). $^{19}F$ NMR (400 MHz, $CD_3OD$): −77.19, −106.56, −114.22, −115.11, −117.83. Mass spectrum (ESI, m/z): Calcd. for $C_{29.4}H_{22.2}Cl_2F_{6.6}N_2O_{3.4}S$, 549.1 (M−1.2CF₃COOH+H). found 549.1.

Example 9

7-(4-chloro-3-methoxyphenyl)-2-((2-chloro-6-fluorobenzyl)thio)-1-(2,3,4-trifluorophenyl)-4,5,6,7-tetrahydro-1H-benzo[d]imidazole Step 1: 3-[3-(4-chloro-3-methoxyphenyl)-2-oxocyclohexyl]-1-(2,3,4-trifluorophenyl)thiourea

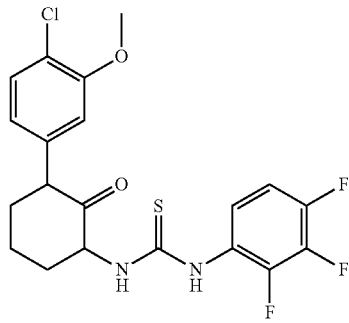 [SMILES: COc1cc(C2CCCC(NC(=S)Nc3ccc(F)c(F)c3F)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1,2,3-trifluoro-4-isothiocyanatobenzene to afford the desired product as a yellow solid. Mass spectrum (ESI, m/z): Calcd. for $C_{20}H_{18}ClF_3N_2O_2S$, 443.1 (M+H). found 443.1.

Step 2: 7-(4-chloro-3-methoxyphenyl)-1-(2,3,4-trifluorophenyl)-4,5,6,7-tetrahydro-1H-1,3-benzodiazole-2-thiol

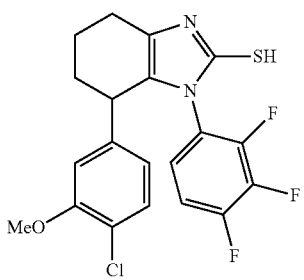 [SMILES: COc1cc(C2CCCc3nc(S)n(-c4ccc(F)c(F)c4F)c32)ccc1Cl]

The title compound was prepared according to the procedure described in Example 1 step 7 by heating 3-[3-(4-chloro-3-methoxyphenyl)-2-oxocyclohexyl]-1-(2,3,4-trifluorophenyl) thiourea in acetic acid to afford the desired product as a white solid. Mass spectrum (ESI, m/z): Calcd. for $C_{20}H_{16}ClF_3N_2OS$, 425.1 (M+H). found 425.1.

Step 3: 7-(4-chloro-3-methoxyphenyl)-2-((2-chloro-6-fluorobenzyl)thio)-1-(2,3,4-trifluorophenyl)-4,5,6,7-tetrahydro-1H-benzo[d]imidazole

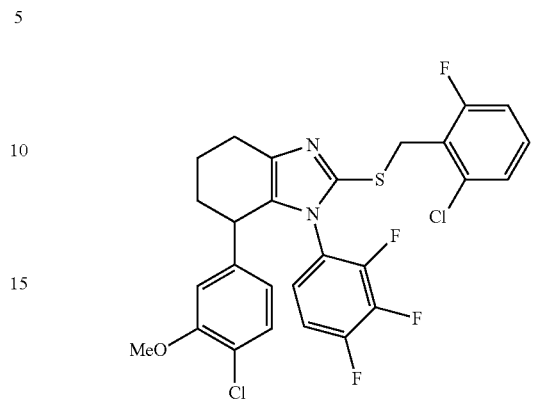

The title compound was prepared according to the procedure described in Example 1 step 8 by coupling 7-(4-chloro-3-methoxyphenyl)-1-(2,3,4-trifluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1H$ NMR (300 MHz, $CD_3OD$): δ 6.59-7.35 (m, 6H), 6.33-6.46 (m, 2H), 3.92-4.30 (m, 3H), 3.70 (d, J=8.7 Hz, 1H), 2.78-2.83 (m, 2H), 1.84-2.29 (m, 4H). Mass spectrum (ESI, m/z): Calcd. for $C_{27}H_{20}Cl_2F_4N_2OS$, 567.1 (M+H). found 567.2.

Example 10

7-(4-chloro-3-methoxyphenyl)-2-((2-chloro-6-fluorobenzyl)thio)-1-(3,4,5-trifluorophenyl)-4,5,6,7-tetrahydro-1H-benzo[d]imidazole Step 1: 3-[3-(4-chloro-3-methoxyphenyl)-2-oxocyclohexyl]-1-(3,4,5-trifluorophenyl)thiourea

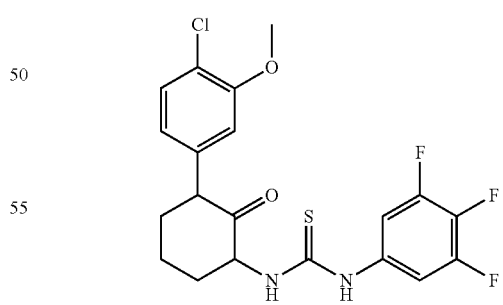

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1,2,3-trifluoro-5-isothiocyanatobenzene to afford the desired product as a yellow solid. Mass spectrum (ESI, m/z): Calcd. for $C_{20}H_{18}ClF_3N_2O_2S$, 443.1 (M+H). found 443.1.

Step 2: 7-(4-chloro-3-methoxyphenyl)-1-(3,4,5-trifluorophenyl)-4,5,6,7-tetrahydro-1H-1,3-benzodiazole-2-thiol

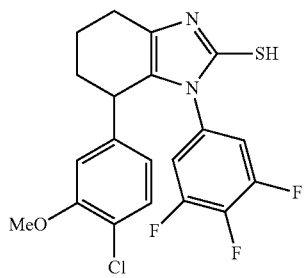 [SMILES: COc1cc(C2CCCc3nc(S)n(-c4cc(F)c(F)c(F)c4)c32)ccc1Cl]

The title compound was prepared according to the procedure described in Example 1 step 7 by heating 3-[3-(4-chloro-3-methoxyphenyl)-2-oxocyclohexyl]-1-(3,4,5-trifluorophenyl) thiourea in acetic acid to afford the desired product as a white solid. Mass spectrum (ESI, m/z): Calcd. for $C_{20}H_{16}ClF_3N_2OS$, 425.1 (M+H). found 425.1.

Step 3: 7-(4-chloro-3-methoxyphenyl)-2-((2-chloro-6-fluorobenzyl)thio)-1-(3,4,5-trifluorophenyl)-4,5,6,7-tetrahydro-1H-benzo[d]imidazole

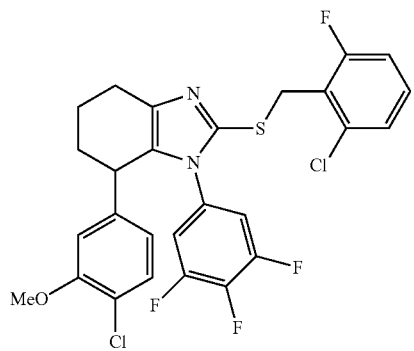 [SMILES: COc1cc(C2CCCc3nc(SCc4c(F)cccc4Cl)n(-c4cc(F)c(F)c(F)c4)c32)ccc1Cl]

The title compound was prepared according to the procedure described in Example 1 step 8 by coupling 7-(4-chloro-3-methoxyphenyl)-1-(3,4,5-trifluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1$H NMR (300 MHz, $CD_3OD$): δ 6.96-7.27 (m, 4H), 6.34-6.51 (m, 3H), 3.89-4.13 (m, 3H), 3.73 (s, 3H), 2.65-2.76 (m, 2H), 2.14-2.22 (m, 1H), 1.74-1.98 (m, 3H). Mass spectrum (ESI, m/z): Calcd. for $C_{27}H_{20}Cl_2F_4N_2OS$, 567.1 (M+H). found 567.1.

Example 11

7-(4-chloro-3-methoxyphenyl)-2-((2-chloro-6-fluorobenzyl)thio)-1-(2, 4, 5-trifluorophenyl)-4,5,6,7-tetrahydro-1H-benzo[d]imidazole Step 1: 3-[3-(4-chloro-3-methoxyphenyl)-2-oxocyclohexyl]-1-(2,4,5-trifluorophenyl)thiourea

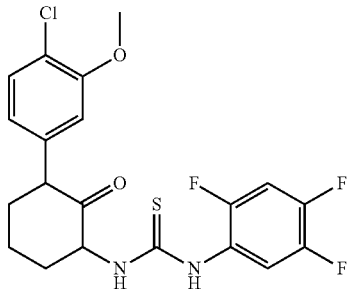 [SMILES: COc1cc(C2CCCC(NC(=S)Nc3cc(F)c(F)cc3F)C2=O)ccc1Cl]

The title compound was prepared according to the procedure described in Example 1 step 6 by coupling 2-amino-6-(4-chloro-3-methoxyphenyl)cyclohexan-1-one hydrochloride (prepared as described in Example 1, Step 5) and 1,2,5-trifluoro-4-isothiocyanatobenzene to afford the desired product as a yellow solid. Mass spectrum (ESI, m/z): Calcd. for $C_{20}H_{18}ClF_3N_2O_2S$, 443.1 (M+H). found 443.1.

Step 2: 7-(4-chloro-3-methoxyphenyl)-1-(2, 4, 5-trifluorophenyl)-4,5,6,7-tetrahydro-1H-1,3-benzodiazole-2-thiol

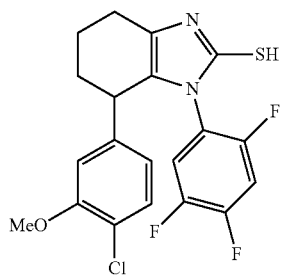 [SMILES: COc1cc(C2CCCc3nc(S)n(-c4cc(F)c(F)cc4F)c32)ccc1Cl]

The title compound was prepared according to the procedure described in Example 1 step 7 by heating 3-[3-(4-chloro-3-methoxyphenyl)-2-oxocyclohexyl]-1-(2,4,5-trifluorophenyl) thiourea in acetic acid to afford the desired product as a white solid. Mass spectrum (ESI, m/z): Calcd. for $C_{20}H_{16}ClF_3N_2OS$, 425.1 (M+H). found 425.1.

Step 3: 7-(4-chloro-3-methoxyphenyl)-2-((2-chloro-6-fluorobenzyl)thio)-1-(2,4,5-trifluorophenyl)-4,5,6,7-tetrahydro-1H-benzo[d]imidazole

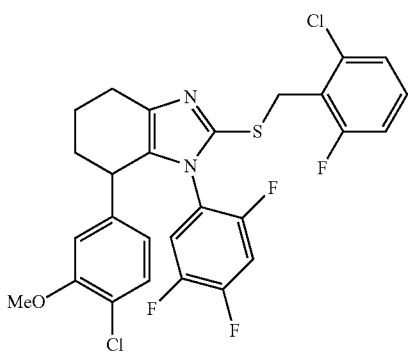 [SMILES: COc1cc(C2CCCc3nc(SCc4c(F)cccc4Cl)n(-c4cc(F)c(F)cc4F)c32)ccc1Cl]

The title compound was prepared according to the procedure described in Example 1 step 8 by coupling 7-(4-chloro-3-methoxyphenyl)-1-(2,4,5-trifluorophenyl)-4,5,6,7-tetrahydro-1H-1,3-benzo diazole-2-thiol with 1-chloro-2-(chloromethyl)-3-fluorobenzene in the presence of $Cs_2CO_3$ to afford the desired product as a white solid. $^1$H NMR (300 MHz, $CD_3OD$): δ 6.99-7.15 (m, 3H), 6.59-6.90 (m, 3H), 6.31-6.42 (m, 2H), 4.28-4.33 (m, 1H), 4.08-4.14 (m, 1H), 3.70-3.79 (m, 4H), 2.72-2.78 (m, 2H), 2.16-2.31 (m, 1H), 1.72-1.89 (m, 4H). Mass spectrum (ESI, m/z): Calcd. for $C_{27}H_{20}Cl_2F_4N_2OS$, 567.1 (M+H). found 567.1.

Example 12

4-((7-(4-chloro-3-methoxyphenyl)-1-(4-fluorophenyl)-4,5,6,7-tetrahydro-1H-benzo[d]imidazol-2-ylthio)methyl)-3,5-difluorobenzoic acid trifluoroacetic acid Step 1: Tert-butyl 3, 5-difluorobenzoate

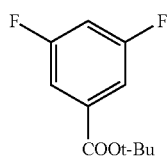

A solution of 3,5-difluorobenzoic acid (7.9 g, 49.97 mmol, 1.00 equiv), tert-butanol (5.55 g, 1.50 equiv), 4-dimethylaminopyridine (610 mg, 4.99 mmol, 0.10 equiv), was treated with TEA (7.07 g, 69.87 mmol, 1.40 equiv) during a period of 20 min at room temperature. The mixture was cooled to 0° C. in a water/ice bath, treated with $Boc_2O$ (14.27 g, 65.38 mmol, 1.30 equiv) was added at the same temperature, warmed to room temperature, and stirred overnight. The reaction was concentrated under vacuum. Silica gel chromatography (ethyl acetate/petroleum ether (1:30)) gave tert-butyl 3,5-difluorobenzoate as a colorless oil.

Step 2: Tert-butyl 3, 5-difluoro-4-formylbenzoate

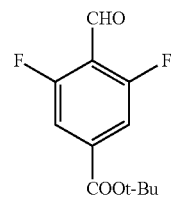

A solution of $(i-Pr)_2NH$ (4.79 g, 47.43 mmol, 1.30 equiv), tetrahydrofuran (80 mL), under nitrogen, at 0° C., was treated with 2.5 M of n-BuLi (20 mL) over a period of 30 min. The mixture was cooled to −78° C., and tert-butyl 3,5-difluorobenzoate (7.8 g, 36.41 mmol, 1.00 equiv) in tetrahydrofuran (20 mL) was added over a period of 30 min. The reaction was stirred for 1 h, treated with N,N-dimethylformamide (4.0 g, 54.73 mmol, 1.50 equiv), and stirred for an additional 1 h while the temperature was maintained at −78° C. The reaction was quenched by the addition of 50 mL of water, extracted with 3×200 mL of ethyl acetate, and the combined organic layers were dried over sodium sulfate, filtered, and concentrated under vacuum. Silica gel chromatography (ethyl acetate/petroleum ether (1:50)) gave tert-butyl 3,5-difluoro-4-formylbenzoate as a light yellow solid.

Step 3: Tert-butyl 3, 5-difluoro-4-(hydroxymethyl)benzoate

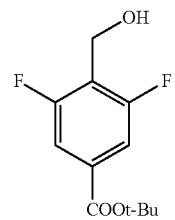

A solution of tert-butyl 3, 5-difluoro-4-formylbenzoate (2.6 g, 10.73 mmol, 1.00 equiv), methanol (50 mL), at 0° C. was treated with $NaBH_4$ (810 mg, 21.41 mmol, 2.00 equiv), and the resulting solution was stirred for 2 h at 0° C., followed by concentration under vacuum. Silica gel chromatography (ethyl acetate/petroleum ether 1:10) gave tert-butyl 3,5-difluoro-4-(hydroxymethyl) benzoate as a off-white solid.

Step 4. Tert-butyl 3,5-difluoro-4-[(methanesulfonyloxy)methyl]benzoate

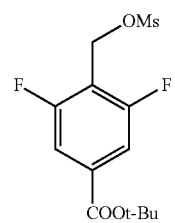

A solution of tert-butyl 3,5-difluoro-4-(hydroxymethyl) benzoate (1.2 g, 4.91 mmol, 1.00 equiv) in dichloromethane (50 mL), TEA (1.50 g, 14.82 mmol, 2.97 equiv), MsCl (1.1 g, 9.57 mmol, 1.95 equiv) was stirred for overnight at room temperature. The resulting mixture was concentrated under vacuum. Silica gel chromatography (petroleum ether/ethyl acetate-5:1) gave tert-butyl 3,5-difluoro-4-[(methanesulfonyloxy)methyl]benzoate as a white solid.

Step 5: tert-butyl 4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorobenzoate

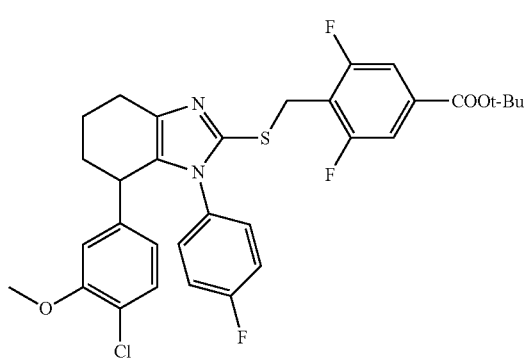

The title compound was prepared according to the procedure described in Example 1 step 8 by coupling 7-(4-chloro-3-methoxyphenyl)-1-(4-fluorophenyl)-4,5,6,7-tetrahydro-1H-1,3-benzo diazole-2-thiol (prepared as described in Example 1, Step 7) with tert-butyl 3,5-difluoro-4-[(methanesulfonyloxy)methyl]benzoate in the presence of $Cs_2CO_3$ to afford the desired product as a white solid.

Mass spectrum (ESI, m/z): Calcd. for: $C_{32}H_{30}ClF_3N_2O_3S$: 614.2 (M+H). found 641.2.

Step 6: 4-((7-(4-chloro-3-methoxyphenyl)-1-(4-fluorophenyl)-4,5,6,7-tetrahydro-1H-benzo[d]imidazol-2-ylthio)methyl)-3,5-difluorobenzoic acid trifluoroacetic acid

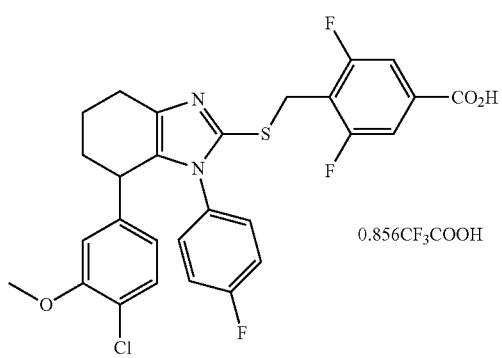 [SMILES: COc1cc(C2CCCc3nc(SCc4c(F)cc(C(=O)O)cc4F)n(-c4ccc(F)cc4)c32)ccc1Cl]

A solution of tert-butyl 4-([[7-(4-chloro-3-methoxyphenyl)-1-(4-fluorophenyl)-4,5,6,7-tetrahydro-1H-1,3-benzodiazol-2-yl]sulfanyl] methyl)-3,5-difluorobenzoate (150 mg, 0.24 mmol, 1.00 equiv), dichloromethane (10 mL), and trifluoroacetic acid (1 mL) was stirred for 3 h at room temperature and concentrated under vacuum. The crude product was purificated by Prep-HPLC With the following conditions (1#waters2767-5): column, SunFire Prep C18, 19*150 mm 5 μm H Prep C-001(T)18600256819513816414 04; Mobile Phase, phase A: water with 0.05% TFA, phase B: CH3CN (40% $CH_3CN$ up to 70% in 8 min, up to 100% in 0.1 min, hold 100% in 1.9 min, down to 40% in 0.1 min, hold 40% in 1.9 min); detector, UV 220 & 254 nm to give 4-((7-(4-chloro-3-methoxyphenyl)-1-(4-fluorophenyl)-4,5,6,7-tetrahydro-1H-benzo[d]imidazol-2-ylthio)methyl)-3,5-difluorobenzoic acid trifluoroacetic acid as a white solid. $^1$H NMR (400 MHz, $CD_3OD$) δ 7.46-7.54 (m, 2H), 7.28 (s, 1H), 6.84-7.21 (m, 3H), 6.33-6.46 (m, 3H), 4.08-4.16 (m, 2H), 3.80 (s, 4H), 2.87-3.08 (m, 2H), 2.03-2.26 (m, 1H), 1.86-1.99 (m, 3H). $^{19}$F NMR (400 MHz, $CD_3OD$) δ−75.742, −108.802, −114.143. Mass spectrum (ESI, m/z): Calcd. for: $C_{29.712}H_{22.856}ClF_{5.568}N_2O_{4.712}S$: 559.2 (M−0.856$CF_3$COOH+H). found 559.2.

Example 13

2-(4-((7-(4-chloro-3-methoxyphenyl)-1-(4-fluorophenyl)-4,5,6,7-tetrahydro-1H-benzo[d]imidazol-2-ylthio)methyl)-3,5-difluorobenzamido)-N,N,N-trimethylethanaminium 2,2,2-trifluoroacetate

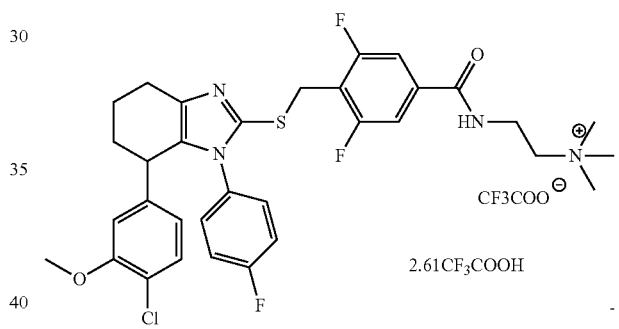

A solution of 4-([[7-(4-chloro-3-methoxyphenyl)-1-(4-fluorophenyl)-4,5,6,7-tetrahydro-1H-1,3-benzodiazol-2-yl] sulfanyl]methyl)-3,5-difluorobenzoic acid (30 mg, 0.05 mmol, 1.00 equiv) in dichloromethane (2 mL) was treated with (2-aminoethyl)trimethylazanium hydrochloride chloride (11.3 mg, 0.06 mmol, 1.20 equiv), HOBt (11 mg, 0.08 mmol, 1.21 equiv), EDCI (12.4 mg, 0.06 mmol, 1.21 equiv), and triethylamine (16.3 mg, 0.16 mmol, 3.00 equiv). The resulting solution was stirred overnight at room temperature. The reaction was then quenched by the addition of 10 mL of water, extracted with 3×10 mL of dichloromethane, and the combined organic layers were dried over sodium sulfate and concentrated under vacuum. The crude product (3 mL) was purificated by Prep-HPLC With the following conditions: (1#waters2767-5) column, SunFire Prep C18, 19*150 mm H Prep C-001(T)18600256819513816414 04; Mobile Phase, phase A: water with 0.05% TFA, phase B: CH3CN (20% $CH_3CN$ up to 50% in 8 min, up to 100% in 0.1 min, hold 100% in 1.9 min, down to 20% in 0.1 min, hold 20% in 1.9 min); Detector, UV 220 & 254 nm. This resulted in 13.6 mg (24%) of PH-ZHS-XZ1-H-125-0 as a light yellow semi-solid. $^1$H NMR (400 MHz, $CD_3OD$) δ7.54 (d, J=8.0 Hz, 2H), 6.95-7.18 (m, 3H), 6.52 (s, 1H), 6.39-6.42 (m, 2H), 4.22 (s, 2H), 4.05 (s, 1H), 3.85-3.89 (m, 3H), 3.73 (s, 3H), 3.61-3.64 (m, 2H), 3.25-3.33 (m, 12H), 2.93 (s, 4H), 2.78-

2.88 (m, 2H), 2.26-2.33 (m, 1H), 1.90-2.08 (m, 3H). 19F NMR (400 MHz, CD$_3$OD) δ −77.08, −111.59, −115.30. Mass spectrum (ESI, m/z): Calcd. for: $C_{40.22}H_{37.61}ClF_{13.83}N_4O_{9.22}S$:643.2 (M−2.61CF$_3$COOH—CF$_3$COO). found 643.2.

Example 14

2-([[7-(4-chloro-3-methoxyphenyl)-1-(4-fluorophenyl)-4,5,6,7-tetrahydro-1H-1,3-benzodiazol-2-yl]sulfanyl]methyl)-3-fluorobenzonitrile

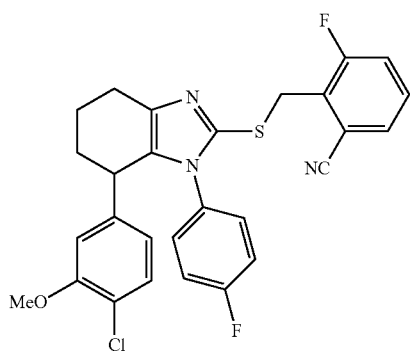 [SMILES: COc1cc(C2CCCc3nc(SCc4c(F)cccc4C#N)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1-cyano-2-(chloromethyl)-3-fluorobenzene in the presence of Cs$_2$CO$_3$ to afford the desired product as a white solid.

$^1$H NMR (400 MHz, CD$_3$OD): δ 7.50-7.54 (m, 2H), 7.40-7.43 (m, 1H), 7.11 (d, J=8.0 Hz, 1H), 6.72 (br, 2H), 6.52 (s, 1H), 6.37-6.42 (m, 1H), 4.02-4.08 (m, 2H), 3.92-3.99 (m, 1H), 3.73 (s, 3H), 2.66-2.88 (m, 2H), 2.21-2.23 (m, 1H), 1.84-1.95 (m, 1H), 1.80-1.83 (m, 2H). Mass spectrum (ESI, m/z): Calcd. for $C_{28}H_{22}ClF_2N_3OS$, 552.1 (M+H). found 552.0.

Example 15

7-(4-chloro-3-methoxyphenyl)-2-([[2-fluoro-6-(trifluoromethyl) phenyl]methyl]sulfanyl)-1-(4-fluorophenyl)-4,5,6,7-tetrahydro-1H-1,3-benzodiazole

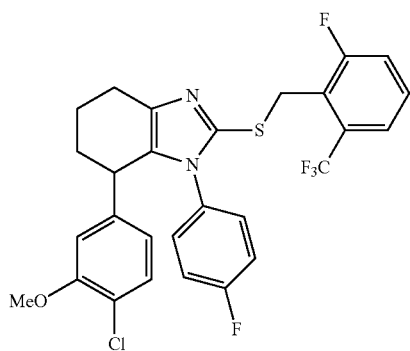 [SMILES: COc1cc(C2CCCc3nc(SCc4c(F)cccc4C(F)(F)F)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1-trifluoromethyl-2-(chloromethyl)-3-fluorobenzene in the presence of Cs$_2$CO$_3$ to afford the desired product as a white solid.

$^1$H NMR (300 MHz, CD$_3$OD): δ 7.43-7.46 (m, 2H), 7.26-7.32 (m, 1H), 7.06-7.09 (m, 1H), 6.63-6.84 (m, 3H), 6.44-6.45 (m, 1H), 6.33-6.37 (m, 1H), 4.03-4.14 (m, 2H), 3.87-3.90 (m, 1H), 3.68 (s, 3H), 2.64-2.76 (m, 2H), 2.12-2.21 (m, 1H), 1.74-1.94 (m, 3H). Mass spectrum (ESI, m/z): Calcd. for $C_{28}H_{22}ClF_5N_2OS$, 565.1 (M+H). found 565.2.

Example 16

7-(4-chloro-3-methoxyphenyl)-2-(2-fluoro-6-methoxybenzylthio)-1-(4-fluorophenyl)-4,5,6,7-tetrahydro-1H-benzo[d]imidazole trifluoroacetic acid

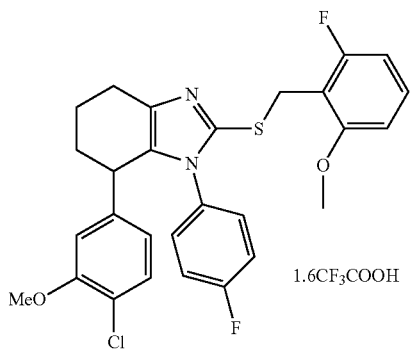 [SMILES: COc1cc(C2CCCc3nc(SCc4c(F)cccc4OC)n(-c4ccc(F)cc4)c32)ccc1Cl]

1.6CF$_3$COOH

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1-methoxy-2-(chloromethyl)-3-fluorobenzene in the presence of Cs$_2$CO$_3$ to afford the desired product as a white solid.

$^1$H NMR (300 MHz, CD$_3$OD): δ 7.30-7.35 (m, 1H), 6.70-7.10 (m, 6H), 6.44-6.45 (m, 1H), 6.31-6.34 (m, 1H), 3.97-4.14 (m, 3H), 3.74 (s, 3H), 3.67 (s, 3H), 2.81-2.91 (m, 2H), 2.21-2.27 (m, 1H), 1.88-2.06 (m, 3H). $^{19}$F NMR (300 MHz, CD$_3$OD): −77.28, −111.53, −119.42. Mass spectrum (ESI, m/z): Calcd. for $C_{31.2}H_{26.6}ClF_{6.8}N_2O_{5.2}S$, 527.3 (M−1.6 CF$_3$COOH+H). found 527.3.

Example 17

2-[[(2-bromo-6-fluorophenyl)methyl]sulfanyl]-7-(4-chloro-3-methoxyphenyl)-1-(4-fluorophenyl)-4,5,6,7-tetrahydro-H-1,3-benzodiazole

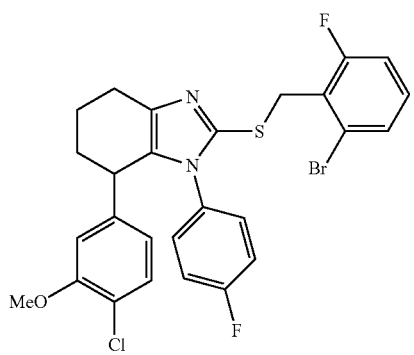

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1-bromo-2-(chloromethyl)-3-fluorobenzene in the presence of $Cs_2CO_3$ to afford the desired product as a white solid.

$^1$H NMR (300 MHz, $CD_3OD$): δ 7.21-7.33 (m, 1H), 7.01-7.19 (m, 3H), 6.81 (br, 2H), 6.43 (d, J=1.8 Hz, 1H), 6.33-6.36 (m, 1H), 4.03-4.14 (m, 2H), 3.85-3.99 (m, 1H), 3.67 (s, 3H), 2.64-2.76 (m, 2H), 2.11-2.20 (m, 1H), 1.74-1.93 (m, 3H). Mass spectrum (ESI, m/z): Calcd. for $C_{27}H_{22}BrClF_2N_2OS$, 577.1 (M+H). found 577.1.

Example 18

7-(4-chloro-3-methoxyphenyl)-2-[[(2-fluoro-6-nitrophenyl)methyl]sulfanyl]-1-(4-fluorophenyl)-4,5,6,7-tetrahydro-1H-1,3-benzodiazole

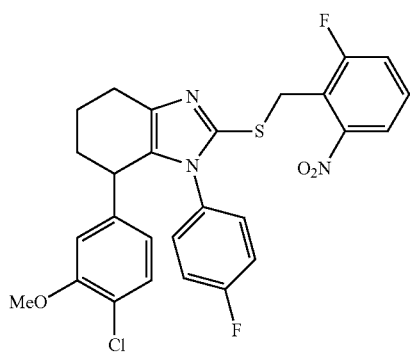

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1-nitro-2-(chloromethyl)-3-fluorobenzene in the presence of $Cs_2CO_3$ to afford the desired product as a white solid. $^1$H NMR (300 MHz, $CD_3OD$): δ 7.53-7.76 (m, 1H), 7.38-7.51 (m, 2H), 7.04-7.07 (m, 1H), 6.48-6.85 (m, 3H), 6.48-6.49 (m, 1H), 6.33-6.36 (m, 1H), 4.20-4.32 (m, 2H), 3.83-3.87 (m, 2H), 3.69 (s, 3H), 2.60-2.69 (m, 2H), 2.11-2.20 (m, 1H), 1.75-2.08 (m, 3H). Mass spectrum (ESI, m/z): Calcd. for $C_{27}H_{22}ClF_2N_3O_3S$, 542.1 (M+H). found 542.2.

Example 19

7-(4-chloro-3-methoxyphenyl)-2-[[(2,5-difluorophenyl)methyl]sulfanyl]-1-(4-fluorophenyl)-4,5,6,7-tetrahydro-1H-1,3-benzodiazole

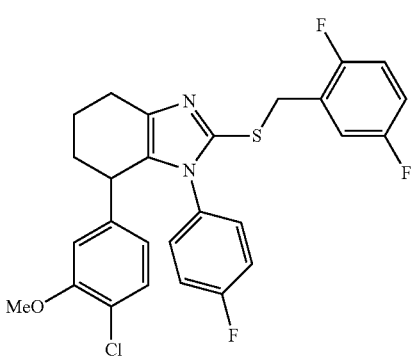 [SMILES: COc1cc(C2CCCc3nc(SCc4cc(F)ccc4F)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1,4-difluoro-2-(chloromethyl)-benzene in the presence of $Cs_2CO_3$ to afford the desired product as a white solid.

$^1$H NMR (300 MHz, $CD_3OD$): δ 7.09-7.28 (m, 5H), 6.87-6.98 (m, 2H), 6.33-6.47 (m, 3H), 3.96-4.15 (m, 3H), 3.68 (s, 3H), 2.73-2.91 (m, 2H), 2.22-2.28 (m, 1H), 1.91-2.20 (m, 3H). Mass spectrum (ESI, m/z): Calcd. for $C_{27}H_{22}ClF_3N_2OS$, 515.1 (M+H). found 515.1.

Example 20

2-[[(2-chloro-3,6-difluorophenyl)methyl]sulfanyl]-7-(4-chloro-3-methoxyphenyl)-1-(4-fluorophenyl)-4,5,6,7-tetrahydro-1H-1,3-benzodiazole

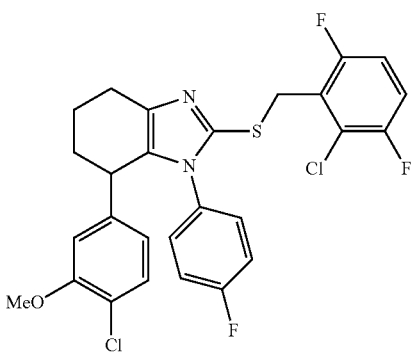 [SMILES: COc1cc(C2CCCc3nc(SCc4c(F)ccc(F)c4Cl)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1, Step 7) with 1-chloro-2-(chloromethyl)-3,6-difluorobenzene in the presence of $Cs_2CO_3$ to afford the desired product as a white solid.

$^1$H-NMR (300 MHz, $CD_3OD$): δ 6.98-7.19 (m, 3H), 6.59-6.85 (m, 3H), 6.32-6.44 (m, 2H), 3.97-4.08 (m, 2H), 3.86-3.88 (m, 1H), 3.67 (s, 3H), 2.59-2.74 (m, 2H), 2.11-2.20 (m, 1H), 1.73-1.94 (m, 3H). Mass spectrum (ESI, m/z): Calcd. for $C_{27}H_{21}Cl_2F_3N_2OS$, 549.1 (M+H). found 549.2.

Example 21

4-((7-(4-chloro-3-methoxyphenyl)-1-(4-fluorophenyl)-4,5,6,7-tetrahydro-1H-benzo[d]imidazol-2-ylthio)methyl)-3,5-difluorobenzenesulfonamide (21a) and 4-((7-(4-chloro-3-methoxyphenyl)-1-(4-fluorophenyl)-4,5,6,7-tetrahydro-1H-benzo[d]imidazol-2-ylthio)methyl)-3,5-difluoro-N-(methylsulfonyl)benzenesulfonamide (21b)

Step 1: [4-(benzylsulfanyl)-2,6-difluorophenyl]methanol

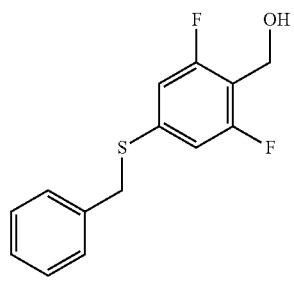 [SMILES: OCc1c(F)cc(SCc2ccccc2)cc1F]

A solution of (4-bromo-2,6-difluorophenyl)methanol (22 g, 98.65 mmol, 1.00 equiv) in 1,4-dioxane (300 mL) was treated with phenylmethanethiol (16 g, 128.82 mmol, 1.31 equiv), $Pd_2(dba)_3$ (2.7 g, 2.95 mmol, 0.03 equiv), Xantphos (5.8 g, 10.02 mmol, 0.10 equiv), and TEA (30 g, 297.03 mmol, 3.01 equiv). The resulting solution was stirred for 3 h at 80° C. and concentrated. Silica gel column chromatography with ethyl acetate/petroleum ether (1:5) gave the title compound as an orange solid. Mass spectrum (ESI, m/z): Calcd. for: $C_{14}H_{12}F_2OS$: 267.1 (M+H). found 267.1.

Step 2: [4-(benzylsulfanyl)-2,6-difluorophenyl]methyl acetate

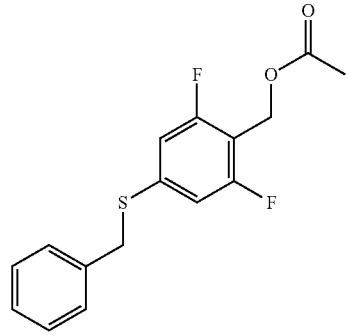 [SMILES: CC(=O)OCc1c(F)cc(SCc2ccccc2)cc1F]

A solution of [4-(benzylsulfanyl)-2,6-difluorophenyl]methanol (5000 mg, 18.78 mmol, 1.00 equiv) in dichloromethane (50 mL) and pyridine (3800 mg, 48.10 mmol, 2.56 equiv) was treated with AcCl (1800 mg, 22.93 mmol, 1.20 equiv) dropwise with stirring at 0° C. The resulting solution was stirred for 2 h at room temperature, concentrated under vacuum, and purified by silica gel chromatography (ethyl acetate/petroleum ether (1:10)) to give the title compound as a red oil. Mass spectrum (ESI, m/z): Calcd. for: $C_{16}H_{14}F_2O_2S$: 308.1 (M+H). found 308.1.

Step 3: [4-(chlorosulfonyl)-2,6-difluorophenyl]methyl acetate

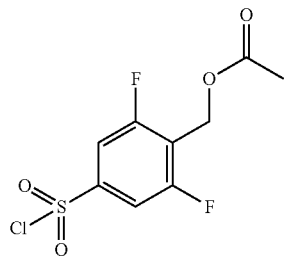 [SMILES: CC(=O)OCc1c(F)cc(S(=O)(=O)Cl)cc1F]

A solution of [4-(benzylsulfanyl)-2,6-difluorophenyl]methyl acetate (4 g, 12.97 mmol, 1.00 equiv), acetic acid (3.9 g, 64.95 mmol, 4.99 equiv), water (1.4 g, 77.78 mmol, 6.00 equiv), and MeCN (50 mL) was treated with NCS (5.2 g, 38.94 mmol, 3.00 equiv), in portions at 0° C. The resulting solution was stirred for 2 h at room temperature, concentrated under vacuum, and diluted with 100 mL of EA. The resulting mixture was washed with 1×50 mL of water, 1×50 mL of brine, dried over sodium sulfate and concentrated under vacuum. Silica gel chromatography (petroleum ether/ EA (10/1)) gave the title compound as a white solid. Mass spectrum (ESI, m/z): Calcd. for: $C_9H_7ClF_2O_4S$: 285.0 (M+H). found 285.0.

Step 4: (2, 6-difluoro-4-sulfamoylphenyl)methyl acetate

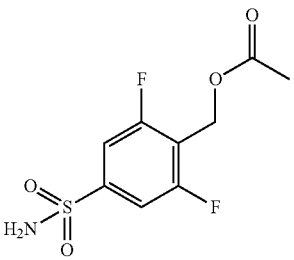 [SMILES: CC(=O)OCc1c(F)cc(S(N)(=O)=O)cc1F]

A solution of [4-(chlorosulfonyl)-2,6-difluorophenyl]methyl acetate (1 g, 3.51 mmol, 1.00 equiv) in tetrahydrofuran (50 mL) was treated with $NH_3(g)$ and stirred for 2 h at 5-10° C. in a water/ice bath. The resulting mixture was concentrated under vacuum and purified by preparatory TLC with ethyl acetate/petroleum ether (1:2.5) to give the title compound as a white solid. Mass spectrum (ESI, m/z): Calcd. for: $C_9H_9F_2NO_4S$: 266.0 (M+H). found 266.0.

Step 5: 3, 5-difluoro-4-(hydroxymethyl)benzene-1-sulfonamide

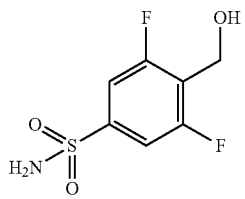 [SMILES: NS(=O)(=O)c1cc(F)c(CO)c(F)c1]

A solution of (2,6-difluoro-4-sulfamoylphenyl)methyl acetate (200 mg, 0.75 mmol, 1.00 equiv) in methanol/H$_2$O (2/2 mL) was treated with LiOH.H$_2$O (160 mg, 3.81 mmol, 5.06 equiv) and stirred for 4 h at room temperature. The resulting mixture was concentrated under vacuum and purified by preparatory TLC with ethyl acetate/petroleum ether (1:1) to give the title compound as a white solid. Mass spectrum (ESI, m/z): Calcd. for: C$_7$H$_7$F$_2$NO$_3$S: 224.0 (M+H). found 224.0.

Step 6: 4-((7-(4-chloro-3-methoxyphenyl)-1-(4-fluorophenyl)-4,5,6,7-tetrahydro-1H-benzo[d]imidazol-2-ylthio)methyl)-3,5-difluorobenzenesulfonamide (21a)

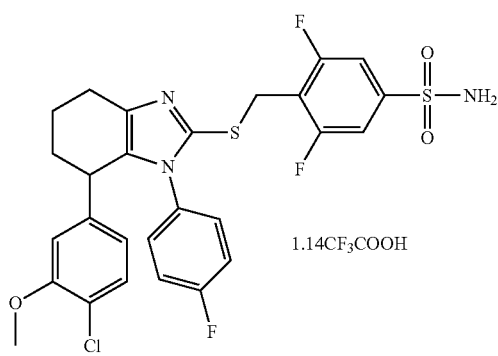 [SMILES: COc1cc(C2CCCc3nc(SCc4c(F)cc(S(N)(=O)=O)cc4F)n(-c4ccc(F)cc4)c32)ccc1Cl]

1.14CF$_3$COOH

A solution of 3,5-difluoro-4-(hydroxymethyl)benzene-1-sulfonamide (110 mg, 0.49 mmol, 1.10 equiv), 7-(4-chloro-3-methoxyphenyl)-1-(4-fluorophenyl)-4,5,6,7-tetrahydro-1H-benzo[d]imidazole-2-thiol (Prepared as described in Example 1 Step 7, 175 mg, 0.45 mmol, 1.00 equiv), n-Bu$_3$P (226 mg, 1.12 mmol, 2.50 equiv), and ADDP (237 mg, 0.95 mmol, 2.10 equiv) in toluene (5 mL) was stirred overnight at 60° C. in an oil bath. The resulting mixture was concentrated under vacuum, purified by silica gel column with dichloromethane/methanol (20/1), followed by Prep-HPLC with the following conditions: (1#waters2767-5) column, SunFire Prep C18, 19*150 mm H Prep C-001(T) 18600256819513816414 04; Mobile Phase, phase A: water with 0.05% TFA, phase B: CH3CN (35% CH$_3$CN up to 70% in 8 min, up to 100% in 0.1 min, hold 100% in 1.9 min, down to 35% in 0.1 min, hold 35% in 1.9 min); Detector, UV 220 & 254 nm. The title compound was obtained as a white solid. $^1$H NMR (400 MHz, CD$_3$OD) δ7.49 (d, J=6.8 Hz, 2H), 6.99-7.17 (m, 4H), 6.50 (d, J=1.6 Hz, 1H), 6.38-6.41 (m, 1H), 4.01-4.16 (m, 3H), 3.73 (s, 3H), 2.73-2.88 (m, 2H), 2.24-2.30 (m, 1H), 1.87-2.05 (m, 3H). 19F NMR (400 MHz, CD$_3$OD) δ −77.08, −81.97, −112.41, −113.74. Mass spectrum (ESI, m/z): Calcd. for: C$_{29.28}$H$_{24.14}$ClF$_{6.42}$N$_3$O$_{5.28}$S$_2$: 594.2 (M−1.14CF$_3$COOH+H). found 594.2.

Step 7: 2, 6-difluoro-4-(N-(methylsulfonyl)sulfamoyl)benzyl methanesulfonate

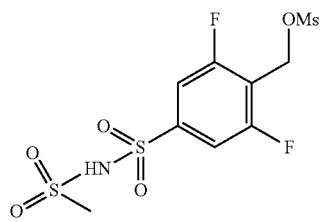 [SMILES: CS(=O)(=O)NS(=O)(=O)c1cc(F)c(COS(C)(=O)=O)c(F)c1]

A solution of 3,5-difluoro-4-(hydroxymethyl)benzene-1-sulfonamide (200 mg, 0.90 mmol, 1.00 equiv), TEA (272 mg, 2.69 mmol, 3.00 equiv), and MsCl (206 mg, 1.79 mmol, 2.00 equiv) in dichloromethane (10 mL) was stirred for 3 h at room temperature. The resulting mixture was concentrated under vacuum and purified by TLC with dichloromethane/methanol (30:1) to give the title compound as a light yellow solid. Mass spectrum (ESI, m/z): Calcd. for: C$_9$H$_{11}$F$_2$NO$_7$S$_3$: 380.0 (M+H). found 380.0.

Step 8: 4-((7-(4-chloro-3-methoxyphenyl)-1-(4-fluorophenyl)-4,5,6,7-tetrahydro-1H-benzo[d]imidazol-2-ylthio)methyl)-3,5-difluoro-N-(methylsulfonyl)benzenesulfonamide (21b)

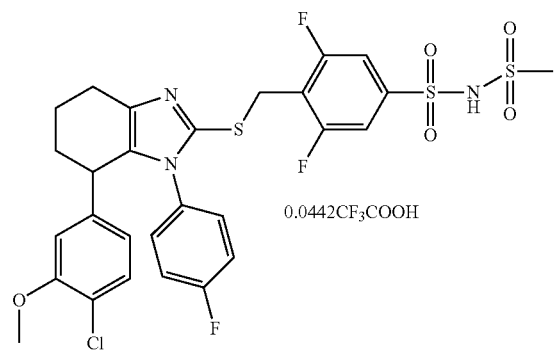 [SMILES: COc1cc(C2CCCc3nc(SCc4c(F)cc(S(=O)(=O)NS(C)(=O)=O)cc4F)n(-c4ccc(F)cc4)c32)ccc1Cl]

0.0442CF$_3$COOH

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 2, 6-difluoro-4-(N-(methyl sulfonyl)sulfamoyl)benzyl methanesulfonate in the presence of Cs$_2$CO$_3$ to afford the desired product as a white solid.

$^1$H NMR (400 MHz, CD$_3$OD) δ7.33 (d, J=7.2 Hz, 2H), 6.91-7.23 (m, 5H), 6.53 (s, 1H), 6.36-6.39 (m, 1H), 4.23 (d, J=20.0 Hz, 1H), 4.06-4.09 (m, 2H), 3.79 (s, 3H), 2.87 (s, 3H), 2.68-2.75 (m, 1H), 2.12-2.18 (m, 1H), 1.72-1.91 (m, 3H). $^{19}$F NMR (400 MHz, CD$_3$OD) δ −74.76, −111.00, −114.27. Mass spectrum (ESI, m/z): Calcd. for: C$_{28.0884}$H$_{25.0442}$ClF$_{3.1326}$N$_3$O$_{5.0884}$S$_3$: 672.1 (M−0.0442CF$_3$COOH+H). found 672.1.

Example 22

3-(4-((7-(4-chloro-3-methoxyphenyl)-1-(4-fluoro-phenyl)-4,5,6,7-tetrahydro-1H-benzo[d]imidazol-2-ylthio)methyl)-3,5-difluorophenylsulfonamido)-N,N,N-trimethylpropan-1-aminium 2,2,2-trifluoroacetate

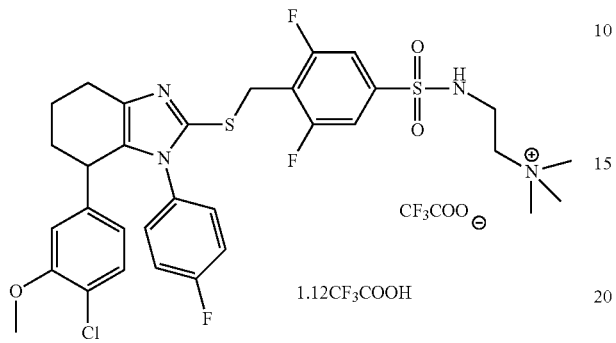

A solution of 4-((7-(4-chloro-3-methoxyphenyl)-1-(4-fluorophenyl)-4,5,6,7-tetrahydro-1H-benzo[d]imidazol-2-ylthio)methyl)-3,5-difluorobenzenesulfonamide (60 mg, 0.10 mmol, 1.00 equiv), potassium methaneperoxoate potassium (41 mg, 0.29 mmol, 3.00 equiv), and (3-bromopropyl)trimethylazanium bromide (29 mg, 0.11 mmol, 1.11 equiv) in N,N-dimethylformamide (1 mL) was stirred overnight at room temperature, filtered and concentrated. Purification by Prep-HPLC with the following conditions: (1#waters2767-5) column, SunFire Prep C18, 19*150 mm H Prep C-001 (T)18600256819513816414 04; Mobile Phase, phase A: water with 0.05% TFA, phase B: CH$_3$CN (25% CH$_3$CN up to 60% in 8 min, up to 100% in 0.1 min, hold 100% in 1.9 min, down to 25% in 0.1 min, hold 25% in 1.9 min); Detector, UV 220 & 254 nm gave the title compound as a white solid. $^1$H NMR (400 MHz, CD$_3$OD) δ7.47-7.51 (m, 2H), 6.99-7.20 (m, 4H), 6.52 (s, 1H), 6.42 (d, J=1.6 Hz, 1H), 4.13 (s, 2H), 4.02 (t, J=10.8 Hz, 1H), 3.74 (s, 3H), 3.46-3.50 (m, 2H), 3.18 (s, 9H), 3.01-3.04 (m, 2H), 2.75-2.85 (m, 2H), 2.24-2.30 (m, 1H), 2.02-2.09 (m, 3H), 1.87-1.90 (m, 2H). 19F NMR (400 MHz, CD$_3$OD) δ −77.14, −112.18, −113.02. Mass spectrum (ESI, m/z): Calcd. for C$_{37.24}$H$_{38.12}$ClF$_{9.36}$N$_4$O$_{7.24}$S$_2$, 693.2 (M−1.12CF$_3$COOH—CF$_3$COO). found 693.2.

Example 23

1-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]-1,4,7,10-tetraoxadodecan-12-ol

Step 1: 3,5-difluoro-4-(hydroxymethyl)phenol

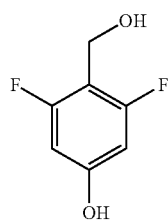

A solution of 2,6-difluoro-4-hydroxybenzaldehyde (2.912 g, 18.42 mmol, 1.00 equiv) in methanol (30 mL) was treated with NaBH$_4$ (1.4 g, 37.01 mmol, 2.01 equiv) in portions at 0° C. and stirred for 5 h at 16° C. The reaction was quenched by the addition of 5 mL of water, extracted with 2×10 mL of ethyl acetate and the organic layers combined and concentrated under vacuum. Silica gel column chromatography with dichloromethane/methanol (10:1) gave the title compound as a white solid.

Step 2: 2-[2-[2-(2-[[(4-methylbenzene)sulfonyl]oxy]ethoxy)ethoxy]ethan-1-ol

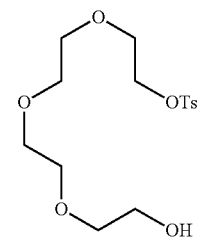 [SMILES: Cc1ccc(S(=O)(=O)OCCOCCOCCOCCO)cc1]

A solution of 2-[2-[2-(2-hydroxyethoxy)ethoxy]ethoxy]ethan-1-ol (38.8 g, 199.77 mmol, 10.00 equiv), TEA (2.02 g, 19.96 mmol, 1.00 equiv), and 4-methylbenzene-1-sulfonyl chloride (3.8 g, 19.93 mmol, 1.00 equiv) in dichloromethane (200 mL) was stirred overnight at 30° C. The reaction was quenched by the addition of 200 mL of water, extracted with 2×200 mL of dichloromethane and the organic layers combined, concentrated under vacuum, and dried in an oven under reduced pressure. Silica gel column chromatography with ethyl acetate/petroleum ether (1:1) gave the title compound as a yellow oil.

Step 3: 2, 2, 3, 3-tetramethyl-4,7,10,13-tetraoxa-3-silapentadecan-15-yl 4-methylbenzene-1-sulfonate

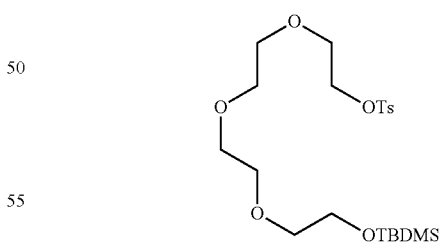

A solution of 2-[2-[2-(2-[[(4-methylbenzene)sulfonyl]oxy]ethoxy)ethoxy]ethan-1-ol (3.48 g, 9.99 mmol, 1.00 equiv) in pyridine (10 mL) was treated with tert-butyldimethylsilyl trifluoromethanesulfonate (5.28 g, 19.97 mmol, 2.00 equiv) dropwise with stirring at 0° C. The resulting solution was stirred for 2 h at 30° C. and concentrated under vacuum. Silica gel column chromatography with ethyl acetate/petroleum ether (1:1) gave the title compound as a yellow oil.

Step 4: [2,6-difluoro-4-[(2,2,3,3-tetramethyl-4,7,10,13-tetraoxa-3-silapentadecan-15-yl)oxy]phenyl] methanol

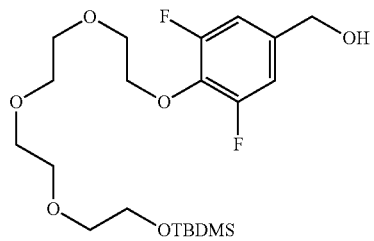 [SMILES: CC(C)(C)[Si](C)(C)OCCOCCOCCOCCOc1c(F)cc(CO)cc1F]

A solution of 3,5-difluoro-4-(hydroxymethyl)phenol (200 mg, 1.25 mmol, 1.00 equiv), 2,2,3,3-tetramethyl-4,7,10,13-tetraoxa-3-silapentadecan-15-yl 4-methylbenzene-1-sulfonate (690 mg, 1.49 mmol, 1.20 equiv), and potassium carbonate (517 mg, 3.74 mmol, 3.00 equiv) in N,N-dimethylformamide (5 mL) was stirred overnight at 40° C. The resulting mixture was concentrated under vacuum and purified by silica gel column chromatography with ethyl acetate/petroleum ether (2:1) to give the title compound as a yellow oil.

Step 5: [2,6-difluoro-4-[(2,2,3,3-tetramethyl-4,7,10,13-tetraoxa-3-silapentadecan-15-yl)oxy]phenyl] methyl methanesulfonate

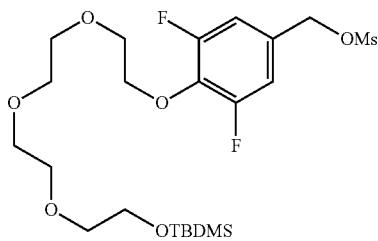 [SMILES: CC(C)(C)[Si](C)(C)OCCOCCOCCOCCOc1c(F)cc(COS(C)(=O)=O)cc1F]

A solution of [2,6-difluoro-4-[(2,2,3,3-tetramethyl-4,7,10,13-tetraoxa-3-silapentadecan-15-yl)oxy]phenyl]methanol (220 mg, 0.49 mmol, 1.00 equiv), TEA (99 mg, 0.98 mmol, 2.00 equiv), MsCl (67 mg, 0.59 mmol, 1.20 equiv) in dichloromethane (5 mL) was stirred for 5 h at 30° C. The resulting mixture was concentrated under vacuum and purified by silica gel column chromatography with ethyl acetate/petroleum ether (1:2) to give the total compound as a yellow solid.

Step 6: 7-(4-chloro-3-methoxyphenyl)-2-([2,6-difluoro-4-[(2,2,3,3-tetramethyl-4,7,10,13-tetraoxa-3-silapentadecan-15-yl)oxy phenyl]methyl)sulfanyl]-1-(4-fluorophenyl)-4,5,6,7-tetrahydro-1H-1,3-benzodiazole

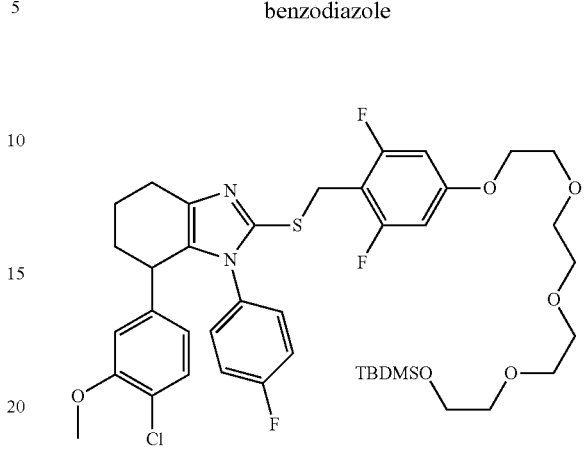

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) and [2,6-difluoro-4-[(2,2,3,3-tetramethyl-4,7,10,13-tetraoxa-3-silapentadecan-15-yl)oxy]phenyl]methyl methanesulfonate in the presence of $Cs_2CO_3$ to afford the desired product as a white oil.

Step 7: 1-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]-1,4,7,10-tetraoxadodecan-12-ol

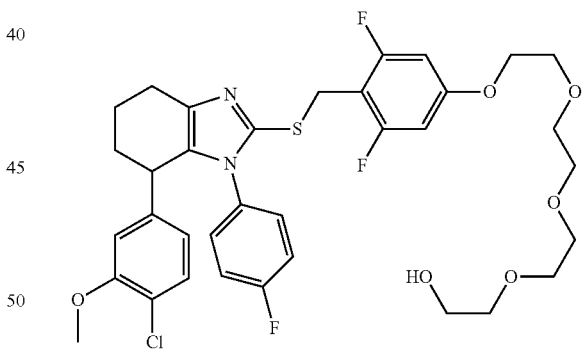

A solution of 7-(4-chloro-3-methoxyphenyl)-2-[([2,6-difluoro-4-[(2,2,3,3-tetramethyl-4,7,10,13-tetraoxa-3-silapentadecan-15-yl)oxy]phenyl]methyl)sulfanyl]-1-(4-fluorophenyl)-4,5,6,7-tetrahydro-1H-1,3-benzodiazole (120 mg, 0.15 mmol, 1.00 equiv) and TBAF (1M, 0.17 mL, 1.20 equiv) in tetrahydrofuran (2 mL) was stirred for 3 h at 30° C. and concentrated under vacuum. Prep-HPLC purification using (1#Waters 2767-1) Column, Sun Fire Prep C18, 5 μm, 19*100 mm; mobile phase, water with 0.05% $NH_4HCO_3$ and $CH_3CN$ (45% $CH_3CN$ up to 78% in 10 min, up to 100% in 2 min, down to 45% in 2 min); Detector, 254 nm gave the title compound as a white solid. $^1H$ NMR (400 MHz, $CD_3OD$) δ7.15-7.17 (d, J=8.0 Hz, 1H), 6.89 (s, 2H), 6.51-6.57 (m, 4H), 6.37-6.40 (m, 1H), 4.11-4.15 (m, 2H), 3.98-

4.02 (d, J=13.2 Hz, 1H), 3.85-3.89 (m, 4H), 3.63-3.74 (m, 13H), 3.56-3.58 (t, J=4.4 Hz, 2H), 2.69-2.80 (m, 2H), 2.16-2.20 (m, 1H), 1.85-1.94 (m, 1H), 1.79-1.83 (m, 2H). $^{19}$F NMR (400 MHz, CD$_3$OD) δ −114.59, −116.14. Mass spectrum (ESI, m/z): Calcd. for C$_{35}$H$_{38}$ClF$_3$N$_2$O$_6$S, 707.1 (M+H). found 707.1.

Example 24

2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)-N,N-dimethylethanamine Trifluoromethylacetic acid salt

Step 1: 2,6-difluoro-4-((4-methoxybenzyl)oxy)benzyl methanesulfonate

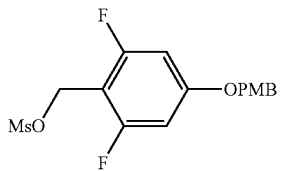

The title compound was prepared according to the procedure described in Example 23 steps 4 and 5 by alkylation of 3,5-difluoro-4-(hydroxymethyl)phenol with p-methoxybenzyl chloride followed by mesylation of the benzyl alcohol to afford the desire product as an off white oil.

Step 2: 7-(4-chloro-3-methoxyphenyl)-2-[((2,6-difluoro-4-[(4-methoxyphenyl)methoxy]phenyl]methyl)sulfanyl]-1-(4-fluorophenyl)-4,5,6,7-tetrahydro-1H-1,3-benzodiazole

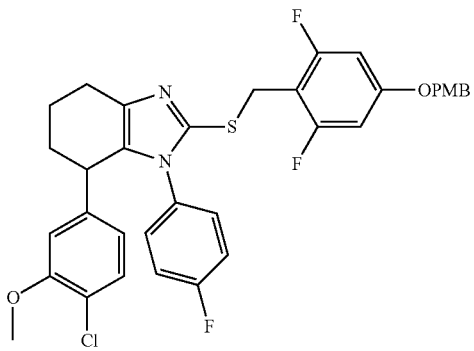

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) and 2,6-difluoro-4-((4-methoxybenzyl)oxy)benzyl methanesulfonate in the presence of Cs$_2$CO$_3$ to afford the desired product as a white oil. Mass spectrum (ESI, m/z): Calcd. for C$_{35}$H$_{30}$ClF$_3$N$_2$O$_3$S, 651.2 (M+H). found 651.2.

Step 3: 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol

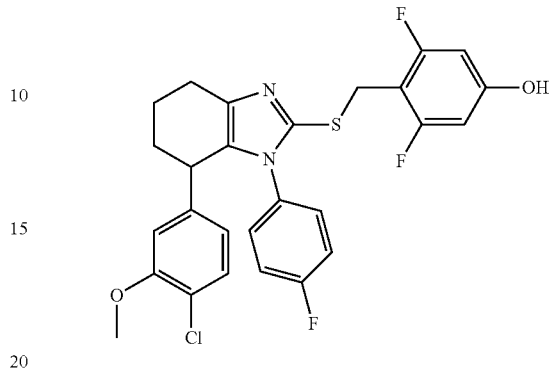

A solution of 7-(4-chloro-3-methoxyphenyl)-2-[((2,6-difluoro-4-[(4-methoxyphenyl)methoxy]phenyl] methyl) sulfanyl]-1-(4-fluorophenyl)-4,5,6,7-tetrahydro-1H-1,3-benzodiazole (1.0 g, 1.54 mmol, 1.00 equiv), dichloromethane (15 mL), and trifluoroacetic acid (1.5 mL) was stirred for 2.0 h at room temperature. The resulting mixture was concentrated under vacuum, diluted with 15 mL of DCM, and washed with 3×15 mL of H$_2$O. The organic layer was dried over anhydrous sodium sulfate, filtered, and concentrated under vacuum to give the title compound as a yellow oil. Mass spectrum (ESI, m/z): Calcd. for C$_{27}$H$_{22}$ClF$_3$N$_2$O$_2$S, 531.1 (M+H). found 531.1.

Step 4: 2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)-N,N-dimethylethanamine

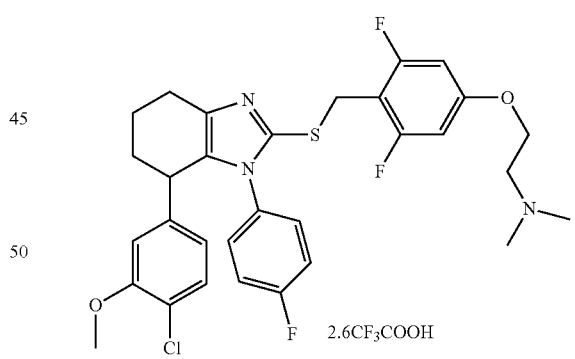

A solution of 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (53 mg, 0.10 mmol, 1.00 equiv), (2-bromoethyl)dimethylamine hydrobromide (28 mg, 0.12 mmol, 1.21 equiv), and potassium methaneperoxoate (41 mg, 0.29 mmol, 3.00 equiv) in N,N-dimethylformamide (2 mL) was stirred for 6 h at room temperature, filtered and concentrated. The crude product was purified by Prep-HPLC With the following conditions: (1#waters2767-5) column, SunFire Prep C18, 19*150 mm H Prep C-001(T)18600256819513816414 04; Mobile Phase, phase A: water with 0.05% TFA, phase B: CH3CN (18% CH$_3$CN up to 32% in 26 min, up to 100% in 0.1 min, hold 100% in 1.9 min, down to 18% in 0.1 min, hold 18% in 1.9 min); Detector, UV 220 & 254 nm to give the title compound as a light yellow oil. $^1$H NMR (300 MHz, CD$_3$OD): δ 7.17-7.20 (m, 4H), 6.78-6.80 (m, 2H), 6.54 (s, 1H), 6.44 (d, J=1.8 Hz, 1H), 4.38-4.42 (m, 2H), 4.04-4.19 (m, 3H), 3.74 (s, 3H), 3.65-3.66 (m, 2H), 3.01 (s, 6H), 2.80-2.96 (m, 2H), 2.23-2.34 (m, 1H), 2.08-2.10 (m, 3H). $^{19}$F NMR (300 MHz, CD$_3$OD): δ −77.20, −111.45, −115.62. Mass spectrum (ESI, m/z): Calcd. for $C_{36.2}H_{33.6}ClF_{10.8}N_3O_{7.2}S$, 602.3 (M−2.6CF$_3$COOH+H). found 602.3.

Step 5: 2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)-N,N-dimethylethanamine HCl salt

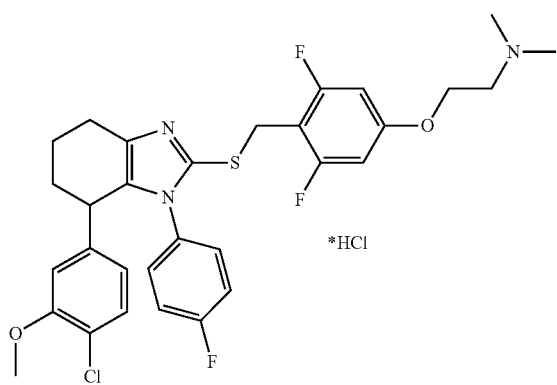 [SMILES: COc1cc(C2CCCc3nc(SCc4c(F)cc(OCCN(C)C)cc4F)n(-c4ccc(F)cc4)c32)ccc1Cl]

A solution of 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (280 mg, 0.53 mmol, 1.00 equiv), potassium carbonate (219 mg, 1.58 mmol, 3.00 equiv), and (2-bromoethyl)dimethylamine (146 mg, 0.63 mmol, 1.20 equiv) in N,N-dimethylformamide (5 mL) was stirred for 6 h at room temperature and filtered. Prep-HPLC purification with the following conditions: (1#waters2767-5) column, SunFire Prep C18, 19*150 mm 5 μm H Prep C-001(T)18600256819513816414 04; Mobile Phase, phase A: water with 0.05% TFA, phase B: CH3CN (30% CH$_3$CN up to 50% in 8 min, up to 100% in 0.1 min, hold 100% in 1.9 min, down to 30% in 0.1 min, hold 30% in 1.9 min); Detector, UV 220 & 254 nm. was followed by concentration under vacuum. Acidification by the addition of 4.0 mL H$_2$O, followed by 4 drops of con. HCl and subsequent evaporation was carried out twice. A final acidification was followed by lyophilization to give the title compound as a white solid. $^1$H NMR (400 MHz, CD$_3$OD): δ 7.33 (br, 1H), 7.14 (d, J=16.0 Hz, 1H), 7.00 (br, 1H), 6.87-6.96 (m, 2H), 6.55 (s, 1H), 6.43-6.45 (m, 1H), 4.38-4.43 (m, 2H), 4.13-4.21 (m, 2H), 4.07-7.10 (m, 1H), 3.75 (s, 3H), 3.62-6.67 (m, 2H), 3.02 (s, 6H), 2.82-2.98 (m, 2H), 2.28-2.33 (m, 1H), 1.96-2.07 (m, 1H), 1.91-1.95 (m, 2H). $^{19}$F NMR (400 MHz, CD$_3$OD): δ −111.16, −115.27.

Example 25

2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)ethanol Step 1: 2-[[(4-[2-[(tert-butyldimethylsilyl)oxy]ethoxy]-2,6-difluorophenyl)methyl]sulfanyl]-7-(4-chloro-3-methoxyphenyl)-1-(4-fluorophenyl)-4,5,6,7-tetrahydro-1H-1,3-benzodiazole

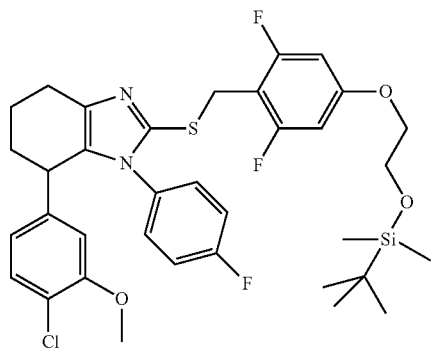 [SMILES: COc1cc(C2CCCc3nc(SCc4c(F)cc(OCCO[Si](C)(C)C(C)(C)C)cc4F)n(-c4ccc(F)cc4)c32)ccc1Cl]

The title compound was prepared according to the procedure described in Example 24 step 4 by coupling 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (Prepared as described in Example 24, Step 3) and (2-bromoethoxy)(tert-butyl) dimethylsilane in the presence of Cs$_2$CO$_3$ to afford the desired product as a white oil. Mass spectrum (ESI, m/z): Calcd. for $C_{35}H_{40}ClF_3N_2O_3SSi$, 575.1 (M−C$_6$H$_{15}$Si+2H). found 575.1.

Step 2: 2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)ethanol

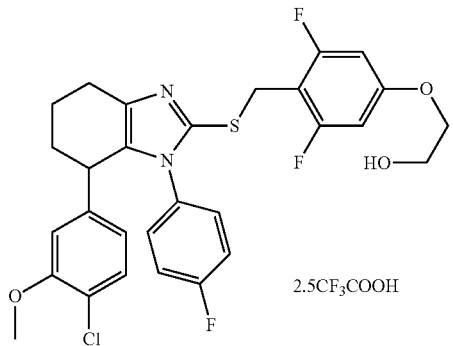 [SMILES: COc1cc(C2CCCc3nc(SCc4c(F)cc(OCCO)cc4F)n(-c4ccc(F)cc4)c32)ccc1Cl]

A solution of 2-[[(4-[2-[(tert-butyldimethylsilyl)oxy]ethoxy]-2,6-difluorophenyl)methyl]sulfanyl]-7-(4-chloro-3-methoxyphenyl)-1-(4-fluorophenyl)-4,5,6,7-tetrahydro-1H-1,3-benzodiazole (20 mg, 0.03 mmol, 1.00 equiv) and TBAF (9.1 mg, 0.03 mmol, 1.20 equiv) in tetrahydrofuran (2 mL) was stirred for 3 h at room temperature and concentrated under vacuum. Purification by Prep-HPLC with the following conditions: (1#waters2767-5) column, SunFire Prep C18, 19*150 mm 5 μm H Prep C-001(T) 18600256819513816414 04; Mobile Phase, phase A: water with 0.05% TFA, phase B: CH₃CN (35% CH₃CN up to 65% in 8 min, up to 100% in 0.1 min, hold 100% in 1.9 min, down to 35% in 0.1 min, hold 35% in 1.9 min); Detector, UV 220 & 254 nm, gave the title compound as a white solid. $^1$H NMR (400 MHz, CD$_3$OD): δ 6.68-7.20 (m, 3H), 6.66-6.70 (m, 2H), 6.52 (d, J=1.6 Hz, 1H), 6.40-6.42 (m, 1H), 4.01-4.14 (m, 5H), 3.90-3.92 (m, 2H), 3.74 (s, 3H), 2.77-2.93 (m, 2H), 2.25-2.316 (m, 1H), 1.90-2.08 (m, 3H). $^{19}$F NMR (400 MHz, CD$_3$OD): δ −77.80, −111.82, −116.58. Mass spectrum (ESI, m/z): Calcd. for C$_{34}$H$_{28.5}$ClF$_{10.5}$N$_2$O$_8$S, 575.3 (M−2.5CF$_3$COOH+H). found 575.3.

Example 26

2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)ethanoic acid Step 1: Methyl 2-[4-(([7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenoxy]acetate

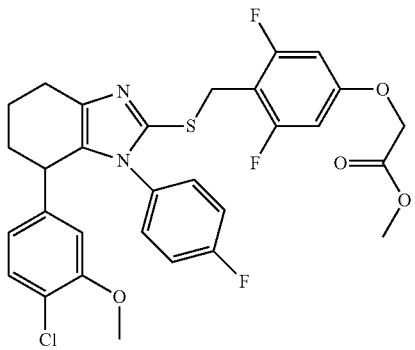 [SMILES: COC(=O)COc1cc(F)c(CSc2nc3c(n2-c2ccc(F)cc2)C(c2ccc(Cl)c(OC)c2)CCC3)c(F)c1]

The title compound was prepared according to the procedure described in Example 24 step 4 by coupling 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (Prepared as described in Example 24, Step 3) and methyl 2-bromoacetate in the presence of Cs$_2$CO$_3$ to afford the desired product as a white oil. Mass spectrum (ESI, m/z): Calcd. for C$_{30}$H$_{26}$ClF$_3$N$_2$O$_4$S, 603.1 (M+H). found 603.1.

Step 2: 2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)ethanoic acid

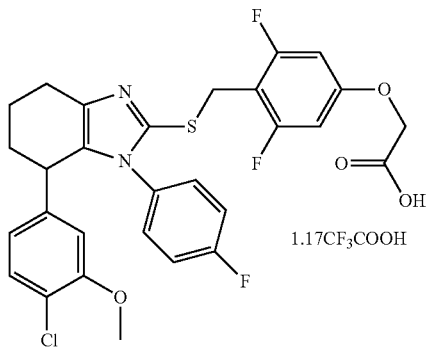 [SMILES: COc1cc(C2CCCc3nc(SCc4c(F)cc(OCC(=O)O)cc4F)n(-c4ccc(F)cc4)c32)ccc1Cl]

1.17CF₃COOH

A solution of methyl 2-[4-(([7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenoxy]acetate (30 mg, 0.05 mmol, 1.00 equiv) and LiOH.H$_2$O (11 mg, 0.26 mmol, 5.00 equiv) in methanol/H$_2$O (3/2 mL) was stirred for 3 h at room temperature and concentrated under vacuum. The pH was adjusted to 5 with hydrogen chloride (2 mol/L). The resulting solution was extracted with 2×5 ml of ethyl acetate and the organic layers combined and concentrated under vacuum. Purification by Prep-HPLC with the following conditions: (1#waters2767-5) column, SunFire Prep C18, 19*150 mm 5 μm H Prep C-001(T) 18600256819513816414 04; Mobile Phase, phase A: water with 0.05% TFA, phase B: CH₃CN (38% CH₃CN up to 60% in 8 min, up to 100% in 0.1 min, hold 100% in 1.9 min, down to 38% in 0.1 min, hold 38% in 1.9 min); Detector, UV 220 & 254 nm, to give the title compound as a white solid. $^1$H NMR (400 MHz, CD$_3$OD) δ7.17 (d, J=8.0 Hz, 4H), 6.66-6.68 (m, 2H), 6.50 (d, J=1.6 Hz, 1H), 6.39-6.41 (m, 1H), 4.79 (s, 2H), 4.01-4.17 (m, 3H), 3.73 (s, 3H), 2.85-2.91 (m, 2H), 1.90-2.31 (m, 4H). $^{19}$F NMR (400 MHz, CD$_3$OD) δ −77.14, −111.57, −116.37. Mass spectrum (ESI, m/z): Calcd. for C31.34H25.17ClF6.51N2O6.34S, 589.3 (M−1.17CF$_3$COOH+H). found 589.3.

Example 27

7-(4-chloro-3-methoxyphenyl)-2-[([2, 6-difluoro-4-[2-(pyrrolidin-1-yl)ethoxy]phenyl]methyl) sulfanyl]-1-(4-fluorophenyl)-4,5,6,7-tetrahydro-1H-1,3-benzodiazole Step 1: 7-(4-chloro-3-methoxyphenyl)-2-([[4-(2-chloroethoxy)-2,6-difluorophenyl]methyl]sulfanyl)-1-(4-fluorophenyl)-4,5,6,7-tetrahydro-1H-1,3-benzodiazole

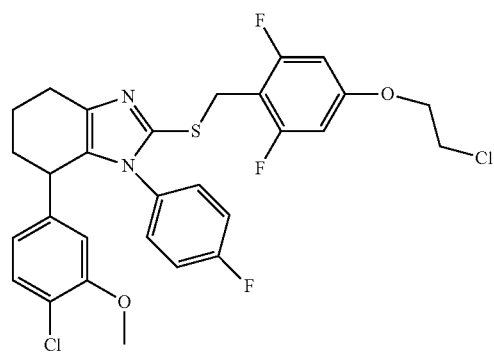 [SMILES: COc1cc(C2CCCc3nc(SCc4c(F)cc(OCCCl)cc4F)n(-c4ccc(F)cc4)c32)ccc1Cl]

The title compound was prepared according to the procedure described in Example 24 step 4 by coupling 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (Prepared as described in Example 24, Step 3) and 1-chloro-2-iodoethane in the presence of Cs$_2$CO$_3$ to afford the desired product as a white oil. $^1$H NMR (400 MHz, CD$_3$OD) δ 7.18 (d, J=8.0 Hz, 1H), 6.96 (s, 3H), 6.63-6.71 (m, 2H), 6.51 (s, 1H), 6.40 (d, J=7.6 Hz, 1H), 4.24-4.33 (m, 2H), 4.10 (s, 1H), 3.89-3.98 (m, 4H), 3.74 (s, 3H), 2.73-2.89 (m, 2H), 2.22-2.29 (m, 1H), 1.89-2.05 (m, 3H). 19F NMR (400 MHz, CD$_3$OD) δ −76.95, −112.73, −116.10. Mass spectrum (ESI, m/z): Calcd. for $C_{29}H_{25}Cl_2F_3N_2O_2S$, 593.2 (M+H). found 593.2.

Step 2: 7-(4-chloro-3-methoxyphenyl)-2-[([2,6-difluoro-4-[2-(pyrrolidin-1-yl)ethoxy]phenyl]methyl)sulfanyl]-1-(4-fluorophenyl)-4,5,6,7-tetrahydro-1H-1,3-benzodiazole

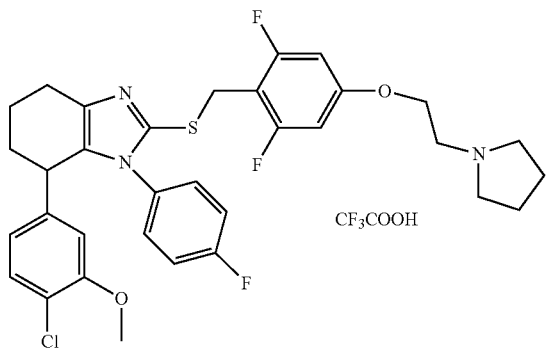 [SMILES: COc1cc(C2CCCc3nc(SCc4c(F)cc(OCCN5CCCC5)cc4F)n(-c4ccc(F)cc4)c32)ccc1Cl ; "CF3COOH"]

A solution of 7-(4-chloro-3-methoxyphenyl)-2-([[4-(2-chloroethoxy)-2,6-difluorophenyl]methyl]sulfanyl)-1-(4-fluorophenyl)-4,5,6,7-tetrahydro-1H-1,3-benzodiazole (50 mg, 0.08 mmol, 1.00 equiv), NaI (1.3 mg, 0.01 mmol, 0.10 equiv), and pyrrolidine (30 mg, 0.42 mmol, 5.01 equiv) in ethanol (2 mL) was stirred for 48 h at 80° C. in an oil bath and concentrated under vacuum. Purification by Prep-HPLC with the following conditions: (1#waters2767-5) column, SunFire Prep C18, 19*150 mm 5 μm H Prep C-001(T) 18600256819513816414 04; Mobile Phase, phase A: water with 0.05% TFA, phase B: CH3CN (25% $CH_3CN$ up to 40% in 8 min, up to 100% in 0.1 min, hold 100% in 1.9 min, down to 25% in 0.1 min, hold 25% in 1.9 min); Detector, UV 220 & 254 nm, gave the title compound as a white solid. $^1H$ NMR (400 MHz, $CD_3OD$) δ7.01-7.12 (m, 2H), 6.96-7.01 (m, 2H), 6.69-6.96 (m, 2H), 6.49 (s, 1H), 6.37-6.39 (m, 1H), 4.33 (s, 2H), 3.97-4.07 (m, 3H), 3.64-3.77 (m, 7H), 2.73-2.88 (m, 2H), 1.86-2.28 (br, 10H), 1.26 (s, 1H). $^{19}F$ NMR (400 MHz, $CD_3OD$) δ −77.12, −111.92, −115.58. Mass spectrum (ESI, m/z): Calcd. for $C_{35}H_{34}ClF_6N_3O_4S$, 628.0 ($M-CF_3COOH+H$). found 628.0.

Example 28

7-(4-chloro-3-methoxyphenyl)-2-([[2,6-difluoro-4-(2,5,8,11-tetraoxatridecan-13-yloxy)phenyl]methyl]sulfanyl)-1-(4-fluorophenyl)-4,5,6,7-tetrahydro-1H-1,3-benzodiazole Step 1. 1-(3,5-difluorophenyl)-1,4,7,10,13-pentaoxatetradecane

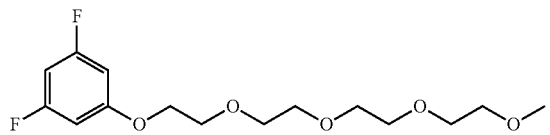 [SMILES: COCCOCCOCCOCCOc1cc(F)cc(F)c1]

A solution 3,5-difluorophenol (2 g, 15.37 mmol, 1.00 equiv), 2,5,8,11-tetraoxatridecan-13-ol (3.36 g, 16.13 mmol, 1.05 equiv), $PPh_3$ (4.84 g, 18.45 mmol, 1.20 equiv), and DIAD (3.73 g, 18.45 mmol, 1.20 equiv) in tetrahydrofuran (30 mL) was stirred overnight at 30° C. The resulting mixture was concentrated under vacuum, extracted with 2×30 mL of ethyl acetate, and the combined organic layers were dried over anhydrous sodium sulfate, filtered, and concentrated. Silica gel column chromatography with ethyl acetate/petroleum ether (1:2) gave the title compound as a yellow oil.

Step 2: 2, 6-difluoro-4-(2,5,8,11-tetraoxatridecan-13-yloxy)benzaldehyde

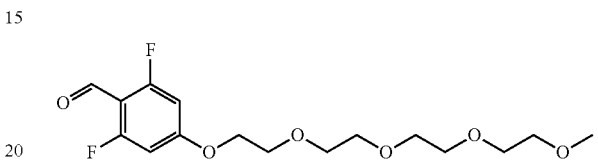

A solution of $(i-Pr)_2NH$ (1.32 g) in tetrahydrofuran (15 mL) was treated with n-BuLi (5.4 mL) dropwise with stirring for 1 h at 0° C., followed by the addition of 1-(3,5-difluorophenyl)-1,4,7,10,13-pentaoxatetradecane (2.79 g, 8.71 mmol, 1.00 equiv). After stirring for 1 h at −78° C., the reaction was treated with N, N-dimethylformamide (1.082 g, 14.80 mmol, 1.70 equiv) and stirred for an additional hour at −78° C. The reaction was quenched by the addition of 5 mL of water and extracted with 3×30 mL of ethyl acetate. The combined organic layers were dried over sodium sulfate, filtered, and concentrated. Silica gel column chromatography with ethyl acetate/petroleum ether (2:1) gave the title compound as a light yellow oil.

Step 3: [2, 6-difluoro-4-(2,5,8,11-tetraoxatridecan-13-yloxy)phenyl]methanol

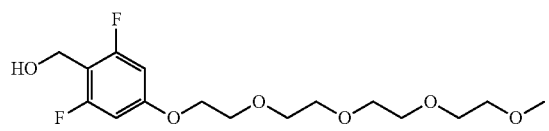 [SMILES: COCCOCCOCCOCCOc1cc(F)c(CO)c(F)c1]

The title compound was prepared according to the procedure described in Example 12 Step 3 by $NaBH_4$ reduction of 2, 6-difluoro-4-(2,5,8,11-tetraoxatridecan-13-yloxy)benzaldehyde to afford the desired product as a yellow oil.

Step 4: [2, 6-difluoro-4-(2,5,8,11-tetraoxatridecan-13-yloxy)phenyl]methyl methanesulfonate

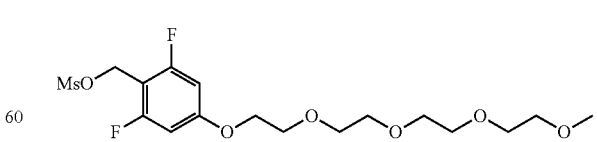

The title compound was prepared according to the procedure described in Example 12 Step 4 by mesylation of [2, 6-difluoro-4-(2,5,8,11-tetraoxatridecan-13-yloxy)phenyl]methanol to afford the desired product as a light yellow solid.

Step 5: 7-(4-chloro-3-methoxyphenyl)-2-([[2,6-difluoro-4-(2,5,8,11-tetraoxatridecan-13-yloxy)phenyl]methyl]sulfanyl)-1-(4-fluorophenyl)-4,5,6,7-tetrahydro-1H-1,3-benzodiazole

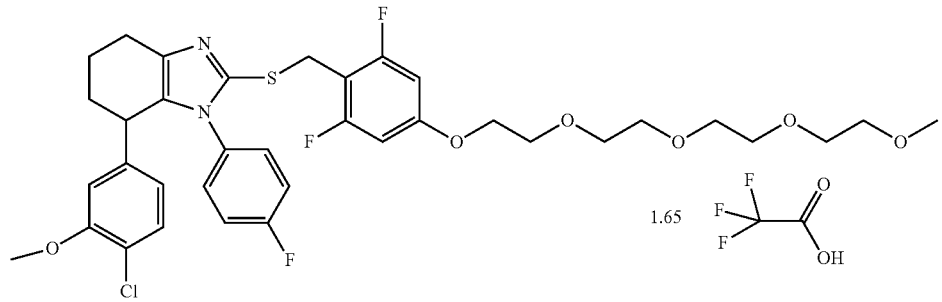

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (prepared as described in Example 1, Step 7) and [2, 6-difluoro-4-(2,5,8,11-tetraoxatridecan-13-yloxy) phenyl]methyl methanesulfonate in the presence of $Cs_2CO_3$ to afford the desired product as a white oil. $^1$H NMR (300 MHz, $CD_3OD$) δ 6.34-7.16 (m, 8H), 3.82-4.13 (m, 7H), 3.48-3.69 (m, 14H), 3.28-3.32 (m, 4H), 2.80-2.86 (m, 2H), 1.84-2.01 (m, 4H). $^{19}$F NMR (300 MHz, $CD_3OD$) δ−75.77, −108.520, −114.107. Mass spectrum (ESI, m/z): Calcd. for $C_{39.3}H_{41.65}ClF_{7.95}N_2O_{9.3}S$, 721.2 (M−1.65$CF_3COOH$+1). found 721.2.

Example 29

2-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenoxy]acetonitrile trifluoroacetic acid

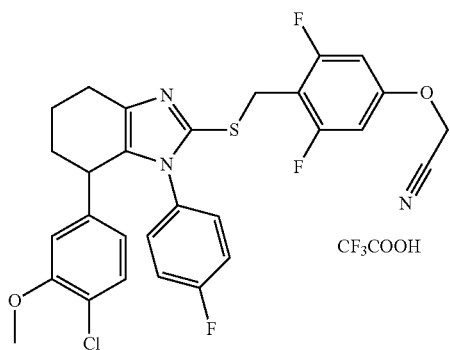 [SMILES: COc1cc(C2CCCc3nc(SCc4c(F)cc(OCC#N)cc4F)n(-c4ccc(F)cc4)c32)ccc1Cl ; "CF3COOH"]

The title compound was prepared according to the procedure described in Example 24 step 4 by coupling 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (Prepared as described in Example 24, Step 3) and 2-chloroacetonitrile in the presence of $Cs_2CO_3$ to afford the desired product as a white solid.

$^1$H NMR (300 MHz, $CD_3OD$) δ: 6.98-7.18 (m, 4H), 6.81-6.86 (m, 2H), 6.51 (s, 1H), 6.39-6.42 (m, 2H), 5.11 (s, 2H), 4.12 (s, 2H), 4.01-4.07 (m, 1H), 3.73 (s, 3H), 2.78-2.95 (m, 2H), 2.24-2.33 (m, 1H), 2.01-2.05 (m, 1H), 1.91-1.92 (m, 2H). $^{19}$F NMR (300 MHz, $CD_3OD$) δ: −77.15, −111.43, −115.17. Mass spectrum (ESI, m/z): Calcd. for $C_{31}H_{24}ClF_6N_3O_4S$, 570.1 (M−$CF_3COOH$+H). found 570.1.

Example 30

7-(4-chloro-3-methoxyphenyl)-2-([[2,6-difluoro-4-(1H-1,2,3,4-tetrazol-5-ylmethoxy)phenyl] methyl]sulfanyl)-1-(4-fluorophenyl)-4,5,6,7-tetrahydro-1H-1,3-benzodiazole

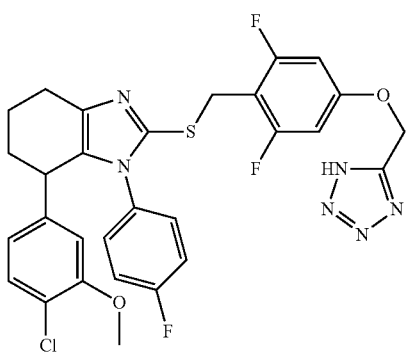 [SMILES: COc1cc(C2CCCc3nc(SCc4c(F)cc(OCc5nnn[nH]5)cc4F)n(-c4ccc(F)cc4)c32)ccc1Cl]

A solution of 2-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenoxy] acetonitrile (60 mg, 0.11 mmol, 1.00 equiv), $NH_4Cl$ (8.3 mg, 0.16 mmol, 1.47 equiv), and $NaN_3$ (10.28 mg, 0.16 mmol, 1.50 equiv), in N,N-dimethylformamide (2 mL) was stirred overnight at 80° C. in an oil bath. The reaction was then quenched by the addition of 5 mL of water and extracted with 2×5 mL of ethyl acetate. The combined organic layers were dried over sodium sulfate and concentrated. Silica gel column chromatography with ethyl acetate/petroleum ether (2:1) gave the title compound as a white solid. $^1$H NMR (300 MHz, $CD_3OD$) δ: 7.06-7.18 (m, 1H), 6.90 (s, 2H), 6.60-6.80 (m, 4H), 6.50 (s, 1H), 6.36-6.39 (m, 1H), 5.40-5.50 (m, 2H), 3.87-3.99 (m, 3H), 3.73 (s, 3H), 2.65-2.80 (m, 2H), 2.22-2.27 (m, 1H), 1.96-2.19 (m, 3H). Mass spectrum (ESI, m/z): Calcd. for $C_{29}H_{24}ClF_3N_6O_2S$, 613.1 (M+H). found 613.1.

Example 31

7-(4-chloro-3-methoxyphenyl)-2-([[3-(2-[2-[2-(dimethylamino) ethoxy]ethoxy] ethoxy)-2,6-difluorophenyl]methyl]sulfanyl)-1-(4-fluorophenyl)-4,5,6,7-tetrahydro-1H-1,3-benzodiazole hydrochloride

Step 1: 2,6-difluoro-3-[(4-methoxyphenyl)methoxy]benzaldehyde

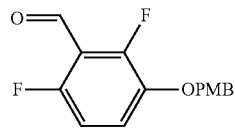

A solution of 2,6-difluoro-3-hydroxybenzaldehyde (1 g, 6.33 mmol, 1.00 equiv), potassium carbonate (2.6 g, 18.81 mmol, 2.97 equiv), and 1-(chloromethyl)-4-methoxybenzene (1.2 g, 7.66 mmol, 1.21 equiv) in N,N-dimethylformamide (20 mL) was stirred overnight at room temperature. The reaction was then quenched by the addition of 30 mL of water and extracted with 3×30 mL of ethyl acetate. The combined organic layers were washed with 1×30 mL of brine, dried over sodium sulfate, and concentrated under vacuum. Silica gel column chromatography with ethyl acetate/petroleum ether (1:5) gave the title compound as a yellow solid. Mass spectrum (ESI, m/z): Calcd. for $C_{15}H_{12}F_2O_3$, 279.1 (M+H). found 279.1.

Step 2: [2,6-difluoro-3-[(4-methoxyphenyl)methoxy]phenyl]methanol

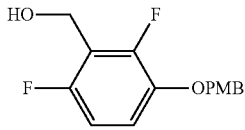

A solution of 2, 6-difluoro-3-[(4-methoxyphenyl)methoxy]benzaldehyde (1.2 g, 4.31 mmol, 1.00 equiv) and sodium borohydride (328 mg, 8.67 mmol, 2.01 equiv) in methanol (10 mL) was stirred for 1 h at room temperature and concentrated under vacuum. The resulting solution was diluted with 50 mL of EA, washed with 20 mL of water, 20 mL of brine, dried over anhydrous sodium sulfate, and concentrated under vacuum to give the title compound as a white solid. Mass spectrum (ESI, m/z): Calcd. for $C_{15}H_{14}F_2O_3$, 281.1 (M+H). found 281.1.

Step 3: 2-(chloromethyl)-1,3-difluoro-4-[(4-methoxyphenyl)methoxy]benzene

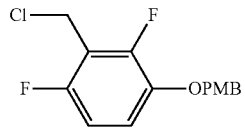

A solution of [2, 6-difluoro-3-[(4-methoxyphenyl)methoxy]phenyl]methanol (1.2 g, 4.28 mmol, 1.00 equiv) and TEA (1.3 g, 12.85 mmol, 3.00 equiv) in dichloromethane (25 mL) was treated with MsCl (986 mg) dropwise with stirring at 5° C. The resulting solution was stirred for 3.0 h at room temperature, concentrated under vacuum, and purified by silica gel column with ethyl acetate/petroleum ether (1:4) to give the title compound as a white solid. Mass spectrum (ESI, m/z): Calcd. for $C_{15}H_{13}ClF_2O_2$ 299.1 (M+H). found 299.1.

Step 4: 7-(4-chloro-3-methoxyphenyl)-2-[([2,6-difluoro-3-[(4-methoxyphenyl) methoxy]phenyl]methyl) sulfanyl]-1-(4-fluorophenyl)-4,5,6,7-tetrahydro-1H-1,3-benzodiazole

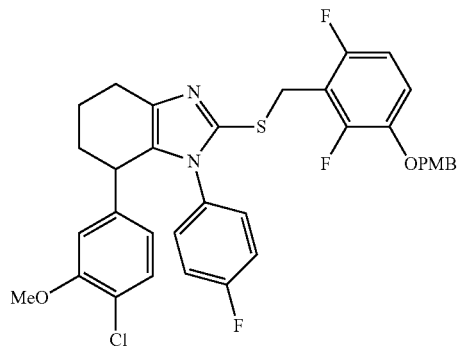

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol and 2-(chloromethyl)-1,3-difluoro-4-[(4-methoxyphenyl)methoxy]benzene in the presence of $Cs_2CO_3$ to afford the desired product as a white solid. Mass spectrum (ESI, m/z): Calcd. for $C_{35}H_{30}ClF_3N_2O_3S$, 651.2 (M+H). found 651.2.

Step 5: 3-([[7-(4-chloro-3-methoxyphenyl)-1-(4-fluorophenyl)-4,5,6,7-tetrahydro-1H-1,3-benzodiazol-2-yl]sulfanyl]methyl)-2,4-difluorophenol

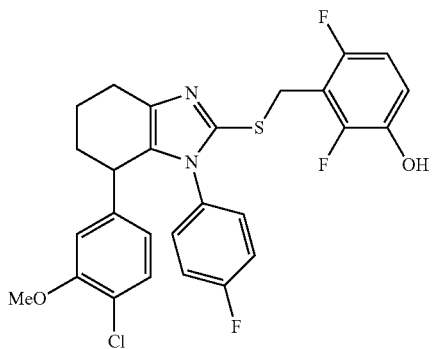 [SMILES: COc1cc(C2CCCc3nc(SCc4c(F)ccc(O)c4F)n(-c4ccc(F)cc4)c32)ccc1Cl]

The title compound was prepared according to the procedure described in Example 24 step 3 by de-benzylation of 7-(4-chloro-3-methoxyphenyl)-2-[([2,6-difluoro-3-[(4-methoxyphenyl) methoxy]phenyl]methyl) sulfanyl]-1-(4-fluorophenyl)-4,5,6,7-tetrahydro-1H-1,3-benzodiazole in the presence of trifluoroacetic acid to afford the desired product as a yellow solid.

Mass spectrum (ESI, m/z): Calcd. for $C_{27}H_{22}ClF_3N_2O_2S$, 531.1 (M+H). found 531.1.

Step 6. [2-[3-([[17-(4-chloro-3-methoxyphenyl)-1-(4-fluorophenyl)-4,5,6,7-tetrahydro-1H-1,3-benzodiazol-2-yl]sulfanyl]methyl]-2,4-difluorophenoxy]ethyl]dimethylamine

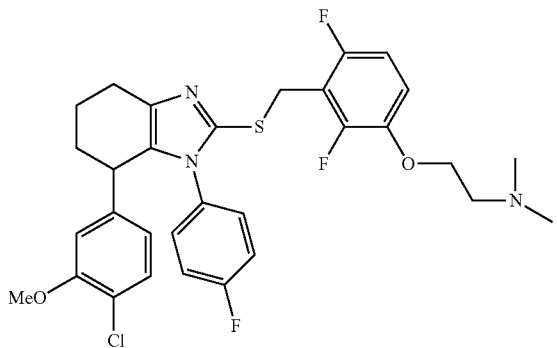 [SMILES: COc1cc(C2CCCc3nc(SCc4c(F)ccc(OCCN(C)C)c4F)n(-c4ccc(F)cc4)c32)ccc1Cl]

The title compound was prepared according to the procedure described in Example 24 step 4 by coupling 3-([[7-(4-chloro-3-methoxyphenyl)-1-(4-fluorophenyl)-4,5,6,7-tetrahydro-1H-1,3-benzodiazol-2-yl]sulfanyl]methyl)-2,4-difluorophenol and 2-chloro-N,N-dimethylethanamine HCl salt in the presence of $Cs_2CO_3$ to afford the desired product as a white solid.
$^1$H-NMR (300 MHz, $CD_3OD$): δ 7.01-7.25 (m, 6H), 6.36-6.49 (m, 3H), 4.37-4.41 (m, 2H), 4.03-4.39 (m, 3H), 3.69 (s, 3H), 3.51-3.62 (m, 2H), 2.80-2.98 (m, 8H), 1.86-2.27 (m, 4H). $^{19}$F-NMR (300 MHz, $CD_3OD$): −115.145, −126.537, −134.694. Mass spectrum (ESI, m/z): Calcd. for $C_{31}H_{31}ClF_3N_3O_2S$, 602.2 (M+H). found 602.2.

Example 32

7-(4-chloro-3-methoxyphenyl)-2-([[3-(2-[2-[2-(dimethylamino) ethoxy]ethoxy]ethoxy)-2,6-difluorophenyl]methyl]sulfanyl)-1-(4-fluorophenyl)-4,5,6,7-tetrahydro-1H-1,3-benzodiazole hydrochloride Step 1: 7-(4-chloro-3-methoxyphenyl)-2-[[(2,6-difluoro-3-[2-[2-(2-iodoethoxy)ethoxy]ethoxy]phenyl)methyl]sulfanyl]-1-(4-fluorophenyl)-4,5,6,7-tetrahydro-1H-1,3-benzodiazole

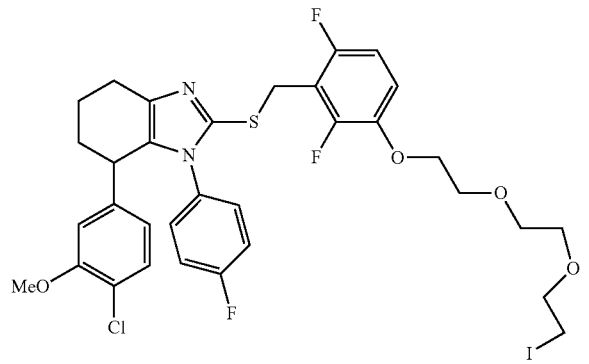 [SMILES: COc1cc(C2CCCc3nc(SCc4c(F)ccc(OCCOCCOCCI)c4F)n(-c4ccc(F)cc4)c32)ccc1Cl]

The title compound was prepared according to the procedure described in Example 24 step 4 by coupling 3-([[7-(4-chloro-3-methoxyphenyl)-1-(4-fluorophenyl)-4,5,6,7-tetrahydro-1H-1,3-benzodiazol-2-yl]sulfanyl]methyl)-2,4-difluorophenol and 1,2-bis(2-iodoethoxy)ethane in the presence of $Cs_2CO_3$ to afford the desired product as a white solid.
Mass spectrum (ESI, m/z): Calcd. for $C_{33}H_{33}ClF_3IN_2O_4S$, 773.1 (M+H). found 773.1.

Step 2: 7-(4-chloro-3-methoxyphenyl)-2-([[3-(2-[2-[2-(dimethylamino) ethoxy]ethoxy]ethoxy)-2,6-difluorophenyl]methyl]sulfanyl)-1-(4-fluorophenyl)-4,5,6,7-tetrahydro-1H-1,3-benzodiazole hydrochloride

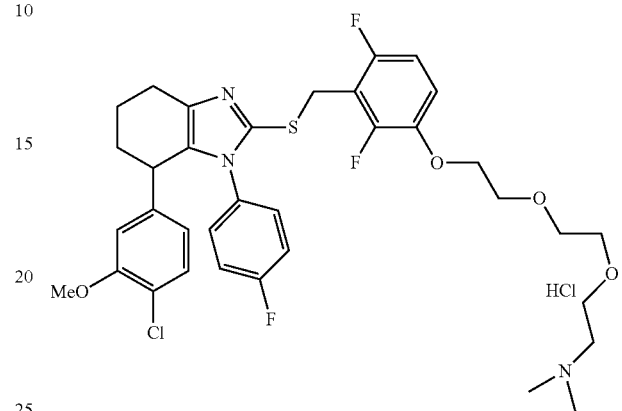

The title compound was prepared according to the procedure described in Example 27 step 2 by coupling 7-(4-chloro-3-methoxyphenyl)-2-[[(2,6-difluoro-3-[2-[2-(2-iodoethoxy)ethoxy] ethoxy]phenyl) methyl]sulfanyl]-1-(4-fluorophenyl)-4,5,6,7-tetrahydro-1H-1,3-benzodiazole and dimethylamine HCl salt in the presence of $Cs_2CO_3$ to afford the desired product as a yellow solid. $^1$H-NMR (300 MHz, $CD_3OD$): δ 7.11-7.17 (m, 3H), 6.91-6.98 (m, 2H), 6.49 (d, J=1.8 Hz, 1H), 6.34-6.49 (m, 1H), 4.15-4.18 (m, 4H), 3.70-4.01 (m, 12H), 2.78-3.05 (m, 8H), 1.89-2.27 (m, 4H). $^{19}$F-NMR (300 MHz, $CD_3OD$): −77.811, −111.157, −128.085, −136.136. Mass spectrum (ESI, m/z): Calcd. for $C_{35}H_{39}ClF_3N_3O_4S$, 690.2 (M−HCl+H). found 690.3.

Example 33

2-(2-(2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)ethoxy)ethoxy)-N,N-dimethylethanamine hydrochloride Step 1: 7-(4-chloro-3-methoxyphenyl)-2-[[(2,6-difluoro-4-[2-[2-(2-iodoethoxy)ethoxy]ethoxy]phenyl)methyl]sulfanyl]-1-(4-fluorophenyl)-4,5,6,7-tetrahydro-1H-1,3-benzodiazole

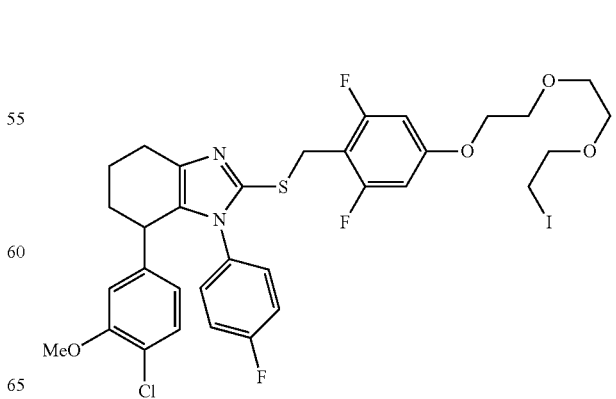

The title compound was prepared according to the procedure described in Example 24 step 4 by coupling 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (Prepared as described in Example 24, Step 3) and 1,2-bis(2-iodoethoxy)ethane in the presence of $Cs_2CO_3$ to afford the desired product as a white solid. Mass spectrum (ESI, m/z): Calcd. for $C_{33}H_{33}ClF_3IN_2O_4S$, 773.1 (M+H). found 773.1.

Step 2: 2-(2-(2-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenoxy)ethoxy)ethoxy)-N,N-dimethylethanamine hydrochloride

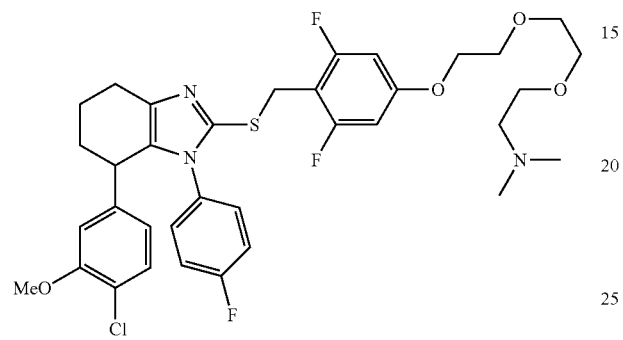

The title compound was prepared according to the procedure described in Example 27 step 2 by coupling 7-(4-chloro-3-methoxyphenyl)-2-[[(2,6-difluoro-4-[2-[2-(2-iodoethoxy)ethoxy]phenyl)methyl]sulfanyl]-1-(4-fluorophenyl)-4,5,6,7-tetrahydro-1H-1,3-benzodiazole and dimethylamine HCl salt in the presence of $Cs_2CO_3$ to afford the desired product as a yellow solid. $^1$H NMR (400 MHz, $CD_3OD$): δ 7.40 (br, 1H), 7.20 (d, J=8.4 Hz, 1H), 6.90 (br, 1H), 6.69 (d, J=10.0 Hz, 2H), 6.55 (s, 1H), 6.42-6.44 (m, 1H), 6.30 (br, 1H), 4.19-4.23 (m, 2H), 4.07-4.14 (m, 2H), 3.90-4.05 (m, 4H), 3.76-3.79 (m, 3H), 3.75 (s, 3H), 3.32-3.39 (m, 2H), 2.95 (s, 6H), 2.84-2.88 (m, 1H), 2.28-2.32 (m, 1H), 2.06-2.17 (m, 1H), 1.97 (br, 2H). $^{19}$F NMR (400 MHz, $CD_3OD$): δ −111.24, −116.20. Mass spectrum (ESI, m/z): Calcd. for $C_{35}H_{39}ClF_3N_3O_4S$, 690.2 (M−HCl+H). found 690.2.

Example 34

(2-[2-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenoxy]ethoxy]ethyl)dimethylamine hydrochloride Step 1: 2-[([4-[2-(2-bromoethoxy)ethoxy]-2,6-difluorophenyl]methyl)sulfanyl]-7-(4-chloro-3-methoxyphenyl)-1-(4-fluorophenyl)-4,5,6,7-tetrahydro-1H-1,3-benzodiazole

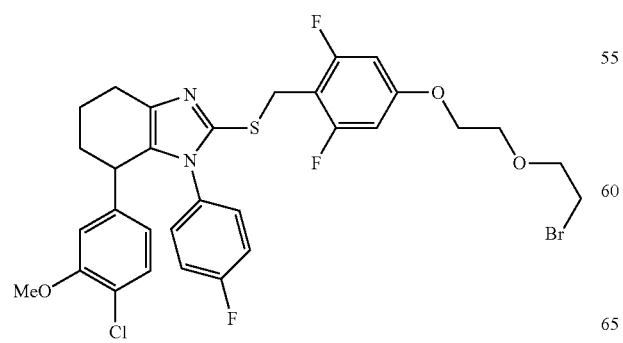

The title compound was prepared according to the procedure described in Example 24 step 4 by coupling 4-((7-(4-chloro-3-methoxyphenyl)-1-(4-fluorophenyl)-4,5,6,7-tetrahydro-1H-benzo[d]imidazol-2-ylthio)methyl)-3,5-difluorophenol (Prepared as described in Example 24, Step 3) and 1-bromo-2-(2-bromo ethoxy)ethane in the presence of $Cs_2CO_3$ to afford the desired product as a white solid. Mass spectrum (ESI, m/z): Calcd. for $C_{31}H_{29}BrClF_3N_2O_3S$, 681.1 (M+H). found 681.1.

Step 2: (2-[2-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenoxy]ethoxy]ethyl)dimethylamine hydrochloride

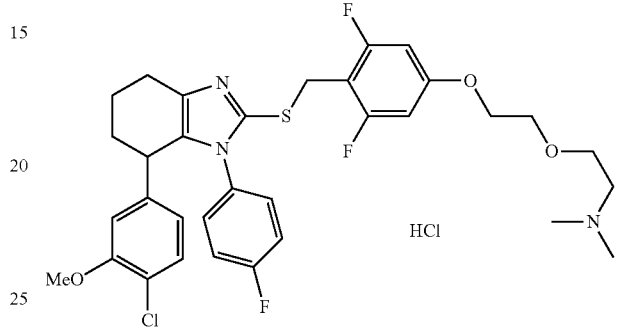

The title compound was prepared according to the procedure described in Example 27 step 2 by coupling 2-[([4-[2-(2-bromoethoxy)ethoxy]-2,6-difluorophenyl]methyl)sulfanyl]-7-(4-chloro-3-methoxyphenyl)-1-(4-fluorophenyl)-4,5,6,7-tetrahydro-1H-1,3-benzodiazole and dimethyl amine HCl salt in the presence of $Cs_2CO_3$ to afford the desired product as a yellow solid. $^1$H NMR (300 MHz, $CD_3OD$) δ: 7.40 (br, 1H), 7.19 (d, J=8.0 Hz, 1H), 6.90 (br, 2H), 6.70 (d, J=10.0 Hz, 2H), 6.54 (s, 1H), 6.42 (d, J=8.4 Hz, 1H), 4.21-4.24 (m, 2H), 4.06-4.18 (m, 3H), 3.91-3.96 (m, 4H), 3.74 (s, 3H), 3.40-3.42 (m, 2H), 2.95-2.97 (m, 7H), 2.83-2.87 (m, 1H), 2.32 (br, 1H), 2.05-2.10 (m, 1H), 1.90 (br, 2H). $^{19}$F NMR (300 MHz, $CD_3OD$) δ: −111.21, −116.14. Mass spectrum (ESI, m/z): Calcd. for $C_{33}H_{36}Cl_2F_3N_3O_3S$, 646.2 (M−HCl+H). found 646.2.

Example 35

(2-[2-[3-([[7-(4-chloro-3-methoxyphenyl)-1-(4-fluorophenyl)-4,5,6,7-tetrahydro-1H-1,3-benzodiazol-2-yl]sulfanyl]methyl)-2,4-difluorophenoxy]ethoxy]ethyl)dimethylamine hydrochloride Step 1: 2-[([3-[2-(2-bromoethoxy)ethoxy]-2,6-difluorophenyl]methyl)sulfanyl]-7-(4-chloro-3-methoxyphenyl)-1-(4-fluorophenyl)-4,5,6,7-tetrahydro-1H-1,3-benzodiazole

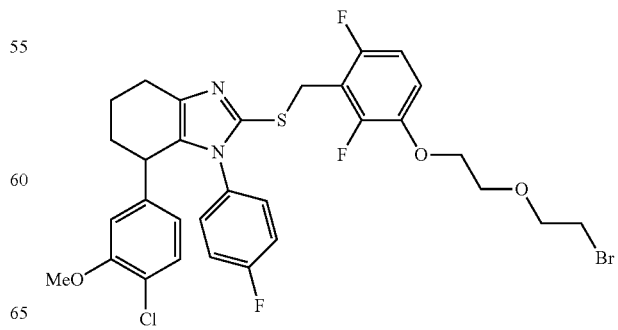

The title compound was prepared according to the procedure described in Example 24 step 4 by coupling 3-([[7-(4-chloro-3-methoxyphenyl)-1-(4-fluorophenyl)-4,5,6,7-tetrahydro-1H-1,3-benzodiazol-2-yl]sulfanyl]methyl)-2,4-difluorophenol and 1-bromo-2-(2-bromo ethoxy)ethane in the presence of Cs$_2$CO$_3$ to afford the desired product as a white solid. Mass spectrum (ESI, m/z): Calcd. for C$_{31}$H$_{29}$BrClF$_3$N$_2$O$_3$S, 681.1 (M+H). found 681.1.

Step 2: (2-[2-[3-([[7-(4-chloro-3-methoxyphenyl)-1-(4-fluorophenyl)-4,5,6,7-tetrahydro-1H-1,3-benzodiazol-2-yl]sulfanyl]methyl)-2,4-difluorophenoxy]ethoxy]ethyl)dimethylamine hydrochloride

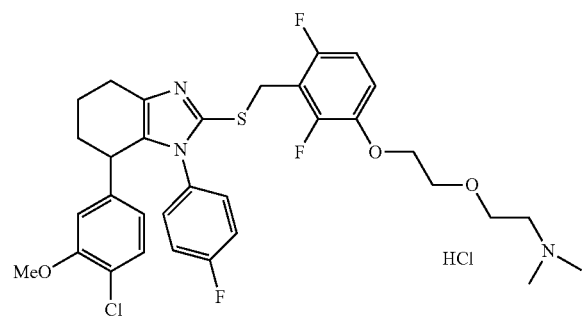 [SMILES: COc1cc(C2CCCc3nc(SCc4c(F)ccc(OCCOCCN(C)C)c4F)n(-c4ccc(F)cc4)c32)ccc1Cl ; Cl]

The title compound was prepared according to the procedure described in Example 27 step 2 by coupling 2-[([3-[2-(2-bromoethoxy)ethoxy]-2,6-difluorophenyl]methyl)sulfanyl]-7-(4-chloro-3-methoxyphenyl)-1-(4-fluorophenyl)-4,5,6,7-tetrahydro-1H-1,3-benzodiazole and dimethyl amine HCl salt in the presence of Cs$_2$CO$_3$ to afford the desired product as a yellow solid. $^1$H NMR (300 MHz, CD$_3$OD) δ: 6.90-7.32 (m, 6H), 6.40-6.54 (m, 3H), 3.91-4.27 (m, 9H), 3.74 (s, 3H), 3.40-3.50 (m, 2H), 2.75-2.97 (m, 9H), 1.91-2.31 (m, 4H). $^{19}$F NMR (300 MHz, CD$_3$OD) δ: −111.16, −128.12, −136.00. Mass spectrum (ESI, m/z): Calcd. for C$_{33}$H$_{36}$Cl$_2$F$_3$N$_3$O$_3$S, 646.2 (M−HCl+H). found 646.3.

Example 36

4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorobenzonitrile Step 1: 4-cyano-2,6-difluorobenzyl methanesulfonate

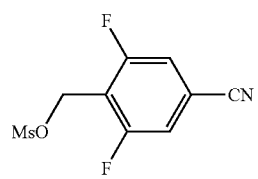 [SMILES: CS(=O)(=O)OCc1c(F)cc(C#N)cc1F]

The title compound was prepared according to the procedure described in Example 12 Step 3-4 by NaBH$_4$ reduction of 3,5-difluoro-4-formylbenzonitrile and mesylation of 3,5-difluoro-4-(hydroxymethyl)benzonitrile to afford the desired product as a white solid.

Step 2: 4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorobenzonitrile

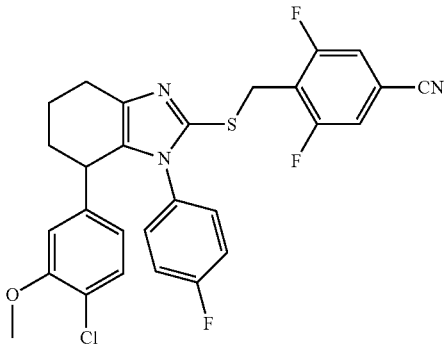 [SMILES: COc1cc(C2CCCc3nc(SCc4c(F)cc(C#N)cc4F)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) and 4-cyano-2,6-difluorobenzyl methanesulfonate in the presence of Cs$_2$CO$_3$ to afford the desired product as a white solid.
$^1$H NMR (300 MHz, CD$_3$OD): δ 7.43-7.45 (m, 2H), 7.08-7.10 (m, 1H), 6.60-6.99 (m, 3H), 6.44 (d, J=1.8 Hz, 1H), 6.31-6.34 (m, 1H), 3.86-3.95 (m, 3H), 3.68 (s, 3H), 2.57-2.72 (m, 2H), 1.75-2.20 (m, 4H). Mass spectrum (ESI, m/z): Calcd. for C$_{28}$H$_{21}$ClF$_3$N$_3$OS, 540.1 (M+H). found 540.1.

Example 37

(5Z)-5-[[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]methylidene]-1,3-thiazolidine-2,4-dione Step 1: 4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorobenzaldehyde

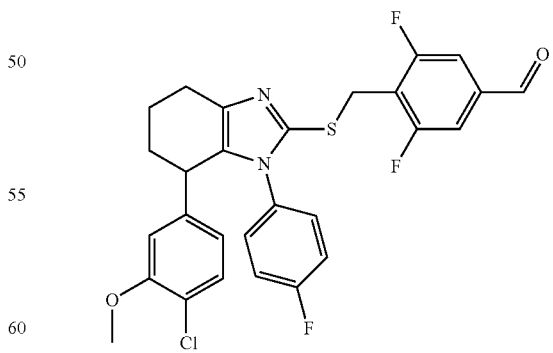

A solution of 4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorobenzonitrile (Prepared as described in Example 36, Step2; 600 mg, 1.11 mmol, 1.00 equiv) in toluene (50 mL) was treated with DIBAL-H (2.2 mL, 2.00 equiv) at 0-5° C. and stirred for 4 h at room temperature. The resulting mixture was concentrated, diluted with 50 mL of H₂O, and extracted with 3×50 mL of ethyl acetate. The combined organic layers were washed with 50 mL of brine, dried over anhydrous sodium sulfate, and purified by silica gel column (P/E 5:1) to give the title compound as a yellow foam. Mass spectrum (ESI, m/z): Calcd. for $C_{28}H_{22}ClF_3N_2O_2S$, 543.1 (M+H). found 543.1.

Step 2: (5Z)-5-[[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]methylidene]-1,3-thiazolidine-2,4-dione

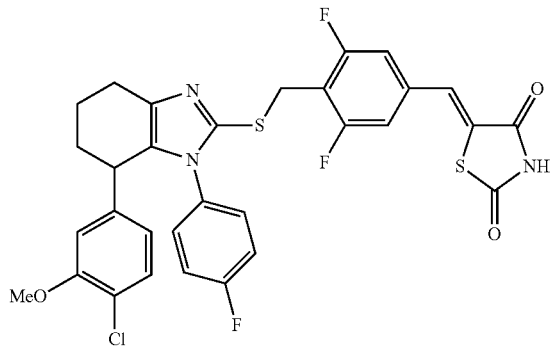 [SMILES: COc1cc(C2CCCc3nc(SCc4c(F)cc(/C=C5\SC(=O)NC5=O)cc4F)n(-c4ccc(F)cc4)c32)ccc1Cl]

A solution of 4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorobenzaldehyde (300 mg, 0.55 mmol, 1.00 equiv), 1,3-thiazolidine-2,4-dione (100 mg, 0.85 mmol, 1.55 equiv), and piperidine (100 mg, 1.12 mmol, 2.03 equiv) in acetic acid (10 mL) was heated to reflux overnight. The resulting mixture was concentrated, diluted with 20 mL of H₂O, and extracted with 3×20 mL of ethyl acetate. The combined organic layers were washed with 20 mL of brine, dried over sodium sulfate, and concentrated. Silica gel column chromatography with PE/EA (1:1) followed by recrystallization from EA/n-Hex in the ratio of 1/1 gave the title compound as an offwhite solid. ¹H NMR (400 MHz, CD₃OD) δ 7.75 (s, 1H), 7.12-7.15 (m, 3H), 6.88 (s, 2H), 6.47 (d, J=2.0 Hz, 1H), 6.35-6.38 (m, 1H), 4.07 (s, 1H), 4.04 (s, 1H), 3.86-3.95 (m, 1H), 3.72 (s, 3H), 2.64-2.79 (m, 2H), 2.17-2.23 (m, 1H), 1.79-2.03 (m, 3H). Mass spectrum (ESI, m/z): Calcd. for $C_{31}H_{23}ClF_3N_3O_3S_2$, 642.1 (M+H). found 642.3.

Example 38

5-(4-((7-(4-chloro-3-methoxyphenyl)-1-(4-fluorophenyl)-4,5,6,7-tetrahydro-1H-benzo[d]imidazol-2-ylthio)methyl)-3,5-difluorobenzyl)thiazolidine-2,4-dione trifluoroacetic acid

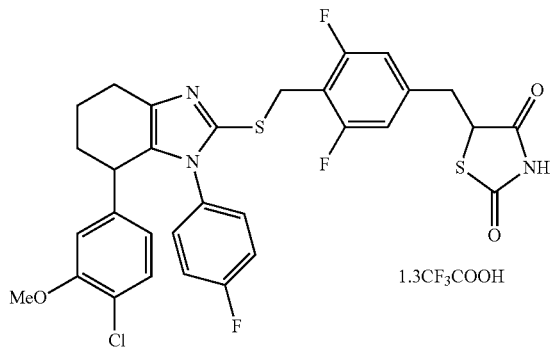 [SMILES: COc1cc(C2CCCc3nc(SCc4c(F)cc(CC5SC(=O)NC5=O)cc4F)n(-c4ccc(F)cc4)c32)ccc1Cl]

A solution of (5Z)-5-[[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]methylidene]-1,3-thiazolidine-2,4-dione (30 mg, 0.05 mmol, 1.00 equiv) and LiBH₄ (2 mg, 0.09 mmol, 1.95 equiv) in tetrahydrofuran/pyridine (6/4 mL) was heated to reflux for 5 h in an oil bath and concentrated under vacuum. Purification by Prep-HPLC With the following conditions: (1#waters2767-5) column, SunFire Prep C18, 19*150 mm 5 μm H Prep C-001(T)18600256819513816414 04; Mobile Phase, phase A: water with 0.05% TFA, phase B: CH3CN (20% CH₃CN up to 38% in 10 min, up to 100% in 0.1 min, hold 100% in 1.9 min, down to 20% in 0.1 min, hold 20% in 1.9 min); Detector, UV 220 & 254 nm, gave the title compound as a white solid. ¹H NMR (400 MHz, CD₃OD) δ 7.17-7.21 (m, 1H), 6.99-7.01 (m, 4H), 6.52 (s, 1H), 6.42 (d, J=8.4 Hz, 1H), 4.83-4.86 (m, 1H), 4.13-4.20 (m, 2H), 4.01 (d, J=5.2 Hz, 1H), 3.74 (s, 3H), 3.43-3.51 (m, 1H), 3.32-3.33 (m, 1H), 2.80-2.89 (m, 2H), 2.25-2.30 (m, 1H), 1.90-2.07 (m, 3H). ¹⁹F NMR (400 MHz, CD₃OD) δ −77.139, −111.45, −116.85, −116.96. Mass spectrum (ESI, m/z): Calcd. for $C_{33.6}H_{26.3}ClF_{6.9}N_3O_{5.6}S_2$, 644.1 (M−1.3CF₃COOH+H). found 644.3.

Example 39

(E)-1-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propyl)-2-methylguanidine hydrochloride (39a) and 3-(4-((7-(4-chloro-3-methoxyphenyl)-1-(4-fluorophenyl)-4,5,6,7-tetrahydro-1H-benzo[d]imidazol-2-ylthio) methyl)-3,5-difluorophenyl)-N,N-dimethylpropan-1-amine trifluoroacetic acid (39b)

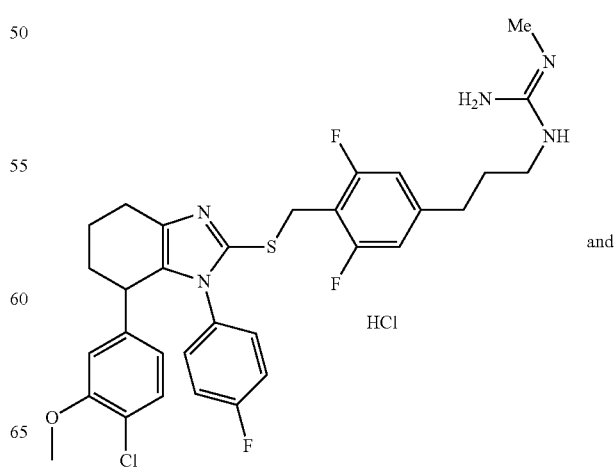

115
-continued

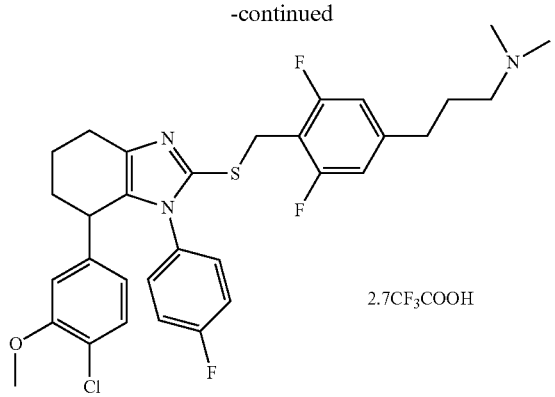

2.7CF₃COOH

A solution of 3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl] propyl methanesulfonate (Prepared as described in Example 43 Step 1, 200 mg, 0.31 mmol, 1.00 equiv), N,N-dimethylformamide (4 mL), potassium carbonate (127 mg, 0.92 mmol, 2.99 equiv), and 1-methylguanidine (45 mg, 0.62 mmol, 2.00 equiv) was stirred overnight at 80° C. The crude product was purified by Prep-HPLC with the following conditions (1#-Waters 2767-5): Column, SunFire Prep C18, 5 μm, 19*100 mm; mobile phase, Water of 0.05% trifluoroacetic acid and CH₃CN (20% CH₃CN up to 55% in 8 min, up to 100% in 0.1 min, hold 100% in 1.9 min, down to 20% in 0.1 min, hold 20% in 1.9 min); Detector, UV 220&254 nm. The solvent was removed under vacuum followed by the addition of 4.0 mL H₂O and 4 drops of concentrated HCl. The evaporation and acid dilution was repeated twice followed by lyophilization to give the title compound as a white solid.

(E)-1-[3-[4-([[7-(4-chloro-3-methoxyphenyl)-1-(4-fluorophenyl)-4,5,6,7-tetrahydro-1H-1,3-benzodiazol-2-yl]sulfanyl]methyl]-3,5-difluorophenyl]propyl]-2-methylguanidine hydrochloride (39a)

¹H NMR (400 MHz, CD₃OD): δ 7.19-7.41 (m, 2H), 6.75-7.09 (m, 4H), 6.54 (s, 1H), 6.42-6.44 (m, 1H), 4.04-4.22 (m, 3H), 3.74 (s, 3H), 3.27-3.37 (m, 2H), 3.08 (s, 1H), 2.88-2.91 (m, 4H), 2.71-2.75 (m, 2H), 2.25-2.35 (m, 1H), 2.08-2.15 (m, 1H), 1.80-2.03 (m, 4H), 1.17-1.21 (m, 1H). ¹⁹F NMR (400 MHz, CD₃OD): δ −111.38, −117.61. Mass spectrum (ESI, m/z): Calcd. for $C_{32}H_{33}ClF_3N_5OS$, 628.2 (M−HCl+H). found 628.3.

3-(4-((7-(4-chloro-3-methoxyphenyl)-1-(4-fluorophenyl)-4,5,6,7-tetrahydro-1H-benzo[d]imidazol-2-ylthio) methyl)-3,5-difluorophenyl)-N,N-dimethylpropan-1-amine trifluoroacetic acid (39b)

¹H NMR (400 MHz, CD₃OD): δ 7.19 (d, J=8.0 Hz, 1H), 6.96 (d, J=8.4 Hz, 4H), 6.53 (d, J=8.0 Hz, 1H), 6.41-6.44 (m, 1H), 4.07-4.17 (m, 2H), 3.99-4.02 (m, 1H), 3.74 (s, 3H), 3.32-3.37 (m, 1H), 3.15-3.20 (m, 2H), 2.92 (s, 6H), 2.80-2.89 (m, 2H), 2.73-2.77 (m, 2H), 2.25-2.29 (m, 1H), 2.01-2.08 (m, 3H), 1.88-1.92 (m, 2H). ¹⁹F NMR (400 MHz, CD₃OD): δ −77.08, −112.04, −117.23. Mass spectrum (ESI, m/z): Calcd. for $C_{32}H_{33}ClF_3N_3OS$, 600.2 (M−2.7CF₃COOH+H). found 600.4.

116
Example 40

Ethyl 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanoate trifluoroacetic acid Step 1: Ethyl (2E)-3-[3,5-difluoro-4-(hydroxymethyl)phenyl]prop-2-enoate

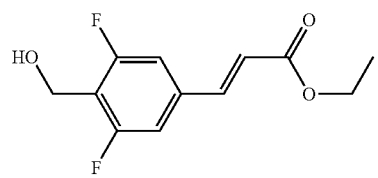 [SMILES: CCOC(=O)/C=C/c1cc(F)c(CO)c(F)c1]

A solution of (4-bromo-2,6-difluorophenyl)methanol (5 g, 22.42 mmol, 1.00 equiv), N,N-dimethylformamide (25 mL), (tolyl)₃P (1.368 g, 4.50 mmol, 0.20 equiv), DIEA (8.72 g, 67.47 mmol, 3.01 equiv), PdCl₂ (396 mg, 2.25 mmol, 0.10 equiv), and ethyl prop-2-enoate (11.26 g, 112.47 mmol, 5.02 equiv) was stirred overnight at 90° C. The reaction was quenched by the addition of 25 mL of water, followed by extraction with 3×100 mL of ethyl acetate. The combined organic layers were concentrated under vacuum. Silica gel column chromatography with ethyl acetate/petroleum ether (1:2) gave the title compound as an orange oil.

Step 2: Ethyl 3-[3,5-difluoro-4-(hydroxymethyl)phenyl]propanoate

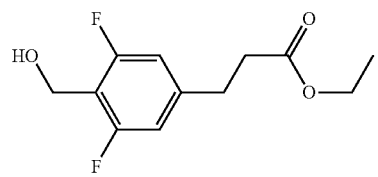 [SMILES: CCOC(=O)CCc1cc(F)c(CO)c(F)c1]

A solution of ethyl (2E)-3-[3,5-difluoro-4-(hydroxymethyl)phenyl]prop-2-enoate (6.5 g, 26.84 mmol, 1.00 equiv) in methanol (25 mL) was treated with palladium carbon (650 mg) and H₂ gas. The resulting solution was stirred overnight at room temperature, filtered, and concentrated to give the title compound as a light yellow oil.

Step 3: Ethyl 3-[3,5-difluoro-4-[(methanesulfonyloxy)methyl]phenyl]propanoate

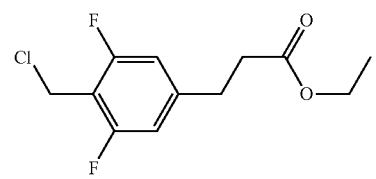 [SMILES: CCOC(=O)CCc1cc(F)c(CCl)c(F)c1]

A solution of ethyl 3-[3, 5-difluoro-4-(hydroxymethyl)phenyl]propanoate (900 mg, 3.68 mmol, 1.00 equiv) in dichloromethane (10 ml) was treated with TEA (1.12 g, 11.07 mmol, 3.00 equiv) dropwise with stirring, followed by MsCl (841 mg, 7.38 mmol, 2.00 equiv) dropwise with stirring. The resulting solution was stirred overnight at room temperature and concentrated under vacuum to give the title compound as a brown oil.

Step 4: Ethyl 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanoate trifluoroacetic acid

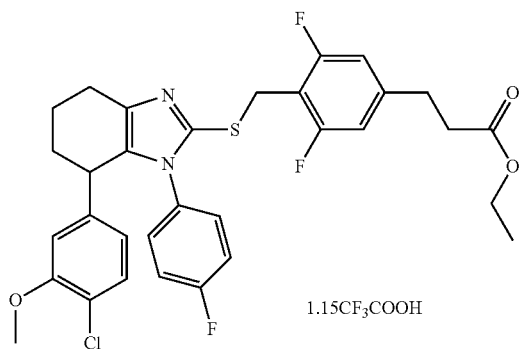 [SMILES: CCOC(=O)CCc1cc(F)c(CSc2nc3c(n2-c2ccc(F)cc2)C(c2ccc(Cl)c(OC)c2)CCC3)c(F)c1]

1.15CF$_3$COOH

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) and ethyl 3-[3,5-difluoro-4-[(methanesulfonyloxy)methyl]phenyl] propanoate in the presence of Cs$_2$CO$_3$ to afford the desired product as a white solid. $^1$H NMR (300 MHz, CD$_3$OD) δ: 7.19 (d, J=8.0 Hz, 1H), 6.92-7.18 (m, 3H), 6.51 (d, J=1.6 Hz, 1H), 6.40-6.42 (m, 1H), 4.12-4.17 (m, 4H), 4.05 (t, J=36.0 Hz, 1H), 3.74 (s, 3H), 278-2.99 (m, 4H), 2.67-2.70 (m, 2H), 2.25-2.31 (m, 1H), 1.90-2.09 (m, 3H), 1.25 (t, J=14.4 Hz, 3H). $^{19}$F NMR (400 Hz, CD$_3$OD) δ: −77.04, −111.60, −117.81. Mass spectrum (ESI, m/z): Calcd. for C$_{34.3}$H$_{31.15}$ClF$_{6.45}$N$_2$O$_{5.3}$S, 615.2 (M−1.15CF$_3$COOH+H). found 615.1.

Example 41

3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propan-1-ol trifluoroacetic acid

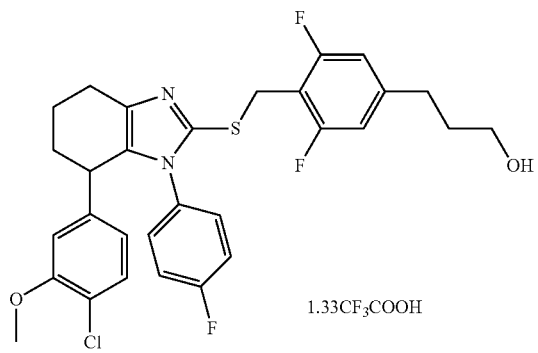 [SMILES: COc1cc(C2CCCc3nc(SCc4c(F)cc(CCCO)cc4F)n(-c4ccc(F)cc4)c32)ccc1Cl]

1.33CF$_3$COOH

A solution of ethyl 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanoate (500 mg, 0.81 mmol, 1.00 equiv) in toluene (5 mL) was treated with DIBAL-H (1M) (2.1 mL) dropwise with stirring at 0° C. The resulting solution was stirred for 2 h at 0° C., quenched with 10 mL of water and filtered. The resulting solution was extracted with 3×20 mL of dichloromethane and the organic layers combined and concentrated under vacuum to give the title compound as a light yellow oil.

$^1$H NMR (300 MHz, CD$_3$OD) δ: 7.19 (d, J=8.0 Hz, 1H), 6.91-7.14 (m, 3H), 6.52 (s, 1H), 6.42 (d, J=8.0 Hz, 1H), 6.20-6.22 (m, 1H), 4.12-4.18 (m, 2H), 4.00 (s, 1H), 3.73 (s, 3H), 3.62 (d, J=6.4 Hz, 2H), 2.73-2.94 (m, 4H), 2.28-2.31 (m, 1H), 1.81-2.06 (m, 5H). $^{19}$F NMR (400 Hz, CD$_3$OD) δ: −77.07, −111.50, −118.14. Mass spectrum (ESI, m/z): Calcd. for C$_{32.66}$H$_{29.33}$ClF$_{6.99}$N$_2$O$_{4.66}$S, 573.1 (M−1.33CF$_3$COOH+H). found 573.1.

Example 42

1-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propyl)guanidine trifluoroacetic acid Step 1: Tert-butyl N-[(1Z)-[[(tert-butoxy)carbonyl]amino]([3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]propyl]amino)methylidene]carbamate

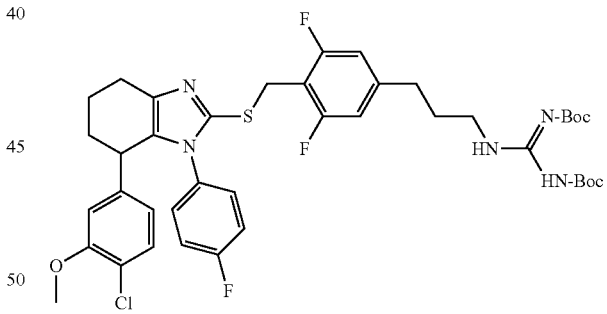

A solution of 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propan-1-ol (200 mg, 0.35 mmol, 1.00 equiv), tert-butyl N-[(1Z)-amino([[(tert-butoxy)carbonyl]amino]) methylidene]carbamate (110.49 mg, 0.43 mmol, 2.00 equiv), PPh$_3$ (137.94 mg, 0.53 mmol, 1.50 equiv), and tetrahydrofuran (5 mL) was treated with DIAD (105.94 mg, 0.52 mmol, 1.50 equiv) dropwise with stirring. The resulting solution was stirred overnight at 30° C. in an oil bath and concentrated under vacuum. Silica gel column chromatography with ethyl acetate/petroleum ether (1:1) gave the title compound as a brown oil. Mass spectrum (ESI, m/z): Calcd. For C$_{41}$H$_{47}$ClF$_3$N$_5$O$_5$S, 814.3 (M+H). found 814.3.

Step 2: 1-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propyl)guanidine trifluoroacetic acid

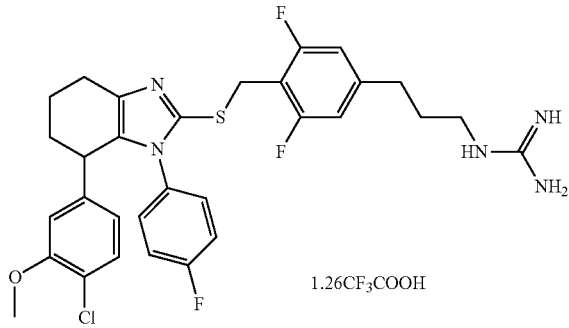 [SMILES: COc1cc(C2CCCc3nc(SCc4c(F)cc(CCCNC(=N)N)cc4F)n(-c4ccc(F)cc4)c32)ccc1Cl]

1.26CF$_3$COOH

A solution of tert-butyl N-[(1Z)-[[(tert-butoxy)carbonyl]amino]([3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]propyl]amino)methylidene]carbamate (280 mg, 0.34 mmol, 1.00 equiv) in dichloromethane (3 mL) was treated with CF$_3$COOH (2 mL) dropwise with stirring. The resulting solution was stirred for 2 h at room temperature and concentrated under vacuum. Prep-HPLC purifications with the following conditions (1#-Waters 2767-5): Column, SunFire Prep C18, 5 μm, 19*100 mm; mobile phase, Water of 0.05% trifluoroacetic acid and CH$_3$CN (20% CH$_3$CN up to 50% in 8 min, up to 100% in 0.1 min, hold 100% in 1.9 min, down to 20% in 0.1 min, hold 20% in 1.9 min); Detector, UV 220&254 nm, gave the title compound as a white solid. $^1$H NMR (300 MHz, CD$_3$OD) δ: 7.19 (d, J=8.1 Hz, 1H), 6.91-7.18 (m, 4H), 6.52 (s, 1H), 6.40-6.43 (m, 1H), 4.11-4.20 (m, 2H), 4.01 (t, J=21.0 Hz, 1H), 3.74 (s, 3H), 3.24 (d, J=6.9 Hz, 2H), 2.71-2.88 (m, 4H), 1.88-2.29 (m, 6H). $^{19}$F NMR (300 Hz, CD$_3$OD): δ −77.05, −111.80, −117.61. Mass spectrum (ESI, m/z): Calcd. for C$_{33.52}$H$_{32.26}$ClF$_{6.78}$NO$_5$O$_{3.52}$S, 614.2 (M−1.26CF$_3$COOH+H). found 614.2.

Example 43

(E)-1-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propyl)-2-cyanoguanidine hydrochloride

Step 1: 3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]propyl methanesulfonate

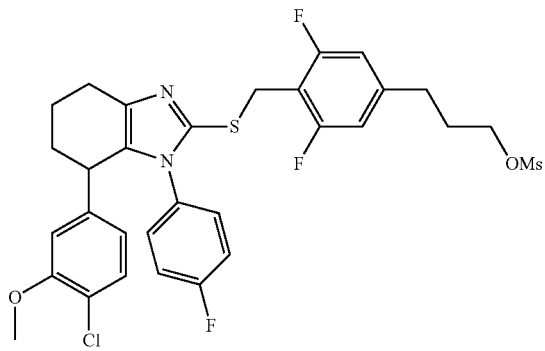 [SMILES: COc1cc(C2CCCc3nc(SCc4c(F)cc(CCCOS(C)(=O)=O)cc4F)n(-c4ccc(F)cc4)c32)ccc1Cl]

The title compound was prepared according to the procedure described in Example 12 Step 4 by mesylation of 3-[4-([[7-(4-chloro-3-methoxyphenyl)-1-(4-fluorophenyl)-4,5,6,7-tetrahydro-1H-1,3-benzodiazol-2-yl] sulfanyl]methyl)-3,5-difluorophenyl]propan-1-ol to afford the desired product as a light yellow solid. Mass spectrum (ESI, m/z): Calcd. For C$_{31}$H$_{30}$ClF$_3$N$_2$O$_4$S$_2$, 651.1 (M+H). found 651.1.

Step 2: (E)-1-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propyl)-2-cyanoguanidine hydrochloride

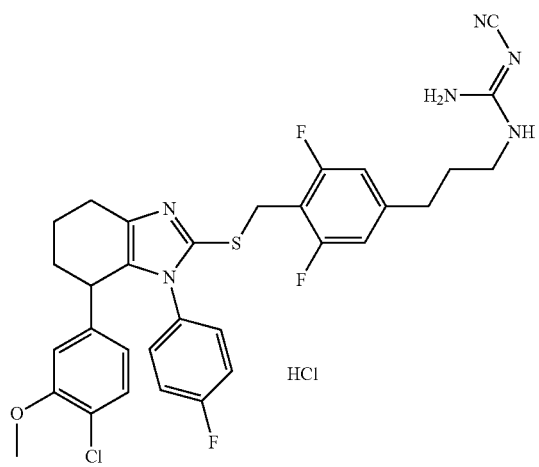 [SMILES: COc1cc(C2CCCc3nc(SCc4c(F)cc(CCCN/C(N)=N/C#N)cc4F)n(-c4ccc(F)cc4)c32)ccc1Cl ; Cl]

A solution of 3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl] propyl methanesulfonate (150 mg, 0.23 mmol, 1.00 equiv), N,N-dimethylformamide (4 mL), sodium hydride (17 mg, 0.71 mmol, 3.07 equiv), and 2-amino-N-cyanoethanimidamide (39 mg, 0.40 mmol, 1.73 equiv) was stirred for 1 h at 60° C. The crude product was purified by Prep-HPLC with the following conditions (1#-Waters 2767-5): Column, SunFire Prep C18, 5 μm, 19*100 mm; mobile phase, mobile phase, Water of 0.05% NH$_4$HCO$_3$ and CH$_3$CN (10% CH$_3$CN up to 30% in 8 min, up to 100% in 0.1 min, hold 100% in 1.9 min, down to 10% in 0.1 min, hold 10% in 1.9 min); Detector, UV 220&254 nm. Then used con.HCl to replace TFA to form HCl salt, to give the title compound as a white solid. $^1$H NMR (400 MHz, CD$_3$OD): δ 7.19-7.23 (m, 3H), 6.94-6.99 (m, 3H), 6.53 (d, J=2.0 Hz, 1H), 6.41-6.44 (m, 1H), 4.16 (s, 2H), 4.02-4.05 (m, 1H), 3.75 (s, 3H), 3.21-3.24 (m, 2H), 2.77-2.97 (m, 2H), 2.69-2.73 (m, 2H), 2.26-2.32 (m, 1H), 2.07-2.08 (m, 1H), 1.84-1.96 (m, 4H). $^{19}$F NMR (400 MHz, CD$_3$OD): δ −111.11, −117.97. Mass spectrum (ESI, m/z): Calcd. For C$_{32}$H$_{31}$Cl$_2$F$_3$N$_6$OS, 639.2 (M−HCl+H). found 639.2.

Example 44

3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanoic acid trifluoroacetic acid

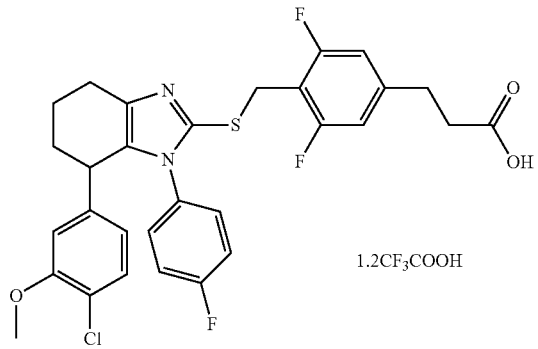 [SMILES: COc1cc(C2CCCc3nc(SCc4c(F)cc(CCC(=O)O)cc4F)n(-c4ccc(F)cc4)c32)ccc1Cl]

1.2CF$_3$COOH

A solution of ethyl 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanoate (55 mg, 0.09 mmol, 1.00 equiv), methanol (3 mL), and LiOH (21.5 mg, 0.90 mmol, 10.04 equiv) was stirred overnight at room temperature. The pH value of the solution was adjusted to 5 with hydrogen chloride solution (2 mol/L). The resulting solution was extracted with 3×2 mL of ethyl acetate and the organic layers combined and concentrated under vacuum. The crude product was purified by Prep-HPLC with the following conditions: Column, SunFire Prep C18, 5 μm, 19*100 mm; mobile phase, Water of 0.05% trifluoroacetic acid and CH$_3$CN (20% CH$_3$CN up to 90% in 10 min, up to 100% in 0.1 min, hold 100% in 1.9 min, down to 20% in 0.1 min, hold 20% in 1.9 min); Detector, UV 220&254 nm, to give the title compound as a white solid. $^1$H NMR (300 MHz, CD$_3$OD) δ: 7.12-7.19 (m, 2H), 6.88-7.07 (m, 4H), 6.45-6.46 (m, 1H), 6.34-6.37 (m, 1H), 4.02-4.13 m (m, 2H), 3.94-3.98 (m, 1H), 3.68 (s, 3H), 2.71-2.94 (m, 4H), 2.60-2.65 (m, 2H), 2.19-2.28 (m, 1H), 1.97-2.05 (m, 1H), 1.86-1.88 (m, 2H). $^{19}$F NMR (300 MHz, CD$_3$OD) δ: −76.72, −111.51, −117.91. Mass spectrum (ESI, m/z): Calcd. for C$_{32.4}$H$_{27.2}$ClF$_{6.6}$N$_2$O$_{5.4}$S, 587.1 (M−1.2CF$_3$COOH+H). found 587.3.

Example 45

3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanamide trifluoroacetic acid

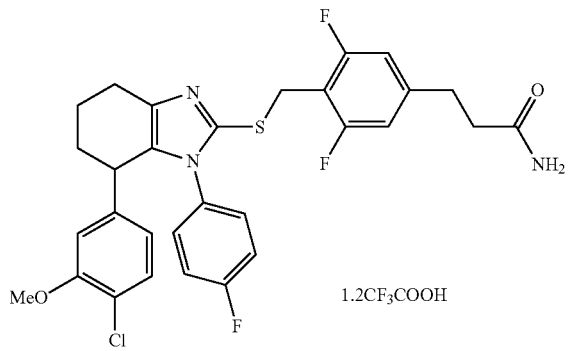 [SMILES: COc1cc(C2CCCc3nc(SCc4c(F)cc(CCC(N)=O)cc4F)n(-c4ccc(F)cc4)c32)ccc1Cl]

1.2CF$_3$COOH

A solution of 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanoic acid (400 mg, 0.65 mmol, 1.00 equiv), methanol (4 mL), and ammonia (10 mL) was stirred overnight at 30° C. The resulting mixture was concentrated under vacuum and was purified by Prep-HPLC with the following conditions: Column, SunFire Prep C18, 5 μm, 19*100 mm; mobile phase, Water of 0.05% trifluoroacetic acid and CH$_3$CN (20% CH$_3$CN up to 90% in 10 min, up to 100% in 0.1 min, hold 100% in 1.9 min, down to 20% in 0.1 min, hold 20% in 1.9 min); Detector, UV 220&254 nm, to give the title compound as a white solid. $^1$H NMR (300 MHz, CD$_3$OD) δ: 7.18 (d, J=8.0 Hz, 3H), 6.94 (d, J=8.8 Hz, 3H), 6.52-6.52 (m, 1H), 6.40-6.43 (m, 1H), 4.09-4.17 (m, 2H), 4.03 (t, J=5.6 Hz, 1H), 3.74 (s, 3H), 2.89-2.99 (m, 3H), 2.78-2.85 (m, 1H), 2.55-2.59 (m, 2H), 2.26-2.33 (m, 1H), 2.07-2.10 (m, 1H), 1.90-1.98 (m, 2H). $^{19}$F NMR (300 MHz, CD$_3$OD) δ:−77.31, −111.29, −118.00. Mass spectrum (ESI, m/z): Calcd. for C$_{32.4}$H$_{28.2}$ClF$_{6.6}$N$_3$O$_{4.4}$S, 586.2 (M−1.2CF$_3$COOH+H). found 586.2.

Example 46

3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanenitrile trifluoroacetic acid

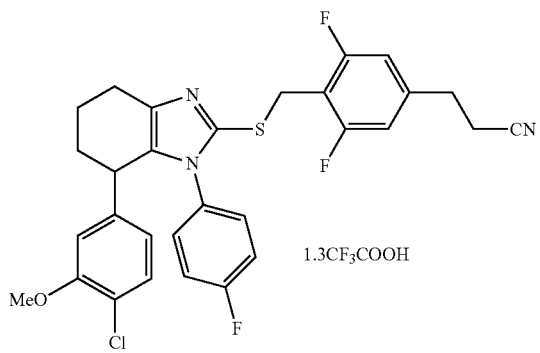 [SMILES: COc1cc(C2CCCc3nc(SCc4c(F)cc(CCC#N)cc4F)n(-c4ccc(F)cc4)c32)ccc1Cl]

1.3CF$_3$COOH

A solution of 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanamide (110 mg, 0.19 mmol, 1.00 equiv), dioxane (6 mL), and pyridine (30 mg, 0.38 mmol, 2.02 equiv) was treated with TFAA (43.4 mg, 0.21 mmol, 1.10 equiv) dropwise at 0° C., and stirred for 4 h at room temperature. The resulting mixture was concentrated under vacuum and purified by Prep-HPLC with the following conditions (1#Waters 2767-5): Column, SunFire Prep C18, 5 μm, 19*100 mm; mobile phase, Water of 0.05% trifluoroacetic acid and CH$_3$CN (20% CH$_3$CN up to 90% in 10 min, up to 100% in 0.1 min, hold 100% in 1.9 min, down to 20% in 0.1 min, hold 20% in 1.9 min); Detector, UV 220&254 nm, to give the title compound as a white solid. $^1$H NMR (300 MHz, CD$_3$OD) δ: 7.18 (d, J=8.4 Hz, 3H), 7.03 (d, J=8.4 Hz, 1H), 6.50-6.51 (m, 1H), 6.40-6.42 (m, 1H), 4.15-4.20 (m, 2H), 4.01-4.02 (m, 1H), 3.73 (s, 3H), 2.82-3.02 (m, 6H), 2.25-2.31 (m, 1H), 2.01-2.10 (m, 1H), 1.89-1.92 (m, 2H). $^{19}$F NMR (300 MHz, CD$_3$OD) δ: −77.75, −111.29, −118.00. Mass spectrum (ESI, m/z): Calcd. for C$_{32.6}$H$_{26.3}$ClF$_{6.9}$N$_3$O$_{3.6}$S, 568.1 (M−1.3CF$_3$COOH+H). found 568.3.

Example 47

(E)-2-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl) propylidene) hydrazinecarboximidamide hydrochloride Step 1: 3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]propanal

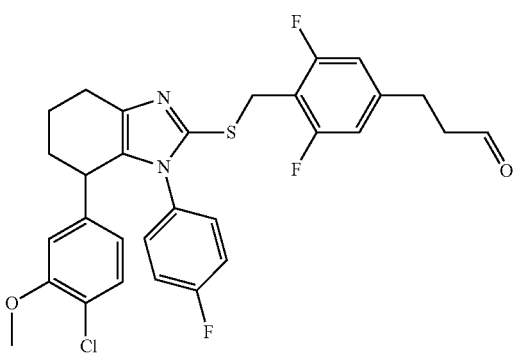 [SMILES: COc1cc(C2CCCc3nc(SCc4c(F)cc(CCC=O)cc4F)n(-c4ccc(F)cc4)c32)ccc1Cl]

The title compound was prepared according to the procedure described in Example 37, step 1 by DIBAL reduction of 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanenitrile to afford the desired product as a white solid. Mass spectrum (ESI, m/z): Calcd. for $C_{30}H_{26}ClF_3N_2O_2S$, 571.1 (M+H). found 571.1.

Step 2: (E)-2-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl) propylidene) hydrazinecarboximidamide hydrochloride

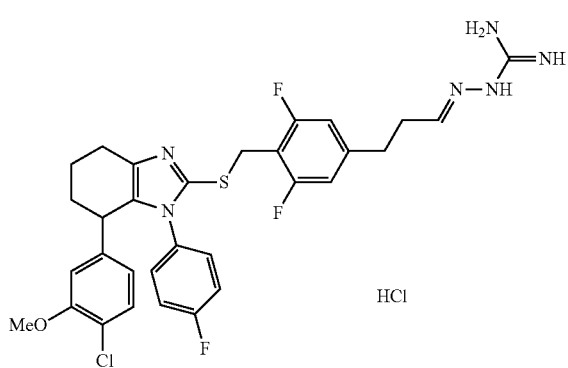 [SMILES: COc1cc(C2CCCc3nc(SCc4c(F)cc(CC/C=N/NC(=N)N)cc4F)n(-c4ccc(F)cc4)c32)ccc1Cl ; Cl]

A solution of 3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]propanal (100 mg, 0.18 mmol, 1.00 equiv), ethanol (4 mL), and 1-aminoguanidine (31 mg, 0.42 mmol, 2.39 equiv) was stirred overnight at 70° C. The crude product was purified by Prep-HPLC with the following conditions: Column, SunFire Prep C18, 5 μm, 19*100 mm; mobile phase, water with 0.05% trifluoroacetic acid and CH$_3$CN (10% CH$_3$CN up to 30% in 8 min, up to 100% in 0.1 min, hold 100% in 1.9 min, down to 10% in 0.1 min, hold 10% in 1.9 min); Detector, UV 220&254 nm. Then used con.HCl to replace TFA to form HCl salt, to give the title compound as a white solid. $^1$H NMR (300 MHz, CD$_3$OD) δ: 7.58-7.60 (m, 1H), 7.12-7.39 (m, 3H), 6.74-7.08 (m, 4H), 6.54 (s, 1H), 6.43-6.45 (d, J=7.6 Hz, 1H), 4.13-4.22 (m, 2H), 4.05 (s, 1H), 3.74 (s, 3H), 2.83-3.00 (m, 4H), 2.66-2.78 (m, 2H), 2.24-2.35 (m, 1H), 2.06-2.11 (m, 1H), 1.93-1.96 (m, 2H). $^{19}$F NMR (300 MHz, CD$_3$OD) δ: −111.14, −117.63. Mass spectrum (ESI, m/z): Calcd. for $C_{31}H_{31}Cl_2F_3N_6OS$, 627.2 (M−HCl+H). found 627.0.

Example 48

(1E,2E)-2-(3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propylidene)-N'-methylhydrazinecarboximidamide hydrochloride

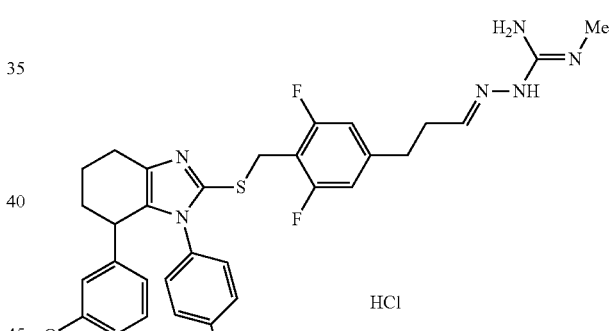

The title compound was prepared according to the procedure described in Example 47 step 2 by coupling 3-[4-([[7-(4-chloro-3-methoxyphenyl)-1-(4-fluorophenyl)-4,5,6,7-tetrahydro-1H-1,3-benzodiazol-2-yl]sulfanyl]methyl)-3,5-difluorophenyl]propanal (Prepared as described in Example 47, Step 1) and (E)-N'-methylhydrazine carboximidamide to afford the desired product as a white solid.

$^1$H NMR (400 MHz, CD$_3$OD): δ 7.58 (s, 1H), 7.19-7.23 (m, 3H), 6.87-7.07 (m, 3H), 6.54 (d, J=1.2 Hz, 1H), 5.95-6.45 (m, 2H), 4.19 (q, 2H), 4.04-4.05 (m, 1H), 3.75 (s, 3H), 2.72-3.02 (m, 6H), 2.64-2.72 (m, 2H), 2.28-2.34 (m, 1H), 2.07-2.11 (m, 1H), 1.94-1.97 (m, 2H). $^{19}$F NMR (400 MHz, CD$_3$OD): δ −111.19, −117.62. Mass spectrum (ESI, m/z): Calcd. for $C_8H_6BrFO_3$, 641.2 (M−HCl+H). found 641.2.

Example 49

2-(4-(2-(1H-tetrazol-5-yl)ethyl)-2,6-difluorobenzylthio)-7-(4-chloro-3-methoxyphenyl)-1-(4-fluorophenyl)-4,5,6,7-tetrahydro-1H-benzo[d]imidazole trifluoroacetic acid

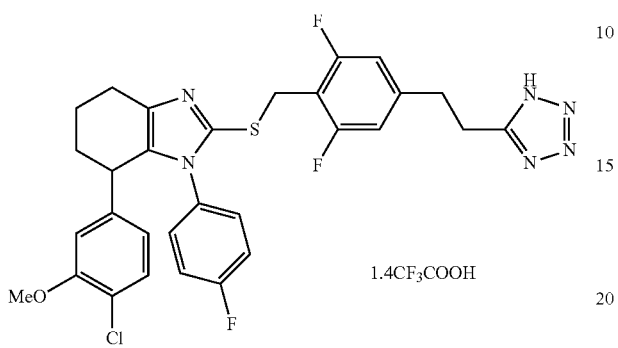

1.4CF₃COOH

A solution of 3-(4-((7-(4-chloro-3-methoxyphenyl)-1-(4-fluorophenyl)-4,5,6,7-tetrahydro-1H-benzo[d]imidazol-2-ylthio)methyl)-3,5-difluorophenyl)propanenitrile (Prepared as described in Example 46, 25 mg, 0.04 mmol, 1.00 equiv), toluene (2 mL), TMS-N₃ (20 mg, 0.17 mmol, 3.95 equiv), and n-Bu₂SnO (11 mg, 0.04 mmol, 1.00 equiv) was stirred overnight at 110° C. The reaction was then quenched by the addition of 5 mL of water, extracted with 2×10 mL of dichloromethane, and the combined organic layers were dried over anhydrous sodium sulfate and concentrated under vacuum. The crude product was purified by Prep-HPLC with the following conditions (1#-Waters 2767-5): Column, SunFire Prep C18, 5 μm, 19*100 mm; mobile phase, Water of 0.05% TFA and CH₃CN (20% CH₃CN up to 50% in 8 min, up to 100% in 0.1 min, hold 100% in 1.9 min, down to 20% in 0.1 min, hold 20% in 1.9 min); Detector, UV 220&254 nm, to give the title compound as an off-white solid. ¹H NMR (300 MHz, CD₃OD) δ: 6.88-7.17 (m, 6H), 6.53-6.53 (m, 1H), 6.40-6.43 (m, 1H), 4.01-4.15 (m, 3H), 3.74 (s, 3H), 3.13-3.19 (m, 2H), 2.77-2.93 (m, 2H), 2.26-2.30 (m, 1H), 2.04-2.06 (m, 1H), 1.87-1.95 (m, 2H). ¹⁹F NMR (300 MHz, CD₃OD) δ: −77.07, −111.75, −117.37. Mass spectrum (ESI, m/z): Calcd. for $C_{32.8}H_{27.4}ClF_{7.2}N_6O_{3.8}S$, 611.2 (M−1.4CF₃COOH+H). found 611.4.

Example 50

7-(4-chloro-3-methoxyphenyl)-2-((3,5-difluoropyridin-4-yl)methylthio)-1-(4-fluorophenyl)-4,5,6,7-tetrahydro-1H-benzo[d]imidazole trifluoroacetic acid Step 1: (3,5-difluoropyridin-4-yl)methanol

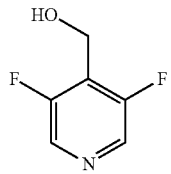

A solution of 3, 5-difluoropyridine-4-carbaldehyde (500 mg, 3.49 mmol, 1.00 equiv) in methanol (10 mL) was cooled to 0° C., treated with NaBH₄ (133 mg, 3.52 mmol, 1.01 equiv), and stirred for 1 h at 0° C. The reaction was then quenched by the addition of 10 mL of water, concentrated under vacuum, extracted with 2×15 mL of ethyl acetate and the organic layers combined and concentrated under vacuum. The residue was applied onto a silica gel column with ethyl acetate/petroleum ether (1:3) to give the title compound as a yellow solid. Mass spectrum (ESI, m/z): Calcd. for $C_6H_5F_2NO$, 146.0 (M+H). found 146.0.

Step 2: (3,5-difluoropyridin-4-yl)methyl methanesulfonate

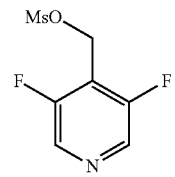 [SMILES: CS(=O)(=O)OCc1c(F)cncc1F]

A solution of (3,5-difluoropyridin-4-yl)methanol (100 mg, 0.69 mmol, 1.00 equiv), dichloromethane (8 mL), and TEA (209 mg, 2.07 mmol, 3.00 equiv) was treated with MsCl (157 mg, 1.38 mmol, 2.00 equiv) dropwise with stirring at 0° C., stirred for 4 h at room temperature and concentrated under vacuum to give the title compound as a yellow oil. Mass spectrum (ESI, m/z): Calcd. for $C_7H_7F_2NO_3S$, 224.0 (M+H). found 224.0.

Step 3: 7-(4-chloro-3-methoxyphenyl)-2-((3,5-difluoropyridin-4-yl)methylthio)-1-(4-fluorophenyl)-4,5,6,7-tetrahydro-1H-benzo[d]imidazole trifluoroacetic acid

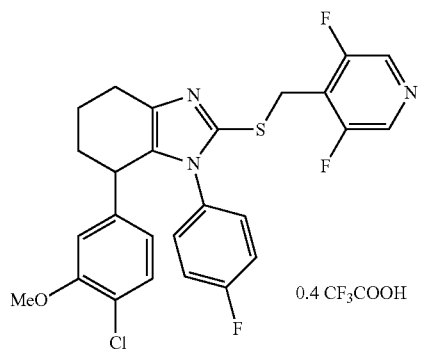 [SMILES: COc1cc(C2CCCc3nc(SCc4c(F)cncc4F)n(-c4ccc(F)cc4)c32)ccc1Cl]

0.4 CF₃COOH

A solution of (3,5-difluoropyridin-4-yl)methyl methanesulfonate (34.3 mg, 0.15 mmol, 1.00 equiv), acetone (6 mL), potassium carbonate (64 mg, 0.46 mmol, 3.01 equiv), and 7-(4-chloro-3-methoxyphenyl)-1-(4-fluorophenyl)-4,5,6,7-tetrahydro-1H-benzo[d]imidazole-2-thiol (Prepared as described in Example 1 Step 7, 60 mg, 0.15 mmol, 1.00 equiv) was stirred overnight at room temperature. The crude product (3 mL) was purified by Prep-HPLC with the following conditions (1#-Waters 2767-5): Column, SunFire Prep C18, 5 μm, 19*100 mm; mobile phase, Water of 0.05% trifluoroacetic acid and CH₃CN (20% CH₃CN up to 90% in 8 min, up to 100% in 0.1 min, hold 100% in 1.9 min, down to 20% in 0.1 min, hold 20% in 1.9 min); Detector, UV 220&254 nm, to give the title compound as a white solid. $^1$H NMR (300 MHz, CD$_3$OD): δ 8.35 (s, 2H), 7.11 (d, J=8.4 Hz, 2H), 6.98 (br, 2H), 6.48 (s, 1H), 6.36 (dd, J=8.1, 2.1 Hz, 1H), 3.99-4.13 (m, 3H), 3.83 (s, 3H), 2.77-2.82 (m, 2H), 2.25-2.28 (m, 1H), 1.94-2.03 (m, 1H), 1.86-1.87 (m, 2H). $^{19}$F NMR (300 MHz, CD$_3$OD): δ −77.00, −112.98, −131.68. Mass spectrum (ESI, m/z): Calcd. for C$_{26}$H$_{21}$ClF$_3$N$_3$OS, 516.0 (M−0.4CF$_3$COOH+H). found 516.0.

Step 4: 7-(4-chloro-3-methoxyphenyl)-2-((3,5-difluoropyridin-4-yl)methylthio)-1-(4-fluorophenyl)-4,5,6,7-tetrahydro-1H-benzo[d]imidazole hydrochloric acid

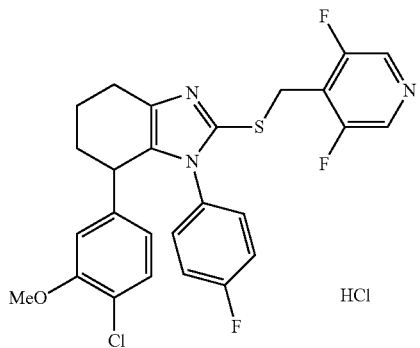 [SMILES: COc1cc(C2CCCc3nc(SCc4c(F)cncc4F)n(-c4ccc(F)cc4)c32)ccc1Cl ; Cl]

A solution of (3,5-difluoropyridin-4-yl)methyl methanesulfonate (86 mg, 0.39 mmol, 1.00 equiv), acetone (6 mL), potassium carbonate (160 mg), and 7-(4-chloro-3-methoxyphenyl)-1-(4-fluorophenyl)-4,5,6,7-tetrahydro-1H-benzo[d]imidazole-2-thiol (Prepared as described in Example 1 Step 7, 150 mg, 0.39 mmol, 1.00 equiv) was stirred overnight at room temperature. The mixture was concentrated under vacuum and purified by Prep-HPLC with the following conditions (1#-Waters 2767-5): Column, SunFire Prep C18, 5 μm, 19*100 mm; mobile phase, mobile phase, Water of 0.05% trifluoroacetic acid and CH$_3$CN (20% CH$_3$CN up to 80% in 8 min, up to 100% in 0.1 min, hold 100% in 1.9 min, down to 20% in 0.1 min, hold 20% in 1.9 min); Detector, UV 220&254 nm. The solvent was removed under vacuum. Then 4.0 mL H$_2$O and 4 drops of con.HCl was added. The water was removed again. This operation was repeated twice. Then after water and HCl were added, it was lyophilized, to give the title compound as a yellow solid. $^1$H-NMR (400 MHz, CD$_3$OD): δ 8.47 (s, 2H), 7.31-7.32 (m, 1H), 7.17 (d, J=8.0 Hz, 1H), 6.95-6.96 (s, 1H), 6.62-6.68 (m, 1H), 6.54 (s, 1H), 6.43 (d, J=7.6 Hz, 1H), 4.10-4.28 (m, 3H), 3.75 (s, 3H), 2.80-2.97 (m, 2H), 2.29-2.33 (m, 1H), 2.08-2.12 (m, 1H), 1.89-1.97 (m, 2H). $^{19}$F-NMR (400 MHz, CD$_3$OD): δ −110.88, −131.59. Mass spectrum (ESI, m/z): Calcd. for C$_{26}$H$_{21}$ClF$_3$N$_3$OS, 516.1 (M−HCl+H). found 516.2.

Example 51

2-((3-fluoropyridin-4-yl)methylthio)-7-(4-chloro-3-methoxyphenyl)-1-(4-fluorophenyl)-4,5,6,7-tetrahydro-1H-benzo[d]imidazole trifluoroacetic acid

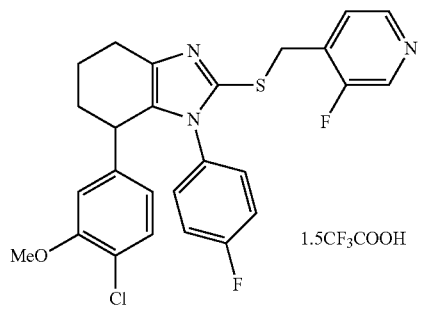

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 4-(bromomethyl)-3-fluoropyridine in the presence of Cs$_2$CO$_3$ to afford the desired product as a white solid.

$^1$H NMR (400 MHz, CD$_3$OD): δ 8.48 (s, 1H), 8.37-8.39 (m, 1H), 7.29-7.32 (m, 1H), 6.51-7.30 (m, 4H), 6.39-6.51 (m, 2H), 4.93 (s, 1H), 4.17-4.25 (m, 1H), 4.05-4.19 (m, 1H), 3.73 (s, 3H), 2.80-3.33 (m, 2H), 2.26-2.33 (m, 1H), 1.88-2.08 (m, 2H). $^{19}$F NMR (400 MHz, CD$_3$OD): −77.29, −111.24, −133.74. Mass spectrum (ESI, m/z): Calcd. for C$_{29}$H$_{23.5}$ClF$_{6.5}$N$_3$O$_4$S, 498.1 (M−1.5CF$_3$COOH+H). found 498.2.

Example 52

2-((3-fluoropyridin-2-yl)methylthio)-7-(4-chloro-3-methoxyphenyl)-1-(4-fluorophenyl)-4,5,6,7-tetrahydro-1H-benzo[d]imidazole trifluoroacetic acid

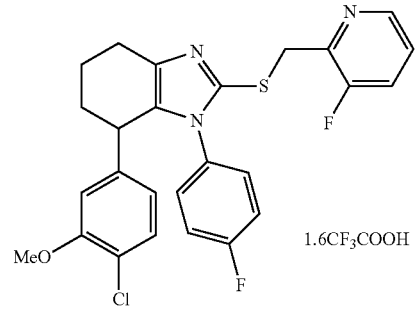

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 2-(bromomethyl)-3-fluoropyridine in the presence of Cs$_2$CO$_3$ to afford the desired product as a yellow solid.

$^1$H NMR (300 MHz, CD$_3$OD): δ 8.34 (d, J=4.8 Hz, 1H), 7.63-7.68 (m, 1H), 7.47-7.50 (m, 1H), 7.28 (br, 4H), 6.44-

6.54 (m, 2H), 4.22 (s, 2H), 4.03-4.07 (m, 1H), 3.73 (s, 3H), 2.76-2.92 (m, 2H), 2.26-2.34 (m, 1H), 1.89-2.08 (m, 3H). $^{19}$F NMR (300 MHz, CD$_3$OD): −77.09, −111.30, −125.10. Mass spectrum (ESI, m/z): Calcd. for C$_{29.2}$H$_{23.6}$ClF$_{6.8}$N$_3$O$_{4.2}$S, 498.1 (M−1.6CF$_3$COOH+H). found 498.1.

Example 53

2-((5-chloropyrimidin-4-yl)methylthio)-7-(4-chloro-3-methoxyphenyl)-1-(4-fluorophenyl)-4,5,6,7-tetrahydro-1H-benzo[d]imidazole trifluoroacetic acid Step 1: 4-(bromomethyl)-5-chloropyrimidine

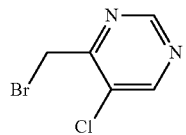

A solution of 5-chloro-4-methylpyrimidine (500 mg, 3.89 mmol, 1.00 equiv), AcOH (10 mL), and Br$_2$ (750 mg, 4.69 mmol, 1.20 equiv) was stirred for 30 min at 80° C. in an oil bath. The resulting mixture was concentrated under vacuum, diluted with 50 mL of H$_2$O, extracted with 3×50 mL of dichloromethane, and the combined organic layers were washed with 1×50 mL of brine, filtered, and concentrated. Chromatography on a silica gel column with ethyl acetate/petroleum ether (1:3), to give the title compound as a light yellow oil.

Step 2: 2-((5-chloropyrimidin-4-yl)methylthio)-7-(4-chloro-3-methoxyphenyl)-1-(4-fluorophenyl)-4,5,6,7-tetrahydro-1H-benzo[d]imidazole trifluoroacetic acid

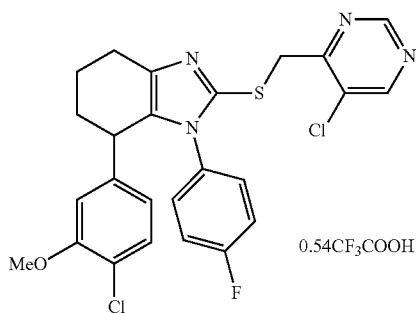

0.54CF$_3$COOH

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 4-(bromomethyl)-5-chloropyrimidine in the presence of Cs$_2$CO$_3$ to afford the desired product as a white solid.

$^1$H NMR (400 MHz, CD$_3$OD): δ 8.87 (s, 1H), 7.51 (s, 1H), 7.18 (d, J=9.0 Hz, 2H), 6.92-7.14 (m, 2H), 6.53 (s, 1H), 6.44 (d, J=1.8 Hz, 1H), 4.15 (d, J=13.5 Hz, 2H), 4.03-4.11 (m, 1H), 3.73 (s, 3H), 2.73-2.92 (m, 2H), 2.25-2.35 (m, 1H), 1.87-2.06 (m, 3H). $^{19}$F NMR (400 MHz, CD$_3$OD): δ −77.14, −111.78. Mass spectrum (ESI, m/z): Calcd. for C$_{26.08}$H$_{21.54}$Cl$_2$F$_{2.62}$N$_4$O$_{2.08}$S, 515.1 (M−0.54CF$_3$COOH+H). found 515.1.

Example 54

4-chloro-3-methoxyphenyl)-2-((3,5-dichloropyridin-4-yl)methylthio)-1-(4-fluorophenyl)-4,5,6,7-tetrahydro-1H-benzo[d]imidazole trifluoroacetic acid

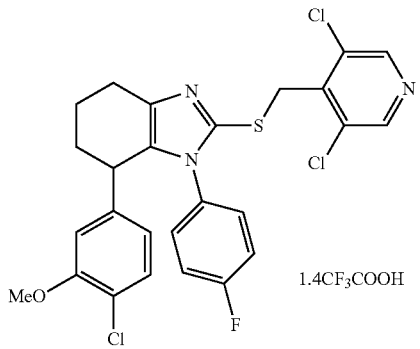

1.4CF$_3$COOH

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 4-(bromomethyl)-3,5-dichloropyridine in the presence of Cs$_2$CO$_3$ to afford the desired product as a white solid.

$^1$H NMR (300 MHz, CD$_3$OD): δ 7.13 (d, J=8.1 Hz, 1H), 6.91-6.96 (m, 1H), 6.76 (d, J=6.0 Hz, 1H), 6.42-6.50 (m, 1H), 4.15-4.26 (m, 2H), 3.92-4.04 (m, 1H), 3.72 (s, 3H), 2.72-2.87 (m, 2H), 2.22-2.30 (m, 1H), 2.02-2.08 (m, 1H), 1.83-1.97 (m, 2H). $^{19}$F NMR (300 MHz, CD$_3$OD): δ −77.04, −113.04. Mass spectrum (ESI, m/z): Calcd. for C$_{28.8}$H$_{22.4}$Cl$_3$F$_{5.2}$N$_3$O$_{3.8}$S, 548.0 (M−1.4CF$_3$COOH+H). found 548.1.

Example 55

7-(4-chloro-3-methoxyphenyl)-2-[[(3-chloro-5-fluoropyridin-4-yl)methyl]sulfanyl]-1-(4-fluorophenyl)-4,5,6,7-tetrahydro-1H-1,3-benzodiazole bis(trifluoroacetic acid)

Step 1: Methyl 3-chloro-5-fluoropyridine-4-carboxylate

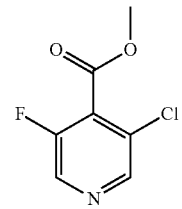

A solution of 3-chloro-5-fluoropyridine-4-carboxylic acid (100 mg, 0.57 mmol, 1.00 equiv) in dichloromethane (2 mL) was treated with thionyl chloride (68 mg) dropwise with stirring at 0° C. After stirring 2.0 h at 40° C., methanol (2 mL) was added, and the resulting solution was stirred for 10 min at room temperature, concentrated under vacuum, and quenched by the addition of 3 mL of sodium bicarbonate/H₂O. The reaction was extracted with 3×3 mL of dichloromethane and the combined organic layers combined were dried over anhydrous sodium sulfate, filtered, and concentrated to give the title compound as a yellow oil. Mass spectrum (ESI, m/z): Calcd. for C₇H₅ClFNO₂, 190.0 (M+H). found 190.0.

Step 2: (3-chloro-5-fluoropyridin-4-yl)methanol

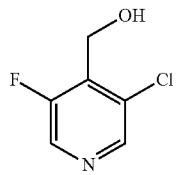

A solution of 3-chloro-5-fluoropyridine-4-carboxylate (80 mg, 0.42 mmol, 1.00 equiv) in tetrahydrofuran (2 mL) was treated with DIBAL-H (0.85 mL, 2.00 equiv) dropwise with stirring at −78° C. The resulting solution was stirred for 3.0 h at room temperature and quenched with 2 mL of water. The reaction was extracted with 4×3 mL of ethyl acetate, and the combined organic layers were dried over anhydrous sodium sulfate, filtered, and concentrated. Preparatory chromatography with ethyl acetate/petroleum ether (1:5) gave the title compound as a yellow oil. Mass spectrum (ESI, m/z): Calcd. for C₆H₅ClFNO, 162.0 (M+H). found 162.0.

Step 3: (3-chloro-5-fluoropyridin-4-yl)methyl methanesulfonate

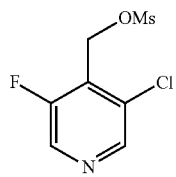 [SMILES: CS(=O)(=O)OCc1c(F)cncc1Cl]

The title compound was prepared according to the procedure described in Example 50 step 2 by mesylation of (3-chloro-5-fluoropyridin-4-yl)methanol to afford the desired product as a white solid.

Mass spectrum (ESI, m/z): Calcd. for C₇H₇ClFNO₃S, 240.0 (M+H). found 240.0.

Step 4: 7-(4-chloro-3-methoxyphenyl)-2-[[(3-chloro-5-fluoropyridin-4-yl)methyl]sulfanyl]-1-(4-fluorophenyl)-4,5,6,7-tetrahydro-1H-1,3-benzodiazole bis(trifluoroacetic acid)

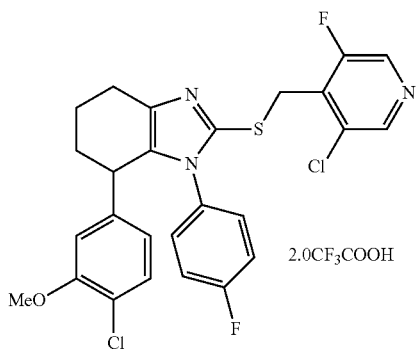 [SMILES: COc1cc(C2CCCc3nc(SCc4c(F)cncc4Cl)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with (3-chloro-5-fluoropyridin-4-yl)methyl methanesulfonate in the presence of Cs₂CO₃ to afford the desired product as a white solid.

¹H NMR: (400 MHz, CD₃OD): δ 8.44-8.48 (m, 2H), 7.56-7.69 (m, 2H), 7.01-7.16 (m, 4H), 6.51 (d, J=1.6 Hz, 1H), 6.40-6.42 (m, 1H), 4.04-4.23 (m, 3H), 3.73 (s, 3H), 2.76-2.91 (m, 2H), 2.26-2.32 (m, 1H), 1.89-2.08 (m, 3H). ¹⁹F NMR (400 MHz, CD₃OD): −77.12, −111.98, −130.52. Mass spectrum (ESI, m/z): Calcd. for C₃₀H₂₃Cl₂F₈N₃O₅S, 532.1 (M−2.0CF₃COOH+H). found 532.2.

Example 56

2-((3-bromo-5-fluoropyridin-4-yl)methylthio)-7-(4-chloro-3-methoxyphenyl)-1-(4-fluorophenyl)-4,5,6,7-tetrahydro-1H-benzo[d]imidazole trifluoroacetic acid Step 1: (3-bromo-5-fluoropyridin-4-yl)methanol

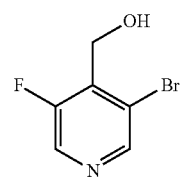

The title compound was prepared according to the procedure described in Example 55 step 1-2 by esterification of 3-bromo-5-fluoroisonicotinic acid followed by DIBAL reduction to afford the desired product as a yellow oil. Mass spectrum (ESI, m/z): Calcd. for C₆H₅BrFNO, 206.0 (M+H). found 206.0.

Step 2: 3-bromo-4-(chloromethyl)-5-fluoropyridine

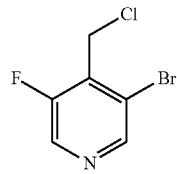

A solution of (3-bromo-5-fluoropyridin-4-yl)methanol (50 mg, 0.24 mmol, 1.00 equiv) in dichloromethane (2 mL) was treated with TEA (73.9 mg, 0.73 mmol, 3.01 equiv) dropwise with stirring at 0° C., followed by MsCl (33.7 mg). The resulting solution was stirred for 2.0 h at room temperature and concentrated under vacuum. Silica gel column chromatography with ethyl acetate/petroleum ether (1:5) gave the title compound as a white oil. Mass spectrum (ESI, m/z): Calcd. for $C_6H_4BrClFN$, 223.9 (M+H). found 223.9.

Step 3: 2-((3-bromo-5-fluoropyridin-4-yl)methylthio)-7-(4-chloro-3-methoxyphenyl)-1-(4-fluorophenyl)-4,5,6,7-tetrahydro-1H-benzo[d]imidazole trifluoroacetic acid

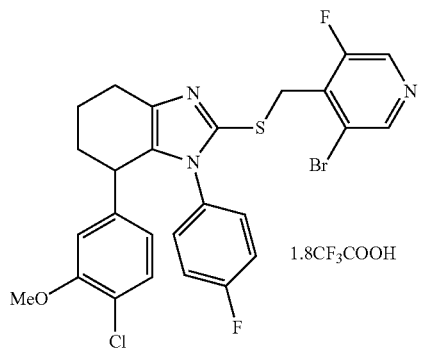 [SMILES: COc1cc(C2CCCc3nc(SCc4c(F)cncc4Br)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 3-bromo-4-(chloromethyl)-5-fluoropyridine in the presence of $Cs_2CO_3$ to afford the desired product as a white solid. $^1$H NMR (300 MHz, $CD_3OD$): δ 8.60 (s, 1H), 8.46 (s, 1H), 7.04-7.16 (m, 4H), 6.40-6.52 (m, 2H), 4.07-4.28 (m, 3H), 3.73 (s, 3H), 2.79-2.96 (m, 2H), 2.27-2.35 (m, 1H), 2.03-2.13 (m, 3H). $^{19}$F NMR (300 MHz, $CD_3OD$): −77.26, −111.35, −128.99. Mass spectrum (ESI, m/z): Calcd. for $C_{29.6}H_{22.8}BrClF_{7.4}N_3O_{4.6}S$, 576.0 (M−1.8CF$_3$COOH+H). found 576.0.

Example 57

7-(4-chloro-3-methoxyphenyl)-1-(4-fluorophenyl)-2-[(pyrimidin-2-ylmethyl)sulfanyl]-4,5,6,7-tetrahydro-1H-1,3-benzodiazole trifluoroacetic acid

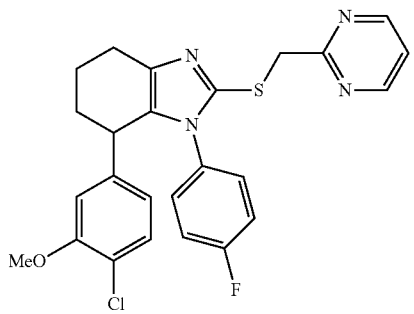 [SMILES: COc1cc(C2CCCc3nc(SCc4ncccn4)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 2-(bromomethyl)pyrimidine in the presence of $Cs_2CO_3$ to afford the desired product as a white solid. $^1$H NMR (300 MHz, $CD_3OD$): δ 8.75 (s, 2H), 7.43-7.46 (m, 1H), 6.97-7.23 (m, 3H), 6.45-6.55 (m, 2H), 4.32-4.48 (m, 2H), 4.05-4.27 (m, 1H), 3.74 (s, 3H), 2.77-2.93 (m, 2H), 2.27-2.35 (m, 1H), 1.91-2.09 (m, 3H). Mass spectrum (ESI, m/z): Calcd. for $C_{29}H_{24}ClF_7N_4O_5S$, 481.0 (M−2CF$_3$COOH+H). found 481.0.

Example 58

2-((3-chlorothiophen-2-yl)methylthio)-7-(4-chloro-3-methoxyphenyl)-1-(4-fluorophenyl)-4,5,6,7-tetrahydro-1H-benzo[d]imidazole trifluoroacetic acid

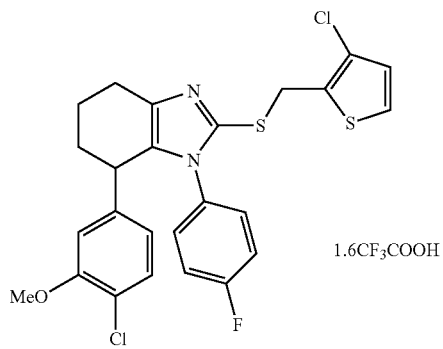 [SMILES: COc1cc(C2CCCc3nc(SCc4sccc4Cl)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 3-chloro-2-(chloromethyl)thiophene in the presence of $Cs_2CO_3$ to afford the desired product as a white solid. $^1$H NMR (300 MHz, $CD_3OD$): δ 7.52 (d, J=5.4 Hz, 1H), 6.91-7.16 (m, 4H), 6.40-6.51 (m, 2H), 4.31-4.41 (m, 2H), 4.01-4.05 (m, 1H), 3.73 (s, 3H), 2.81-2.94 (m, 2H), 2.25-2.33 (m, 1H), 2.08-2.10 (m). $^{19}$F NMR (300 MHz, $CD_3OD$): δ −77.11, −111.77. Mass spectrum (ESI, m/z): Calcd. for $C_{28.2}H_{22.6}Cl_2F_{5.8}N_2O_{4.2}S_2$, 519.0 (M−1.6CF$_3$COOH+H). found 519.0.

Example 59

4-((7-(4-chloro-3-methoxyphenyl)-1-(4-fluorophenyl)-4,5,6,7-tetrahydro-1H-benzo[d]imidazol-2-ylthio)methyl)-3,5-difluoropyridine 1-oxide trifluoroacetic acid Step 1: 3,5-difluoro-4-(hydroxymethyl)pyridin-1-ium-1-olate

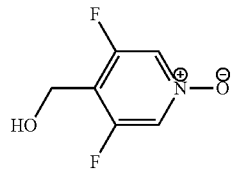 [SMILES: [O-][n+]1cc(F)c(CO)c(F)c1]

A solution of (3,5-difluoropyridin-4-yl)methanol (150 mg, 1.03 mmol, 1.00 equiv), ethylene glycol dimethyl ether (2 mL), and heptane (4 mL) was treated with mCPBA (178 mg, 1.03 mmol, 1.00 equiv) in several batches at 0° C. The resulting solution was stirred overnight at room temperature and filtered to give the title compound as a white solid. Mass spectrum (GC, m/z): Calcd. for $C_6H_5F_2NO_2$, 162.0 (M+1). found 162.0.

Step 2: 3, 5-difluoro-4-[(methanesulfonyloxy)methyl]pyridin-1-ium-1-olate

The title compound was prepared according to the procedure described in Example 50 step 2 by mesylation of 3,5-difluoro-4-(hydroxymethyl)pyridin-1-ium-1-olate to afford the desired product as a white solid. Mass spectrum (ESI, m/z): Calcd. for $C_7H_7F_2NO_4S$, 240.0 (M+H). found 240.0.

Step 3: 4-((7-(4-chloro-3-methoxyphenyl)-1-(4-fluorophenyl)-4,5,6,7-tetrahydro-1H-benzo[d]imidazol-2-ylthio)methyl)-3,5-difluoropyridine 1-oxide trifluoroacetic acid

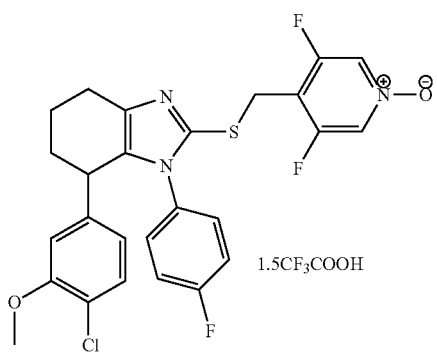 [SMILES: COc1cc(C2CCCc3nc(SCc4c(F)c[n+]([O-])cc4F)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with 3, 5-difluoro-4-[(methanesulfonyloxy)methyl]pyridin-1-ium-1-olate in the presence of Cs$_2$CO$_3$ to afford the desired product as a white solid. $^1$H NMR (400 MHz, CD$_3$OD): 8.40-8.43 (m, 2H), 7.05-7.17 (m, 5H), 6.53 (d, J=2.0 Hz, 1H), 6.41-6.43 (m, 1H), 4.03-4.14 (m, 3H), 3.74 (s, 3H), 2.78-2.92 (m, 2H), 2.27-2.33 (m, 1H), 2.02-2.08 (m, 1H), 1.88-1.96 (m, 2H). $^{19}$F NMR (400 MHz, CD$_3$OD): δ −77.37, −111.56, −127.30. Mass spectrum (ESI, m/z): Calcd. for $C_{29}H_{22.5}ClF_{7.5}N_3O_5S$, 532.1 (M+H). found 532.1.

Example 60

2-((3,5-dibromopyridin-4-yl)methylthio)-7-(4-chloro-3-methoxyphenyl)-1-(4-fluorophenyl)-4,5,6,7-tetrahydro-1H-benzo[d]imidazole Step 1: (3,5-dibromopyridin-4-yl)methyl methanesulfonate

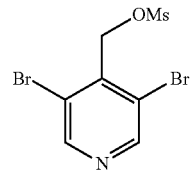

The title compound was prepared according to the procedure described in Example 50 step 2 by mesylation of (3,5-dibromopyridin-4-yl)methanol to afford the desired product as a white solid. Mass spectrum (ESI, m/z): Calcd. for $C_7H_7Br_2NO_3S$, 343.9 (M+H). found 343.9.

Step 2: 2-((3,5-dibromopyridin-4-yl)methylthio)-7-(4-chloro-3-methoxyphenyl)-1-(4-fluorophenyl)-4,5,6,7-tetrahydro-1H-benzo[d]imidazole

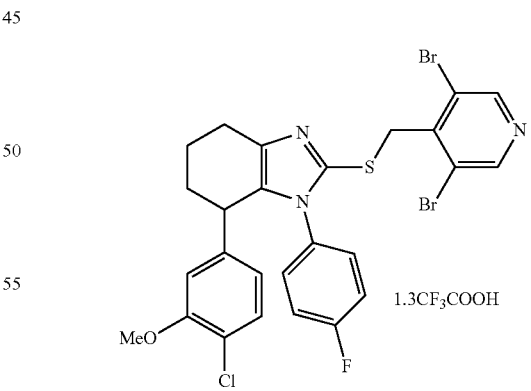

The title compound was prepared according to the procedure described in Example 1 step 8 by coupling 7-(4-chloro-3-methoxyphenyl)-1-(4-fluorophenyl)-4,5,6,7-tetrahydro-1H-benzo[d]imidazole-2-thiol (Prepared as described in Example 1 Step 7) with (3,5-dibromopyridin-4-yl)methyl methanesulfonate in the presence of Cs$_2$CO$_3$ to afford the desired product as a white solid. $^1$H NMR (400 MHz, CD$_3$OD): δ 8.65 (s, 2H), 6.97-7.27 (m, 3H), 6.51-6.64 (m, 1H), 6.43-6.45 (m, 1H), 4.25-4.37 (m, 2H), 4.11-4.13 (m, 1H), 3.73 (s, 3H), 2.81-2.95 (m, 2H), 2.29-2.35 (m, 1H), 2.07-2.11 (m, 1H), 1.87-1.96 (m, 2H). $^{19}$FNMR (400 MHz, CD$_3$OD): δ −77.26, −111.55. Mass spectrum (ESI, m/z): Calcd. for C$_{28.6}$H$_{22.3}$Br$_2$ClF$_{4.9}$N$_3$O$_{3.6}$S, 635.9.9 (M−1.3 CF$_3$COOH+H). found 635.9.

Example 61

7-(4-chloro-3-methoxyphenyl)-2-[[(2-chloro-6-fluorophenyl)methyl]sulfanyl]-1-(4-fluorophenyl)-5-methyl-4,5,6,7-tetrahydro-1H-1,3-benzodiazole Step 1: 2-(4-chloro-3-methoxyphenyl)-4-methylcyclohexan-1-one

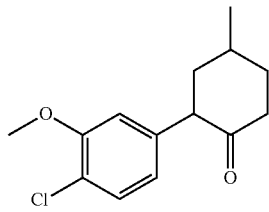 [SMILES: COc1cc(C2CC(C)CCC2=O)ccc1Cl]

The title compound was prepared according to the procedure described in Example 1 step 1 by coupling 4-methylcyclohexanone and 4-bromo-1-chloro-2-methoxybenzene to afford the desired product as a yellow solid. Mass spectrum (ESI, m/z): Calcd. for C$_{14}$H$_{17}$C$_1$O$_2$, 253.1 (M+H). found 253.1.

Step 2: 7-(4-chloro-3-methoxyphenyl)-1-(4-fluorophenyl)-5-methyl-4,5,6,7-tetrahydro-1H-1,3-benzodiazole-2-thiol

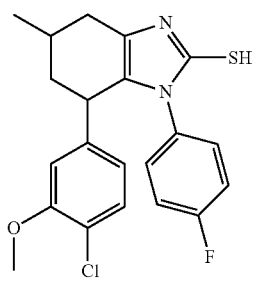 [SMILES: COc1cc(C2CC(C)Cc3nc(S)n(-c4ccc(F)cc4)c32)ccc1Cl]

The title compound was prepared according to the procedure described in Example 1 step 2-7 to afford the desired product as a yellow solid. Mass spectrum (ESI, m/z): Calcd. for C$_{21}$H$_{20}$ClFN$_2$OS, 403.1 (M+H). found 403.1.

Step 3: 7-(4-chloro-3-methoxyphenyl)-2-[[(2-chloro-6-fluorophenyl)methyl]sulfanyl]-1-(4-fluorophenyl)-5-methyl-4,5,6,7-tetrahydro-1H-1,3-benzodiazole

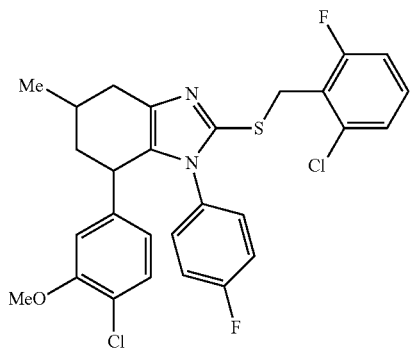 [SMILES: COc1cc(C2CC(C)Cc3nc(SCc4c(F)cccc4Cl)n(-c4ccc(F)cc4)c32)ccc1Cl]

The title compound was prepared according to the procedure described in Example 1 step 8 by coupling 7-(4-chloro-3-methoxyphenyl)-1-(4-fluorophenyl)-5-methyl-4,5,6,7-tetrahydro-1H-1,3-benzodiazole-2-thiol with 2-(bromomethyl)-1-chloro-3-fluorobenzene in the presence of Cs$_2$CO$_3$ to afford the desired product as a white solid. $^1$H NMR (300 MHz, CD$_3$OD) δ: 7.15-7.25 (m, 2H), 6.95-7.01 (m, 4H), 6.29-6.32 (m, 2H), 4.01-4.02 (m, 2H), 3.85-3.95 (m, 1H), 3.62 (s, 3H), 3.65-3.75 (m, 1H), 2.30-2.40 (m, 1H), 2.00-2.15 (m, 2H), 1.40-1.55 (m, 1H), 1.10 (d, J=6.6 Hz, 3H). Mass spectrum (ESI, m/z): Calcd. for C$_{28}$H$_{24}$Cl$_2$F$_2$N$_2$OS, 545.1 (M+H). found 545.1.

Example 62

2-((2-chloro-6-fluorobenzyl)thio)-7-(3,4-dimethoxyphenyl)-1-(4-fluorophenyl)-4,5,6,7-tetrahydro-1H-benzo[d]imidazole Step 1: 2-(3,4-dimethoxyphenyl)cyclohexanone

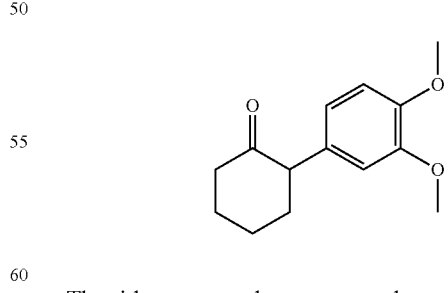

The title compound was prepared according to the procedure as described in Example 1 step 1 reacting cyclohexanone and 1-bromo-3,4-dimethoxybenzene as a white solid. $^1$H NMR (400 MHz, CDCl$_3$) δ 6.85 (d, J=8.1 Hz, 1H), 6.68 (d, J=7.8 Hz, 1H), 6.65 (s, 1H), 3.87 (s, 6H), 3.55 (dd, J=8.5, 5.2 Hz, 1H), 2.51 (m, 2H), 2.31 (m, 1H), 2.15 (m, 1H), 2.03 (m, 2H), 1.82 (m, 2H).

Step 2: 2-bromo-6-(3,4-dimethoxyphenyl)cyclo-hexanone and 2-bromo-6-(2-bromo-4,5-dimethoxyphenyl)cyclohexanone and 2-bromo-6-(2,3-dibromo-4,5-dimethoxyphenyl)cyclohexanone

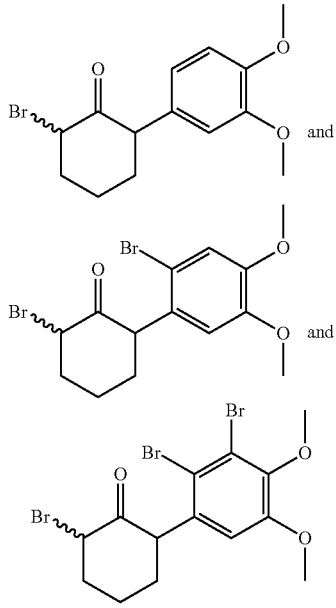

The title compound was prepared according to the procedure as described in Example 1 step 2-3 reacting 2-(3,4-dimethoxyphenyl)cyclohexanone with TMSOTf/TEA followed by NBS as mixtures of a light yellow solid.

2-bromo-6-(3,4-dimethoxyphenyl)cyclohexanone (major isomer):

¹H NMR (400 MHz, CDCl₃) δ 7.05 (s, 1H), 6.85 (1H), 4.15 (m, 1H), 3.89 (s, 6H), 2.82 (m, 1H), 2.10 (m, 2H), 1.38 (m, 2H), 1.10 (m, 2H).

2-bromo-6-(2-bromo-4,5-dimethoxyphenyl)cyclohexanone

ESI-MS (m/z): Calcd. For C₁₄H₁₆Br₂O₃: 392.1. found: 312 (M−Br+H).

2-bromo-6-(2,3-dibromo-4,5-dimethoxyphenyl)cyclohexanone

ESI-MS (m/z): Calcd. For C₁₄H₁₅Br₃O₃: 471.0. found: 391 (M−Br+H).

Step 3: 2-azido-6-(3,4-dimethoxyphenyl)cyclohexanone

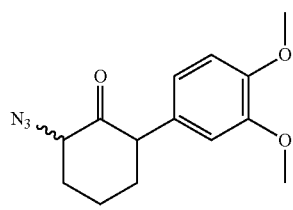 [SMILES: COc1ccc(C2CCCC(N=[N+]=[N-])C2=O)cc1OC]

The title compound was prepared according to the procedure as described in Example 1 step 4 reacting 2-bromo-6-(3,4-dimethoxyphenyl)cyclohexanone with NaN₃ as light yellow solid.

ESI-MS (m/z): Calcd. For C₄H₁₇N₃O₃: 275.3. found: 234 (M−N₃+H).

Step 4: 2-amino-6-(3,4-dimethoxyphenyl)cyclohexanone hydrogen chloride

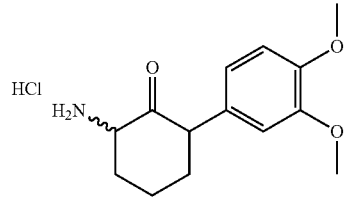 [SMILES: Cl ; COc1ccc(C2CCCC(N)C2=O)cc1OC]

The title compound was prepared as brown solid according to the procedure as described in Example 1 step 5 by reacting 2-azido-6-(3,4-dimethoxyphenyl)cyclohexanone with 5% Pd on carbon under 50 psi hydrogen in acetic acid.

ESI-MS (m/z): Calcd. For Cl₄H₁₉NO₃: 249.3. found: 250 (M+H).

Step 5: 1-(3-(3,4-dimethoxyphenyl)-2-oxocyclohexyl)-3-(4-fluorophenyl)thiourea

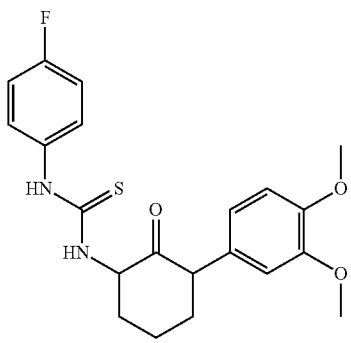 [SMILES: COc1ccc(C2CCCC(NC(=S)Nc3ccc(F)cc3)C2=O)cc1OC]

The title compound was prepared according to the procedure as described in Example 1 step 6 reacting 2-amino-6-(3,4-dimethoxyphenyl)cyclohexanone hydrogen chloride salt and 1-fluoro-4-isothiocyanatobenzene as off yellow solid.

¹H NMR (400 MHz, CDCl₃) δ 7.75 (br, s, 1H), 7.24 (d, J=7.5 Hz, 2H), 7.16 (s, 1H), 7.05 (s, 1H), 6.81 (s, 1H), 6.65 (d, J=7.5 Hz, 2H), 4.15 (m, 1H), 3.85 (s, 6H), 3.72 (m, 1H), 2.05 (m, 4H).

Step 6: 7-(3,4-dimethoxyphenyl)-1-(4-fluorophenyl)-4,5,6,7-tetrahydro-1H-benzo[d]imidazole-2-thiol

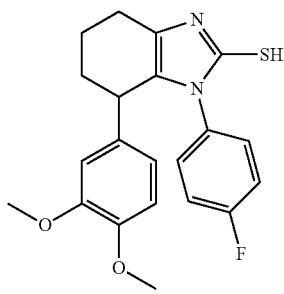 [SMILES: COc1ccc(C2CCCc3nc(S)n(-c4ccc(F)cc4)c32)cc1OC]

The title compound was prepared according to the procedure as described in Example 1 step 7 reacting 1-(3-(3,4-dimethoxyphenyl)-2-oxocyclohexyl)-3-(4-fluorophenyl) thiourea in acetic acid as off yellow solid.

$^1$H NMR (400 MHz, CDCl$_3$) δ 6.96 (m, 4H), 6.65 (d, J=7.2 Hz, 1H), 6.38 (d, J=6.5 Hz, 1H), 6.32 (s, 1H), 3.82 (s, 3H), 3.75 (s, 3H), 3.65 (m, 1H), 2.60 (m, 2H), 2.12 (m, 1H), 1.87 (m, 1H), 1.75 (m, 2H).

Step 7: 2-((2-chloro-6-fluorobenzyl)thio)-7-(3,4-dimethoxyphenyl)-1-(4-fluorophenyl)-4,5,6,7-tetrahydro-1H-benzo[d]imidazole

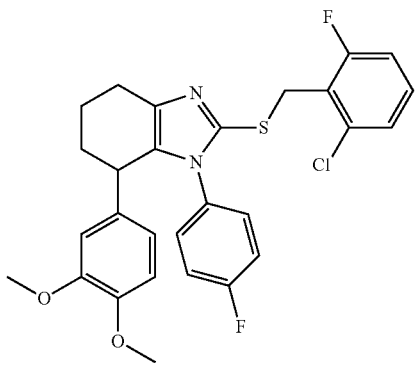 [SMILES: COc1ccc(C2CCCc3nc(SCc4c(F)cccc4Cl)n(-c4ccc(F)cc4)c32)cc1OC]

The title compound was prepared according to the procedure as described in Example 1 step 8 reacting 7-(3,4-dimethoxyphenyl)-1-(4-fluorophenyl)-4,5,6,7-tetrahydro-1H-benzo[d]imidazole-2-thiol and 2-(bromomethyl)-1-chloro-3-fluorobenzene as an off-white solid.

$^1$H NMR (400 MHz, CDCl$_3$) δ 7.11 (m, 3H), 6.90 (t, J=6.5 Hz, 1H), 6.78 (m, 2H), 6.61 (s, 1H), 6.58 (d, J=7.5 Hz, 1H), 6.35 (d, J=4.5 Hz, 2H), 4.25 (abq, J=10.5 Hz, 2H), 3.82 (s, 3H), 3.72 (s, 3H), 3.70 (m, 1H), 2.85 (m, 1H), 2.72 (m, 1H), 2.18 (m, 1H), 1.95 (m, 1H), 1.77 (m, 2H).

Example 63

(R*)-2-((2-chloro-6-fluorobenzyl)thio)-7-(3,4-dimethoxyphenyl)-1-(4-fluorophenyl)-4,5,6,7-tetrahydro-1H-benzo[d]imidazole (63a) and (S*)-2-((2-chloro-6-fluorobenzyl)thio)-7-(3,4-dimethoxyphenyl)-1-(4-fluorophenyl)-4,5,6,7-tetrahydro-1H-benzo[d]imidazole (63b)

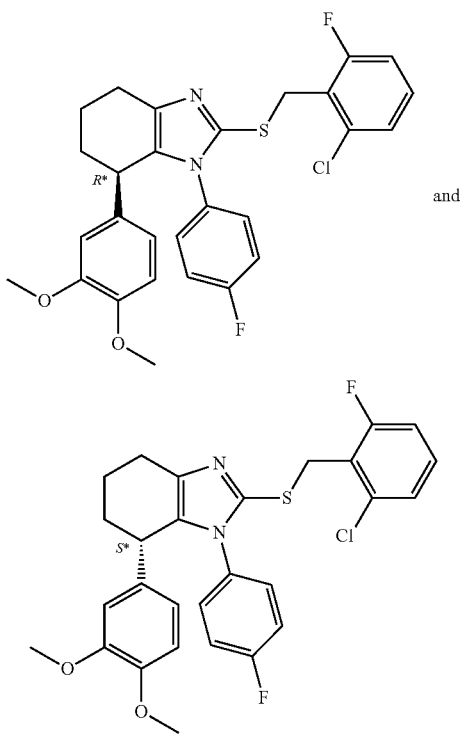

2-((2-chloro-6-fluorobenzyl)thio)-7-(3,4-dimethoxyphenyl)-1-(4-fluorophenyl)-4,5,6,7-tetrahydro-1H-benzo[d] imidazole as a racemate (50 mg) was purified by chiral SFC (CHIRALPAK AD-H 5 μM 250×20 mm) using mobile phase of 80% CO$_2$ and 20% i-PrOH to yield 20 mg R* enantiomer and 21 mg S* enantiomer as white solids. Absolute stereochemistry is arbitually assigned.

(R*)-2-((2-chloro-6-fluorobenzyl)thio)-7-(3,4-dimethoxyphenyl)-1-(4-fluorophenyl)-4,5,6,7-tetrahydro-1H-benzo[d]imidazole (63a)

First peak, ESI-MS (m/z): Calcd. For C$_{28}$H$_{25}$ClF$_2$N$_2$O$_2$S: 527.03. found: 527 (M+H).

(S*)-2-((2-chloro-6-fluorobenzyl)thio)-7-(3,4-dimethoxyphenyl)-1-(4-fluorophenyl)-4,5,6,7-tetrahydro-1H-benzo[d]imidazole (63b)

Second peak, ESI-MS (m/z): Calcd. For C$_{28}$H$_{25}$ClF$_2$N$_2$O$_2$S: 527.03. found: 527 (M+H).

Example 64

4-(((7-(3,4-dimethoxyphenyl)-1-(4-fluorophenyl)-4,5,6,7-tetrahydro-1H-benzo[d]imidazol-2-yl)thio)methyl)-3,5-difluorobenzonitrile

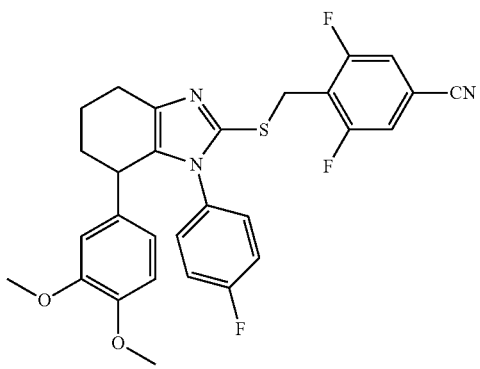 [SMILES: COc1ccc(C2CCCc3nc(SCc4c(F)cc(C#N)cc4F)n(-c4ccc(F)cc4)c32)cc1OC]

The title compound was prepared according to the procedure as described in Example 1 step 8 reacting 7-(3,4-dimethoxyphenyl)-1-(4-fluorophenyl)-4,5,6,7-tetrahydro-1H-benzo[d]imidazole-2-thiol (Prepared as described in Example 62, Step 6) and 4-cyano-2,6-difluorobenzyl methanesulfonate as an off-white solid.

$^1$H NMR (400 MHz, CDCl$_3$) δ 7.15 (d, J=6.0 Hz, 2H), 6.85 (br, m, 2H), 6.71 (br, m, 1H), 6.63 (d, J=6.5 Hz, 2H), 6.32 (d, J=5.5 Hz, 2H), 4.12 (abq, J=8.8 Hz, 2H), 3.82 (s, 3H), 3.71 (s, 3H), 3.70 (m, 1H), 2.80 (m, 1H), 2.72 (m, 1H), 1.90 (m, 1H), 1.75 (m, 2H).

Example 65

4-(((7-(3,4-dimethoxyphenyl)-1-(4-fluorophenyl)-4,5,6,7-tetrahydro-1H-benzo[d]imidazol-2-yl)thi)methyl)-3,5-difluorobenzoic acid

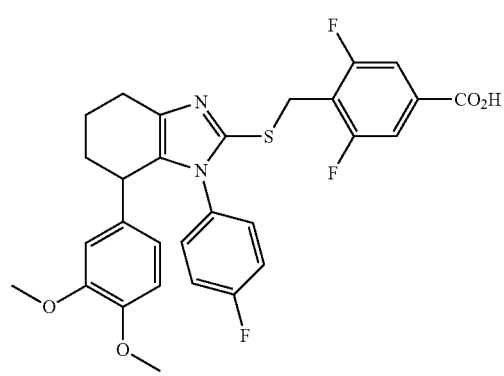 [SMILES: COc1ccc(C2CCCc3nc(SCc4c(F)cc(C(=O)O)cc4F)n(-c4ccc(F)cc4)c32)cc1OC]

4-(((7-(3,4-dimethoxyphenyl)-1-(4-fluorophenyl)-4,5,6,7-tetrahydro-1H-benzo[d]imidazol-2-yl)thio)methyl)-3,5-difluorobenzonitrile (500 mg, 0.94 mmol) in mixed solvent of MeOH (2 mL), THF (2 mL) and 1N NaOH solution (4 mL) were heated at 80° C. for 4 hours. The solvent was removed and the residue was acidified by 1N HCl to pH ~4. The residue was then extracted 3 times by ethyl acetate and the combined organic layer was washed with water and brine. The solvent was dried over anhydrous Na$_2$SO$_4$, filtered anc concentrated and purified by silica gel column chromatography system to afford the title product as a white solid (400 mg, 77% yield)

$^1$H NMR (400 MHz, CDCl$_3$) δ 7.35 (d, J=5.8 Hz, 2H), 6.90 (br, m, 2H), 6.81 (m, 1H), 6.60 (d, J=5.5 Hz, 2H), 6.35 (d, J=6.0 Hz, 2H), 4.15 (abq, J=7.5 Hz, 2H), 3.80 (s, 3H), 3.72 (s, 3H), 3.68 (m, 1H), 2.92 (m, 1H), 2.50 (m, 1H), 2.15 (m, 1H), 1.92 (m, 1H), 1.82 (m, 2H).

Example 66

4-(((7-(3,4-dimethoxyphenyl)-1-(4-fluorophenyl)-4,5,6,7-tetrahydro-1H-benzo[d]imidazol-2-yl)thio)methyl)-3,5-difluoro-N-(2,5,8,11-tetraoxatridecan-13-yl)benzamide

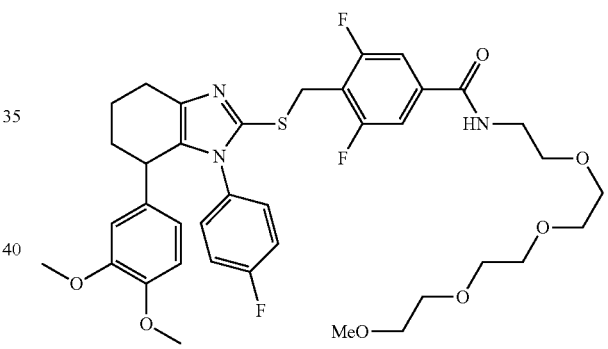

4-(((7-(3,4-dimethoxyphenyl)-1-(4-fluorophenyl)-4,5,6,7-tetrahydro-1H-benzo[d]imidazol-2-yl)thio)methyl)-3,5-difluorobenzoic acid (43 mg, 0.0775 mmol), 2,5,8,11-tetraoxatridecan-13-amine (32 mg, 0.155 mmol), HATU (59 mg, 0.155 mmol), DIPEA (0.04 mL, 0.233 mol) in DMF (1 mL) at room temperature were stirred overnight. The reaction was partitioned between DCM and water, washed with brine, dried and silica gel column purification with EA to EA (5% MeOH) to obtain the desired product as a colorless oil. The compound was dissolved in CH$_3$CN and water (1:1) and lyophilized overnight to give white solid (40 mg, 69% yield).

$^1$H NMR (400 MHz, CDCl$_3$) δ 7.81 (br, s, 1H), 7.42 (d, J=7.5 Hz, 2H), 7.02 (br, s, 3H), 6.68 (d, J=7.2 Hz, 1H), 6.35 (d, J=4.5 Hz, 2H), 6.32 (br, s, 1H), 4.21 (abq, J=9.8 Hz, 2H), 3.82 (s, 3H), 3.72 (s, 3H), 3.68 (m, 15H), 3.52 (s, 2H), 3.32 (s, 3H), 3.05 (m, 1H), 2.85 (m, 1H), 2.22 (m, 1H), 1.99 (m, 1H), 1.85 (m, 2H).

Example 67

2-((4-(2-chloroethoxy)-2,6-difluorobenzyl)thio)-7-(3,4-dimethoxyphenyl)-1-(4-fluorophenyl)-4,5,6,7-tetrahydro-1H-benzo[d]imidazole Step 1: 4-(2-chloroethoxy)-2,6-difluorobenzyl methanesulfonate

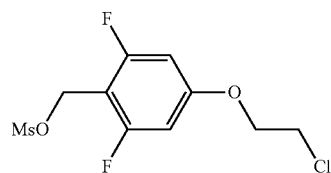 [SMILES: CS(=O)(=O)OCc1c(F)cc(OCCCl)cc1F]

The title compound was prepared according to the procedure as described in Example 23 step 1-5 starting with 3,5-difluoro-4-(hydroxymethyl)phenol and 1-iodo-2-chloroethane to afford the product as an off-white solid.

Step 2: 2-((4-(2-chloroethoxy)-2,6-difluorobenzyl)thio)-7-(3,4-dimethoxyphenyl)-1-(4-fluorophenyl)-4,5,6,7-tetrahydro-1H-benzo[d]imidazole

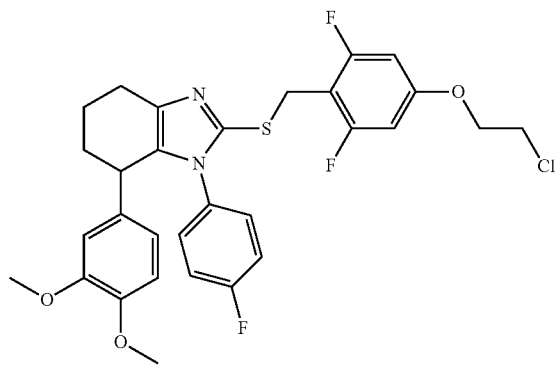 [SMILES: COc1ccc(C2CCCc3nc(SCc4c(F)cc(OCCCl)cc4F)n(-c4ccc(F)cc4)c32)cc1OC]

The title compound was prepared according to the procedure as described in Example 1 step 8 reacting 7-(3,4-dimethoxyphenyl)-1-(4-fluorophenyl)-4,5,6,7-tetrahydro-1H-benzo[d]imidazole-2-thiol (Prepared as described in Example 62, Step 6) and 4-(2-chloroethoxy)-2,6-difluorobenzyl methanesulfonate as an off-white solid.

$^1$H NMR (400 MHz, CDCl$_3$) δ 7.31 (s, 1H), 7.00 (br, s, 3H), 6.72 (d, J=6.5 Hz, 1H), 6.42 (d, J=5.8 Hz, 2H), 6.31 (m, 2H), 4.25 (abq, J=9.5 Hz, 2H), 4.18 (m, 2H), 3.88 (s, 3H), 3.85 (m, 2H), 3.78 (s, 3H), 3.70 (m, 1H), 3.05 (m, 1H), 2.90 (m, 1H), 2.20 (m, 1H), 2.02 (m, 1H), 1.85 (m, 2H).

Example 68

4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluoro-N-(2, 5, 8,11-tetraoxatridecan-13-yl)benzamide (68a) and 4-(((7-(2,3-dibromo-4,5-dimethoxyphenyl)-1-(4-fluorophenyl)-4,5,6,7-tetrahydro-1H-benzo[d]imidazol-2-yl)thio)methyl-3,5-difluoro-N-(2,5,8,11-tetraoxatridecan-13-yl) benzamide (68b)

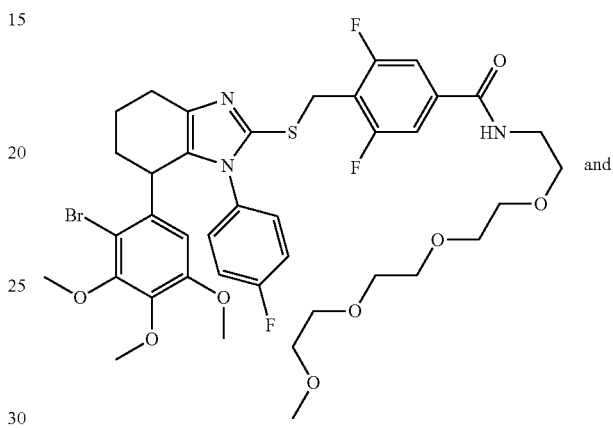

and

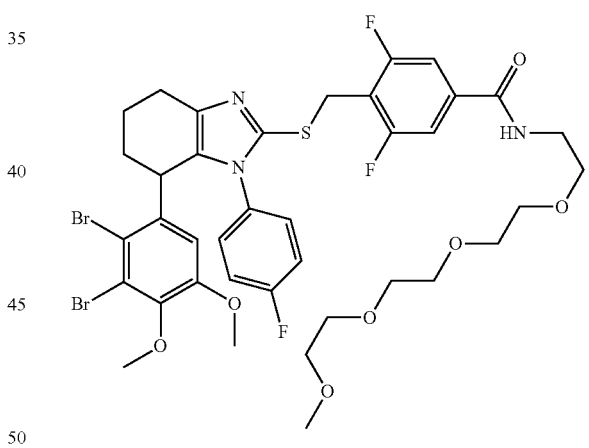

Step 1: 2-azido-6-(2-bromo-4,5-dimethoxyphenyl)cyclohexanone and 2-azido-6-(2,3-dibromo-4,5-dimethoxyphenyl)cyclohexanone

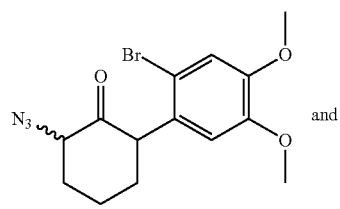

and

-continued

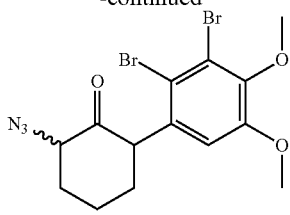

The title compounds were prepared according to the procedure as described in Example 1 step 4 by reacting the mixtures of 2-bromo-6-(3,4-dimethoxy-6-bromo-phenyl)cyclohexanone and 2-bromo-6-(3,4-dimethoxy-5,6-dibromophenyl)cyclohexanone with NaN₃ to obtain the title compounds as a light yellow solid.

Step 2: 2-amino-6-(2-bromo-4,5-dimethoxyphenyl)cyclohexanone hydrogen chloride and 2-amino-6-(2,3-dibromo-4,5-dimethoxyphenyl)cyclohexanone hydrogen chloride

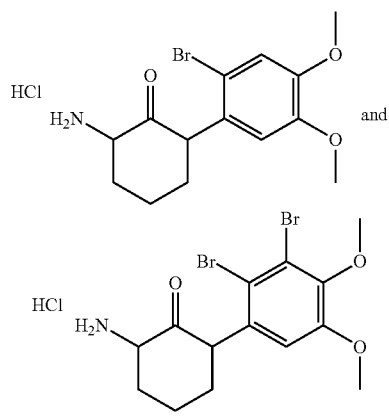

The title compounds were prepared as a brown solid according to the procedure as described in Example 1 step 5 by reacting the mixtures of 2-azido-6-(2-bromo-4,5-dimethoxyphenyl)cyclohexanone and 2-azido-6-(2,3-dibromo-4,5-dimethoxyphenyl) cyclohexanone with 5% Pd on carbon under 50 psi hydrogen in acetic acid.

Step 3: 1-(3-(2-bromo-4,5-dimethoxyphenyl)-2-oxocyclohexyl)-3-(4-fluorophenyl)thiourea and 1-(3-(2,3-dibromo-4,5-dimethoxyphenyl)-2-oxocyclohexyl)-3-(4-fluorophenyl)thiourea

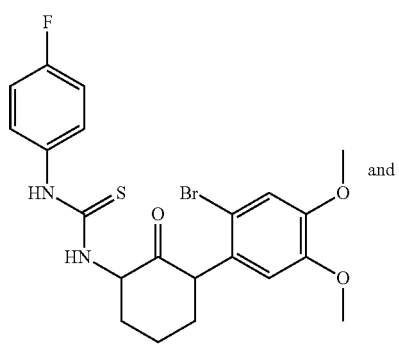

-continued

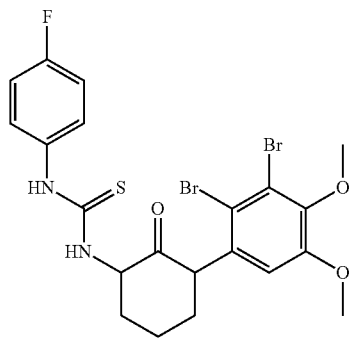

The title compounds were prepared as a mixture according to the procedure as described in Example 1 step 6 by reacting 2-amino-6-(2-bromo-4,5-dimethoxyphenyl)cyclohexanone hydrogen chloride and 2-amino-6-(2,3-dibromo-4,5-dimethoxyphenyl)cyclohexanone hydrogen chloride and 1-fluoro-4-isothiocyanatobenzene to obtain the title compounds as an off yellow solid.

Step 4: 7-(2-bromo-4,5-dimethoxyphenyl)-1-(4-fluorophenyl)-4,5,6,7-tetrahydro-1H-benzo[d]imidazole-2-thiol and 7-(2,3-dibromo-4,5-dimethoxyphenyl)-1-(4-fluorophenyl)-4,5,6,7-tetrahydro-1H-benzo[d]imidazole-2-thiol

The title compounds were prepared as a mixture according to the procedure as described in Example 1 step 7 by reacting 1-(3-(2-bromo-4,5-dimethoxyphenyl)-2-oxocyclohexyl)-3-(4-fluorophenyl)thiourea and 1-(3-(2,3-dibromo-4,5-dimethoxyphenyl)-2-oxocyclohexyl)-3-(4-fluorophenyl)thiourea in acetic acid to obtain the title compounds as an off yellow solid.

Step 5: 4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluorobenzonitrile and 4-(((7-(2,3-dibromo-4,5-dimethoxyphenyl)-1-(4-fluorophenyl)-4,5,6,7-tetrahydro-1H-benzo[d]imidazol-2-yl)thio)methyl)-3,5-difluorobenzonitrile

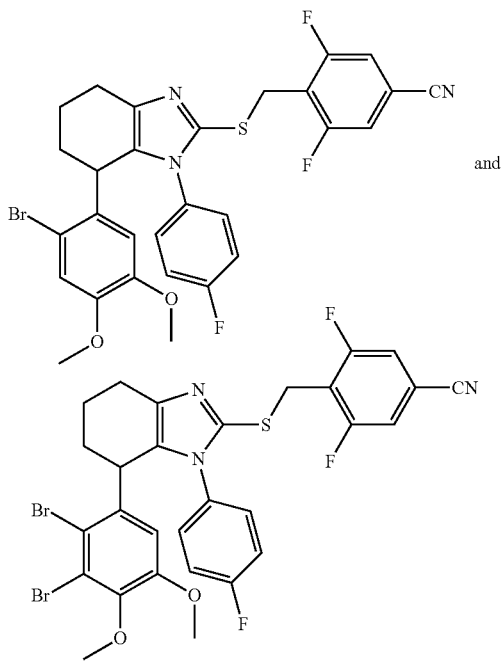

and

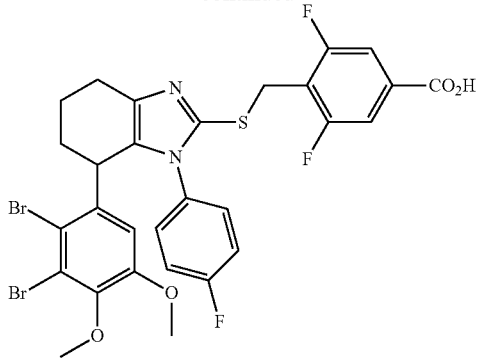

The title compound were prepared as a mixture according to the procedure as described in Example 1 step 8 by reacting 7-(2-bromo-4,5-dimethoxyphenyl)-1-(4-fluorophenyl)-4,5,6,7-tetrahydro-1H-benzo[d]imidazole-2-thiol and 7-(2,3-dibromo-4,5-dimethoxyphenyl)-1-(4-fluorophenyl)-4,5,6,7-tetrahydro-1H-benzo[d]imidazole-2-thiol and 4-cyano-2,6-difluorobenzyl methanesulfonate to obtain the title compounds as an off-white solid.

Step 6: 4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluorobenzoic acid and 4-(((7-(2,3-dibromo-4,5-dimethoxyphenyl)-1-(4-fluorophenyl)-4,5,6,7-tetrahydro-1H-benzo[d]imidazol-2-yl)thio)methyl)-3,5-difluorobenzoic acid

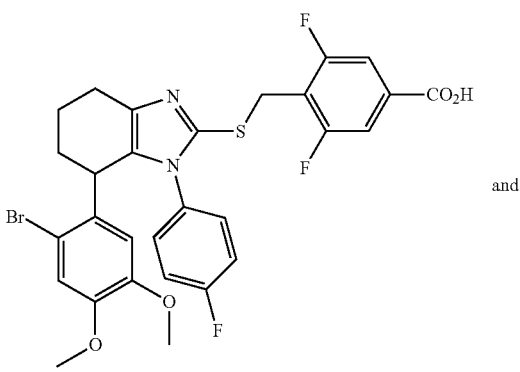

and

The title compounds were prepared according to the procedure as described in Example 65 by hydrolysis of 4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluorobenzonitrile and 4-(((7-(2, 3-dibromo-4,5-dimethoxyphenyl)-1-(4-fluorophenyl)-4,5,6,7-tetrahydro-1H-benzo[d]imidazol-2-yl)thio)methyl)-3,5-difluorobenzonitrile with NaOH in water and purified by silica gel column to afford 4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluorobenzoic acid and 4-(((7-(2,3-dibromo-4,5-dimethoxyphenyl)-1-(4-fluorophenyl)-4,5,6,7-tetrahydro-1H-benzo[d]imidazol-2-yl)thio)methyl)-3,5-difluorobenzoic acid as two off-white solids.

4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluorobenzoic acid ESI-MS (m/z): Calcd. For $C_{29}H_{24}BrF_3N_2O_4S$: 633.48. found: 634 (M+H).

4-(((7-(2,3-dibromo-4,5-dimethoxyphenyl)-1-(4-fluorophenyl)-4,5,6,7-tetrahydro-1H-benzo[d]imidazol-2-yl)thio)methyl)-3,5-difluorobenzoic acid ESI-MS (m/z): Calcd. For $C_{28}H_{25}ClF_2N_2O_2S$: 712.37. found: 713 (M+H).

Step 7: 4-(((7-(2-bromo-4,5-dimethoxyphenyl)-1-(4-fluorophenyl)-4,5,6,7-tetrahydro-1H-benzo[d]imidazol-2-yl)thio)methyl)-3,5-difluoro-N-(2,5,8,11-tetraoxatridecan-13-yl)benzamide (68a)

The title compound was prepared according to the procedure as described in Example 66 by coupling 4-(((7-(2-bromo-4,5-dimethoxyphenyl)-1-(4-fluorophenyl)-4,5,6,7-tetrahydro-1H-benzo[d] imidazol-2-yl)thio)methyl)-3,5-difluorobenzoic acid (prepared through synthetic sequences in Example 1 step 4-7) with 2,5,8,11-tetraoxatridecan-13-amine using HATU to obtain the title compound as a white solid.

$^1$H NMR (400 MHz, CDCl$_3$) δ 7.82 (br, s, 1H), 7.42 (d, J=7.6 Hz, 2H), 6.50 (s, 1H), 6.23 (s, 1H), 4.21 (m, 2H), 3.81 (s, 3H), 3.75 (s, 3H), 3.65 (m, 16H), 3.54 (m, 1H), 3.31 (s, 3H), 2.95 (m, 1H), 2.22 (m, 1H), 2.05 (m, 1H), 1.85 (m, 2H).

Step 8: 4-(((7-(2,3-dibromo-4,5-dimethoxyphenyl)-1-(4-fluorophenyl)-4,5,6,7-tetrahydro-1H-benzo[d] imidazol-2-yl)thio)methyl)-3,5-difluoro-N-(2,5,8,11-tetraoxatridecan-13-yl) benzamide (68b)

The title compound was prepared according to the procedure as described in Example 66 by coupling 4-(((7-(2,3- dibromo-4,5-dimethoxyphenyl)-1-(4-fluorophenyl)-4,5,6,7-tetrahydro-1H-benzo[d]imidazol-2-yl)thio)methyl)-3,5-difluorobenzoic acid (prepared through synthetic sequences in Example 1 step 4-7) with 2,5,8,11-tetraoxatridecan-13-amine using HATU to obtain the title compound as a white solid.

$^1$H NMR (400 MHz, CDCl$_3$) δ 7.81 (br, s, 1H), 7.42 (d, J=7.8 Hz, 2H), 6.38 (s, 1H), 4.51 (m, 1H), 4.25 (m, 2H), 3.81 (s, 6H), 3.72 (m, 14H), 3.55 (m, 2H), 3.31 (s, 3H), 2.95 (m, 2H), 2.21 (m, 1H), 2.02 (m, 1H), 1.85 (m, 1H), 1.77 (m, 1H).

Example 69

2-((2,6-difluoro-4-(2-(pyrrolidin-1-yl)ethoxy)benzyl)thio)-7-(3,4-dimethoxyphenyl)-1-(4-fluorophenyl)-4,5,6,7-tetrahydro-1H-benzo[d]imidazole

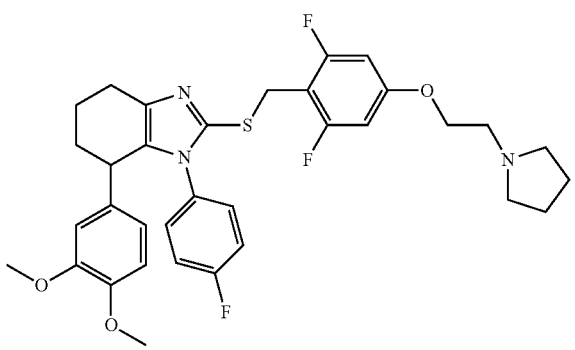 [SMILES: COc1ccc(C2CCCc3nc(SCc4c(F)cc(OCCN5CCCC5)cc4F)n(-c4ccc(F)cc4)c32)cc1OC]

The title compound was prepared according to the procedure described in Example 27 step 2 by coupling 2-((4-(2-chloroethoxy)-2,6-difluorobenzyl)thio)-7-(3,4-dimethoxyphenyl)-1-(4-fluorophenyl)-4,5,6,7-tetrahydro-1H-benzo[d]imidazole (prepared as described in Example 67 Step 2) and pyrrolidine in the presence of Cs$_2$CO$_3$ to afford the desired product as a yellow solid.

$^1$H NMR (400 MHz, CDCl$_3$) δ 7.55 (s, 1H), 6.86 (m, 2H), 6.72 (br, s, 1H), 6.62 (d, J=6.5 Hz, 1H), 6.38 (m, 4H), 4.15 (abq, J=8.5 Hz, 2H), 4.05 (t, J=6.5 Hz, 2H), 3.82 (s, 3H), 3.75 (s, 3H), 3.68 (m, 1H), 2.85 (t, J=6.5 Hz, 2H), 2.80 (m, 1H), 2.75 (m, 1H), 2.65 (m, 4H), 2.10 (m, 1H), 1.95 (m, 1H), 1.85 (m, 2H), 1.80 (m, 4H).

Example 70

2-((2-chloro-6-fluorobenzyl)thio)-1-(4-fluorophenyl)-7-(3-methoxyphenyl)-4, 5, 6, 7-tetrahydro-1H-benzo[d]imidazole Step 1:
2-bromo-6-(3-methoxyphenyl)cyclohexanone

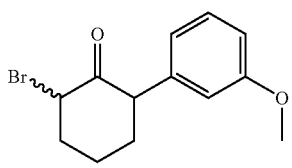 [SMILES: COc1cccc(C2CCCC(Br)C2=O)c1]

The title compound was prepared according to the procedure as described in Example 1 step 2-3 reacting 2-(3-methoxyphenyl)cyclohexanone (Aldrich) with TMSOTf/TEA followed by NBS as light yellow solid.

ESI-MS (m/z): Calcd. For C$_{13}$H$_{15}$BrO$_2$: 283.16. found: 203 (M+H).

Step 2: 2-azido-6-(3-methoxyphenyl)cyclohexanone

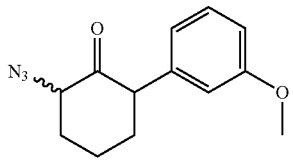

The title compound was prepared according to the procedure as described in Example 1 step 4 reacting 2-bromo-6-(3-methoxyphenyl)cyclohexanone with NaN$_3$ as light yellow solid.

ESI-MS (m/z): Calcd. For C$_{13}$H$_{15}$N$_3$O$_2$: 245.28. found: 204 (M−N$_3$+H).

Step 3:
2-amino-6-(3-methoxyphenyl)cyclohexanone hydrogen chloride

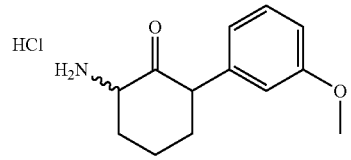 [SMILES: Cl ; COc1cccc(C2CCCC(N)C2=O)c1]

The title compound was prepared as brown solid according to the procedure as described in Example 1 step 5 by reacting 2-azido-6-(3-methoxyphenyl)cyclohexanone with 5% Pd on carbon under 50 psi hydrogen gas.

ESI-MS (m/z): Calcd. For C$_{13}$H$_{17}$NO$_2$: 219.28. found: 220 (M+H).

Step 4: 1-(3-(3-methoxyphenyl)-2-oxocyclohexyl)-3-(4-fluorophenyl)thiourea

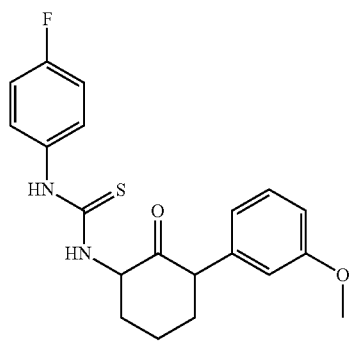 [SMILES: COc1cccc(C2CCCC(NC(=S)Nc3ccc(F)cc3)C2=O)c1]

The title compound was prepared according to the procedure as described in Example 1 step 6 reacting 2-amino- 6-(3-methoxyphenyl)cyclohexanone hydrogen chloride salt and 1-fluoro-4-isothiocyanatobenzene as off yellow solid.

ESI-MS (m/z): Calcd. For $C_{20}H_{21}FN_2O_2S$: 372.46. found: 373 (M+H).

Step 5: 7-(3-methoxyphenyl)-1-(4-fluorophenyl)-4,5,6,7-tetrahydro-1H-benzo[d]imidazole-2-thiol

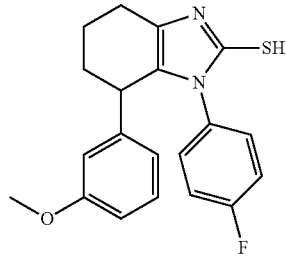 [SMILES: COc1cccc(C2CCCc3nc(S)n(-c4ccc(F)cc4)c32)c1]

The title compound was prepared according to the procedure as described in Example 1 step 7 reacting 1-(3-(3-methoxyphenyl)-2-oxocyclohexyl)-3-(4-fluorophenyl)thiourea in acetic acid as off yellow solid.

$^1$H NMR (400 MHz, CDCl$_3$) δ 6.85 (m, 4H), 6.70 (d, J=7.5 Hz, 1H), 6.42 (d, J=7.5 Hz, 1H), 3.75 (s, 3H), 3.66 (m, 1H), 2.68 (m, 2H), 2.20 (m, 1H), 1.85 (m, 1H), 1.73 (m, 2H).

Step 6: 2-((2-chloro-6-fluorobenzyl)thio)-1-(4-fluorophenyl)-7-(3-methoxyphenyl)-4,5,6,7-tetrahydro-1H-benzo[d]imidazole

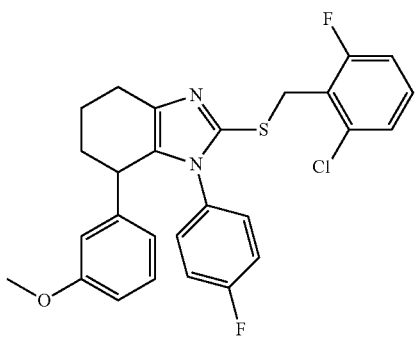 [SMILES: COc1cccc(C2CCCc3nc(SCc4c(F)cccc4Cl)n(-c4ccc(F)cc4)c32)c1]

The title compound was prepared according to the procedure as described in Example 1 step 8 reacting 7-(3-methoxyphenyl)-1-(4-fluorophenyl)-4,5,6,7-tetrahydro-1H-benzo[d]imidazole-2-thiol and 2-(bromomethyl)-1-chloro-3-fluorobenzene as an off-white solid.

$^1$H NMR (400 MHz, CDCl$_3$) δ 7.15 (m, 3H), 7.08 (t, J=7.5 Hz, 1H), 6.91 (t, J=6.0 Hz, 1H), 6.75 (m, 2H), 6.62 (d, J=6.5 Hz, 1H), 6.60 (m, 1H), 6.42 (d, J=7.0 Hz, 1H), 6.35 (s, 1H), 4.25 (abq, J=14.5, 8.9 Hz, 2H), 3.72 (s, 3H), 2.85 (m, 1H), 2.72 (m, 1H), 2.15 (m, 1H), 1.90 (m, 1H), 1.81 (m, 2H).

Example 71

2-(((3,5-difluoropyridin-4-yl)methyl)thio)-1-(4-fluorophenyl)-7-(3-methoxyphenyl)-4,5,6,7-tetrahydro-1H-benzo[d]imidazole

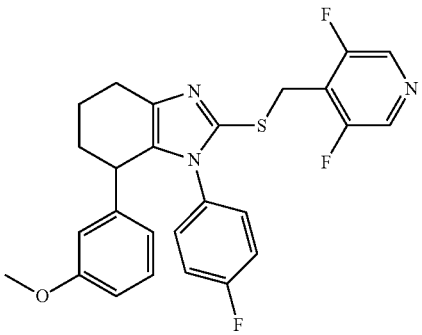 [SMILES: COc1cccc(C2CCCc3nc(SCc4c(F)cncc4F)n(-c4ccc(F)cc4)c32)c1]

The title compound was prepared according to the procedure as described in Example 1 step 8 reacting 7-(3-methoxyphenyl)-1-(4-fluorophenyl)-4,5,6,7-tetrahydro-1H-benzo[d]imidazole-2-thiol and (3,5-difluoropyridin-4-yl)methyl methanesulfonate to give the title compound as an off-white solid.

ESI-MS (m/z): Calcd. For $C_{26}H_{22}N_3OS$: 481.53. found: 482 (M+H).

Example 72

2-(((3,5-difluoropyridin-4-yl)methyl)thio)-1-(4-fluoro-3-methoxyphen)-7-(3-methoxyphenyl)-4,5,6,7-tetrahydro-1H-benzo[d]imidazole Step 1: 1-(4-fluoro-3-methoxyphenyl)-7-(3-methoxyphenyl)-4,5,6,7-tetrahydro-1H-benzo[d]imidazole-2-thiol

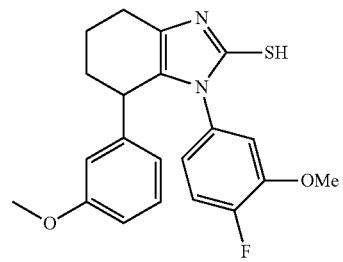 [SMILES: COc1cccc(C2CCCc3nc(S)n(-c4ccc(F)c(OC)c4)c32)c1]

The title compound was prepared according to the procedure as described in Example 70 step 4 by reacting 2-amino-6-(3-methoxyphenyl)cyclohexanone hydrogen chloride salt (Prepared as described in Example 70, Step 3) with 1-fluoro-2-methoxy-4-isothiocyanatobenzene, followed by further reaction with 1-(3-(3-methoxyphenyl)-2-oxocyclohexyl)-3-(3-methoxy-4-fluorophenyl)thiourea in acetic acid according to the procedure described in Example 70, Step 5, to afford the title product as a white solid.

ESI-MS (m/z): Calcd. For $C_{21}H_{21}N_2O_2S$: 384.47. found: 385 (M+H).

Step 2: 2-(((3,5-difluoropyridin-4-yl)methyl)thio)-1-(4-fluoro-3-methoxyphenyl)-7-(3-methoxyphenyl)-4,5,6,7-tetrahydro-1H-benzo[d]imidazole

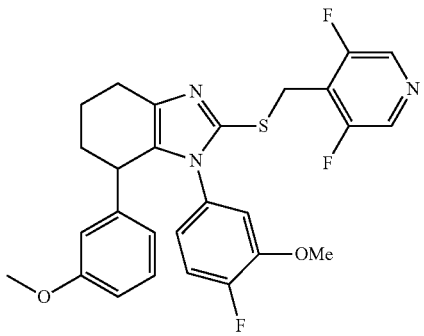 [SMILES: COc1cccc(C2CCCc3nc(SCc4c(F)cncc4F)n(-c4ccc(F)c(OC)c4)c32)c1]

The title compound was prepared according to the procedure as described in Example 1 step 8 reacting 1-(4-fluoro-3-methoxyphenyl)-7-(3-methoxyphenyl)-4,5,6,7-tetrahydro-1H-benzo[d]imidazole-2-thiol and (3,5-difluoropyridin-4-yl)methyl methanesulfonate as an off-white solid.

ESI-MS (m/z): Calcd. For $C_{27}H_{24}F_3N_3O_2S$: 511.56. found: 512 (M+H).

Example 73

3,5-difluoro-4-(((7-(4-fluoro-3-methoxyphenyl)-1-(4-fluorophenyl)-4,5,6,7-tetrahydro-1H-benzo[d]imidazol-2-yl)thio)methyl)benzonitrile Step 1: 2-(3-methoxy-4-fluorophenyl)cyclohexanone

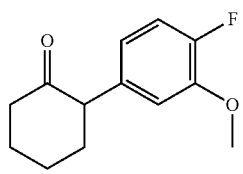 [SMILES: COc1cc(C2CCCCC2=O)ccc1F]

The title compound was prepared according to the procedure as described in Example 1 step 1 reacting cyclohexanone and 4-bromo-1-fluoro-2-methoxybenzene as a white solid.

Step 2: 2-bromo-6-(3-methoxy-4-fluorophenyl)cyclohexanone

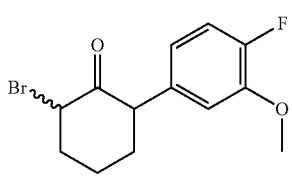 [SMILES: COc1cc(C2CCCC(Br)C2=O)ccc1F]

The title compound was prepared according to the procedure as described in Example 1 step 2-3 reacting 2-(3-methoxy-4-fluorophenyl)cyclohexanone with TMSOTf/TEA followed by NBS as light yellow solid.

ESI-MS (m/z): Calcd. For $C_{13}H_{14}BrFO_2$: 301.15. found: 221 (M–Br+H).

Step 3: 2-azido-6-(3-methoxy4-fluorophenyl)cyclohexanone

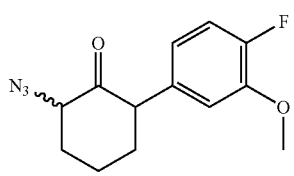 [SMILES: COc1cc(C2CCCC(N=[N+]=[N-])C2=O)ccc1F]

The title compound was prepared according to the procedure as described in Example 1 step 4 reacting 2-bromo-6-(3-methoxy-4-fluorophenyl)cyclohexanone with $NaN_3$ as light yellow solid.

ESI-MS (m/z): Calcd. For $C_{13}H_{14}FN_3O_2$: 263.27. found: 222 (M–$N_3$+H).

Step 4: 2-amino-6-(3-methoxy-4-fluorophenyl)cyclohexanone hydrogen chloride

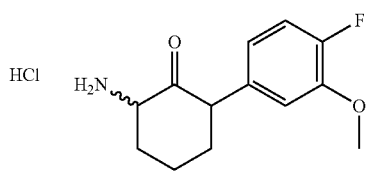 [SMILES: Cl ; COc1cc(C2CCCC(N)C2=O)ccc1F]

The title compound was prepared as brown solid according to the procedure as described in Example 1 step 5 by reacting 2-azido-6-(3-methoxy4-fluorophenyl)cyclohexanone with 5% Pd on carbon under 50 psi hydrogen gas.

ESI-MS (m/z): Calcd. For $C_{13}H_{16}FNO_2$: 237.27. found: 238 (M+H).

Step 5: 1-(3-(3-methoxy-4-fluorophenyl)-2-oxocyclohexyl)-3-(4-fluorophenyl)thiourea

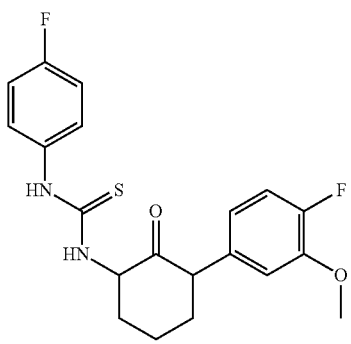 [SMILES: COc1cc(C2CCCC(NC(=S)Nc3ccc(F)cc3)C2=O)ccc1F]

The title compound was prepared according to the procedure as described in Example 1 step 6 reacting 2-amino- 6-(3-methoxy-4-fluorophenyl)cyclohexanone hydrogen chloride salt and 1-fluoro-4-isothiocyanatobenzene as off yellow solid.

ESI-MS (m/z): Calcd. For $C_{20}H_{20}F_2N_2O_2S$: 390.45. found: 391 (M+H).

Step 6: 7-(3-methoxy-4-fluorophenyl)-1-(4-fluorophenyl)-4,5,6,7-tetrahydro-1H-benzo[d]imidazole-2-thiol

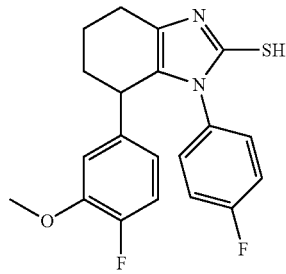 [SMILES: COc1cc(C2CCCc3nc(S)n(-c4ccc(F)cc4)c32)ccc1F]

The title compound was prepared as off yellow solid by reacting 1-(3-(3-methoxy-4-fluorophenyl)-2-oxocyclohexyl)-3-(4-fluorophenyl)thiourea with acetic acid according to the procedure as described in Example 1 step 7.

ESI-MS (m/z): Calcd. For $C_{20}H_{22}F_2N_2O_3S$: 372.43. found: 373 (M+H).

Step 7: 3,5-difluoro-4-(((7-(4-fluoro-3-methoxyphenyl)-1-(4-fluorophenyl)-4,5,6,7-tetrahydro-1H-benzo[d]imidazol-2-yl)thio)methyl)benzonitrile

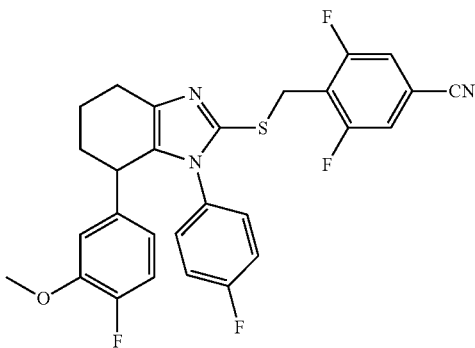 [SMILES: COc1cc(C2CCCc3nc(SCc4c(F)cc(C#N)cc4F)n(-c4ccc(F)cc4)c32)ccc1F]

The title compound was prepared according to the procedure as described in Example 1 step 8 reacting 7-(3-methoxy-4-fluorophenyl)-1-(4-fluorophenyl)-4,5,6,7-tetrahydro-1H-benzo[d]imidazole-2-thiol and 4-cyano-2,6-difluorobenzyl methanesulfonate as an off-white solid.

$^1$H NMR (400 MHz, CDCl$_3$) δ 7.15 (d, J=6.8 Hz, 2H), 6.82 (m, 2H), 6.80 (m, J=8.8 Hz, 2H), 6.72 (m, 1H), 6.42 (d, J=6.5 Hz, 1H), 6.30 (m, J=4.0 Hz, 1H), 4.10 (s, 2H), 3.75 (s, 3H), 3.70 (m, 1H), 2.78 (m, 1H), 2.64 (m, 1H), 2.18 (m, 1H), 1.85 (m, 1H), 1.74 (m, 2H).

Example 74

3,5-difluoro-4-(((7-(4-fluoro-3-methoxyphenyl)-1-(4-fluorophenyl)-4,5,6,7-tetrahydro-1H-benzo[d]imidazol-2-yl)thio)methyl)benzoic acid

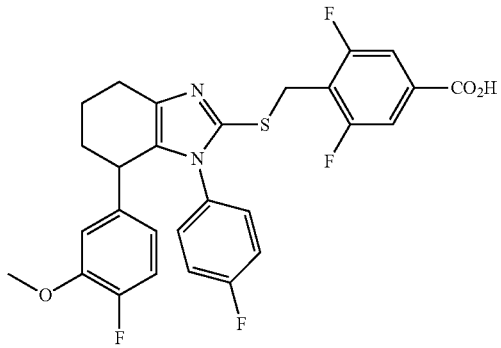 [SMILES: COc1cc(C2CCCc3nc(SCc4c(F)cc(C(=O)O)cc4F)n(-c4ccc(F)cc4)c32)ccc1F]

The title compound was prepared according to the procedure as described in Example 65 by reacting 3,5-difluoro-4-(((7-(4-fluoro-3-methoxyphenyl)-1-(4-fluorophenyl)-4,5,6,7-tetrahydro-1H-benzo[d]imidazol-2-yl)thio)methyl)benzonitrile (Prepared as described in Example 73, Step 7) in aqueous alkaline solution to give the title compound as a white solid.

$^1$H NMR (400 MHz, CDCl$_3$) δ 7.28 (d, J=7.1 Hz, 2H), 6.82 (d, J=7.0 Hz, 3H), 6.65 (m, 1H), 6.48 (d, J=6.5 Hz, 1H), 6.31 (d, J=6.1 Hz, 1H), 5.81 (m, 1H), 4.05 (abq, J=12.5, 7.0 Hz, 2H), 3.78 (s, 3H), 3.70 (m, 1H), 2.75 (m, 2H), 2.12 (m, 1H), 1.90 (m, 1H), 1.75 (m, 2H).

Example 75

3,5-difluoro-4-(((7-(4-fluoro-3-methoxyphenyl)-1-(4-fluorophenyl)-4,5,6,7-tetrahydro-1H-benzo[d]imidazol-2-yl)thio)methyl)-N-(2,5,8,11-tetraoxatridecan-13-yl)benzamide

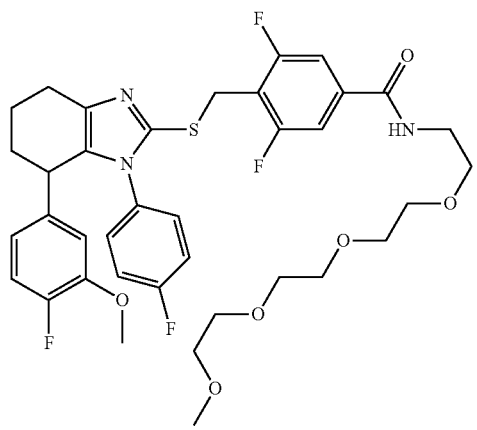 [SMILES: COCCOCCOCCOCCNC(=O)c1cc(F)c(CSc2nc3c(n2-c2ccc(F)cc2)C(c2ccc(F)c(OC)c2)CCC3)c(F)c1]

The title compound was prepared according to the procedure as described in Example 66 coupling 3,5-difluoro-4-(((7-(4-fluoro-3-methoxyphenyl)-1-(4-fluorophenyl)-4,5,6,7-tetrahydro-1H-benzo[d]imidazol-2-yl)thio)methyl)benzoic acid with 2,5,8,11-tetraoxatridecan-13-amine using HATU to give the title compound as a white solid.

¹H NMR (400 MHz, CDCl₃) δ 8.05 (s, 1H), 7.32 (d, J=8.1 Hz, 2H), 6.98 (m, 1H), 6.82 (t, J=7.2 Hz, 2H), 6.67 (br, s, 1H), 6.42 (d, J=6.8 Hz, 1H), 6.31 (m, 1H), 4.15 (m, 2H), 3.75 (s, 3H), 3.70 (s, 3H), 3.65 (m, 16H), 3.51 (m, 1H), 3.32 (s, 3H), 2.75 (m, 2H), 2.15 (m, 1H), 1.90 (m, 1H), 1.78 (m, 2H).

Example 76

7-(3-chloro-4-methoxyphenyl)-2-(2-chloro-6-fluorobenzylthio)-1-(4-fluorophenyl)-4,5,6,7-tetrahydro-1H-benzo[d]imidazole trifluoroacetic acid Step 1: 2-(3-chloro-4-methoxyphenyl)cyclohexan-1-one

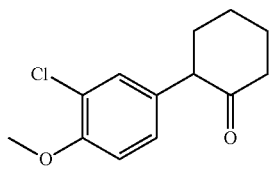 [SMILES: COc1ccc(C2CCCCC2=O)cc1Cl]

The title compound was prepared according to the procedure as described in Example 1 step 1 reacting cyclohexanone and 4-bromo-1-chloro-2-methoxybenzene as a white solid.

Mass spectrum (ESI, m/z): Calcd. for C₁₃H₁₅C₁O₂, 239.1 (M+H). found 239.1.

Step 2: 7-(3-chloro-4-methoxyphenyl)-1-(4-fluorophenyl)-4,5,6,7-tetrahydro-1H-1,3-benzodiazole-2-thiol

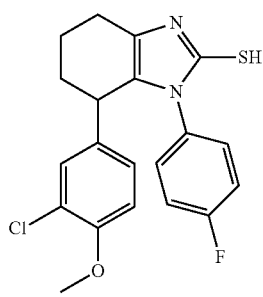 [SMILES: COc1ccc(C2CCCc3nc(S)n(-c4ccc(F)cc4)c32)cc1Cl]

The title compound was prepared according to the procedure as described in Example 1 step 2-7 to afford the product as a white solid. Mass spectrum (ESI, m/z): Calcd. for C₂₀H₁₈ClFN₂OS, 389.1 (M+H). found 389.1.

Step 3: 7-(3-chloro-4-methoxyphenyl)-2-(2-chloro-6-fluorobenzylthio)-1-(4-fluorophenyl)-4,5,6,7-tetrahydro-1H-benzo[d]imidazole trifluoroacetic acid

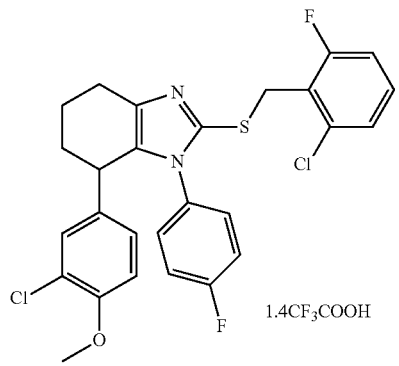 [SMILES: COc1ccc(C2CCCc3nc(SCc4c(F)cccc4Cl)n(-c4ccc(F)cc4)c32)cc1Cl]

1.4CF₃COOH

The title compound was prepared according to the procedure as described in Example 1 step 8 by reacting 7-(3-chloro-4-methoxyphenyl)-1-(4-fluorophenyl)-4,5,6,7-tetrahydro-1H-1,3-benzodiazole-2-thiol and 2-(bromomethyl)-1-chloro-3-fluorobenzene to afford the product as an off-white solid.

¹H NMR (300 MHz, CD₃OD) δ: 7.23-7.33 (m, 2H), 7.04-7.10 (m, 1H), 6.76-6.80 (m, 4H), 6.65-6.68 (m, 1H), 4.07-4.23 (m, 2H), 3.83-3.8 (m, 1H), 3.78 (s, 3H), 2.70-2.78 (m, 2H), 1.76-1.93 (m, 4H). ¹⁹F NMR (300 MHz, CD₃OD) δ: −76.97, −112.81, −115.13. Mass spectrum (ESI, m/z): Calcd. for C₂₉.₈H₂₃.₄Cl₂F₆.₂N₂O₃.₈S, 531.1 (M−1.4CF₃COOH+H). found 531.2.

Example 77

2-[[(2-chloro-6-fluorophenyl)methyl]sulfanyl]-7-(2,3-dihydro-1, 4-benzodioxin-6-yl)-1-(4-fluorophenyl)-4,5,6,7-tetrahydro-1H-1,3-benzodiazole Step 1: 2-(2,3-dihydro-1,4-benzodioxin-6-yl)cyclohexan-1-one

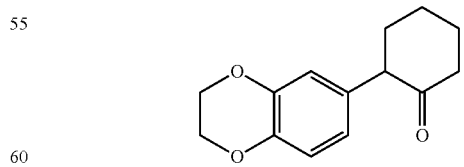

The title compound was prepared according to the procedure as described in Example 1 step 1 reacting cyclohexanone and 6-bromo-2,3-dihydrobenzo[b][1,4]dioxine as a white solid. Mass spectrum (ESI, m/z): Calcd. for C₁₄H₁₆O₃, 233.1 (M+H). found 233.1.

161

Step 2: 7-(2,3-dihydro-1,4-benzodioxin-6-yl)-1-(4-fluorophenyl)-4,5,6,7-tetrahydro-1H-1,3-benzodiazole-2-thiol

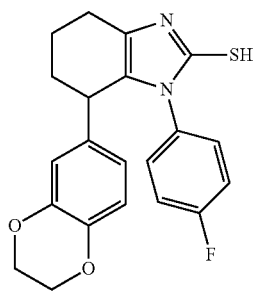 [SMILES: Fc1ccc(-n2c(S)nc3c2C(c2ccc4c(c2)OCCO4)CCC3)cc1]

The title compound was prepared according to the procedure as described in Example 1 step 2-7 to afford the product as a white solid. Mass spectrum (ESI, m/z): Calcd. for $C_{21}H_{19}FN_2O_2S$, 383.1 (M+H). found 383.1.

Step 3: 2-[[(2-chloro-6-fluorophenyl)methyl]sulfanyl]-7-(2,3-dihydro-1,4-benzodioxin-6-yl)-1-(4-fluorophenyl)-4,5,6,7-tetrahydro-1H-1,3-benzodiazole

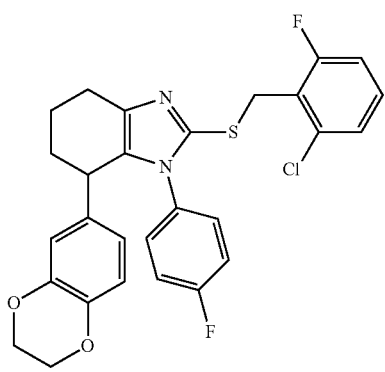 [SMILES: Fc1ccc(-n2c(SCc3c(F)cccc3Cl)nc3c2C(c2ccc4c(c2)OCCO4)CCC3)cc1]

The title compound was prepared according to the procedure as described in Example 1 step 8 reacting 7-(2,3-dihydro-1,4-benzodioxin-6-yl)-1-(4-fluorophenyl)-4,5,6,7-tetrahydro-1H-1,3-benzodiazole-2-thiol and 2-(bromomethyl)-1-chloro-3-fluorobenzene to afford the product as an off-white solid. $^1$H NMR (300 MHz, CD$_3$OD) δ: 7.21-7.31 (m, 2H), 7.01-7.19 (m, 1H), 6.81 (br, 1H), 6.66-6.69 (m, 1H), 6.47-6.58 (m, 1H), 6.21-6.32 (m, 2H), 4.14-4.26 (m, 5H), 3.95-4.00 (m, 1H), 3.67-3.71 (m, 1H), 2.59-2.76 (m, 2H), 2.06-2.15 (m, 1H), 1.82-1.95 (m, 1H), 1.69-1.78 (m, 2H). Mass spectrum (ESI, m/z): Calcd. for $C_{28}H_{23}ClF_2N_2O_2S$, 525.1 (M+H). found 525.1.

162

Example 78

7-(4-chloro-3-methoxyphenyl)-2-[[(2-chloro-6-fluorophenyl)methyl]sulfanyl]-1-(4-fluorophenyl)-7-methyl-4,5,6,7-tetrahydro-1H-1,3-benzodiazole Step 1: 2-(4-chloro-3-methoxyphenyl)-2-methylcyclohexan-1-one

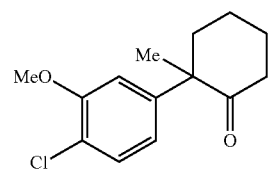 [SMILES: COc1cc(C2(C)CCCCC2=O)ccc1Cl]

A solution of 2-(4-chloro-3-methoxyphenyl) cyclohexan-1-one (10 g, 41.89 mmol, 1.00 equiv), tert-butanol (40 mL), and t-BuOK (5 g, 44.56 mmol, 1.05 equiv) was stirred for 30 min at room temperature followed by the addition of iodomethane (12 g, 84.54 mmol, 2.00 equiv). The resulting solution was stirred for 3 h at room temperature, quenched by the addition of 300 mL of water, and concentrated under vacuum. The reaction was extracted with 3×500 mL of dichloromethane and the combined organic layers were washed with 1×500 mL of brine, dried over Na$_2$SO$_4$, filtered, and concentrated under vacuum. Chromatography using a C18 column with H$_2$O/MeCN as mobile phase (10%-90% in 45 mins) gave the title compound as an off-white solid. Mass spectrum (ESI, m/z): Calcd. for $C_{14}H_{17}C_1O_2$, 253.2 (M+H). found 253.2.

Step 2: [[6-(4-chloro-3-methoxyphenyl)-6-methylcyclohex-1-en-1-yl]oxy]trimethylsilane

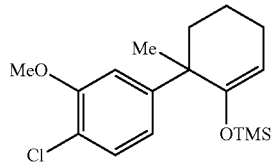

A solution of 2-(4-chloro-3-methoxyphenyl)-2-methylcyclohexan-1-one (7.5 g, 29.68 mmol, 1.00 equiv), dichloromethane (20 mL), TEA (4.5 g, 44.47 mmol, 1.50 equiv), and TMSOTf (7.9 g, 1.20 equiv) was stirred for 30 min at 0° C. The resulting mixture was concentrated under vacuum to give the title compound as a light yellow solid.

Step 3: 6-bromo-2-(4-chloro-3-methoxyphenyl)-2-methylcyclohexan-1-one

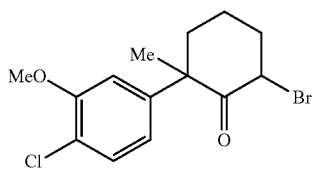

A solution of [[6-(4-chloro-3-methoxyphenyl)-6-methyl-cyclohex-1-en-1-yl]oxy]trimethylsilane (9.6 g, 29.55 mmol, 1.00 equiv) in tetrahydrofuran (20 mL) was treated with NBS (5.3 g, 29.78 mmol, 1.00 equiv) batchwise at 0° C. The reaction was stirred for 30 min at 0° C. and concentrated under vacuum to give the title compound as a light yellow solid.

Step 4: 6-azido-2-(4-chloro-3-methoxyphenyl)-2-methylcyclohexan-1-one

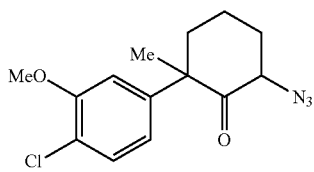 [SMILES: COc1cc(C2(C)CCCC(N=[N+]=[N-])C2=O)ccc1Cl]

A solution of 6-bromo-2-(4-chloro-3-methoxyphenyl)-2-methylcyclohexan-1-one (9.8 g, 29.55 mmol, 1.00 equiv), N,N-dimethylformamide (10 mL), and NaN$_3$ (9.7 g, 149.21 mmol, 5.00 equiv) was stirred for 1 h at room temperature and quenched by the addition of 30 mL of water. The reaction was extracted with 3×50 mL of ethyl acetate, and the combined organic layers were washed with 1×50 mL of brine, dried over anhydrous sodium sulfate, filtered, and concentrated under vacuum. Silica gel column chromatography with ethyl acetate/petroleum ether (1:10) gave the title compound as a light yellow solid. Mass spectrum (ESI, m/z): Calcd. for $C_{14}H_{16}ClN_3O_2$, 294.1 (M+H). found 294.1.

Step 5: 6-amino-2-(4-chloro-3-methoxyphenyl)-2-methylcyclohexanone hydrochloride

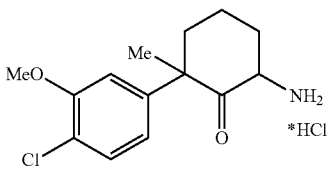 [SMILES: COc1cc(C2(C)CCCC(N)C2=O)ccc1Cl]

A suspension of 6-azido-2-(4-chloro-3-methoxyphenyl)-2-methylcyclohexan-1-one (6 g, 20.43 mmol, 1.00 equiv), methanol (30 mL), hydrogen chloride (3 mL), and palladium carbon (6 g) under H$_2$ atmosphere was stirred for 1 h at room temperature, filtered, and concentrated under vacuum to give the title compound as a light yellow solid. Mass spectrum (ESI, m/z): Calcd. for $C_{14}H_{18}ClNO_2$, 268.1 (M–HCl+H). found 268.1.

Step 6: 3-[3-(4-chloro-3-methoxyphenyl)-3-methyl-2-oxocyclohexyl]-1-(4-fluorophenyl)thiourea

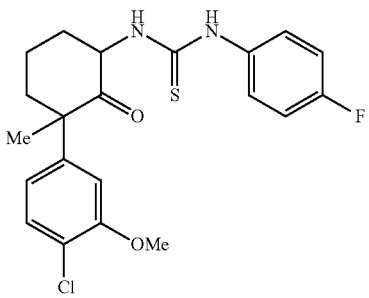 [SMILES: COc1cc(C2(C)CCCC(NC(=S)Nc3ccc(F)cc3)C2=O)ccc1Cl]

A solution of 6-amino-2-(4-chloro-3-methoxyphenyl)-2-methylcyclohexan-1-one hydrochloride (6 g, 19.72 mmol, 1.00 equiv), dichloromethane (20 mL), TEA (6.8 g, 67.20 mmol, 3.00 equiv), and 1-fluoro-4-isothiocyanatobenzene (6.8 g, 44.39 mmol, 2.00 equiv) was stirred for 1 h at room temperature and concentrated under vacuum to give the title compound which was used in the next step directly. Mass spectrum (ESI, m/z): Calcd. for $C_{21}H_{22}ClFN_2O_2S$, 421.1 (M+H). found 421.1.

Step 7: 7-(4-chloro-3-methoxyphenyl)-1-(4-fluoro-phenyl)-7-methyl-4,5,6,7-tetrahydro-1H-benzo[d]imidazole-2-thiol

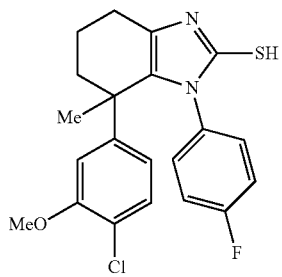 [SMILES: COc1cc(C2(C)CCCc3nc(S)n(-c4ccc(F)cc4)c32)ccc1Cl]

A solution of 3-[3-(4-chloro-3-methoxyphenyl)-3-methyl-2-oxocyclohexyl]-1-(4-fluorophenyl)thiourea (9 g, 21.38 mmol, 1.00 equiv) and AcOH (30 mL) was stirred overnight at 60° C. in an oil bath and concentrated under vacuum. Silica gel column chromatography with ethyl acetate/petroleum ether (1:1) gave the title compound as a light yellow solid. Mass spectrum (ESI, m/z): Calcd. for $C_{21}H_{20}ClFN_2OS$, 403.1 (M+H). found 403.1.

Step 8: 7-(4-chloro-3-methoxyphenyl)-2-[[(2-chloro-6-fluorophenyl)methyl]sulfanyl]-1-(4-fluorophenyl)-7-methyl-4,5,6,7-tetrahydro-1H-1,3-benzodiazole

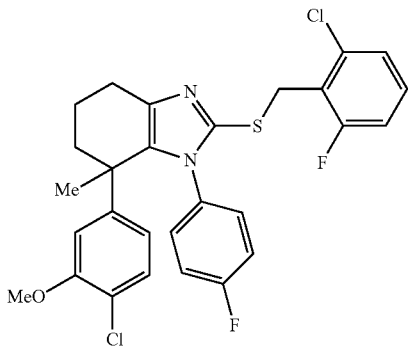 [SMILES: COc1cc(C2(C)CCCc3nc(SCc4c(F)cccc4Cl)n(-c4ccc(F)cc4)c32)ccc1Cl]

A solution of 7-(4-chloro-3-methoxyphenyl)-1-(4-fluorophenyl)-7-methyl-4,5,6,7-tetrahydro-1H-benzo[d]imidazole-2-thiol (100 mg, 0.25 mmol, 1.00 equiv), N,N-dimethylformamide (3 mL), potassium carbonate (103 mg, 0.75 mmol, 3.00 equiv), and 2-(bromomethyl)-1-chloro-3-fluorobenzene (82 mg, 0.37 mmol, 1.50 equiv) was stirred overnight at room temperature. The reaction was then quenched by the addition of 30 mL of water, extracted with 3×30 mL of dichloromethane and the organic layers combined. The reaction was washed with 1×30 mL of brine, dried over anhydrous sodium sulfate, filtered, and concentrated under vacuum. Silica gel column chromatography with ethyl acetate/petroleum ether (1:2) gave the title compound as a white solid. $^1$H NMR (400 MHz, CD$_3$OD): δ 7.22-7.32 (m, 3H), 7.00-7.07 (m, 3H), 6.68 (d, J=2.0 Hz, 1H), 6.56-6.60 (m, 2H), 5.87-5.90 (m, 1H), 4.19 (d, J=12.0 Hz, 1H), 4.00 (d, J=12.0 Hz, 1H), 3.77 (s, 3H), 2.72-2.78 (m, 2H), 1.84-1.96 (m, 4H), 1.36 (s, 3H). Mass spectrum (ESI, m/z): Calcd. for C$_{28}$H$_{24}$Cl$_2$F$_2$N$_2$OS, 545.1 (M+H). found 545.0.

Example 79

7-(4-chloro-3-methoxyphenyl)-2-({[4-(2-[2-[2-(dimethylamino)ethoxy]ethoxy] ethoxy)-2,6-difluorophenyl]methyl]sulfanyl)-1-(4-fluorophenyl)-7-methyl-4,5,6,7-tetrahydro-1H-1,3-benzodiazole bis (trifluoroacetic acid)

Step 1: 7-(4-chloro-3-methoxyphenyl)-2-[([2,6-difluoro-4-[(4-methoxyphenyl)methoxy]phenyl]methyl) sulfanyl]-1-(4-fluorophenyl)-7-methyl-4,5,6,7-tetrahydro-1H-1,3-benzodiazole

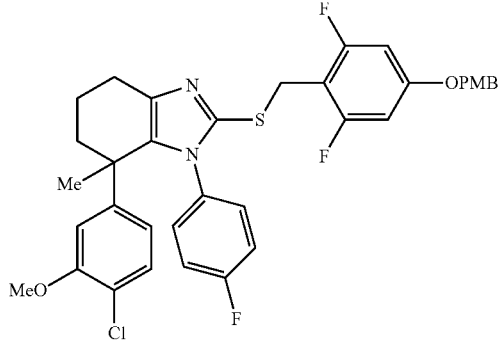

The title compound was prepared according to the procedure as described in Example 78 step 8 reacting 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 2,6-difluoro-4-((4-methoxybenzyl)oxy)benzyl methanesulfonate to afford the product as white solid. Mass spectrum (ESI, m/z): Calcd. for C$_{36}$H$_{32}$ClF$_3$N$_2$O$_3$S, 665.2 (M+H). found 665.2.

Step 2: 4-([[7-(4-chloro-3-methoxyphenyl)-1-(4-fluorophenyl)-7-methyl-4,5,6,7-tetrahydro-1H-1,3-benzodiazol-2-yl]sulfanyl]methyl)-3,5-difluorophenol trifluoroacetic acid

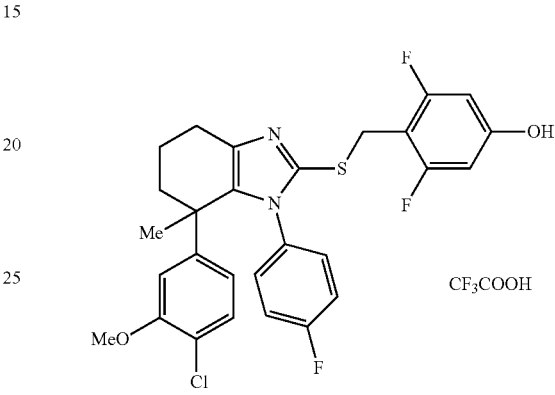

The title compound was prepared according to the procedure as described in Example 24 step 3 reacting 7-(4-chloro-3-methoxyphenyl)-2-[([2,6-difluoro-4-[(4-methoxyphenyl)methoxy]phenyl]methyl) sulfanyl]-1-(4-fluorophenyl)-7-methyl-4,5,6,7-tetrahydro-1H-1,3-benzodiazole in TFA to afford the product as white solid. $^1$H NMR (400 MHz, CD$_3$OD): δ 7.23-7.31 (m, 3H), 6.74-6.78 (m, 1H), 6.68 (s, 1H), 6.52-6.55 (m, 1H), 6.45-6.47 (m, 2H), 6.06-6.10 (m, 1H), 4.18 (d, J=13.6 Hz, 1H), 4.01 (d, J=13.6 Hz, 1H), 3.78 (s, 3H), 2.86-2.91 (m, 2H), 2.01-2.11 (m, 1H), 1.95-1.99 (m, 3H), 1.48 (s, 3H). $^{19}$F NMR (400 MHz, CD$_3$OD): δ −77.13, −111.11, −117.28. Mass spectrum (ESI, m/z): Calcd. for C$_{30}$H$_{25}$ClF$_6$N$_2$O$_4$S, 545.1 (M−CF$_3$COOH+H). found 545.1.

Step 3: 7-(4-chloro-3-methoxyphenyl)-2-[[(2,6-difluoro-4-[2-[2-(2-iodoethoxy)ethoxy]ethoxy]phenyl) methyl] sulfanyl]-1-(4-fluorophenyl)-7-methyl-4,5,6,7-tetrahydro-1H-1,3-benzodiazole

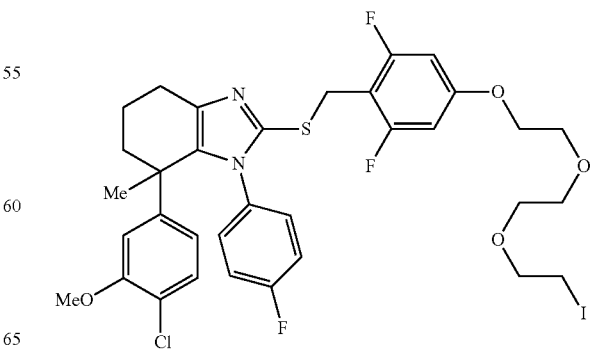

The title compound was prepared according to the procedure as described in Example 24 step 4 by coupling 4-([[7-(4-chloro-3-methoxyphenyl)-1-(4-fluorophenyl)-7-methyl-4,5,6,7-tetrahydro-1H-1,3-benzodiazol-2-yl]sulfanyl]methyl)-3,5-difluorophenol and 1,2-bis(2-idodethyox)ethane in the presence of $Cs_2CO_3$ to afford the desired product as a white solid. Mass spectrum (ESI, m/z): Calcd. for $C_{34}H_{35}ClF_3IN_2O_4S$, 787.1 (M+H). found 787.1.

Step 4: 7-(4-chloro-3-methoxyphenyl)-2-([[4-(2-[2-[2-(dimethylamino)ethoxy]ethoxy]ethoxy)-2,6-difluorophenyl]methyl]sulfanyl)-1-(4-fluorophenyl)-7-methyl-4,5,6,7-tetrahydro-1H-1,3-benzodiazole bis (trifluoroacetic acid)

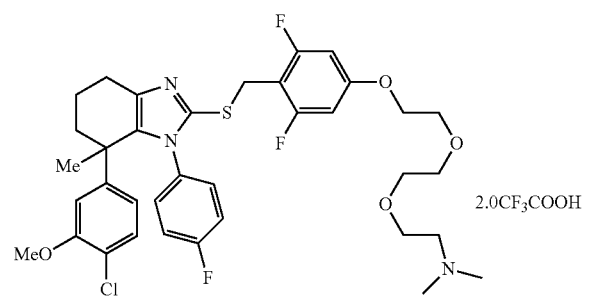 [SMILES: COc1cc(C2(C)CCCc3nc(SCc4c(F)cc(OCCOCCOCCN(C)C)cc4F)n(-c4ccc(F)cc4)c32)ccc1Cl]

The title compound was prepared according to the procedure as described in Example 27 step 2 by coupling 7-(4-chloro-3-methoxyphenyl)-2-[[(2,6-difluoro-4-[2-[2-(2-iodoethoxy)ethoxy]ethoxy]phenyl)methyl]sulfanyl]-1-(4-fluorophenyl)-7-methyl-4,5,6,7-tetrahydro-1H-1,3-benzodiazole and dimethylamine to afford the desired product as a white solid. $^1H$ NMR (300 MHz, $CD_3OD$): δ 7.23-7.32 (m, 3H), 6.68-6.74 (m, 4H), 6.54-6.57 (m, 1H), 5.92-5.94 (m, 1H), 4.18-4.25 (m, 3H), 4.00-4.18 (m, 1H), 3.74-3.92 (m, 12H), 3.32-3.38 (m, 2H), 2.88-2.93 (m, 8H), 1.95-2.09 (m, 3H), 1.45 (s, 3H). $^{19}F$ NMR (300 MHz, $CD_3OD$): δ −77.17, −111.23, −115.97. Mass spectrum (ESI, m/z): Calcd. for $C_{40}H_{43}ClF_9N_3O_8S$, 704.2 (M−2.0 $CF_3COOH$+H). found 704.3.

Example 80

2-(4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorophenoxy)-N,N-dimethylethanamine

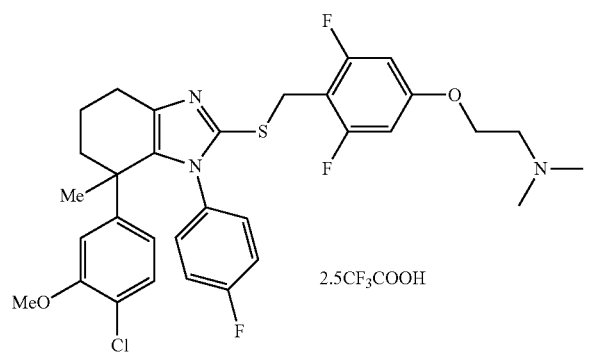 [SMILES: COc1cc(C2(C)CCCc3nc(SCc4c(F)cc(OCCN(C)C)cc4F)n(-c4ccc(F)cc4)c32)ccc1Cl]

The title compound was prepared according to the procedure as described in Example 24 step 4 by coupling 4-([[7-(4-chloro-3-methoxyphenyl)-1-(4-fluorophenyl)-7-methyl-4,5,6,7-tetrahydro-1H-1,3-benzodiazol-2-yl]sulfanyl]methyl)-3,5-difluorophenol (Prepared as described in Example 79, Step 2) and 2-chloro-N,N-dimethylethanamine HCl salt in the presence of $Cs_2CO_3$ to afford the desired product as a white solid. $^1H$ NMR (400 MHz, $CD_3OD$): δ 7.25-7.36 (m, 3H), 6.79-6.80 (m, 3H), 6.75 (s, 1H), 6.58-6.60 (m, 1H), 6.07-6.11 (m, 1H), 4.41-4.43 (m, 2H), 4.19 (d, J=13.6 Hz, 1H), 4.06 (d, J=13.6 Hz, 1H), 3.79 (s, 3H), 3.65-3.67 (m, 2H), 3.02 (s, 6H), 2.88-2.99 (m, 2H), 1.97-2.11 (m, 4H), 1.48 (s, 3H). $^{19}F$ NMR (400 MHz, $CD_3OD$): δ −77.08, −111.02, −115.50. Mass spectrum (ESI, m/z): Calcd. for $C_{37}H_{35.5}ClF_{10.5}N_3$ Example 81

4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid trifluoroacetic acid Step 1: Tert-butyl 4-([[7-(4-chloro-3-methoxyphenyl)-1-(4-fluorophenyl)-7-methyl-4,5,6,7-tetrahydro-1H-1,3-benzodiazol-2-yl]sulfanyl]methyl)-3,5-difluorobenzoate

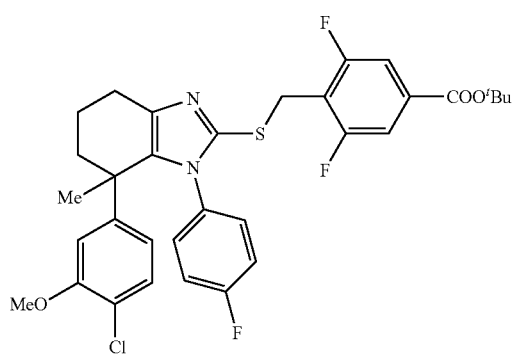

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and tert-butyl 3,5-difluoro-4-(((methylsulfonyl)oxy) methyl) benzoate in the presence of $Cs_2CO_3$ to afford the desired product as a white solid. Mass spectrum (ESI, m/z): Calcd. for $C_{33}H_{32}ClF_3N_2O_3S$, 629.2 (M+H). found 629.2.

Step 2: 4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid trifluoroacetic acid

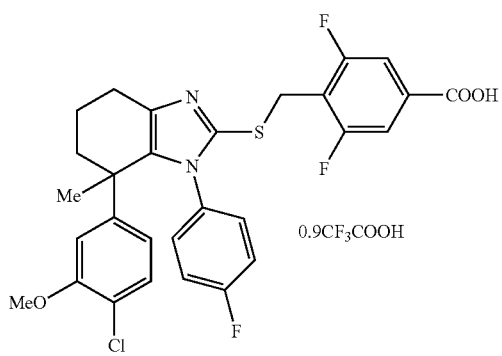 [SMILES: COc1cc(C2(C)CCCc3nc(SCc4c(F)cc(C(=O)O)cc4F)n(-c4ccc(F)cc4)c32)ccc1Cl]

The title compound was prepared according to the procedure as described in Example 12 step 6 by treatment of tert-butyl 4-([[7-(4-chloro-3-methoxyphenyl)-1-(4-fluorophenyl)-7-methyl-4,5,6,7-tetrahydro-1H-1,3-benzodiazol-2-yl]sulfanyl]methyl)-3,5-difluorobenzoate in TFA to afford the desired product as a white solid. $^1$H NMR (400 MHz, CD$_3$OD) δ 7.66 (d, J=8.0 Hz, 2H), 7.21-7.33 (m, 3H), 6.66-6.73 (m, 2H), 6.54-6.57 (m, 1H), 5.90-5.94 (m, 1H), 4.25 (d, J=13.6 Hz, 1H), 4.08 (d, J=13.6 Hz, 1H), 3.77 (s, 3H), 2.79-2.95 (m, 2H), 1.95-2.13 (m, 4H), 1.47 (s, 3H). $^{19}$F NMR (400 MHz, CD$_3$OD) δ −77.11, −111.22, −115.66. Mass spectrum (ESI, m/z): Calcd. for C$_{30.8}$H$_{24.9}$ClF$_{5.7}$N$_2$O$_{4.8}$S, 573.1 (M+H). found 573.3.

Example 82

(S)-methyl 2-(4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzamido)-5-guanidinopentanoate trifluoroacetic acid

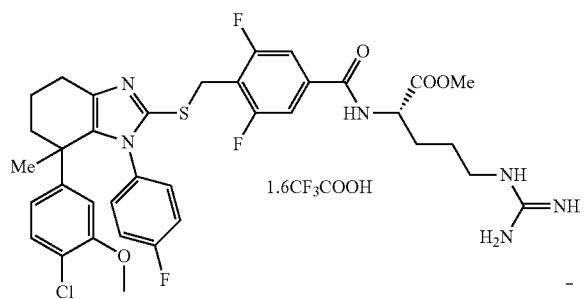 [SMILES: COC(=O)[C@H](CCCNC(=N)N)NC(=O)c1cc(F)c(CSc2nc3c(n2-c2ccc(F)cc2)C(C)(c2ccc(Cl)c(OC)c2)CCC3)c(F)c1]

A solution of 4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid (200 mg, 0.35 mmol, 1.00 equiv) in dichloromethane (4 mL), HOBt (71 mg, 0.42 mmol, 1.21 equiv), EDCI (80 mg, 0.42 mmol, 1.20 equiv), triethylamine (141 mg, 1.39 mmol, 4.02 equiv), and methyl (2S)-2-amino-5-carbamimidamidopentanoate (109 mg, 0.42 mmol, 1.21 equiv) was stirred overnight at 40° C. in an oil bath. The reaction was quenched by the addition of 10 mL of H$_2$O, diluted with 10 mL of DCM, extracted with 3×10 mL of dichloromethane and the organic layers combined. The resulting mixture was washed with 1×10 mL of brine, dried over sodium sulfate and concentrated under vacuum. Silica gel chromatography with ethyl acetate/petroleum ether (1:2), followed by Prep-HPLC with the following conditions: (1#waters2767-5) column, SunFire Prep C18, 19*150 mm 5 μm H Prep C-001(T) 18600256819513816414 04; Mobile Phase, phase A: water with 0.05% TFA, phase B: CH3CN (15% CH$_3$CN up to 60% in 8 min, up to 100% in 0.1 min, hold 100% in 1.9 min, down to 15% in 0.1 min, hold 15% in 1.9 min); Detector, UV 220 & 254 nm, gave the title compound as a white solid. $^1$H NMR (400 MHz, CD$_3$OD) δ 7.57-7.60 (m, 2H), 7.22-7.31 (m, 3H), 6.67-6.76 (m, 2H), 6.54-6.57 (m, 1H), 5.90-6.02 (m, 1H), 4.72 (t, J=4.0 Hz, 1H), 4.23 (d, J=3.6 Hz, 1H), 4.06-4.10 (m, 1H), 3.78 (s, 3H), 3.77 (s, 3H), 3.26-3.29 (m, 2H), 2.84-2.89 (m, 2H), 1.75-2.10 (m, 8H), 1.46 (s, 3H). $^{19}$F NMR (400 MHz, CD$_3$OD) δ −77.09, −111.45, −115.31. Mass spectrum (ESI, m/z): Calcd. for C$_{39.2}$H$_{39.6}$ClF$_{7.8}$N$_6$O$_{7.2}$S, 743.2 (M−1.6CF$_3$COOH+H). found 743.5.

Example 83

(S)-2-(4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzamido)-5-guanidinopentanoic acid trifluoroacetic acid

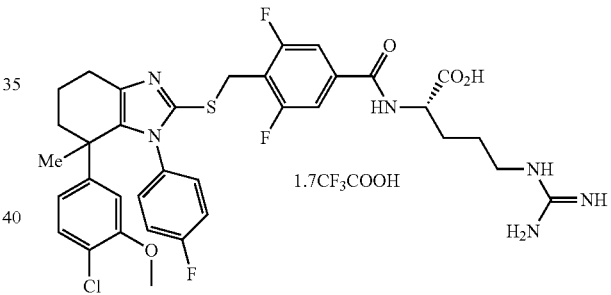

A solution of (S)-methyl 2-(4-((7-(4-chloro-3-methoxyphenyl)-1-(4-fluorophenyl)-4, 5, 6, 7-tetrahydro-7-methyl-1H-benzo[d]imidazol-2-ylthio)methyl)-3,5-difluorobenzamido)-5-guanidinopentanoate (80 mg, 0.11 mmol, 1.00 equiv) in methanol-H$_2$O (2/1 mL), and LiOH monohydrate (21 mg, 0.50 mmol, 4.65 equiv) was stirred for 2 h at room temperature. The resulting mixture was concentrated under vacuum and purified by Prep-HPLC With the following conditions: (1#waters2767-5) column, SunFire Prep C18, 19*150 mm 5 μm H Prep C-001(T)18600256819513816414 04; Mobile Phase, phase A: water with 0.05% TFA, phase B: CH3CN (15% CH$_3$CN up to 50% in 8 min, up to 100% in 0.1 min, hold 100% in 1.9 min, down to 15% in 0.1 min, hold 15% in 1.9 min); Detector, UV 220 & 254 nm, to give the title compound as a white solid. $^1$H NMR (400 MHz, CD$_3$OD) δ7.57-7.60 (m, 2H), 7.22-7.30 (m, 3H), 6.66-6.77 (m, 2H), 6.55-6.57 (m, 1H), 6.03 (t, J=4.8 Hz, 1H), 4.68-4.71 (m, 1H), 4.21 (d, J=13.2 Hz, 1H), 4.07 (d, J=13.6 Hz, 1H), 3.78 (s, 3H), 3.27-3.29 (m, 2H), 2.83-2.88 (m, 2H), 1.76-2.11 (m, 8H), 1.46 (d, J=4.8 Hz, 3H). $^{19}$F NMR (400 MHz, CD$_3$OD) δ −77.07, −111.58, −115.38. Mass spectrum (ESI, m/z): Calcd. for C$_{38.4}$H$_{37.7}$ClF$_{8.1}$N$_6$O$_{7.4}$S, 729.2 (M−1.7CF$_3$COOH+H). found 729.5.

Example 84

4-((7-(4-chloro-3-methoxyphenyl)-1-(4-fluorophenyl)-7-methyl-4,5,6,7-tetrahydro-1H-benzo[d]imidazol-2-ylthio)methyl)-3,5-difluoro-N-(2-(2-(2-(2-hydroxyethoxy)ethoxy)ethoxy)ethyl)benzamide trifluoroacetic acid

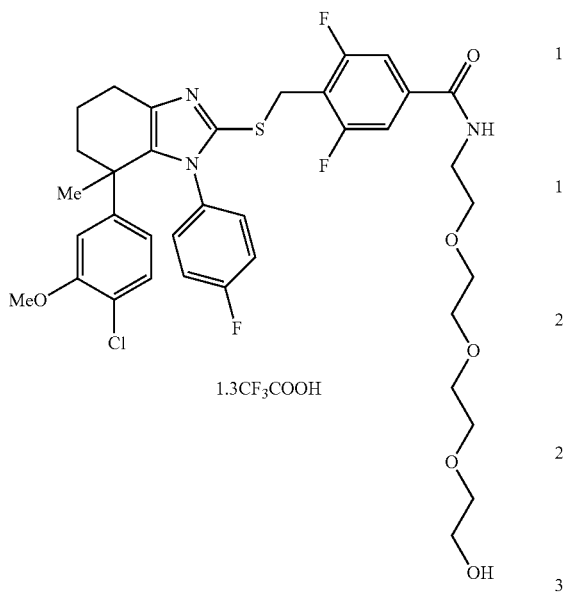

The title compound was prepared according to the procedure as described in Example 82 by coupling 4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid (Prepared as described in Example 81, Step 2) and 2-(2-(2-(2-aminoethoxy)ethoxy)ethoxy)ethanol in the presence of EDCI and HOBt to afford the desired product as a white solid. $^1$H NMR (400 MHz, CD$_3$OD) δ 7.57 (d, J=8.4 Hz, 2H), 7.24-7.33 (m, 3H), 6.760 (t, J=8.4 Hz, 1H), 6.67 (d, J=2.0 Hz, 1H), 6.53-6.56 (m, 1H), 5.93-5.96 (m, 1H), 4.27 (d, J=13.6 Hz, 1H), 4.10 (d, J=13.6 Hz, 1H), 3.77 (s, 3H), 3.55-3.73 (m, 16H), 2.87-2.91 (m, 2H), 1.96-2.11 (m, 4H), 1.47 (s, 3H). $^{19}$F NMR (400 MHz, CD$_3$OD) δ −77.12, −110.95, −115.49. Mass spectrum (ESI, m/z): Calcd. for C$_{39.6}$H$_{42.3}$ClF$_{6.9}$N$_3$O$_{8.6}$S, 748.2 (M−1.3CF$_3$COOH+H). found 748.5.

Example 85

7-(4-chloro-3-methoxyphenyl)-1-(4-fluorophenyl)-7-methyl-2-(pyrimidin-2-ylmethylthio)-4,5,6,7-tetrahydro-1H-benzo[d]imidazole

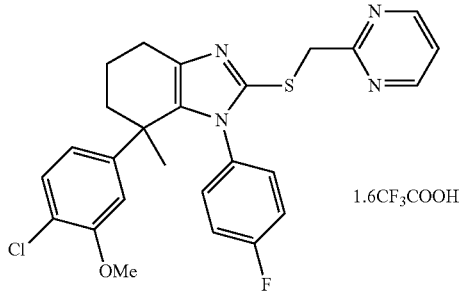 [SMILES: COc1cc(C2(C)CCCc3nc(SCc4ncccn4)n(-c4ccc(F)cc4)c32)ccc1Cl]

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 2-(chloromethyl)pyrimidine HCl salt in the presence of Cs$_2$CO$_3$ followed by HPLC purification using ACN (TFA) and water (TFA) as eluent to afford the desired product as a white solid. $^1$H NMR (400 MHz, CD$_3$OD): δ 8.79 (d, J=4.8 Hz, 2H), 7.45-7.50 (m, 2H), 7.25-7.32 (m, 2H), 6.83-6.88 (m, 1H), 6.66-6.72 (m, 2H), 6.41-6.51 (m, 1H), 4.26-4.35 (m, 2H), 3.80 (s, 3H), 2.82-2.93 (m, 2H), 1.96-2.11 (m, 4H), 1.51 (s, 3H). $^{19}$F NMR (400 MHz, CD$_3$OD): δ −77.17, −110.77. Mass spectrum (ESI, m/z): Calcd. for C$_{29.2}$H$_{25.6}$ClF$_{5.8}$N$_4$O$_{4.2}$S, 495.1 (M−1.6CF$_3$COOH+H). found 495.1.

Example 86

7-(4-chloro-3-methoxyphenyl)-2-((5-chloropyrimidin-4-yl)methylthio)-1-(4-fluorophenyl)-7-methyl-4,5,6,7-tetrahydro-1H-benzo[d]imidazole trifluoroacetic acid

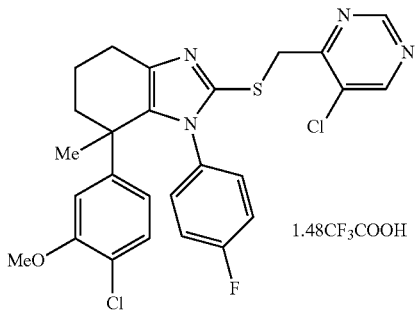 [SMILES: COc1cc(C2(C)CCCc3nc(SCc4ncncc4Cl)n(-c4ccc(F)cc4)c32)ccc1Cl]

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 5-chloro-4-(chloromethyl)pyrimidine HCl salt in the presence of Cs$_2$CO$_3$ to afford the desired product as a white solid. $^1$H NMR (300 MHz, CD$_3$OD): δ 8.90 (s, 1H), 7.52 (s, 1H), 7.19-7.36 (m, 3H), 6.77-6.84 (m, 1H), 6.69 (s, 1H), 6.58-6.61 (m, 1H), 6.35-6.36 (m, 1H), 4.04-4.16 (m, 2H), 3.78 (s, 3H), 2.73-2.88 (m, 2H), 1.80-2.20 (m, 4H), 1.435 (s, 3H). $^{19}$F NMR (300 MHz, CD$_3$OD): δ −77.05. Mass spectrum (ESI, m/z): Calcd. for C$_{28.96}$H$_{24.48}$Cl$_2$F$_{5.44}$N$_4$O$_{3.96}$S, 529.1 (M−1.48CF$_3$COOH+H). found 529.3.

Example 87

2-(benzylsulfanyl)-7-(4-chloro-3-methoxyphenyl)-1-(4-fluorophenyl)-7-methyl-4,5,6,7-tetrahydro-1H-1,3-benzodiazole

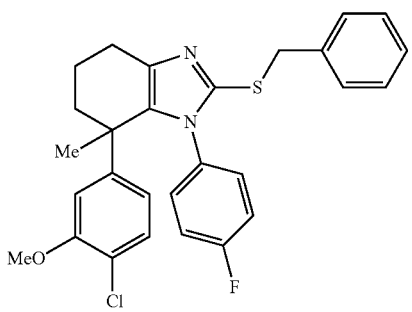 [SMILES: COc1cc(C2(C)CCCc3nc(SCc4ccccc4)n(-c4ccc(F)cc4)c32)ccc1Cl]

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and benzyl bromide in the presence of $Cs_2CO_3$ to afford the desired product as a white solid. $^1$H NMR (400 MHz, $CD_3OD$): δ 7.27-7.31 (m, 3H), 7.19 (d, J=8.4 Hz, 1H), 6.99-7.07 (m, 3H), 6.72-6.75 (m, 1H), 6.57-6.61 (m, 1H), 5.76-5.79 (m, 1H), 4.09 (d, J=12.8 Hz, 1H), 4.00 (d, J=12.8 Hz, 1H), 3.71 (s, 3H), 2.75-2.81 (m, 2H), 1.84-1.94 (m, 4H), 1.32 (s, 3H). Mass spectrum (ESI, m/z): Calcd. for $C_{28}H_{26}ClFN_2OS$, 493.1 (M+H). found 493.1.

Example 88

2-(benzylsulfanyl)-7-(4-chloro-3-methoxyphenyl)-1-(4-fluorophenyl)-7-methyl-4,5,6,7-tetrahydro-1H-1,3-benzodiazole

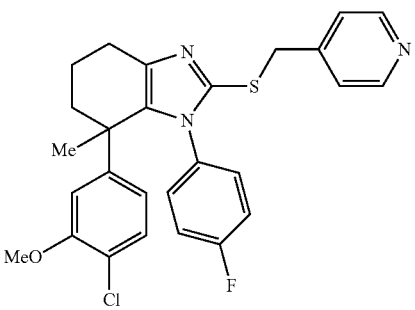 [SMILES: COc1cc(C2(C)CCCc3nc(SCc4ccncc4)n(-c4ccc(F)cc4)c32)ccc1Cl]

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 4-(bromomethyl)pyridine in the presence of $Cs_2CO_3$ to afford the desired product as a white solid. $^1$H NMR (400 MHz, $CD_3OD$): δ 8.44-8.46 (m, 2H), 7.17-7.24 (m, 3H), 7.07-7.09 (m, 1H), 6.94-6.97 (m, 1H), 6.61-6.68 (m, 2H), 6.43-6.45 (m, 1H), 5.88-5.92 (m, 1H), 4.14 (d, J=13.2 Hz, 1H), 4.03 (d, J=13.2 Hz, 1H), 3.72 (s, 3H), 2.56-2.96 (m, 2H), 1.84-1.93 (m, 4H), 1.34 (s, 3H). Mass spectrum (ESI, m/z): Calcd. for $C_{27}H_{25}ClFN_3OS$, 494.1 (M+H). found 494.2.

Example 89

4-((7-(4-chloro-3-methoxyphenyl)-1-(4-fluorophenyl)-7-methyl-4,5,6,7-tetrahydro-1H-benzo[d]imidazol-2-ylthio)methyl)-3,5-difluorobenzonitrile trifluoroacetic acid

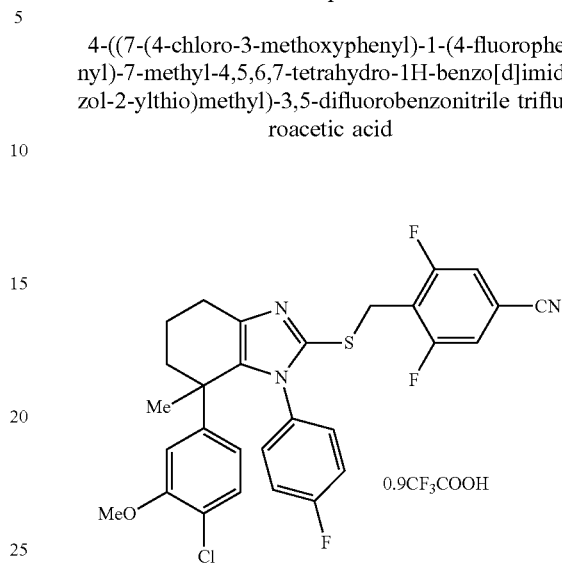

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 4-cyano-2,6-difluorobenzyl methanesulfonate in the presence of $Cs_2CO_3$ to afford the desired product as a white solid. $^1$H NMR (400 MHz, $CD_3OD$): δ 7.58-7.60 (m, 2H), 7.23-7.36 (m, 3H), 6.80-6.83 (m, 1H), 6.69 (s, 1H), 6.57-6.60 (m, 1H), 6.17-6.21 (m, 1H), 4.15 (d, J=13.6 Hz, 1H), 4.05 (d, J=13.6 Hz, 1H), 3.79 (s, 3H), 2.70-2.90 (m, 2H), 2.00-2.09 (m, 1H), 1.95-1.99 (m, 3H), 1.48 (s, 3H). $^{19}$F NMR (400 MHz, $CD_3OD$): δ −77.13, −111.42, −113.48. Mass spectrum (ESI, m/z): Calcd. for $C_{30.8}H_{23.9}ClF_{5.7}N_3O_{2.8}S$, 554.1 (M−0.9CF$_3$COOH+H). found 554.1.

Example 90

7-(4-chloro-3-methoxyphenyl)-2-(2,6-difluoro-4-(2H-tetrazol-5-yl)benzylthio)-1-(4-fluorophenyl)-7-methyl-4,5,6,7-tetrahydro-1H-benzo[d]imidazole trifluoroacetic acid

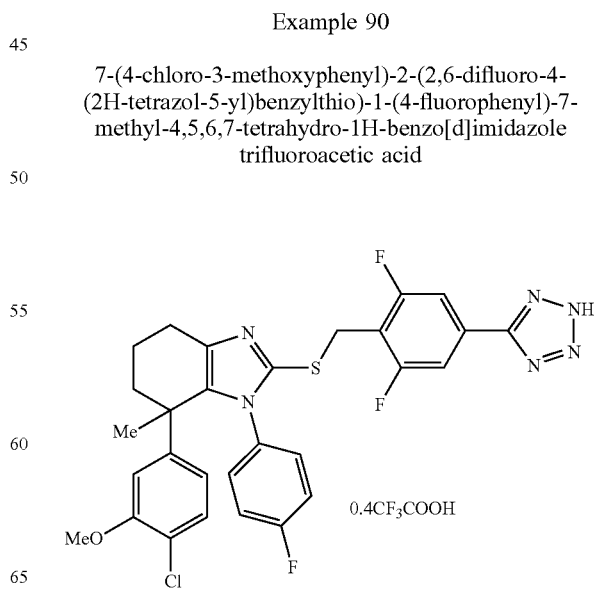

The title compound was prepared according to the procedure as described in Example 30 by reacting 4-((7-(4-chloro-3-methoxyphenyl)-1-(4-fluorophenyl)-7-methyl-4,5,6,7-tetrahydro-1H-benzo[d]imidazol-2-ylthio)methyl)-3,5-difluorobenzonitrile trifluoroacetic acid in the presence of NH₄Cl and NaN₃ to afford the desired product as a white solid. $^1$H NMR (400 MHz, CD₃OD): δ 7.75 (d, J=8.0 Hz, 2H), 7.20-7.31 (m, 3H), 6.80-6.84 (m, 1H), 6.67 (s, 1H), 6.35-6.65 (m, 1H), 6.08 (br, 1H), 4.18 (d, J=13.2 Hz, 1H), 4.08 (d, J=13.2 Hz, 1H), 3.72 (s, 3H), 2.51-2.74 (m, 2H), 1.88-1.93 (m, 1H), 1.76-1.82 (m, 2H), 1.67-1.69 (m, 1H), 1.31 (s, 3H). $^{19}$F NMR (400 MHz, CD₃OD): δ −74.25, −111.78, −112.65. Mass spectrum (ESI, m/z): Calcd. for $C_{29.8}H_{24.4}ClF_{4.2}N6O_{1.8}S$, 597.1 (M−0.4CF₃COOH+H). found 597.2.

Example 91

4-((7-(4-chloro-3-methoxyphenyl)-1-(4-fluorophenyl)-7-methyl-4,5,6,7-tetrahydro-1H-benzo[d]imidazol-2-ylthio)methyl)-3,5-difluoro-N-methylbenzamide trifluoroacetic acid

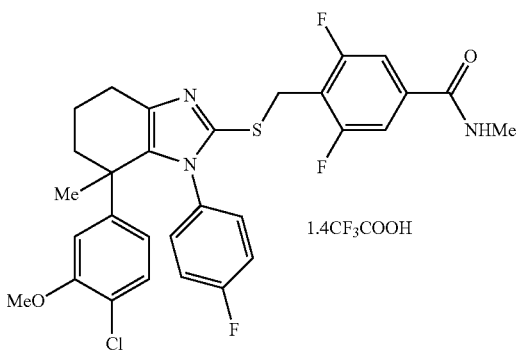 [SMILES: CNC(=O)c1cc(F)c(CSc2nc3c(n2-c2ccc(F)cc2)C(C)(c2ccc(Cl)c(OC)c2)CCC3)c(F)c1]

1.4CF₃COOH

The title compound was prepared according to the procedure as described in Example 82 by coupling 4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid (Prepared as described in Example 81, Step 2) and methylamide THF solution in the presence of EDCI and HOBt to afford the desired product as a white solid. $^1$H NMR (400 MHz, CD₃OD) δ 7.53 (d, J=8.4 Hz, 2H), 7.21-7.32 (m, 3H), 6.73-6.78 (m, 1H), 6.66 (d, J=2.0 Hz, 1H), 6.52-6.55 (m, 1H), 5.86-5.90 (m, 1H), 4.26 (d, J=13.6 Hz, 1H), 4.08 (d, J=13.2 Hz, 1H), 3.77 (s, 3H), 2.99 (s, 3H), 2.81-2.92 (m, 2H), 1.95-2.11 (m, 4H), 1.47 (s, 3H). $^{19}$F NMR (400 MHz, CD₃OD) δ −77.22, −111.12, −115.49. Mass spectrum (ESI, m/z): Calcd. for $C_{32.8}H_{28.4}ClF_{7.2}N_3O_{4.8}S$, 586.2 (M−1.4CF₃COOH+H). found 586.3.

Example 92

4-([[7-(4-chloro-3-methoxyphenyl)-1-(4-fluorophenyl)-7-methyl-4,5,6,7-tetrahydro-1H-1,3-benzodiazol-2-yl]sulfanyl]methyl)-3,5-difluoro-N,N-dimethylbenzamide

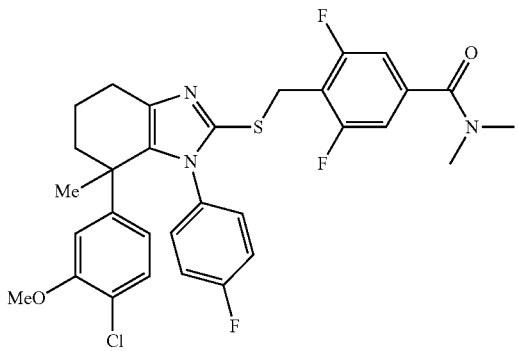 [SMILES: COc1cc(C2(C)CCCc3nc(SCc4c(F)cc(C(=O)N(C)C)cc4F)n(-c4ccc(F)cc4)c32)ccc1Cl]

The title compound was prepared according to the procedure as described in Example 82 by coupling 4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid (Prepared as described in Example 81, Step 2) and dimethylamide THF solution in the presence of EDCI and HOBt to afford the desired product as a white solid. $^1$H NMR (400 MHz, CD₃OD) δ7.26 (d, J=8.4 Hz, 1H), 7.03-7.12 (m, 4H), 6.67-6.72 (m, 2H), 6.56 (t, J=8.4 Hz, 1H), 5.60-6.04 (m, 1H), 4.04 (d, J=13.6 Hz, 1H), 3.91 (d, J=13.2 Hz, 1H), 3.79 (s, 3H), 3.15 (s, 3H), 3.03 (s, 3H), 2.66-2.79 (m, 2H), 1.84-1.95 (m, 4H), 1.37 (s, 3H). $^{19}$F NMR (400 MHz, CD₃OD) δ−113.94, −115.24. Mass spectrum (ESI, m/z): Calcd. for $C_{31}H_{29}ClF_3N_3O_2S$, 600.2 (M+H). found 600.3.

Example 93

7-(4-chloro-3-methoxyphenyl)-2-[([2,6-difluoro-4-[(morpholin-4-yl)carbonyl]phenyl]methyl)sulfanyl]-1-(4-fluorophenyl)-7-methyl-4,5,6,7-tetrahydro-1H-1,3-benzodiazole

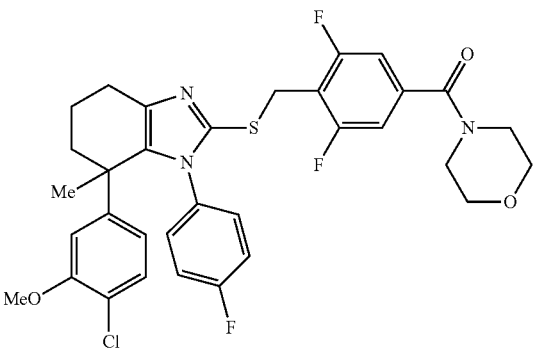

The title compound was prepared according to the procedure as described in Example 82 by coupling 4-((7-(4-chloro-3-methoxyphenyl)-1-(4-fluorophenyl)-4,5,6,7-tetrahydro-7-methyl-1H-benzo[d]imidazol-2-ylthio)methyl)-3, 5-difluorobenzoic acid (Prepared as described in Example 81, Step 2) and morpholine in the presence of EDCI and HOBt to afford the desired product as a white solid. $^1$H NMR (400 MHz, CD$_3$OD) δ 7.26 (d, J=8.4 Hz, 1H), 7.05-7.13 (m, 4H), 6.68-6.73 (m, 2H), 6.56-6.59 (m, 1H), 6.04-6.07 (m, 1H), 4.01 (d, J=13.6 Hz, 1H), 3.90 (d, J=13.6 Hz, 1H), 3.77 (s, 3H), 3.48-3.69 (m, 8H), 2.68-2.75 (m, 2H), 1.84-1.96 (m, 4H), 1.31 (s, 3H). 19F NMR (400 MHz, CD$_3$OD) δ −113.94, −115.00. Mass spectrum (ESI, m/z): Calcd. for C$_{33}$H$_{31}$ClF$_3$N$_3$O$_3$S, 642.2 (M+H). found 642.4.

Example 94

4-((7-(4-chloro-3-methoxyphenyl)-1-(4-fluorophenyl)-7-methyl-4,5,6,7-tetrahydro-1H-benzo[d]imidazol-2-ylthio)methyl)-3,5-difluoro-N-(2-hydroxyethyl)benzamide trifluoroacetic acid

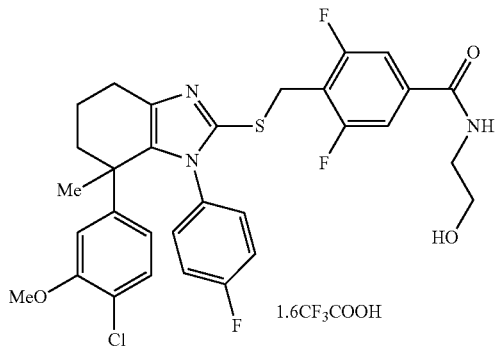 [SMILES: COc1cc(C2(C)CCCc3nc(SCc4c(F)cc(C(=O)NCCO)cc4F)n(-c4ccc(F)cc4)c32)ccc1Cl]

The title compound was prepared according to the procedure as described in Example 82 by coupling 4-((7-(4-chloro-3-methoxyphenyl)-1-(4-fluorophenyl)-4,5,6,7-tetrahydro-7-methyl-1H-benzo[d]imidazol-2-ylthio)methyl)-3,5-difluorobenzoic acid (Prepared as described in Example 81, Step 2) and 2-aminoethanol in the presence of EDCI and HOBt to afford the desired product as a white solid. $^1$H NMR (400 MHz, CD$_3$OD) δ7.55 (d, J=8.4 Hz, 2H), 7.22-7.29 (m, 3H), 6.73-6.78 (m, 1H), 6.67 (d, J=2.0 Hz, 1H), 6.53-6.56 (m, 1H), 5.96-6.00 (m, 1H), 4.21 (d, J=13.6 Hz, 1H), 4.06 (d, J=13.6 Hz, 1H), 3.78 (s, 5H), 3.56 (t, J=11.6 Hz, 2H), 2.82-2.88 (m, 2H), 1.94-2.11 (m, 4H), 1.42 (s, 3H). $^{19}$F NMR (400 MHz, CD$_3$OD) δ −77.10, −111.54, −115.55. Mass spectrum (ESI, m/z): Calcd. for C$_{34.2}$H$_{30.6}$ClF$_{7.8}$N$_3$O$_{6.2}$S, 616.2 (M−1.6CF$_3$COOH+H). found 616.4.

Example 95

3-((7-(4-chloro-3-methoxyphenyl)-1-(4-fluorophenyl)-7-methyl-4,5,6,7-tetrahydro-1H-benzo[d]imidazol-2-ylthio)methyl)-2,4-difluorophenol trifluoroacetic acid Step 1: 7-(4-chloro-3-methoxyphenyl)-2-[([2,6-difluoro-3-[(4-methoxyphenyl)methoxy]phenyl]methyl)sulfanyl]-1-(4-fluorophenyl)-7-methyl-4,5,6,7-tetrahydro-1H-1,3-benzodiazole

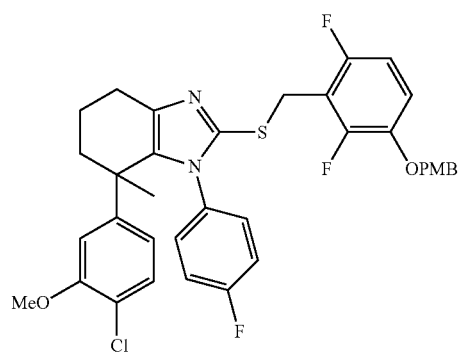

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 2-(chloromethyl)-1,3-difluoro-4-[(4-methoxyphenyl)methoxy]nenzene in the presence of Cs$_2$CO$_3$ to afford the desired product as a white solid. Mass spectrum (ESI, m/z): Calcd. for C$_{36}$H$_{32}$ClF$_3$N$_2$O$_3$S, 665.2 (M+H). found 655.2.

Step 2: 3-((7-(4-chloro-3-methoxyphenyl)-1-(4-fluorophenyl)-7-methyl-4,5,6,7-tetrahydro-1H-benzo[d]imidazol-2-ylthio)methyl)-2,4-difluorophenol trifluoroacetic acid

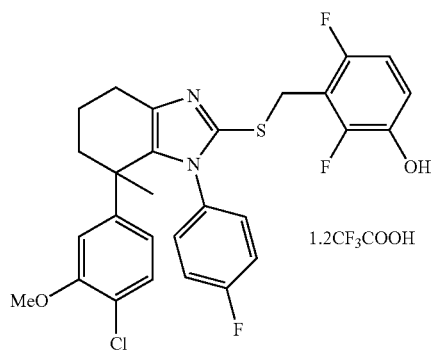 [SMILES: COc1cc(C2(C)CCCc3nc(SCc4c(F)ccc(O)c4F)n(-c4ccc(F)cc4)c32)ccc1Cl]

The title compound was prepared according to the procedure as described in Example 24 step 3 by treatment of 7-(4-chloro-3-methoxyphenyl)-2-[([2,6-difluoro-3-[(4-methoxyphenyl) methoxy]phenyl]methyl)sulfanyl]-1-(4-fluorophenyl)-7-methyl-4,5,6,7-tetrahydro-1H-1,3-benzodiazole in TFA to afford the desired product as a white solid. $^1$H NMR (400 MHz, CD$_3$OD): δ 7.21-7.32 (m, 3H), 6.85-

7.00 (m, 2H), 6.67-6.74 (m, 2H), 6.52-6.55 (m, 1H), 5.94-5.98 (m, 1H), 4.24 (d, J=13.6 Hz, 1H), 4.06 (d, J=13.6 Hz, 1H), 3.78 (s, 3H), 2.83-2.95 (m, 2H), 1.95-2.12 (m, 4H), 1.468 (s, 3H). $^{19}$F NMR (400 MHz, CD$_3$OD): −77.14, −111.15, −129.95, −139.97. Mass spectrum (ESI, m/z): Calcd. for C$_{3.4}$H$_{25.2}$ClF$_{6.6}$N$_2$O$_{4.4}$S, 545.1 (M−1.2CF$_3$COOH+H). found 545.3.

Example 96

2-(3-((7-(4-chloro-3-methoxyphenyl)-1-(4-fluorophenyl)-7-methyl-4,5,6,7-tetrahydro-1H-benzo[d]imidazol-2-ylthio)methyl)-2,4-difluorophenoxy)-N,N-dimethylethanamine trifluoroacetic acid

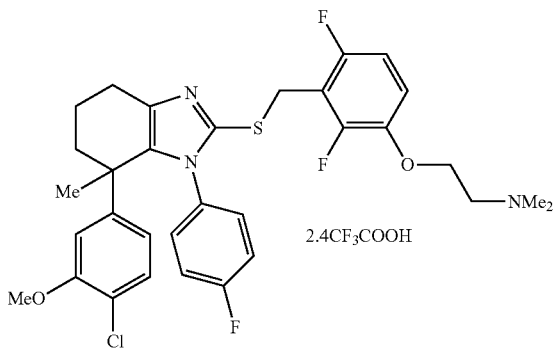 [SMILES: COc1cc(C2(C)CCCc3nc(SCc4c(F)ccc(OCCN(C)C)c4F)n(-c4ccc(F)cc4)c32)ccc1Cl]

The title compound was prepared according to the procedure as described in Example 24 step 4 by coupling 3-((7-(4-chloro-3-methoxyphenyl)-1-(4-fluorophenyl)-7-methyl-4, 5, 6, 7-tetrahydro-1H-benzo[d]imidazol-2-ylthio)methyl)-2,4-difluorophenol and 2-chloro-N,N-dimethylethanamine HCl salt in the presence of Cs$_2$CO$_3$ to afford the desired product as a white solid. $^1$H NMR (400 MHz, CD$_3$OD): δ 7.23-7.31 (m, 4H), 7.02-7.07 (m, 1H), 6.70-6.79 (m, 2H), 6.56-6.59 (m, 1H), 6.15 (s, 1H), 4.43-4.45 (m, 2H), 4.11-4.24 (m, 2H), 3.79 (s, 3H), 3.64-3.66 (m, 2H), 3.02 (s, 3H), 2.84-2.91 (m, 2H), 1.96-2.10 (m, 4H), 1.47 (s, 3H). $^{19}$F NMR (400 MHz, CD$_3$OD): −77.13, −111.14, −126.25, −134.52. Mass spectrum (ESI, m/z): Calcd. for C$_{36.8}$H$_{35.4}$ClF$_{10.2}$N$_3$O$_{6.8}$S, 616.2 (M−2.4CF$_3$COOH+H). found 616.4.

Example 97

7-(4-chloro-3-methoxyphenyl)-2-[[(2, 6-difluoro-3-[2-[2-(2-iodoethoxy)ethoxy]ethoxy]phenyl) methyl]sulfanyl]-1-(4-fluorophenyl)-7-methyl-4,5,6,7-tetrahydro-1H-1,3-benzodiazole

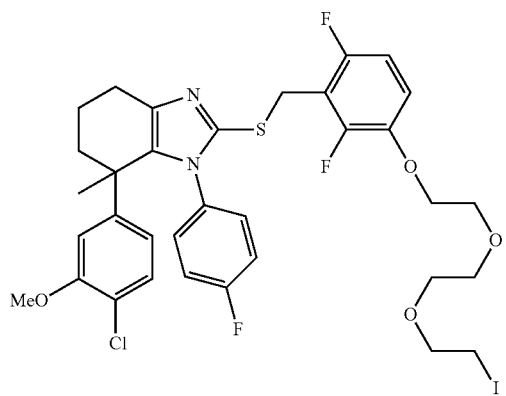 [SMILES: COc1cc(C2(C)CCCc3nc(SCc4c(F)ccc(OCCOCCOCCI)c4F)n(-c4ccc(F)cc4)c32)ccc1Cl]

The title compound was prepared according to the procedure as described in Example 24 step 4 by coupling 3-((7-(4-chloro-3-methoxyphenyl)-1-(4-fluorophenyl)-7-methyl-4,5, 6, 7-tetrahydro-1H-benzo[d]imidazol-2-ylthio) methyl)-2,4-difluorophenol (Prepared as described in Example 95, Step 2) and 1,2-bis(2-idodethyoxy)ethane in the presence of Cs$_2$CO$_3$ to afford the desired product as a white solid. Mass spectrum (ESI, m/z): Calcd. for C$_{34}$H$_{35}$ClF$_3$IN$_2$O$_4$S, 787.1 (M+H). found 787.1.

Step 2: 2-(2-(2-(3-((7-(4-chloro-3-methoxyphenyl)-1-(4-fluorophenyl)-7-methyl-4,5,6,7-tetrahydro-1H-benzo[d]imidazol-2-ylthio)methyl)-2,4-difluorophenoxy)ethoxy)ethoxy)-N,N-dimethylethanamine trifluoroacetic acid

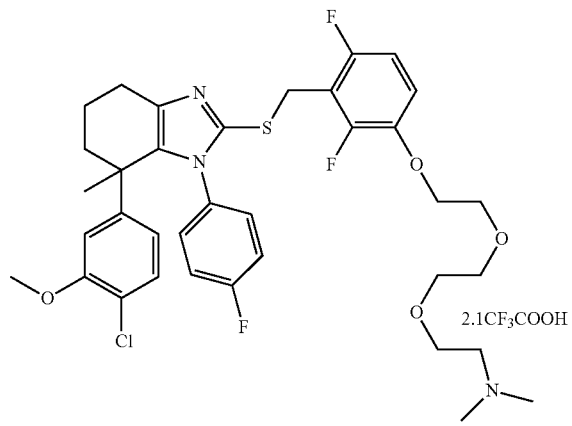

The title compound was prepared according to the procedure as described in Example 27 step 2 by coupling 7-(4-chloro-3-methoxyphenyl)-2-[[(2,6-difluoro-3-[2-[2-(2-iodoethoxy)ethoxy]ethoxy]phenyl) methyl]sulfanyl]-1-(4-fluorophenyl)-7-methyl-4,5,6,7-tetrahydro-1H-1,3-benzodiazole and dimethylamine to afford the desired product as a white solid. $^1$H NMR (400 MHz, CD$_3$OD): δ 7.19-7.32 (m, 4H), 6.95-7.05 (m, 1H), 6.69-6.76 (m, 2H), 6.55-6.57 (m, 1H), 6.06-6.12 (m, 1H), 4.12-4.25 (m, 4H), 3.72-3.91 (m, 11H), 2.88-2.92 (m, 7H), 1.97-1.98 (m, 4H), 1.47 (s, 3H). $^{19}$F NMR (400 MHz, CD$_3$OD): −76.96, −110.92, −127.92, −136.07. Mass spectrum (ESI, m/z): Calcd. for C$_{40.2}$H$_{43.1}$ClF$_{9.3}$N$_3$O$_{8.2}$S, 704.3 (M−2.1CF$_3$COOH+H). found 704.4.

Example 98

2-((3,5-difluoropyridin-4-yl)methylthio)-7-(4-chloro-3-methoxyphenyl)-1-(4-fluorophenyl)-4,5,6,7-tetrahydro-7-methyl-1H-benzo[d]imidazole trifluoroacetic acid

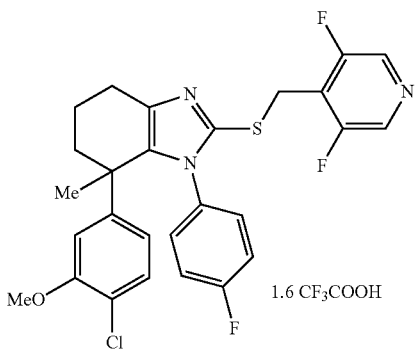 [SMILES: COc1cc(C2(C)CCCc3nc(SCc4c(F)cncc4F)n(-c4ccc(F)cc4)c32)ccc1Cl]

1.6 CF₃COOH

The title compound was prepared according to the procedure as described in Example 78 step 8 by coupling 7-(4-chloro-3-methoxyphenyl)-1-(4-fluorophenyl)-7-methyl-4,5,6,7-tetrahydro-1H-benzo[d]imidazole-2-thiol (Prepared as described in Example 78, Step 7) and 4-(chloromethyl)-3,5-difluoropyridine in the presence of Cs₂CO₃ to afford the desired product as a white solid. $^1$H NMR (400 MHz, CD₃OD): δ 8.47 (s, 2H), 7.23-7.35 (m, 3H), 6.78-6.83 (m, 1H), 6.70-6.71 (m, 1H), 6.56-6.58 (m, 1H), 6.19-6.23 (m, 1H), 4.07-4.20 (m, 2H), 3.80 (s, 3H), 2.79-2.93 (m, 2H), 2.01-2.12 (m, 1H), 1.95-1.98 (m, 3H), 1.48 (s, 3H). $^{19}$F NMR (400 MHz, CD₃OD): δ −77.29, −111.16, −131.62. Mass spectrum (ESI, m/z): Calcd. for $C_{30.2}H_{24.6}ClF_{7.8}N_3O_{4.2}S$, 530.1 (M−1.6CF₃COOH+H). found 530.2.

Example 99

2-(benzylthio)-7-(3,4-dimethoxyphenyl)-1-(4-fluorophenyl)-7-methyl-4, 5, 6, 7-tetrahydro-1H-benzo[d]imidazole Step 1:
2-(3,4-dimethoxyphenyl)-2-methylcyclohexanone

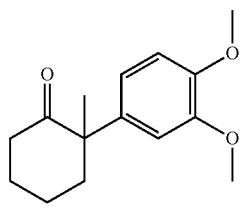

The title compound was prepared according to the procedure as described in Example 78 step 1 reacting 2-(3,4-dimethoxyphenyl)cyclohexanone with NaH followed by MeI as light yellow solid.

$^1$H NMR (400 MHz, CDCl₃) δ 6.82 (d, J=8.2 Hz, 1H), 6.76 (d, J=7.9 Hz, 1H), 6.64 (s, 1H), 3.88 (s, 3H), 2.55 (d, J=7.5 Hz, 1H), 2.38 (m, 1H), 2.31 (d, J=7.5 Hz, 1H), 1.99 (m, 1H), 1.72 (m, 4H), 1.24 (s, 3H).

Step 2: 6-bromo-2-(3,4-dimethoxyphenyl)-2-methylcyclohexanone

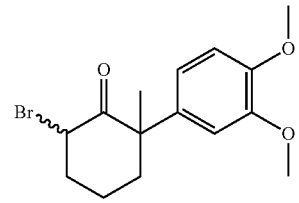 [SMILES: COc1ccc(C2(C)CCCC(Br)C2=O)cc1OC]

The title compound was prepared according to the procedure as described in Example 78 step 2-3 reacting 2-(3,4-dimethoxyphenyl)-2-methylcyclohexanone with TMSOTf/TEA followed by NBS as light yellow solid.
ESI-MS (m/z): Calcd. For $C_{15}H_{19}BrO_3$: 327.21. found: 247 (M−Br+H).

Step 3: 7-(3,4-dimethoxyphenyl)-1-(4-fluorophenyl)-7-methyl-4,5,6,7-tetrahydro-1H-benzo[d]imidazole-2-thiol

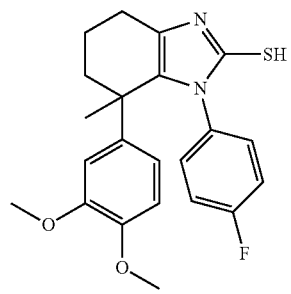 [SMILES: COc1ccc(C2(C)CCCc3nc(S)n(-c4ccc(F)cc4)c32)cc1OC]

The title compound was prepared according to the procedure as described in Example 78 step 4-7 to afford the product as off yellow solid.

Step 4: 2-(benzylthio)-7-(3,4-dimethoxyphenyl)-1-(4-fluorophenyl)-7-methyl-4,5,6,7-tetrahydro-1H-benzo[d]imidazole

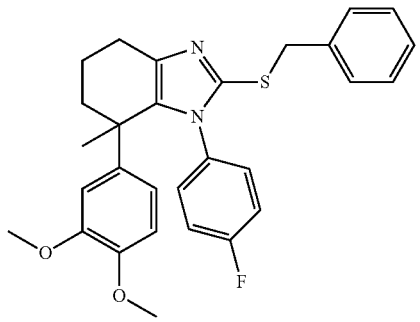 [SMILES: COc1ccc(C2(C)CCCc3nc(SCc4ccccc4)n(-c4ccc(F)cc4)c32)cc1OC]

The title compound was prepared according to the procedure as described in Example 78 step 8 reacting 7-(3,4- dimethoxyphenyl)-1-(4-fluorophenyl)-7-methyl-4,5,6,7-tetrahydro-1H-benzo[d]imidazole-2-thiol and benzyl bromide as an off-white solid.

¹H NMR (400 MHz, CDCl₃) δ 7.25 (m, 4H), 7.18 (m, 1H), 6.88 (t, J=6.5 Hz, 1H), 6.72 (m, 1H), 6.68 (d, J=7.0 Hz, 1H), 6.58 (m, 1H), 6.55 (d, J=7.1 Hz, 1H), 6.43 (d, J=7.5 Hz, 1H), 5.98 (s, 1H), 4.18 (s, 2H), 3.88 (s, 3H), 3.72 (s, 3H), 2.80 (m, 2H), 1.82 (m, 4H), 1.25 (s, 3H).

Example 100

2-((2-chloro-6-fluorobenzyl)thio)-7-(3,4-dimethoxyphenyl)-1-(4-fluorophenyl)-7-methyl-4,5,6,7-tetrahydro-1H-benzo[d]imidazole

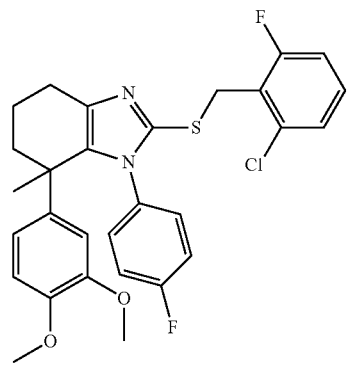 [SMILES: COc1ccc(C2(C)CCCc3nc(SCc4c(F)cccc4Cl)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol(prepared as described in Example 99, Step 3) and 2-(bromomethyl)-1-chloro-3-fluorobenzene as an off-white solid.

¹H NMR (400 MHz, CDCl₃) δ 7.15 (m, 2H), 6.98 (m, 3H), 6.71 (d, J=7.5 Hz, 1H), 6.55 (m, 3H), 6.02 (s, 1H), 4.25 (abq, J=11.5, 7.0 Hz, 2H), 3.85 (s, 3H), 3.80 (s, 3H), 2.81 (m, 2H), 1.82 (m, 4H).

Example 101

(R*)-2-((2-chloro-6-fluorobenzyl)thio)-7-(3,4-dimethoxyphenyl)-1-(4-fluorophenyl)-7-methyl-4,5,6,7-tetrahydro-1H-benzo[d]imidazole (101a) and (S*)-2-((2-chloro-6-fluorobenzyl)thio)-7-(3,4-dimethoxyphenyl)-1-(4-fluorophenyl)-7-methyl-4, 5, 6, 7-tetrahydro-1H-benzo[d]imidazole (101b)

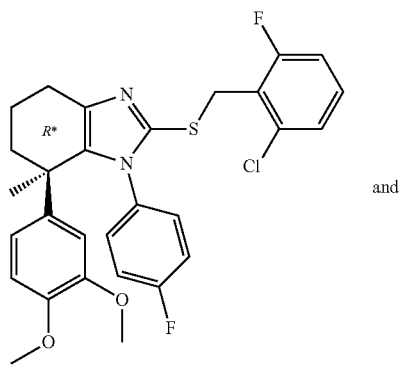
and
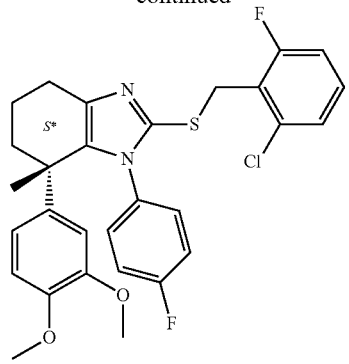

2-((2-chloro-6-fluorobenzyl)thio)-7-(3,4-dimethoxyphenyl)-1-(4-fluorophenyl)-7-methyl-4,5,6,7-tetrahydro-1H-benzo[d]imidazole as a racemate (100 mg) was purified by chiral SFC (CHIRALPAK AD-H 5 μM 250×20 mm) using mobile phase of 80% CO₂ and 20% i-PrOH to yield 45 mg R* enantiomer and 40 mg S* enantiomer as white solids. Absolute stereochemistry is arbitually assigned.

(R*)-2-((2-chloro-6-fluorobenzyl)thio)-7-(3,4-dimethoxyphenyl)-1-(4-fluorophenyl)-7-methyl-4,5,6,7-tetrahydro-1H-benzo[d]imidazole (101a)

First peak, ESI-MS (m/z): Calcd. For $C_{29}H_{27}ClF_2N_2O_2S$: 541.05. found: 541 (M+H).

(S*)-2-((2-chloro-6-fluorobenzyl)thio)-7-(3,4-dimethoxyphenyl)-1-(4-fluorophenyl)-7-methyl-4,5,6,7-tetrahydro-1H-benzo[d]imidazole (101b)

Second peak, ESI-MS (m/z): Calcd. For $C_{29}H_{27}ClF_2N_2O_2S$: 541.05. found: 541 (M+H).

Example 102

4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorobenzonitrile

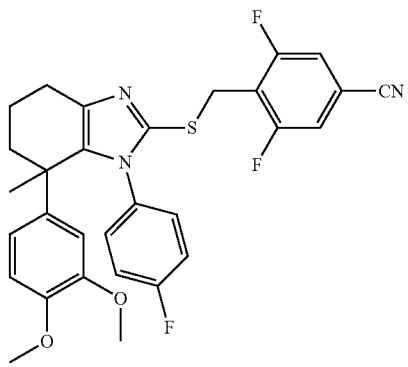 [SMILES: COc1ccc(C2(C)CCCc3nc(SCc4c(F)cc(C#N)cc4F)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol(Prepared as described in Example 99, Step 3) and 4-cyano-2,6-difluorobenzyl methanesulfonate as an off-white solid.

¹H NMR (400 MHz, CDCl₃) δ 7.18 (d, J=6.2 Hz, 2H), 7.05 (m, 2H), 6.71 (d, J=7.0 Hz, 1H), 6.62 (m, 1H), 6.58 (s, 1H), 6.55 (d, J=6.5 Hz, 1H), 6.12 (m, 1H), 4.10 (abq, J=12.8, 7.6 Hz, 2H), 3.91 (s, 3H), 3.82 (s, 3H), 2.72 (m, 2H), 1.83 (m, 4H), 1.31 (s, 3H).

Example 103

4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorobenzoic acid

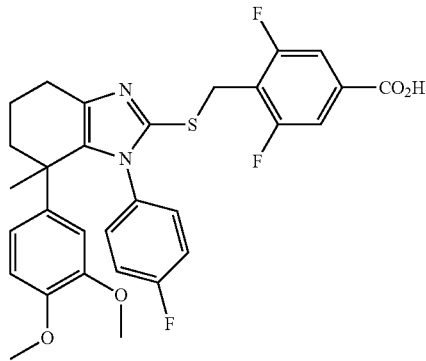 [SMILES: COc1ccc(C2(C)CCCc3nc(SCc4c(F)cc(C(=O)O)cc4F)n(-c4ccc(F)cc4)c32)cc1OC]

The title compound was prepared according to the procedure as described in Example 65 reacting 4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorobenzonitrile in aqueous alkaline solution as a white solid.

¹H NMR (400 MHz, CDCl₃) δ 7.45 (d, J=7.8 Hz, 2H), 7.25 (m, 1H), 7.16 (t, J=6.2 Hz, 1H), 6.75 (m, 2H), 6.68 (s, 1H), 6.58 (d, J=6.0 Hz, 1H), 6.42 (m, 1H), 3.92 (s, 3H), 3.85 (s, 3H), 3.50 (s, 2H), 3.21 (m, 2H), 2.82 (m, 2H), 1.85 (m, 4H), 1.32 (s, 3H).

Example 104

4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorobenzamide

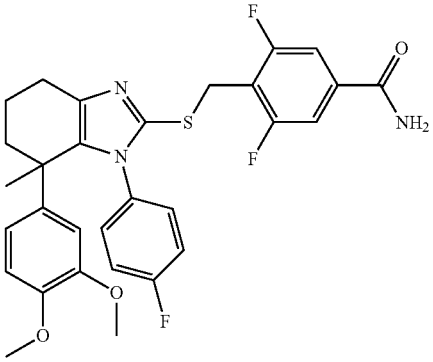 [SMILES: COc1ccc(C2(C)CCCc3nc(SCc4c(F)cc(C(N)=O)cc4F)n(-c4ccc(F)cc4)c32)cc1OC]

The title compound was prepared according to the procedure as described in Example 65 reacting 4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorobenzonitrile (Prepared as described in Example 102) in aqueous alkaline solution as a side product as a while solid.

¹H NMR (400 MHz, CDCl₃) δ 7.26 (d, J=8.0 Hz, 2H), 7.02 (m, 2H), 6.71 (d, J=7.8 Hz, 1H), 6.68 (s, 1H), 6.52 (d, J=5.6 Hz, 1H), 6.45 (t, J=6.1 Hz, 1H), 6.35 (br, s, 1H), 5.18 (m, 1H), 5.10 (br, s, 1H), 4.12 (abq, J=9.5 Hz, 4.3 Hz, 2H), 3.89 (s, 3H), 3.85 (s, 3H), 2.75 (m, 2H), 1.83 (m, 4H), 1.22 (s, 3H).

Example 105

4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluoro-N-(2-(2-(2-(2-hydroxyethoxy)ethoxy) ethoxy)ethyl)benzamide

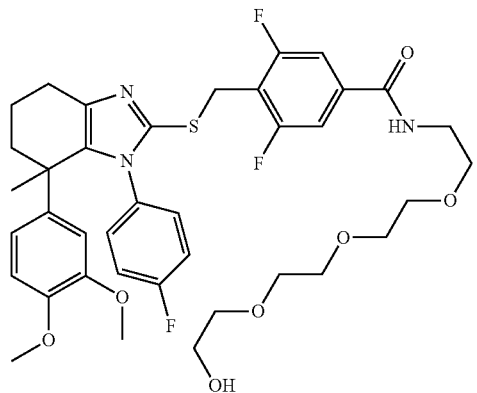 [SMILES: COc1ccc(C2(C)CCCc3nc(SCc4c(F)cc(C(=O)NCCOCCOCCOCCO)cc4F)n(-c4ccc(F)cc4)c32)cc1OC]

The title compound was prepared according to the procedure as described in Example 66 coupling 4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorobenzoic acid (Prepared as described in Example 103) with 2-(2-(2-(2-aminoethoxy)ethoxy) ethoxy) ethanol using HATU as white solid.

¹H NMR (400 MHz, CDCl₃) δ 8.38 (br, s, 1H), 7.42 (d, J=7.0 Hz, 2H), 7.05 (m, 2H), 6.72 (d, J=7.5 Hz, 1H), 6.62 (m, 1H), 6.53 (s, 1H), 6.50 (d, J=6.2 Hz, 1H), 6.16 (m, 1H), 3.98 (abq, J=11.5, 7.0 Hz, 2H), 3.88 (s, 3H), 3.78 (s, 3H), 3.66 (m, 16H), 2.72 (m, 2H), 1.96 (br, s, 1H), 1.80 (m, 4H), 1.25 (s, 3H).

Example 106

2-(2-(2-(4-(((7-(3,4-dimethoxyphenyl)-1-(4-fluorophenyl)-7-methyl-4, 5, 6, 7-tetrahydro-1H-benzo[d]imidazol-2-yl)thio)methyl)-3,5-difluorophenoxy) ethoxy)ethoxy)-N,N-dimethylethanamine Step 1: 4-(2-(2-(2-chloroethoxy)ethoxy)ethoxy)-2,6-difluorobenzyl methanesulfonate

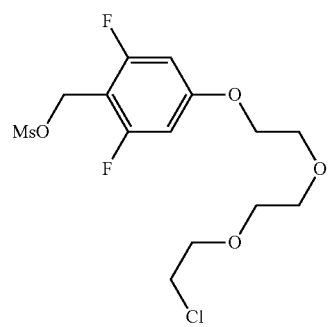 [SMILES: CS(=O)(=O)OCc1c(F)cc(OCCOCCOCCCl)cc1F]

3,5-Difluoro-4-(hydroxymethyl)phenol (2.98 g, 18.6 mmol), 2-(2-(2-chloroethoxy)ethoxy)ethyl methanesulfonate (0.6 g, 18.6 mmol) and K$_2$CO$_3$ (3.85 g, 27.8 mmol) in DMF (10 mL) were heated at 70° C. for 4 hours. The reaction was partitioned between ethyl acetate and water. The organic layer was washed with brine, dried and concentrated to give the (4-(2-(2-(2-chloroethoxy)ethoxy)ethoxy)-2,6-difluorophenyl)methanol as crude material for next step. (4-(2-(2-(2-Chloroethoxy)ethoxy)ethoxy)-2,6-difluorophenyl)methanol (1.28 g, 4.2 mmol) in DCM (10 mL) at 0° C. was treated with TEA (0.63 mL, 4.5 mmol) followed by MsCl (0.34 ml, 4.3 mmol) for 2 hours. The reaction was warmed up to room temperature and partitioned between DCM and saturated sodium bicarbonate. The organic layer was washed with water, brind and dried and concentrated to afford the title product as a colorless oil.

ESI-MS (m/z): Calcd. For C$_{14}$H$_{19}$ClF$_2$O$_6$S: 388.81. found: 412 (M+Na).

Step 2: 2-((4-(2-(2-(2-chloroethoxy)ethoxy)ethoxy)-2,6-difluorobenzyl)thio)-7-(3,4-dimethoxyphenyl)-1-(4-fluorophenyl)-7-methyl-4,5,6,7-tetrahydro-1H-benzo[d]imidazole

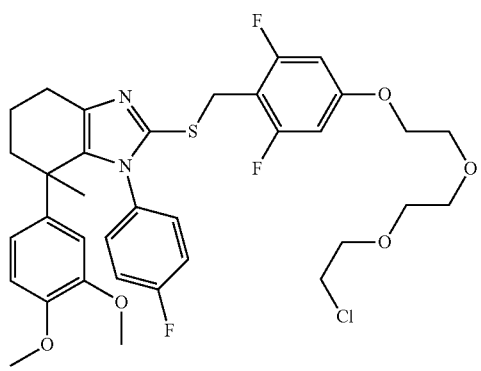 [SMILES: COc1ccc(C2(C)CCCc3nc(SCc4c(F)cc(OCCOCCOCCCl)cc4F)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and 4-(2-(2-(2-chloroethoxy)ethoxy)ethoxy)-2,6-difluorobenzyl methane sulfonate as an off-white solid. $^1$H NMR (400 MHz, CDCl$_3$) δ 7.00 (m, 3H), 6.71 (d, J=6.5 Hz, 1H), 6.60 (s, 1H), 6.55 (m, 2H), 6.42 (d, J=6.5 Hz, 2H), 6.12 (m, 1H), 4.14 (abq, J=11.5, 6.6 Hz, 2H), 4.05 (m, 2H), 3.92 (s, 3H), 3.87 (m, 2H), 3.85 (s, 3H), 3.75 (m, 2H), 3.70 (m, 2H), 3.60 (m, 4H), 2.80 (m, 2H), 2.35 (s, 6H), 1.80 (m, 4H), 1.28 (s, 3H). ESI-MS (m/z): Calcd. For C$_{35}$H$_{38}$ClF$_3$N$_2$O$_5$S: 691.20. found: 691 (M+H).

Step 3: 2-(2-(2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenoxy)ethoxy)ethoxy)-N,N-dimethylethanamine

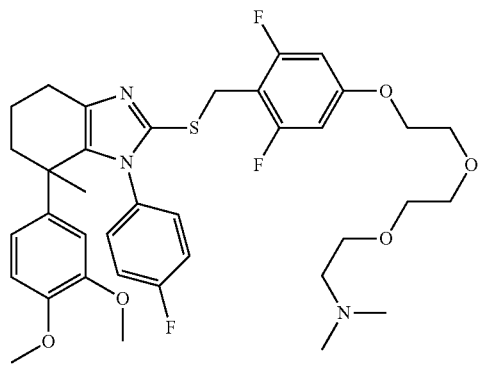 [SMILES: COc1ccc(C2(C)CCCc3nc(SCc4c(F)cc(OCCOCCOCCN(C)C)cc4F)n(-c4ccc(F)cc4)c32)cc1OC]

The title compound was prepared according to the procedure as described in Example 27 step 2 reacting 2-((4-(2-(2-(2-chloroethoxy)ethoxy)ethoxy)-2,6-difluorobenzyl)thio)-7-(3,4-dimethoxyphenyl)-1-(4-fluorophenyl)-7-methyl-4,5,6,7-tetrahydro-1H-benzo[d]imidazole and dimethyl amine as an off-white solid.
$^1$H NMR (400 MHz, CDCl$_3$) δ 7.05 (m, 2H), 6.72 (d, J=7.5 Hz, 1H), 6.62 (s, 1H), 6.54 (m, 2H), 6.42 (d, J=7.5 Hz, 2H), 6.15 (m, 1H), 4.15 (abq, J=10.5, 5.6 Hz, 2H), 4.08 (m, 2H), 3.92 (s, 3H), 3.85 (m, 2H), 3.82 (s, 3H), 3.73 (m, 2H), 3.69 (m, 2H), 3.61 (m, 4H), 2.82 (m, 2H), 2.35 (s, 6H), 1.85 (m, 4H), 1.38 (s, 3H).

Example 107

2-((4-(2-chloroethoxy)-2,6-difluorobenzyl)thio)-7-(3,4-dimethoxyphenyl)-1-(4-fluorophenyl)-7-methyl-4,5,6,7-tetrahydro-1H-benzo[d]imidazole

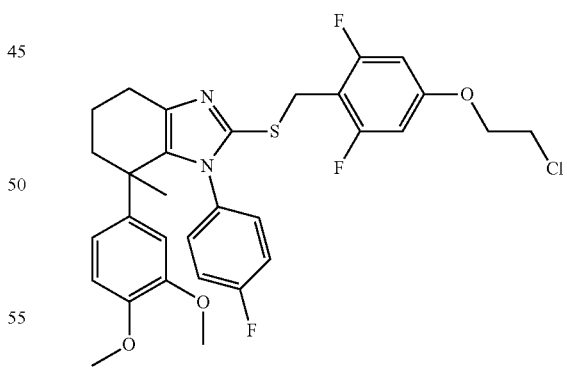

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and 4-(2-chloroethoxy)-2,6-difluorobenzyl methanesulfonate as an off-white solid.
$^1$H NMR (400 MHz, CDCl$_3$) δ 7.02 (m, 2H), 6.72 (d, J=6.5 Hz, 1H), 6.65 (s, 1H), 6.55 (d, J=6.8 Hz, 2H), 6.39 (d, J=7.5 Hz, 2H), 6.08 (m, 1H), 4.18 (m, 2H), 4.10 (abq, J=12.5, 7.5 Hz, 2H), 3.89 (s, 3H), 3.81 (s, 3H), 3.77 (m, 2H), 2.75 (m, 2H), 1.82 (m, 4H), 1.28 (s, 3H).

Example 108

2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenoxy)-N,N-dimethyl-ethanamine

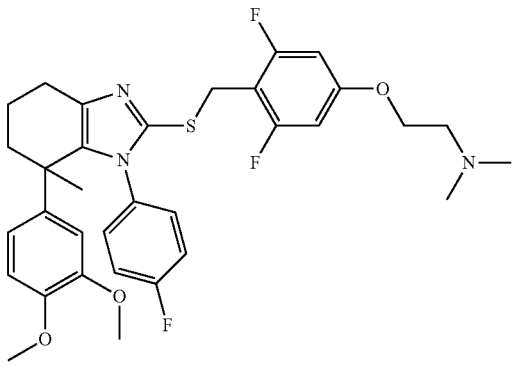 [SMILES: COc1ccc(C2(C)CCCc3nc(SCc4c(F)cc(OCCN(C)C)cc4F)n(-c4ccc(F)cc4)c32)cc1OC]

The title compound was prepared according to the procedure as described in Example 27 step 2 reacting 2-((4-(2-chloroethoxy)-2,6-difluorobenzyl)thio)-7-(3,4-dimethoxyphenyl)-1-(4-fluorophenyl)-7-methyl-4,5,6,7-tetrahydro-1H-benzo[d]imidazole and dimethyl amine as an off-white solid.

$^1$H NMR (400 MHz, CDCl$_3$) δ 7.02 (m, 2H), 6.72 (d, J=7.8 Hz, 1H), 6.61 (d, J=7.5 Hz, 1H), 6.55 (m, 1H), 6.38 (d, J=8.2 Hz, 2H), 6.15 (m, 1H), 4.12 (abq, J=10.5, 6.5 Hz, 2H), 4.02 (t, J=6.8 Hz, 2H), 3.89 (s, 3H), 3.81 (s, 3H), 2.78 (m, 2H), 2.70 (t, J=6.8 Hz, 2H), 2.31 (s, 6H), 1.82 (m, 4H), 1.25 (s, 3H).

Example 109

2-((4-bromo-2,6-difluorobenzyl)thio)-7-(3,4-dimethoxyphenyl)-1-(4-fluorophenyl)-7-methyl-4,5,6,7-tetrahydro-1H-benzo[d]imidazole

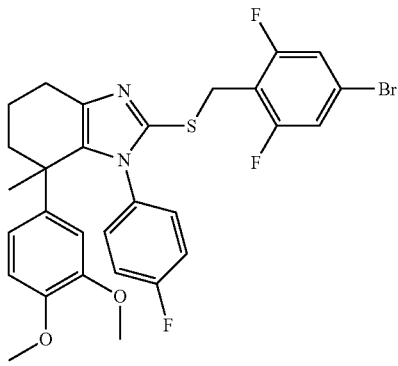 [SMILES: COc1ccc(C2(C)CCCc3nc(SCc4c(F)cc(Br)cc4F)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and 4-bromo-2,6-difluorobenzyl methanesulfonate as an off-white solid.

$^1$H NMR (400 MHz, CDCl$_3$) δ 7.02 (s, 1H), 7.00 (m, 3H), 6.73 (d, J=6.0 Hz, 1H), 6.61 (s, 1H), 6.52 (m, 2H), 6.08 (m, 1H), 4.05 (abq, J=13.1, 8.2 Hz, 2H), 3.89 (s, 3H), 3.78 (s, 3H), 2.75 (m, 2H), 1.80 (m, 4H), 1.25 (s, 3H).

Example 110

(E)-7-(3,4-dimethoxyphenyl)-2-((4-(2-ethoxyvinyl)-2,6-difluorobenzyl)thio)-1-(4-fluorophenyl)-7-methyl-4,5,6,7-tetrahydro-1H-benzo[d]imidazole

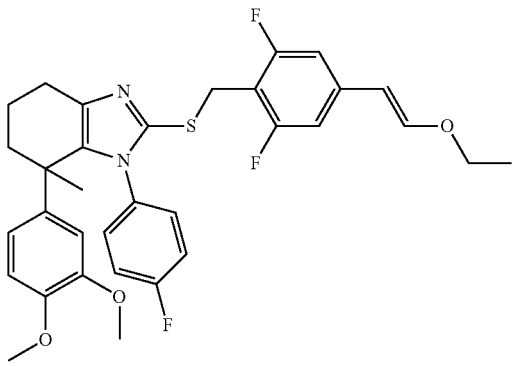 [SMILES: CCO/C=C/c1cc(F)c(CSc2nc3c(n2-c2ccc(F)cc2)C(C)(c2ccc(OC)c(OC)c2)CCC3)c(F)c1]

2-((4-Bromo-2,6-difluorobenzyl)thio)-7-(3,4-dimethoxyphenyl)-1-(4-fluorophenyl)-7-methyl-4,5,6,7-tetrahydro-1H-benzo[d]imidazole (150 mg, 0.25 mmol) and (E)-2-(2-ethoxyvinyl)-4,4,5,5-tetramethyl-1,3,2-dioxaborolane (102 mg, 0.50 mmol), Pd(PPh$_3$)$_4$ (28 mg, 0.025 mmol), 2M Na$_2$CO$_3$ solution (1 mL) in toluene (2 mL) and EtOH (1 mL) were heated at 100° C. in a sealed tube for 2 hours. The reaction was filtered and washed with ethyl acetate. The reaction was partitioned between ethyl acetate and water. The organic layer was washed with brine, dried and concentrated to give the crude product which was then purified by silica gel column chromatography to give the title product as a colorless oil (102 mg, 69%). $^1$H NMR (400 MHz, CDCl$_3$) δ 7.10 (d, J=7.5 Hz, 2H), 6.75 (t, J=7.0 Hz, 1H), 6.62 (d, J=6.5 Hz, 1H), 6.58 (m, 1H), 6.52 (d, J=6.8 Hz, 2H), 6.25 (m, 1H), 6.03 (m, 1H), 5.68 (d, J=9.8 Hz, 1H), 5.10 (d, J=9.5 Hz, 1H), 4.10 (abq, J=13.0, 9.5 Hz, 2H), 3.89 (q, J=8.5 Hz, 2H), 3.85 (s, 3H), 3.78 (s, 3H), 2.80 (m, 2H), 1.81 (m, 4H), 1.32 (s, 3H), 1.28 (t, J=9.3 Hz, 3H).

Example 111

2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)-N,N-dimethyl-ethanamine Step 1: 2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)acetaldehyde

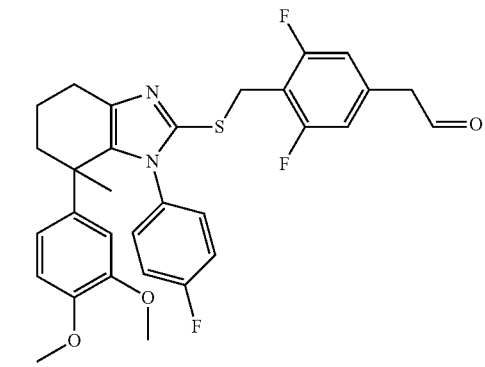 [SMILES: COc1ccc(C2(C)CCCc3nc(SCc4c(F)cc(CC=O)cc4F)n(-c4ccc(F)cc4)c32)cc1OC]

(E)-7-(3,4-dimethoxyphenyl)-2-((4-(2-ethoxyvinyl)-2,6-difluorobenzyl)thio)-1-(4-fluorophenyl)-7-methyl-4,5,6,7-tetrahydro-1H-benzo[d]imidazole (120 mg, 0.202 mmol) in mixed solvent of concentrated HCl (1 mL) and THF (2 mL) was stirred at room temperature for 2 hours. The reaction was neutralized by saturated NaHCO₃ and extracted with ethyl acetate. The organic layer was washed with brine, dried and concentrated to give the crude product: 2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)acetaldehyde as a yellowish oil.

Step 2: 2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)-N,N-dimethylethanamine

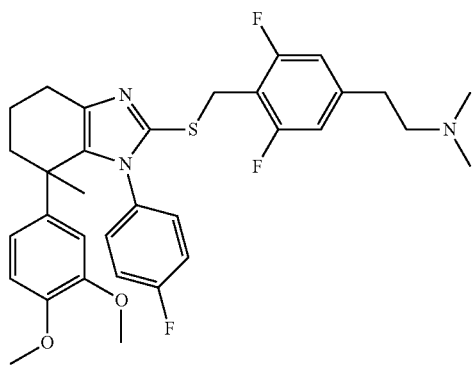 [SMILES: COc1ccc(C2(C)CCCc3nc(SCc4c(F)cc(CCN(C)C)cc4F)n(-c4ccc(F)cc4)c32)cc1OC]

To 2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)acetaldehyde (15 mg, 0.027 mmol) was added dimethyl amine MeOH solution (2M, 0.07 mL) and NaBH(OAc)₃ (17 mg, 0.08 mmol) in DCM (2 mL). The reaction was stirred at room temperature for 2 hours. The solution was partitioned between DCM and saturated NaHCO₃ and then washed with brine. The organic layer was then dried concentrated and purified by silica gel column chromatography to give the title product as a white solid.

¹H NMR (400 MHz, CDCl₃) δ 6.98 (m, 2H), 6.72 (t, J=7.5 Hz, 3H), 6.61 (s, 2H), 6.52 (d, J=6.2 Hz, 1H), 6.08 (m, 1H), 4.15 (abq, J=9.8, 4.6 Hz, 2H), 3.85 (s, 3H), 3.80 (s, 3H), 2.80 (d, J=6.2 Hz, 2H), 2.55 (m, 2H), 2.35 (s, 6H), 1.82 (m, 4H), 1.25 (s, 3H).

Example 112

4-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenethyl)morpholine

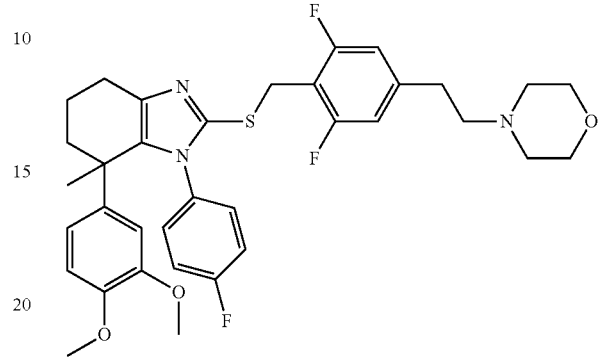

The title compound was prepared according to the procedure as described in Example 111 by reductive amination of 2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)acetaldehyde (prepared as described in Example 111, Step 1) with morpholine to afford the product as an off-white solid.

¹H NMR (400 MHz, CDCl₃) δ 7.05 (m, 2H), 6.68 (d, J=8.5 Hz, 1H), 6.65 (d, J=7.0 Hz, 1H), 6.62 (d, J=8.0 Hz, 2H), 6.57 (d, J=6.5 Hz, 1H), 6.15 (m, 1H), 4.11 (abq, J=9.5, 6.1 Hz, 2H), 3.89 (s, 3H), 3.85 (s, 3H), 3.75 (t, J=5.8 Hz, 4H), 2.76 (m, 2H), 2.58 (m, 2H), 2.52 (m, 4H), 1.38 (s, 3H).

Example 113

2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)ethanol

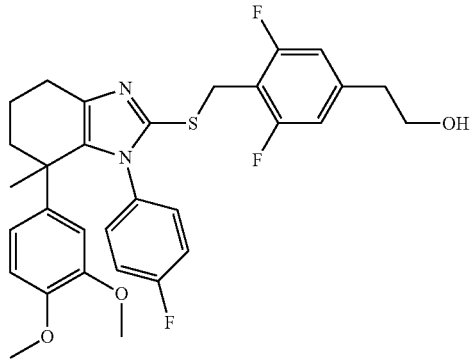 [SMILES: COc1ccc(C2(C)CCCc3nc(SCc4c(F)cc(CCO)cc4F)n(-c4ccc(F)cc4)c32)cc1OC]

A solution of 2-(4-(((7-(3,4-dimethoxyphenyl)-1-(4-fluorophenyl)-7-methyl-4,5,6,7-tetrahydro-1H-benzo[d]imidazol-2-yl)thio)methyl)-3,5-difluorophenyl)acetaldehyde (prepared as described in Example 111, Step 1) (15 mg, 0.027 mmol) in MeOH (1 mL) at room temperature was treated with sodium borohydride (5 mg, 0.1 mmol) for 10 min. The solution was partitioned between ethyl acetate and water and then washed with brine. The organic layer was then dried concentrated and purified by silica gel column chromatography to give the title product as a white solid. ¹H NMR (400 MHz, CDCl₃) δ 7.28 (s, 1H), 7.02 (m, 2H), 6.71 (d, J=7.5 Hz, 2H), 6.62 (s, 1H), 6.55 (m, 2H), 6.10 (m, 1H), 4.05 (abq, J=12.5, 7.0 Hz, 2H), 3.90 (s, 3H), 3.85 (s, 3H), 3.84 (m, 2H), 2.80 (t, J=6.5 Hz, 2H), 2.72 (m, 2H), 1.82 (m, 4H), 1.25 (s, 3H).

Example 114

2-((2,6-dichlorobenzyl)thio)-7-(3,4-dimethoxyphenyl)-1-(4-fluorophenyl)-7-methyl-4,5,6,7-tetrahydro-1H-benzo[d]imidazole

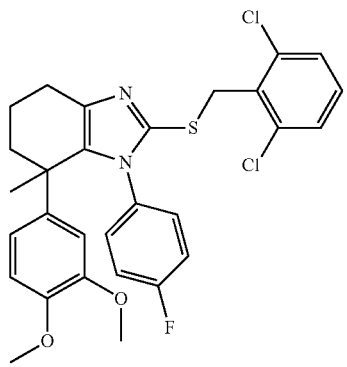 [SMILES: COc1ccc(C2(C)CCCc3nc(SCc4c(Cl)cccc4Cl)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and 2-(bromomethyl)-1,3-dichlorobenzene as an off-white solid.

¹H NMR (400 MHz, CDCl₃) δ 7.23 (d, J=7.8 Hz, 2H), 7.11 (dd, J=7.5, 5.2 Hz, 1H), 6.95 (m, 2H), 6.72 (d, J=6.5 Hz, 1H), 6.59 (s, 1H), 6.55 (m, 1H), 6.50 (t, J=6.0 Hz, 1H), 6.05 (m, 1H), 4.42 (abq, J=12.5, 7.5 Hz, 2H), 3.88 (s, 3H), 3.80 (s, 3H), 2.82 (m, 2H), 1.86 (m, 4H), 1.28 (s, 3H).

Example 115

7-(3,4-dimethoxyphenyl)-2-((2-fluoro-6-nitrobenzyl)thio)-1-(4-fluorophenyl)-7-methyl-4,5,6,7-tetrahydro-1H-benzo[d]imidazole

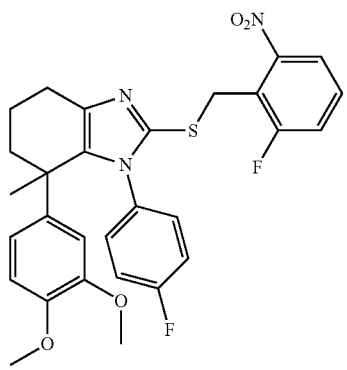 [SMILES: COc1ccc(C2(C)CCCc3nc(SCc4c(F)cccc4[N+](=O)[O-])n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and 2-(bromomethyl)-1-fluoro-3-nitrobenzene as an off-white solid.

¹H NMR (400 MHz, CDCl₃) δ 7.74 (d, J=7.5 Hz, 1H), 7.36 (dd, J=7.8, 4.5 Hz, 1H), 7.31 (d, J=6.9 Hz, 1H), 7.02 (m, 2H), 6.68 (d, J=7.3 Hz, 1H), 6.60 (s, 1H), 6.55 (m, 1H), 6.12 (m, 1H), 4.42 (s, 1H), 3.88 (s, 3H), 3.81 (s, 3H), 2.75 (m, 2H), 1.82 (m, 4H), 1.25 (s, 3H).

Example 116

2-(((3,5-difluoropyridin-4-yl)methyl)thio)-7-(3,4-dimethoxyphenyl)-1-(4-fluorophenyl)-7-methyl-4,5,6,7-tetrahydro-1H-benzo[d]imidazole

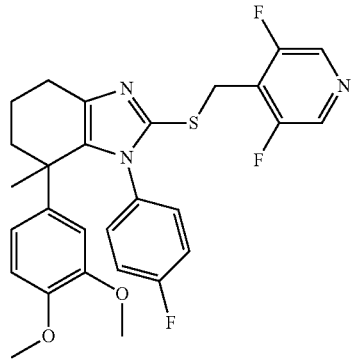 [SMILES: COc1ccc(C2(C)CCCc3nc(SCc4c(F)cncc4F)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and 4-(chloromethyl)-3,5-difluoropyridine HCl salt as an off-white solid.

¹H NMR (400 MHz, CDCl₃) δ 8.25 (s, 2H), 7.02 (d, J=5.8 Hz, 2H), 6.71 (d, J=7.5 Hz, 1H), 6.58 (s, 1H), 6.55 (m, 1H), 6.51 (d, J=5.8 Hz, 1H), 6.10 (m, 1H), 4.10 (abq, J=12.8, 7.4 Hz, 2H), 3.88 (s, 3H), 3.80 (s, 3H), 2.75 (m, 2H), 1.82 (m, 4H), 1.27 (s, 3H).

Example 117

2-(((7-(3,4-dimethoxyphenyl)-1-(4-fluorophenyl)-7-methyl-4,5,6,7-tetrahydro-1H-benzo[d]imidazol-2-yl)thio)methyl)thiazole

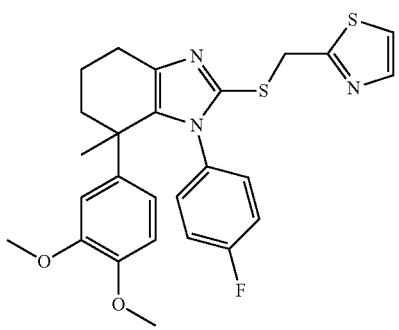 [SMILES: COc1ccc(C2(C)CCCc3nc(SCc4nccs4)n(-c4ccc(F)cc4)c32)cc1OC]

The title compound was prepared according to the procedure as described in Example 78 step 8 reacting 7-(3,4-dimethoxyphenyl)-1-(4-fluorophenyl)-7-methyl-4,5,6,7-tetrahydro-1H-benzo[d]imidazole-2-thiol (Prepared as described in Example 99, Step 3) and thiazol-2-ylmethyl methanesulfonate as an off-white solid.

$^1$H NMR (400 MHz, CDCl$_3$) δ 7.65 (s, 1H), 7.23 (s, 1H), 6.98 (m, 2H), 6.72 (d, J=6.1 Hz, 1H), 6.62 (t, J=5.5 Hz, 1H), 6.55 (m, 2H), 6.18 (m, 1H), 4.57 (abq, J=12.5 Hz, 2H), 3.87 (s, 3H), 3.76 (s, 3H), 2.80 (m, 2H), 1.82 (m, 4H), 1.28 (s, 3H).

Example 118

3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzonitrile Step 1:
2-(3-methoxy-4-fluorophenyl)-2-methylcyclohexanone

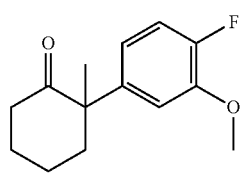 [SMILES: COc1cc(C2(C)CCCCC2=O)ccc1F]

The title compound was prepared according to the procedure as described in Example 78 step 1 reacting 2-(3-methoxy-4-fluorophenyl)cyclohexanone with NaH followed by MeI as light yellow solid. $^1$H NMR (400 MHz, CDCl$_3$) δ 7.05 (dd, J=8.0, 5.5 Hz, 1H), 6.75 (m, 2H), 3.89 (s, 6H), 2.68 (m, 1H), 2.37 (m, 2H), 2.01 (m, 1H), 1.72 (m, 4H), 1.28 (s, 3H), Step 2: 7-(3-methoxy-4-fluorophenyl)-1-(4-fluorophenyl)-7-methyl-4,5,6,7-tetrahydro-1H-benzo[d]imidazole-2-thiol

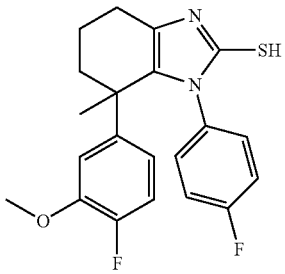 [SMILES: COc1cc(C2(C)CCCc3nc(S)n(-c4ccc(F)cc4)c32)ccc1F]

The title compound was prepared according to the procedure as described in Example 78 step 2-7 to afford the product as a yellow solid.

$^1$H NMR (400 MHz, CDCl$_3$) δ 7.32 (m, 2H), 7.08 (d, J=8.8 Hz, 2H), 7.02 (dd, J=10.5, 7.5 Hz, 1H), 6.83 (d, J=7.0 Hz, 1H), 6.80 (m, 1H), 3.82 (s, 3H), 2.81 (m, 2H), 1.85 (m, 4H).

Step 3: 2-[[(2-chloro-6-fluorophenyl)methyl]sulfanyl]-7-(4-fluoro-3-methoxyphenyl)-1-(4-fluorophenyl)-7-methyl-4,5,6,7-tetrahydro-1H-1,3-benzodiazole

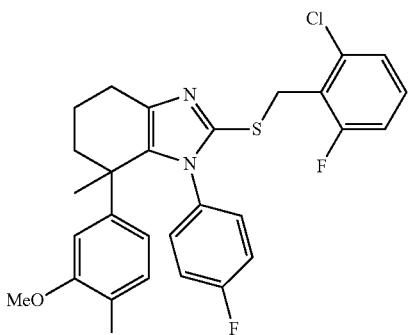

The title compound was prepared according to the procedure as described in Example 78 step 8 reacting 7-(3-methoxy-4-fluorophenyl)-1-(4-fluorophenyl)-7-methyl-4,5,6,7-tetrahydro-1H-benzo[d]imidazole-2-thiol and 2-(bromomethyl)-1-chloro-3-fluorobenzene as an off-white solid. $^1$H NMR (400 MHz, CD$_3$OD): δ 7.22-7.31 (m, 2H), 6.95-7.08 (m, 4H), 6.70-6.73 (m, 1H), 6.54-6.59 (m, 2H), 5.85-5.88 (m, 1H), 4.19 (d, J=13.2 Hz, 1H), 4.00 (d, J=1.6 Hz, 1H), 3.78 (s, 3H), 2.72-2.76 (m, 2H), 1.84-1.95 (m, 4H), 1.31-1.35 (m, 3H). Mass spectrum (ESI, m/z): Calcd. for C$_{28}$H$_{24}$ClF$_3$N$_2$OS, 529.1 (M+H). found 529.3.

Example 119

3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzonitrile

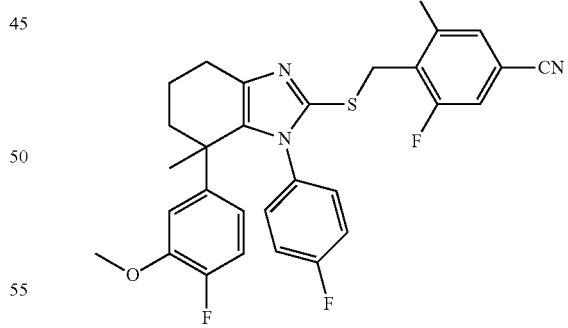

The title compound was prepared according to the procedure as described in Example 78 step 8 reacting 7-(3-methoxy-4-fluorophenyl)-1-(4-fluorophenyl)-7-methyl-4,5,6,7-tetrahydro-1H-benzo[d]imidazole-2-thiol and 4-cyano-2,6-difluorobenzyl methanesulfonate as an off-white solid.

$^1$H NMR (400 MHz, CDCl$_3$) δ 7.18 (d, J=7.5 Hz, 2H), 7.08 (m, 2H), 7.95 (t, J=8.8 Hz, 1H), 6.68 (m, 2H), 5.54 (m, 1H), 6.18 (m, 1H), 4.08 (abq, J=10.5, 4.2 Hz, 2H), 3.78 (s, 3H), 2.75 (m, 2H), 1.82 (m, 4H), 1.28 (s, 3H).

Example 120

3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzoic acid

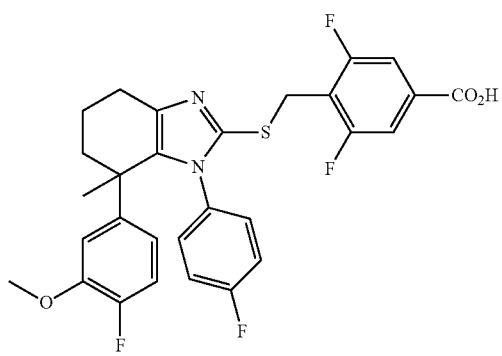

The title compound was prepared according to the procedure as described in Example 65 reacting 3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzonitrile in aqueous alkaline solution as a white solid.

$^1$H NMR (400 MHz, CDCl$_3$) δ 7.42 (d, J=7.2 Hz, 2H), 7.25 (m, J=6.0 Hz, 1H), 7.15 (t, J=6.2 Hz, 1H), 6.95 (t, J=8.5 Hz, 1H), 6.75 (m, 2H), 6.58 (m, 1H), 6.42 (m, 1H), 3.85 (s, 3H), 3.54 (m, 2H), 3.15 (m, 1H), 2.82 (m, 1H), 1.85 (m, 4H), 1.35 (s, 3H).

Example 121

2-((2,6-difluoro-4-(1H-tetrazol-5-yl)benzyl)thio)-7-(4-fluoro-3-methoxyphenyl)-1-(4-fluorophenyl)-7-methyl-4,5,6,7-tetrahydro-1H-benzo[d]imidazole

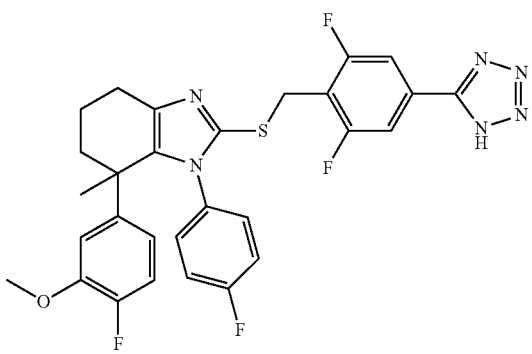 [SMILES: COc1cc(C2(C)CCCc3nc(SCc4c(F)cc(-c5nnn[nH]5)cc4F)n(-c4ccc(F)cc4)c32)ccc1F]

The title compound was prepared according to the procedure as described in Example 30 reacting 3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzonitrile (Prepared as described in Example 119) in NH$_4$Cl and NaN$_3$ solution to afford the product as a white solid.

$^1$H NMR (400 MHz, CDCl$_3$) δ 7.98 (br, s, 1H), 7.62 (d, J=7.8 Hz, 2H), 7.08 (m, 2H), 6.95 (t, J=9.8 Hz, 1H), 6.64 (d, J=5.5 Hz, 2H), 6.53 (m, 1H), 6.12 (m, 1H), 3.98 (abq, J=10.5, 6.1 Hz, 2H), 3.82 (s, 3H), 2.72 (m, 2H), 1.83 (m, 4H).

Example 122

(3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)phenyl) (morpholino)methanone

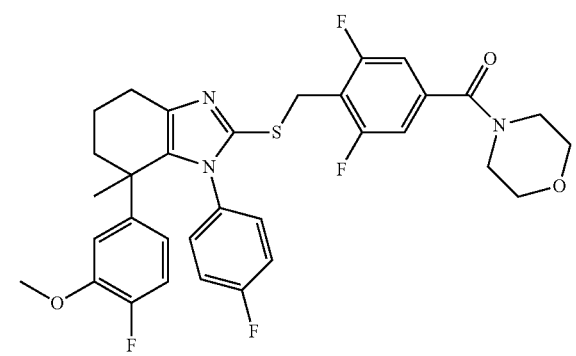 [SMILES: COc1cc(C2(C)CCCc3nc(SCc4c(F)cc(C(=O)N5CCOCC5)cc4F)n(-c4ccc(F)cc4)c32)ccc1F]

The title compound was prepared according to the procedure as described in Example 66 coupling 3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzoic acid (Prepared as described in Example 120) with morpholine using HATU as white solid.

$^1$H NMR (400 MHz, CDCl$_3$) δ 7.08 (m, 2H), 6.95 (t, J=7.5 Hz, 1H), 6.88 (d, J=6.0 Hz, 2H), 6.67 (d, J=6.5 Hz, 2H), 6.56 (m, J=4.0 Hz, 1H), 6.18 (m, 1H), 4.12 (abq, J=9.5, 4.0 Hz, 2H), 3.80 (s, 3H), 3.68 (m, 6H), 3.50 (m, 2H), 2.72 (m, 2H), 1.80 (m, 2H), 1.73 (m, 2H), 1.32 (s, 3H).

Example 123

3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)-N-(2-(2-(2-(2-hydroxyethoxy)ethoxy)ethoxy)ethyl) benzamide

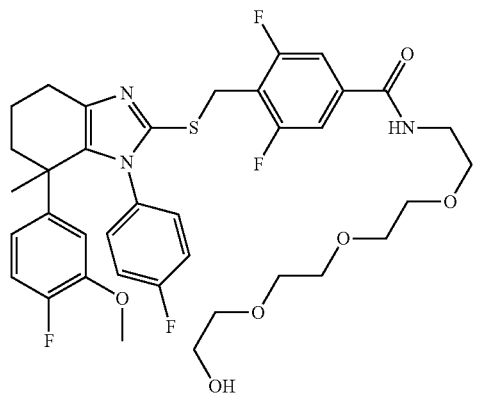 [SMILES: COc1cc(C2(C)CCCc3nc(SCc4c(F)cc(C(=O)NCCOCCOCCOCCO)cc4F)n(-c4ccc(F)cc4)c32)ccc1F]

The title compound was prepared according to the procedure as described in Example 66 coupling 3,5-difluoro- 4-(((7-(4-fluoro-3-methoxyphenyl)-1-(4-fluorophenyl)-7-methyl-4,5,6,7-tetrahydro-1H-benzo[d]imidazol-2-yl)thio)methyl)benzoic acid (Prepared as described in Example 120) with 2-(2-(2-(2-aminoethoxy)ethoxy) ethoxy) ethanol using HATU as white solid.

¹H NMR (400 MHz, CDCl₃) δ 8.32 (br, s, 1H), 7.48 (d, J=6.2 Hz, 2H), 7.12 (m, J=5.7 Hz, 1H), 7.02 (t, J=6.0 Hz, 2H), 6.72 (t, J=6.1 Hz, 1H), 6.60 (d, J=5.8 Hz, 1H), 6.48 (s, 1H), 6.02 (br, s, 1H), 4.21 (abq, J=10.5, 6.5 Hz, 2H), 3.78 (s, 3H), 3.70 (m, 16H), 2.95 (m, 2H), 1.92 (m, 4H), 1.35 (s, 3H).

Example 124

3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)-N-(2-methoxyethyl)benzamide

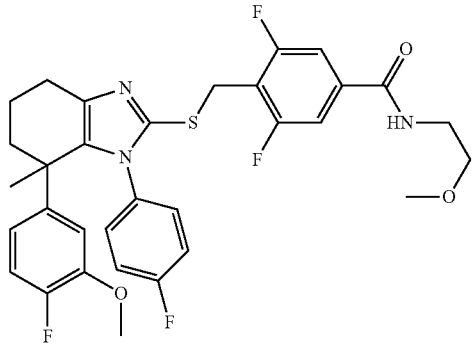 [SMILES: COCCNC(=O)c1cc(F)c(CSc2nc3c(n2-c2ccc(F)cc2)C(C)(c2ccc(F)c(OC)c2)CCC3)c(F)c1]

The title compound was prepared according to the procedure as described in Example 66 coupling 3,5-difluoro-4-(((7-(4-fluoro-3-methoxyphenyl)-1-(4-fluorophenyl)-7-methyl-4,5,6,7-tetrahydro-1H-benzo[d]imidazol-2-yl)thio)methyl)benzoic acid (Prepared as described in Example 120) with 2-methoxyethanamine using HATU as white solid.

¹H NMR (400 MHz, CDCl₃) δ 7.42 (d, J=4.8 Hz, 2H), 7.08 (m, 1H), 6.97 (m, J=5.6 Hz, 1H), 6.90 (t, J=8.6 Hz, 1H), 6.65 (d, J=7.1 Hz, 2H), 6.50 (m, 1H), 6.21 (br, s, 1H), 3.83 (m, 2H), 3.72 (s, 3H), 3.42 (t, J=6.5 Hz, 2H), 3.31 (s, 3H), 2.88 (t, J=6.5 Hz, 2H), 2.62 (m, 2H), 1.78 (m, 4H), 1.28 (s, 3H).

Example 125

2-([[4-(2-[2-[2-(dimethylamino)ethoxy]ethoxy]ethoxy)-2,6-difluorophenyl]methyl]sulfanyl)-7-(4-fluoro-3-methoxyphenyl)-1-(4-fluorophenyl)-7-methyl-4,5,6,7-tetrahydro-1H-1,3-benzodiazole hydrochloride Step 1: 2-[((2,6-difluoro-4-[(4-methoxyphenyl)methoxy]phenyl]methyl)sulfanyl]-7-(4-fluoro-3-methoxyphenyl)-1-(4-fluorophenyl)-7-methyl-4,5,6,7-tetrahydro-1H-1, 3-benzodiazole

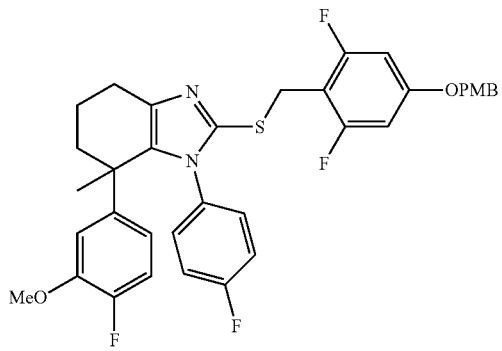

The title compound was prepared according to the procedure as described in Example 78 step 8 reacting 7-(3-methoxy-4-fluorophenyl)-1-(4-fluorophenyl)-7-methyl-4,5,6,7-tetrahydro-1H-benzo[d]imidazole-2-thiol (Prepared as described in Example 118, Step 2) and 2,6-difluoro-4-((4-methoxybenzyl)oxy)benzyl methanesulfonate as an off-white solid. Mass spectrum (ESI, m/z): Calcd. for C₃₆H₃₂F₄N₂O₃S, 649.2 (M+H). found 649.2.

Step 2: 3, 5-difluoro-4-([[7-(4-fluoro-3-methoxyphenyl)-1-(4-fluorophenyl)-7-methyl-4,5,6,7-tetrahydro-1H-1,3-benzodiazol-2-yl]sulfanyl]methyl)phenol

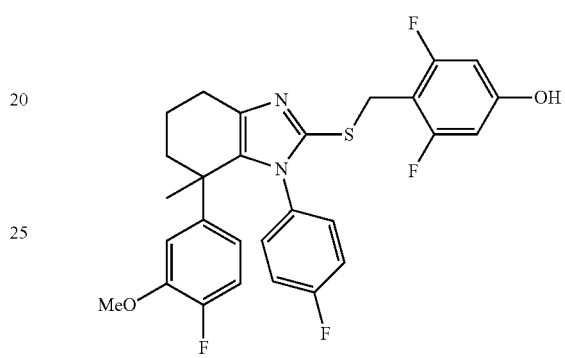

The title compound was prepared according to the procedure as described in Example 24 step 3 reacting 2-[([2,6-difluoro-4-[(4-methoxyphenyl)methoxy]phenyl]methyl)sulfanyl]-7-(4-fluoro-3-methoxyphenyl)-1-(4-fluorophenyl)-7-methyl-4,5,6,7-tetrahydro-1H-1, 3-benzodiazole in TFA to afford the product as an off-white solid. ¹H NMR (300 MHz, CD₃OD): δ 6.99-7.09 (m, 2H), 6.84-6.96 (m, 1H), 6.66-6.72 (m, 1H), 6.39-6.59 (m, 4H), 5.98-6.04 (m, 1H), 4.18-4.32 (m, 2H), 3.79 (s, 3H), 2.93-2.95 (m, 2H), 1.86-1.95 (m, 4H), 1.25-1.35 (m, 3H). Mass spectrum (ESI, m/z): Calcd. for C₂₈H₂₄F₄N₂O₂S, 529.1 (M+H). found 529.1.

Step 3: 2-[[(2,6-difluoro-4-[2-[2-(2-iodoethoxy)ethoxy]ethoxy]phenyl)methyl]sulfanyl]-7-(4-fluoro-3-methoxyphenyl)-1-(4-fluorophenyl)-7-methyl-4,5,6,7-tetrahydro-1H-1,3-benzodiazole

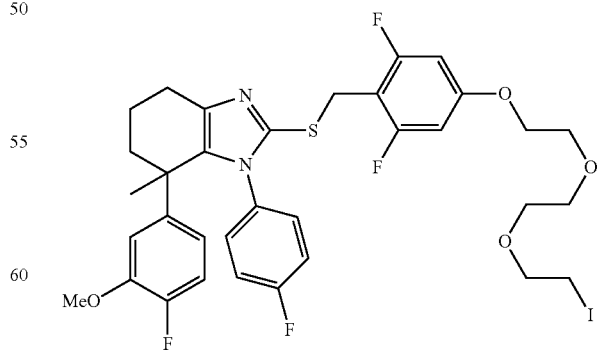

The title compound was prepared according to the procedure as described in Example 24 step 4 by coupling 3, 5-difluoro-4-([[7-(4-fluoro-3-methoxyphenyl)-1-(4-fluorophenyl)-7-methyl-4,5,6,7-tetrahydro-1H-1,3-benzodiazol-2-yl]sulfanyl]methyl)phenol and 1,2-bis(2-idodethyox)ethane in the presence of Cs$_2$CO$_3$ to afford the desired product as a white solid. Mass spectrum (ESI, m/z): Calcd. for C$_{34}$H$_{35}$F$_4$IN$_2$O$_4$S, 771.1 (M+H). found 771.1.

Step 4: 2-([[4-(2-[2-[2-(dimethylamino)ethoxy]ethoxy]ethoxy)-2,6-difluorophenyl]methyl]sulfanyl)-7-(4-fluoro-3-methoxyphenyl)-1-(4-fluorophenyl)-7-methyl-4,5,6,7-tetrahydro-1H-1,3-benzodiazole hydrochloride

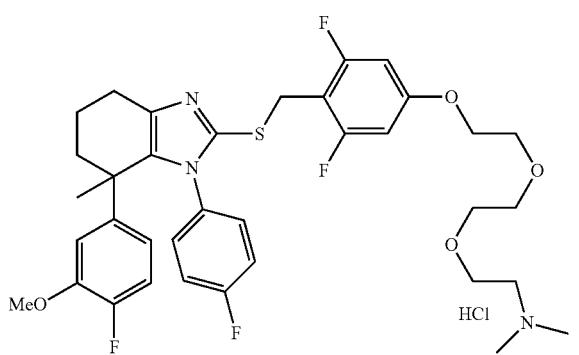 [SMILES: COc1cc(C2(C)CCCc3nc(SCc4c(F)cc(OCCOCCOCCN(C)C)cc4F)n(-c4ccc(F)cc4)c32)ccc1F ; Cl]

The title compound was prepared according to the procedure as described in Example 27 step 2 by coupling 2-[[(2,6-difluoro-4-[2-[2-(2-iodoethoxy)ethoxy]ethoxy]phenyl)methyl]sulfanyl]-7-(4-fluoro-3-methoxyphenyl)-1-(4-fluorophenyl)-7-methyl-4,5,6,7-tetrahydro-1H-1,3-benzodiazole and dimethylamine to afford the desired product as a white solid. $^1$H NMR (400 MHz, CD$_3$OD): δ 7.25-7.34 (m, 2H), 7.03-7.04 (m, 1H), 6.71-6.80 (m, 4H), 6.53-6.56 (m, 1H), 5.96-5.97 (m, 1H), 4.19-4.27 (m, 3H), 4.09-4.20 (m, 1H), 3.77-3.92 (m, 11H), 3.32-3.39 (m, 2H), 2.90-2.94 (m, 8H), 1.99-2.11 (m, 4H), 1.46 (s, 3H). $^{19}$F NMR (400 MHz, CD$_3$OD): −110.89, −116.00, −138.74. Mass spectrum (ESI, m/z): Calcd. for C$_{36}$H$_{42}$ClF$_4$N$_3$O$_4$S, 688.3 (M−HCl+H). found 688.5.

Example 126

7-(4-fluoro-3-methoxyphenyl)-1-(4-fluorophenyl)-7-methyl-2-((pyrimidin-2-ylmethyl)thio)-4,5,6,7-tetrahydro-1H-benzo[d]imidazole

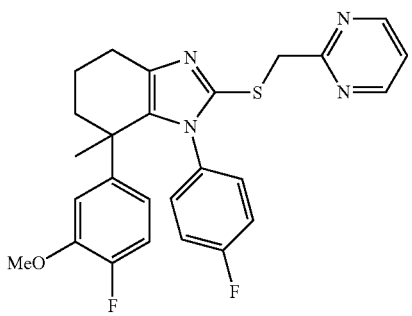 [SMILES: COc1cc(C2(C)CCCc3nc(SCc4ncccn4)n(-c4ccc(F)cc4)c32)ccc1F]

The title compound was prepared according to the procedure as described in Example 78 step 8 reacting 7-(3-methoxy-4-fluorophenyl)-1-(4-fluorophenyl)-7-methyl-4,5,6,7-tetrahydro-1H-benzo[d]imidazole-2-thiol (Prepared as described in Example 118, Step 2) and pyrimidin-2-ylmethyl methanesulfonate as an off-white solid. Mass spectrum (ESI, m/z): Calcd. for C$_{26}$H$_{24}$F$_2$N$_4$OS, 478.56. found 479 (M+H).

Example 127

7-(4-chloro-3-methoxyphenyl)-2-[[(2-chloro-6-fluorophenyl)methyl]sulfanyl]-7-ethyl-1-(4-fluorophenyl)-4,5,6,7-tetrahydro-1H-1,3-benzodiazole Step 1: 2-(4-chloro-3-methoxyphenyl)-2-ethylcyclohexan-1-one

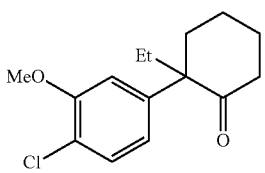 [SMILES: CCC1(c2ccc(Cl)c(OC)c2)CCCCC1=O]

The title compound was prepared according to the procedure as described in Example 78 step 1 reacting 2-(3-methoxy-4-chlorophenyl)cyclohexanone with NaH followed by EtI as light yellow solid. Mass spectrum (ESI, m/z): Calcd. for C$_{15}$H$_{19}$ClO$_2$, 267.2 (M+H). found 267.2.

Step 2: 7-(4-chloro-3-methoxyphenyl)-7-ethyl-1-(4-fluorophenyl)-4,5,6,7-tetrahydro-1H-1,3-benzodiazole-2-thiol

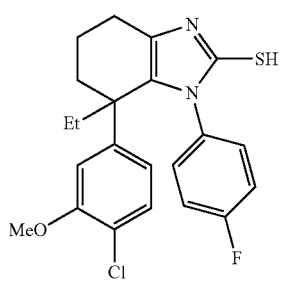 [SMILES: CCC1(c2ccc(Cl)c(OC)c2)CCCc2nc(S)n(-c3ccc(F)cc3)c21]

The title compound was prepared according to the procedure as described in Example 78 step 2-7 to afford the product as a yellow solid. Mass spectrum (ESI, m/z): Calcd. for C$_{22}$H$_{22}$ClFN$_2$OS, 417.1 (M+H). found 417.1.

Step 3: 7-(4-chloro-3-methoxyphenyl)-2-[[(2-chloro-6-fluorophenyl)methyl]sulfanyl]-7-ethyl-1-(4-fluorophenyl)-4,5,6,7-tetrahydro-1H-1,3-benzodiazole

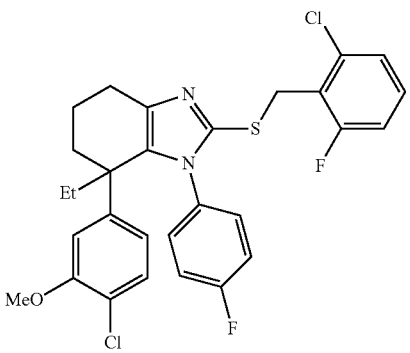

The title compound was prepared according to the procedure as described in Example 78 step 8 reacting 7-(4-chloro-3-methoxyphenyl)-7-ethyl-1-(4-fluorophenyl)-4,5,6,7-tetrahydro-1H-1,3-benzodiazole-2-thiol and 2-(bromomethyl)-1-chloro-3-fluorobenzene as an off-white solid. $^1$H NMR (CD$_3$OD, 300 MHz): δ 7.20-7.30 (m, 3H), 6.98-7.07 (m, 3H), 6.76 (d, J=2.1 Hz, 1H), 6.56-6.61 (m, 2H), 5.91-6.10 (m, 1H), 4.17-4.22 (m, 1H), 4.01 (d, J=1.8 Hz, 1H), 3.79 (s, 3H), 2.67-2.75 (m, 2H), 2.10-2.30 (m, 1H), 1.95-2.05 (m, 1H), 1.79-1.82 (m, 2H), 1.62 (br, 1H), 1.27-1.29 (m, 1H), 0.74-0.79 (m, 3H). Mass spectrum (ESI, m/z): Calcd. for C$_{29}$H$_{26}$Cl$_2$F$_2$N$_2$OS, 559.1 (M+H). found 559.3.

Example 128

(4-(4-chloro-3-methoxyphenyl)-2-(2-chloro-6-fluorobenzylthio)-3-(4-fluorophenyl)-4,5,6,7-tetrahydro-3H-benzo[d]imidazol-4-yl)methanol trifluoroacetic acid Step 1: 2-(4-chloro-3-methoxyphenyl)-2-[[2-(trimethylsilyl)ethoxy]methyl]cyclohexan-1-one

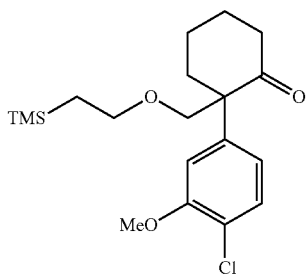 [SMILES: COc1cc(C2(COCC[Si](C)(C)C)CCCCC2=O)ccc1Cl]

The title compound was prepared according to the procedure as described in Example 78 step 1 reacting 2-(3-methoxy-4-chlorophenyl)cyclohexanone with NaH followed by SEMCl as light yellow oil. Mass spectrum (ESI, m/z): Calcd. for C$_{19}$H$_{29}$ClO$_3$Si, 369.2 (M+H). found 369.2.

Step 2: [7-(4-chloro-3-methoxyphenyl)-1-(4-fluorophenyl)-2-sulfanyl-4,5,6,7-tetrahydro-1H-1,3-benzodiazol-7-yl]methanol

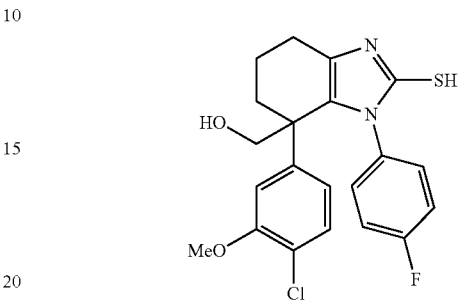

The title compound was prepared according to the procedure as described in Example 78 step 2-7 to afford the product as a yellow solid. Mass spectrum (ESI, m/z): Calcd. for C$_{21}$H$_{20}$ClFN$_2$O$_2$S, 419.1 (M+H). found 419.1.

Step 3. (4-(4-chloro-3-methoxyphenyl)-2-(2-chloro-6-fluorobenzylthio)-3-(4-fluorophenyl)-4,5,6,7-tetrahydro-3H-benzo[d]imidazol-4-yl)methanol trifluoroacetic acid

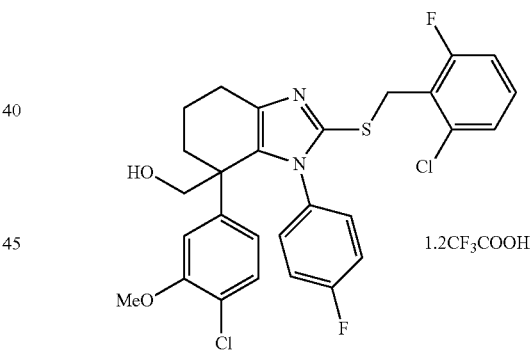

The title compound was prepared according to the procedure as described in Example 78 step 8 reacting [7-(4-chloro-3-methoxyphenyl)-1-(4-fluorophenyl)-2-sulfanyl-4,5,6,7-tetrahydro-1H-1,3-benzodiazol-7-yl]methanol and 2-(bromomethyl)-1-chloro-3-fluorobenzene as an off-white solid. $^1$H NMR (400 MHz, CD$_3$OD): δ 7.44-7.16 (m, 6H), 6.77-6.69 (m, 2H), 6.54-6.52 (m, 1H), 6.12-6.14 (m, 1H), 4.35 (d, J=13.2 Hz, 1H), 4.22 (d, J=13.2 Hz, 1H), 3.96 (d, J=10.8 Hz, 1H), 3.79 (s, 3H), 3.37 (s, 1H), 2.82-2.89 (m, 2H), 2.47-2.51 (m, 1H), 1.88-1.92 (m, 3H). $^{19}$F NMR (300 MHz, CD$_3$OD): −77.11, −111.06, −115.02. Mass spectrum (ESI, m/z): Calcd. for C$_{30.4}$H$_{25.2}$Cl$_2$F$_{5.6}$N$_2$O$_{4.4}$S, 561.1 (M−1.2CF$_3$COOH+H). found 561.1.

Example 129

7-(4-chloro-3-methoxyphenyl)-2-(2-chloro-6-fluorobenzylthio)-7-(fluoromethyl)-1-(4-fluorophenyl)-4,5,6,7-tetrahydro-1H-benzo[d]imidazole trifluoroacetic acid

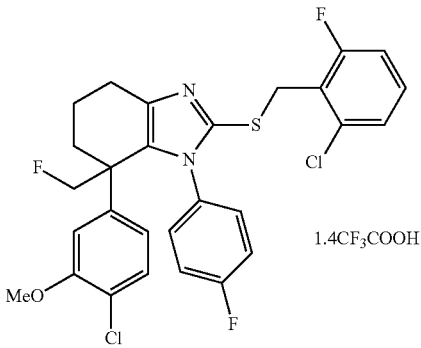 [SMILES: COc1cc(C2(CF)CCCc3nc(SCc4c(F)cccc4Cl)n(-c4ccc(F)cc4)c32)ccc1Cl]

A solution of (4-(4-chloro-3-methoxyphenyl)-2-(2-chloro-6-fluorobenzylthio)-3-(4-fluorophenyl)-4,5,6,7-tetrahydro-3H-benzo[d]imidazol-4-yl)methanol (20 mg, 0.04 mmol, 1.00 equiv), in dichloromethane (1 mL) was treated with BAST (9.45 mg) at −78° C. and stirred for 1.0 h at room temperature. The reaction was quenched by the addition of 1 mL of sodium carbonate/H$_2$O, extracted with 3×3 mL of dichloromethane, and the combined organic layers were dried over anhydrous sodium sulfate, filtered, and concentrated under vacuum. The crude product was purified by Prep-HPLC with the following conditions: (1#waters2767-5) Column, SunFire Prep C18, 19*150 mm 5 µm; mobile phase, Phase A: water with 0.05% TFA, Phase B: CH$_3$CN (40% CH$_3$CN up to 80% in 10 min, up to 100% in 0.1 min, hold 100% in 1.9 min, down to 40% in 0.1 min, hold 40% in 1.9 min); Detector, UV 254 nm, to give the title compound as colorless oil $^1$H NMR (400 MHz, CD$_3$OD): δ 7.25-7.43 (m, 5H), 7.03-7.16 (m, 4H), 6.81-6.91 (m, 1H), 4.16-4.29 (m, 2H), 3.88 (s, 3H), 3.50-3.51 (m, 1H), 2.99-3.16 (m, 1H), 2.71-2.76 (m, 1H), 2.40-2.71 (m, 2H), 2.02-2.07 (m, 2H). $^{19}$F NMR (400 MHz, CD$_3$OD): −77.11, −110.83, −115.30, −156.88. Mass spectrum (ESI, m/z): Calcd. for C$_{30.8}$H$_{24.4}$Cl$_2$F$_{7.2}$N$_2$O$_{3.8}$S, 563.1 (M−1.4CF$_3$COOH+H). found 563.2.

Example 130

4-(4-chloro-3-methoxyphenyl)-2-(2-chloro-6-fluorobenzylthio)-3-(4-fluorophenyl)-4,5,6,7-tetrahydro-3H-benzo[d]imidazole-4-carbaldehyde trifluoroacetic acid

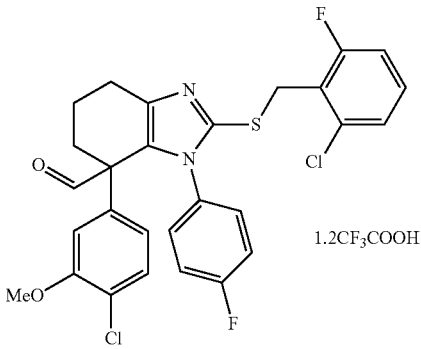 [SMILES: COc1cc(C2(C=O)CCCc3nc(SCc4c(F)cccc4Cl)n(-c4ccc(F)cc4)c32)ccc1Cl]

A solution of (4-(4-chloro-3-methoxyphenyl)-2-(2-chloro-6-fluorobenzylthio)-3-(4-fluorophenyl)-4,5,6,7-tetrahydro-3H-benzo[d]imidazol-4-yl)methanol (Prepared as described in Example 128, 15 mg, 0.03 mmol, 1.00 equiv), dichloromethane (2 mL), and Dess-Martin periodinane (22.7 mg) was stirred for 2.0 h at room temperature. The reaction was quenched by the addition of 1 mL of sodium bicarbonate/H$_2$O, extracted with 3×3 mL of dichloromethane, and the combined organic layers combined were dried over anhydrous sodium sulfate, filtered, and concentrated under vacuum. The crude product (1 mL) was purified by Prep-HPLC with the following conditions: (1#waters2767-5) Column, SunFire Prep C18, 19*150 mm 5 µm; mobile phase, Phase A: water with 0.05% TFA, Phase B: CH$_3$CN (40% CH3CN up to 80% in 10 min, up to 100% in 0.1 min, hold 100% in 1.9 min, down to 40% in 0.1 min, hold 40% in 1.9 min); Detector, UV 254 nm, to give the title compound as a yellow solid. $^1$H NMR (400 MHz, CD$_3$OD): δ 9.83 (s, 1H), 7.32-7.45 (m, 2H), 7.17-7.22 (m, 2H), 7.06-7.15 (m, 1H), 6.92-6.92 (m, 1H), 6.68-6.92 (m, 1H), 6.46-6.55 (m, 2H), 6.14 (s, 1H), 4.21-4.34 (m, 2H), 3.77 (s, 3H), 2.81-2.98 (m, 2H), 2.58-2.62 (m, 1H), 2.27-2.47 (m, 1H), 1.73-1.81 (m, 1H). $^{19}$F NMR (400 MHz, CD$_3$OD): −77.22, −111.68, −114.99. Mass spectrum (ESI, m/z): Calcd. for C$_{30.4}$H$_{23.2}$Cl$_2$F$_{5.6}$N$_2$O$_{4.4}$S, 559.1 (M−1.2CF$_3$COOH+H). found 559.1.

Example 131

2-((2-chloro-6-fluorobenzyl)thio)-4-(3,4-dimethoxyphenyl)-3-(4-fluorophenyl)-3,4,6,7-tetrahydropyrano[3, 4-d]imidazole Step 1: 1-(4-fluorophenyl)-1H-imidazole

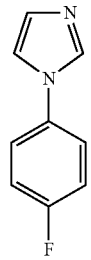 [SMILES: Fc1ccc(-n2ccnc2)cc1]

Imidazole (0.29 g, 4.3 mmol), 4-F-phenylboronic acid (500 mg, 3.57 mmol), copper (I) oxide (107 mg, 0.72 mmol) in MeOH (12 mL) under air were stirred overnight. The solution was filtered and concentrated. The residue was partitioned between ethyl acetate and saturate ammonium chloride and brine. The solution was then dried and concentrated and purified by silica gel column chromatography to give the title compound as a yellow oil. $^1$H NMR (400 MHz, CD$_3$OD) δ 7.80 (s, 1H), 7.35 (m, 2H), 7.21 (m, 4H).

Step 2: 2-((2-chloro-6-fluorobenzyl)thio)-1-(4-fluorophenyl)-1H-imidazole

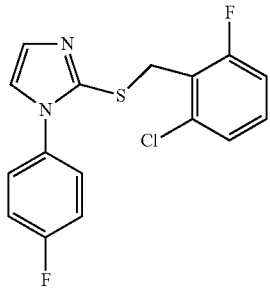 [SMILES: Fc1ccc(-n2ccnc2SCc2c(F)cccc2Cl)cc1]

1-(4-Fluorophenyl)-1H-imidazole (1.4 g, 8.63 mmol) in THF (5 mL) at −78° C. was dropwisely treated with n-BuLi (2.5 M, 3.45 mL, 8.63 mmol) for 30 min. Then S-2-chloro-6-fluorobenzyl 4-methylbenzenesulfonothioate (2.86 g, 8.63 mmol) in THF (5 mL) was slowly dropped into the reaction and stirring was kept at −78° C. for another 2 hours. The reaction was quenched with NH$_4$Cl and warmed up to room temperature. The solvent was removed and the residue was partitioned between ethyl acetate and saturate ammonium chloride and brine. The solution was then dried and concentrated and purified by silica gel column chromatography to give the title compound as a white solid (1.6 g, 55% yield). $^1$H NMR (400 MHz, CDCl$_3$) δ 7.25 (s, 1H), 7.21 (m, 3H), 7.12 (m, 4H), 6.89 (t, J=7.2 Hz, 1H), 4.32 (s, 2H).

Step 3: 2-((2-chloro-6-fluorobenzyl)thio)-1-(4-fluorophenyl)-4,5-diiodo-1H-imidazole

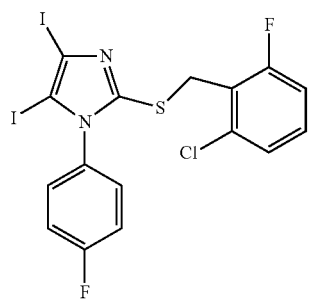 [SMILES: Fc1ccc(-n2c(SCc3c(F)cccc3Cl)nc(I)c2I)cc1]

2-((2-Chloro-6-fluorobenzyl)thio)-1-(4-fluorophenyl)-1H-imidazole (200 mg, 0.60 mmol) and NIS (280 mg, 1.25 mmol), pTSA (3 mg) in DCM (10 mL) were stirred at 50° C. for 6 hours. The reaction was cooled down and washed with saturated sodium thiosulfate and brine. The organic layer was then dried and concentrated and purified by silica gel column chromatography to give the title compound as a white solid (110 mg, 31%). $^1$H NMR (400 MHz, CDCl$_3$) δ 7.20 (m, 6H), 6.95 (t, J=7.0 Hz, 1H), 4.40 (s, 2H).

Step 4: (2-((2-chloro-6-fluorobenzyl)thio)-1-(4-fluorophenyl)-4-iodo-1H-imidazol-5-yl)(3,4-dimethoxyphenyl)methanol

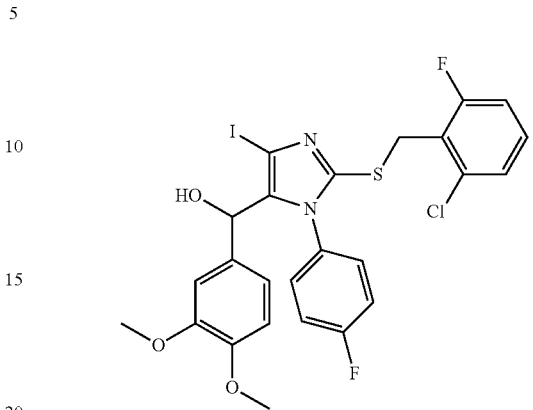

2-((2-Chloro-6-fluorobenzyl)thio)-1-(4-fluorophenyl)-4,5-diiodo-1H-imidazole (170 mg, 0.29 mmol) in THF (2 mL) at 0° C. was treated with i-PrMgBr (2.9 M, 0.1 mL, 0.29 mmol) dropwisely. The reaction was stirred at 0° C. for 10 min and then 3,4-dimethoxybenzaldhyde in THF (2 mL) was dropwisely added into the reaction and stirring was kept for another 2 hours. The reaction was partitioned between ethyl acetate and saturated ammonium chloride. The organic layer was washed with brine then dried and concentrated and purified by silica gel column chromatography to give the title compound as a colorless oil (150 mg, 83% yield). $^1$H NMR (400 MHz, CDCl$_3$) δ 7.18 (m, 3H), 6.91 (t, J=6.8 Hz, 3H), 6.68 (d, J=7.5 Hz, 2H), 6.58 (s, 1H), 6.52 (d, J=6.0 Hz, 1H), 5.90 (s, 1H), 4.38 (s, 2H), 3.83 (s, 3H), 3.72 (s, 3H).

Step 5: (Z)-(2-((2-chloro-6-fluorobenzyl)thio)-4-(2-ethoxyvinyl)-1-(4-fluorophenyl)-1H-imidazol-5-yl)(3,4-dimethoxyphenyl)methanol

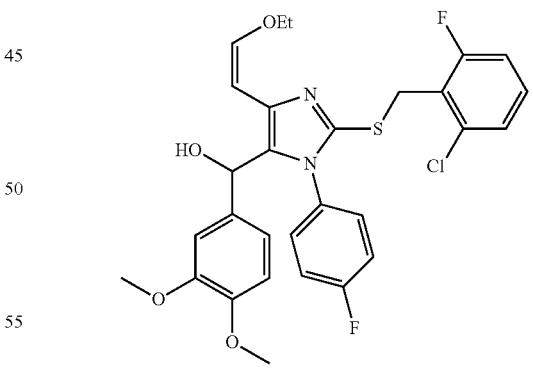

(2-((2-Chloro-6-fluorobenzyl)thio)-1-(4-fluorophenyl)-4-iodo-1H-imidazol-5-yl)(3,4-dimethoxyphenyl)methanol (250 mg, 0.4 mmol), (Z)-tributyl(2-ethoxyvinyl)stannane (287 mg, 0.8 mmol), Pd$_2$(dba)$_3$ (18 mg, 0.02 mmol), triphenyl phosphine (16 mg, 0.06 mmol) in dioxane (6 mL) in a sealed tube were heated at 100° C. for 30 min. The reaction was partitioned between ethyl acetate and saturated ammonium chloride. The organic layer was washed with brine then dried and concentrated and purified by silica gel column chromatography to give the title compound as a colorless oil. Mass spectrum (ESI, m/z): Calcd. for $C_{29}H_{27}ClF_2N_2O_4S$, 573.05. found 574 (M+H).

Step 6: 2-(2-((2-chloro-6-fluorobenzyl)thio)-5-((3,4-dimethoxyphenyl)(hydroxy)methyl)-1-(4-fluorophenyl)-1H-imidazol-4-yl)ethanol

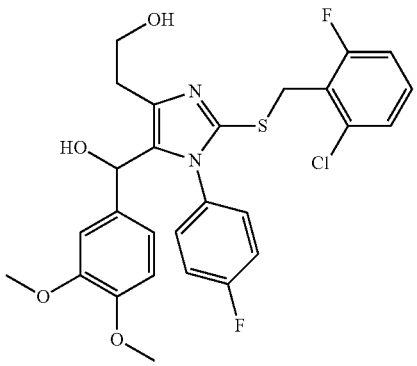 [SMILES: COc1ccc(C(O)c2c(CCO)nc(SCc3c(F)cccc3Cl)n2-c2ccc(F)cc2)cc1OC]

(Z)-(2-((2-chloro-6-fluorobenzyl)thio)-4-(2-ethoxyvinyl)-1-(4-fluorophenyl)-1H-imidazol-5-yl)(3,4-dimethoxyphenyl)methanol (90 mg, 0.15 mmol) in 1 mL concentrated HCl and 2 mL THF was stirred at room temperature for 2 hours. The reaction was neutralized with saturated NaHCO$_3$ and extracted with ethyl acetate. The organic layer was washed with brine then dried and concentrated and purified by silica gel column chromatography to give the title compound as a colorless oil. To this oil in MeOH (1 mL) was added sodium borohydride (20 mg, 0.55 mmol) at 0° C. The reaction was warmed up to room temperature for 10 min and the solvent was removed. The residue was partitioned between ethyl acetate and saturated ammonium chloride. The organic layer was washed with brine then dried and concentrated and purified by silica gel column chromatography to give the title compound as a colorless oil. Mass spectrum (ESI, m/z): Calcd. for $C_{27}H_{25}ClF_2N_2O_4S$, 547.01. found 578 (M+H).

Step 7: 2-((2-chloro-6-fluorobenzyl)thio)-4-(3,4-dimethoxyphenyl)-3-(4-fluorophenyl)-3,4,6,7-tetrahydropyrano[3,4-d]imidazole

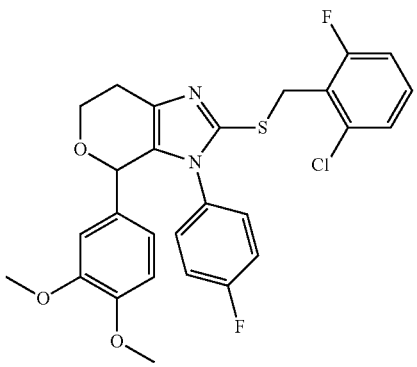 [SMILES: COc1ccc(C2OCCc3nc(SCc4c(F)cccc4Cl)n(-c4ccc(F)cc4)c32)cc1OC]

2-(2-((2-Chloro-6-fluorobenzyl)thio)-5-((3,4-dimethoxyphenyl)(hydroxy)methyl)-1-(4-fluorophenyl)-1H-imidazol-4-yl)ethanol (120 mg, 0.224 mmol) and pTSA (4 mg, 0.022 mmol) in toluene (5 mL) were heated to reflux for 2 hours. The solvent was removed and the residue was purified by silica gel column chromatography to give the title compound as a white solid (54 mg, 47%).

$^1$H NMR (400 MHz, CDCl$_3$) δ 7.24 (m, J=7.2 Hz, 2H), 7.19 (d, J=6.5 Hz, 1H), 7.02 (t, J=6.8 Hz, 1H), 6.85 (m, 2H), 6.62 (d, J=7.0 Hz, 2H), 6.51 (s, 1H), 6.38 (d, J=5.8 Hz, 1H), 5.38 (s, 1H), 4.36 (abq, J=10.5, 6.5 Hz, 2H), 4.25 (m, 1H), 3.95 (m, 1H), 3.85 (s, 3H), 3.72 (s, 3H), 3.21 (m, 1H), 3.08 (m, 1H).

Example 132

4-(4-chloro-3-methoxyphenyl)-2-((2-chloro-6-fluorobenzyl)thio)-3-(4-fluorophenyl)-3,4,6,7-tetrahydropyrano[3, 4-d]imidazole Step 1: 2-(tert-butyldimethylsilyl)-1-(4-fluorophenyl)-1H-imidazole

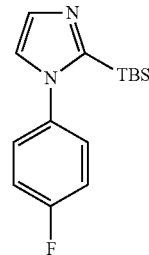

The title compound was prepared according to the procedure as described in Example 131 step 2 reacting 1-(4-fluorophenyl)-1H-imidazole and TBSCl in the presence of n-BuLi at −78° C. to afford the product off-white solid. $^1$H NMR (400 MHz, CDCl$_3$) δ 7.28 (m, 3H), 7.10 (m, J=7.02 Hz, 2H), 7.06 (s, 1H), 0.76 (s, 9H), 0.10 (s, 6H).

Step 2: 4,5-dibromo-2-(tert-butyldimethylsilyl)-1-(4-fluorophenyl)-1H-imidazole

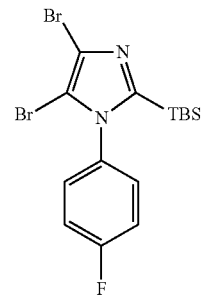

2-(tert-Butyldimethylsilyl)-1-(4-fluorophenyl)-1H-imidazole (4.4 g, 16 mmol) and NBS (5.95 g, 33.4 mmol) in DCM (20 mL) were stirred at room temperature for 4 hours. The reaction was cooled down and washed with saturated sodium thiosulfate and brine. The organic layer was then dried and concentrated and purified by silica gel column chromatography to give the title compound as a white solid (4.85, 70%). $^1$H NMR (400 MHz, CDCl$_3$) δ 7.25 (m, 4H), 0.95 (s, 9H), 0.02 (s, 6H).

Step 3: (4-bromo-2-(tert-butyldimethylsilyl)-1-(4-fluorophenyl)-1H-imidazol-5-yl)(4-chloro-3-methoxyphenyl)methanol

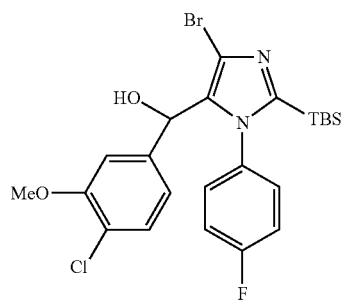

4,5-Dibromo-2-(tert-butyldimethylsilyl)-1-(4-fluorophenyl)-1H-imidazole (1.5 g, 3.45 mmol) in THF (5 mL) at −78° C. was treated with n-BuLi (2.5 M, 1.4 mL, 3.45 mmol) dropwise for 30 min and then 3-methoxy-4-chlorobenzaldehyde (574 mg, 3.5 mmol) in THF (1 mL) was added into the reaction. The reaction was slowly warmed to room temperature for another 2 hour and quenched with saturated NH$_4$Cl. The solvent was removed and the residue was partitioned between ethyl acetate and saturated ammonium chloride. The organic layer was washed with brine then dried and concentrated and purified by silica gel column chromatography to give the title compound as a colorless oil. Mass spectrum (ESI, m/z): Calcd. for $C_{23}H_{27}BrClFN_2O_2Si$, 525.91. found 526 (M+H).

Step 4: (Z)-(2-(tert-butyldimethylsilyl)-4-(2-ethoxyvinyl)-1-(4-fluorophenyl)-1H-imidazol-5-yl)(4-chloro-3-methoxyphenyl)methanol

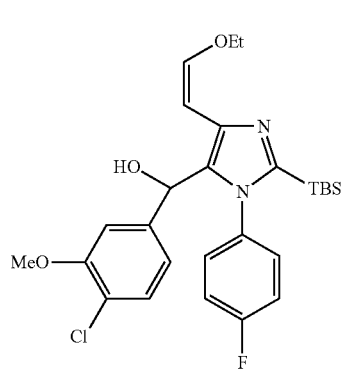

The title compound was prepared according to the procedure as described in Example 131 step 5 reacting (4-bromo-2-(tert-butyldimethylsilyl)-1-(4-fluorophenyl)-1H-imidazol-5-yl)(4-chloro-3-methoxyphenyl)methanol with (Z)-2-(2-ethoxyvinyl)-4,4,5,5-tetramethyl-1,3,2-dioxaborolane with Pd$_2$(dba)$_3$ and BINAP to give a yellow solid. Mass spectrum (ESI, m/z): Calcd. for $C_{27}H_{34}ClFN_2O_3Si$, 517.11. found 518 (M+H).

Step 5: 2-(2-(tert-butyldimethylsilyl)-5-((4-chloro-3-methoxyphenyl)(hydroxy)methyl)-1-(4-fluorophenyl)-1H-imidazol-4-yl)ethanol

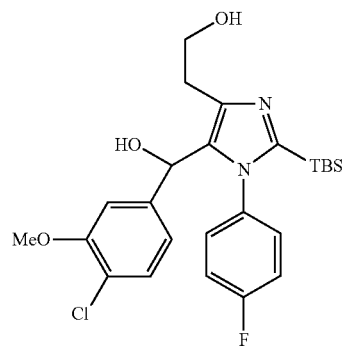

The title compound was prepared according to the procedure as described in Example 131 step 6 reacting (Z)-(2-(tert-butyldimethylsilyl)-4-(2-ethoxyvinyl)-1-(4-fluorophenyl)-1H-imidazol-5-yl)(4-chloro-3-methoxyphenyl)methanol in aqueous HCl solution followed by NaBH$_4$ reduction of the corresponding aldehyde to give a yellow solid. Mass spectrum (ESI, m/z): Calcd. for $C_{25}H_{32}ClFN_2O_3Si$, 491.07. found 492 (M+H).

Step 6: 2-(tert-butyldimethylsilyl)-4-(4-chloro-3-methoxyphenyl)-3-(4-fluorophenyl)-3,4,6,7-tetrahydropyrano[3,4-d]imidazole

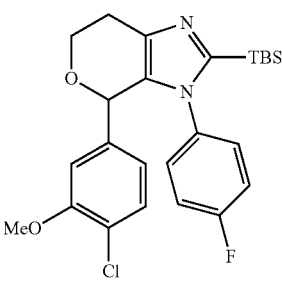

The title compound was prepared according to the procedure as described in Example 131 step 7 reacting 2-(2-(tert-butyldimethylsilyl)-5-((4-chloro-3-methoxyphenyl)(hydroxy)methyl)-1-(4-fluorophenyl)-1H-imidazol-4-yl)ethanol in pTSA toluene solution to give an off white solid. Mass spectrum (ESI, m/z): Calcd. for $C_{25}H_{30}ClFN_2O_2Si$, 473.05. found 474 (M+H).

Step 7: 4-(4-chloro-3-methoxyphenyl)-3-(4-fluorophenyl)-3,4,6,7-tetrahydropyrano[3,4-d]imidazole

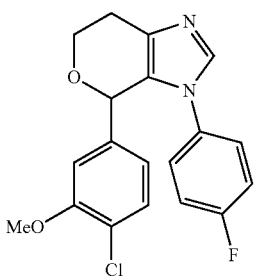 [SMILES: COc1cc(C2OCCc3ncn(-c4ccc(F)cc4)c32)ccc1Cl]

2-(tert-butyldimethylsilyl)-4-(4-chloro-3-methoxyphenyl)-3-(4-fluorophenyl)-3,4,6,7-tetrahydropyrano[3,4-d]imidazole (80 mg) was treated with 1 N TBAF (0.3 mL, 0.34 mmol) at room temperature for 5 min. The solvent was removed and the residue was purified by silica gel column chromatography to afford the title compound as a white solid. Mass spectrum (ESI, m/z): Calcd. for $C_{19}H_{16}ClFN_2O_2$, 358.79. found 359 (M+H).

Step 8: 4-(4-chloro-3-methoxyphenyl)-2-((2-chloro-6-fluorobenzyl)thio)-3-(4-fluorophenyl)-3,4,6,7-tetrahydropyrano[3,4-d]imidazole

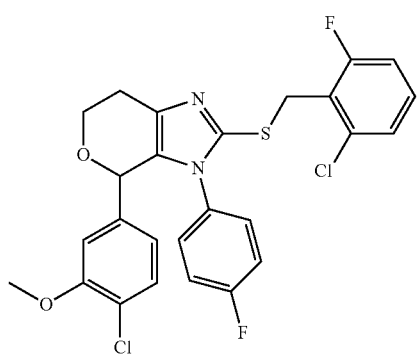 [SMILES: COc1cc(C2OCCc3nc(SCc4c(F)cccc4Cl)n(-c4ccc(F)cc4)c32)ccc1Cl]

The title compound was prepared according to the procedure as described in Example 131 step 2 reacting 4-(4-chloro-3-methoxyphenyl)-3-(4-fluorophenyl)-3,4,6,7-tetrahydropyrano[3,4-d]imidazole and S-2-chloro-6-fluorobenzyl 4-methylbenzenesulfonothioate in the presence of n-BuLi at −78° C. to afford the product off-white solid. $^1$H NMR (400 MHz, CDCl$_3$) δ 7.18 (d, J=7.5 Hz, 2H), 7.11 (d, J=6.5 Hz, 2H), 6.92 (t, J=7.1 Hz, 1H), 6.81 (t, J=7.8 Hz, 2H), 6.62 (m, 1H), 6.55 (s, 1H), 6.44 (m, 1H), 5.42 (s, 1H), 4.28 (abq, J=10.5, 5.8 Hz, 2H), 4.20 (m, 1H), 3.95 (m, 1H), 3.74 (s, 3H), 3.08 (m, 1H), 2.79 (m, 1H).

Example 133

4-(4-chloro-3-methoxyphenyl)-2-((4-(2-(2-(2-chloroethoxy)ethoxy)ethoxy)-2,6-difluorobenzyl)thio)-3-(4-fluorophenyl)-3,4,6,7-tetrahydropyrano[3,4-d]imidazole

Step 1: S-4-(2-(2-(2-chloroethoxy)ethoxy)ethoxy)-2,6-difluorobenzyl 4-methylbenzenesulfonothioate

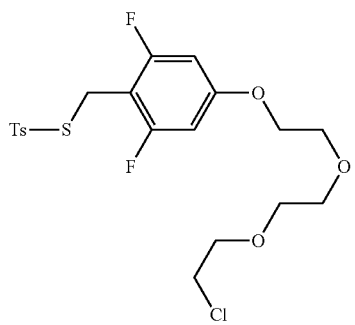 [SMILES: Cc1ccc(S(=O)(=O)SCc2c(F)cc(OCCOCCOCCCl)cc2F)cc1]

4-(2-(2-(2-Chloroethoxy)ethoxy)ethoxy)-2,6-difluorobenzyl methanesulfonate (800 mg, 2.14 mmol) was added solution of p-toluenethiosulfonic acid potassium salt (500 mg, 2.14 mmol) in 10 mL of acetone at room temperature. The solution was stirred overnight. The solid was filtered off. The filtrate was concentrated. It was partitioned between ethyl acetate and water. The organic layer was washed with water and brine and dried and concentrated to give the title product as a white solid (950 mg, 92% yield). $^1$H NMR (400 MHz, CDCl$_3$) δ 7.85 (d, J=7.8 Hz, 2H), 7.30 (d, J=8.5 Hz, 2H), 6.42 (d, J=7.2 Hz, 2H), 4.21 (s, 2H), 4.08 (m, 2H), 3.88 (d, J=6.5 Hz, 2H), 3.75 (m, 4H), 3.62 (m, 4H). 2.48 (s, 3H).

Step 2: 4-(4-chloro-3-methoxyphenyl)-2-((4-(2-(2-(2-chloroethoxy)ethoxy)ethoxy)-2,6-difluorobenzyl)thio)-3-(4-fluorophenyl)-3,4,6,7-tetrahydropyrano[3,4-d]imidazole

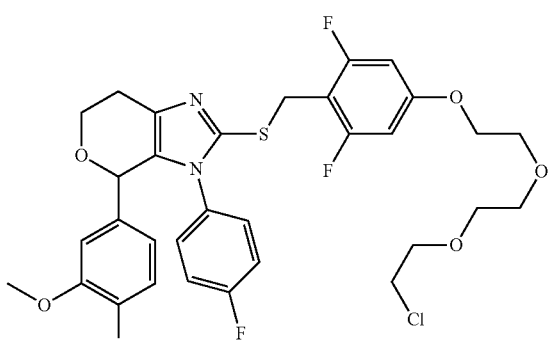

The title compound was prepared according to the procedure as described in Example 131 step 2 reacting 4-(4-chloro-3-methoxyphenyl)-3-(4-fluorophenyl)-3,4,6,7-tetrahydropyrano[3,4-d]imidazole (Prepared as described in Example 132, Step 7) and S-4-(2-(2-(2-chloroethoxy)ethoxy)-2,6-difluorobenzyl 4-methylbenzenesulfonothioate in the presence of n-BuLi at −78° C. to afford the product off-white solid.

$^1$H NMR (400 MHz, CDCl$_3$) δ 7.82 (d, J=7.8 Hz, 1H), 7.39 (d, J=7.5 Hz, 1H), 7.18 (d, J=7.2 Hz, 1H), 6.98 (m, 2H), 6.55 (s, 1H), 6.47 (d, J=8.1 Hz, 2H), 6.38 (m, 2H), 5.42 (s, 1H), 4.65 (abq, J=10.5 Hz, 2H), 4.25 (m, 2H), 4.18 (m, 2H), 3.70 (m, 10H), 3.65 (s, 3H), 3.21 (m, 1H), 3.05 (m, 1H).

Example 134

2-((2-chloro-6-fluorobenzyl)thio)-4-(4-fluoro-3-methoxyphenyl)-3-(4-fluorophenyl)-3,4,6,7-tetrahydropyrano[3,4-d]imidazole Step 1: (2-((2-chloro-6-fluorobenzyl)thio)-1-(4-fluorophenyl)-4-iodo-1H-imidazol-5-yl)(3-methoxy-4-fluorophenyl)methanol

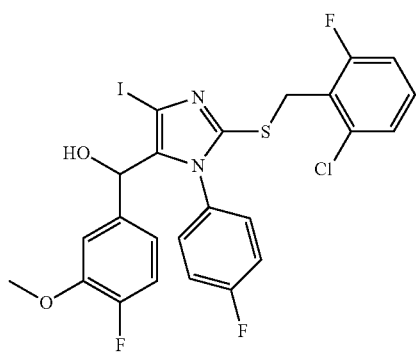 [SMILES: COc1cc(C(O)c2c(I)nc(SCc3c(F)cccc3Cl)n2-c2ccc(F)cc2)ccc1F]

The title compound was prepared according to the procedure as described in Example 131 step 4 reacting 2-((2-chloro-6-fluorobenzyl)thio)-1-(4-fluorophenyl)-4,5-diiodo-1H-imidazole (Prepared as described in Example 131, Step 3) with i-Pr—MgBr followed by 4-fluoro-3-methoxybenzaldehyde to give an off-white solid.). $^1$H NMR (400 MHz, CDCl$_3$) δ 7.25 (m, 6H), 6.91 (t, J=6.8 Hz, 1H), 6.72 (m, 1H), 6.48 (d, J=6.5 Hz, 1H), 6.21 (m, 1H), 5.95 (s, 1H), 4.39 (abq, 2H), 3.73 (s, 3H).

Step 2: (Z)-(2-((2-chloro-6-fluorobenzyl)thio)-4-(2-ethoxyvinyl)-1-(4-fluorophenyl)-1H-imidazol-5-yl)(3-methoxy-4-fluorophenyl)methanol

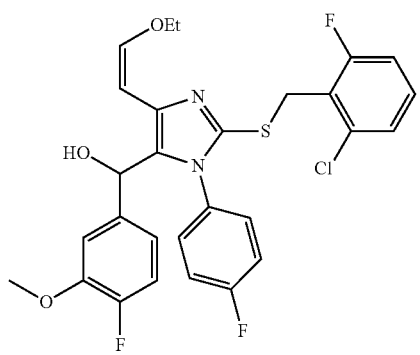 [SMILES: CCO/C=C\c1nc(SCc2c(F)cccc2Cl)n(-c2ccc(F)cc2)c1C(O)c1ccc(F)c(OC)c1]

The title compound was prepared according to the procedure as described in Example 131 step 5 reacting (2-((2-chloro-6-fluorobenzyl)thio)-1-(4-fluorophenyl)-4-iodo-1H-imidazol-5-yl)(3-methoxy-4-fluorophenyl)methanol with (Z)-2-(2-ethoxyvinyl)-4,4,5,5-tetramethyl-1,3,2-dioxaborolane with Pd$_2$(dba)$_3$ and BINAP to give a yellow solid. Mass spectrum (ESI, m/z): Calcd. for C$_{28}$H$_{24}$ClF$_3$N$_2$O$_3$S, 561.01. found 562 (M+H).

Step 3: 2-(2-((2-chloro-6-fluorobenzyl)thio)-5-((3-methoxy4-fluorophenyl)(hydroxy)methyl)-1-(4-fluorophenyl)-1H-imidazol-4-yl)ethanol

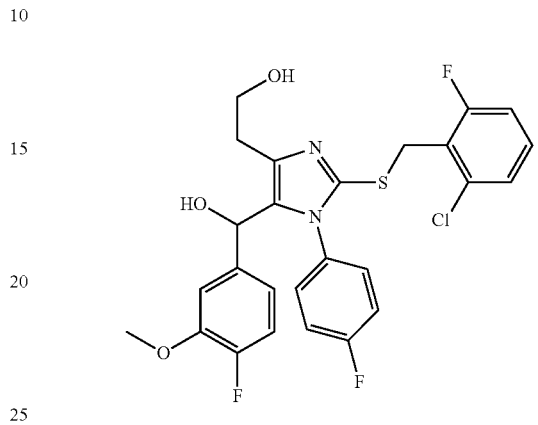

The title compound was prepared according to the procedure as described in Example 131 step 6 reacting (Z)-(2-((2-chloro-6-fluorobenzyl)thio)-4-(2-ethoxyvinyl)-1-(4-fluorophenyl)-1H-imidazol-5-yl)(3-methoxy-4-fluorophenyl)methanol in aqueous HCl solution followed by NaBH$_4$ reduction of the corresponding aldehyde to give a yellow solid. Mass spectrum (ESI, m/z): Calcd. for C$_{26}$H$_{22}$ClF$_3$N$_2$O$_3$S, 534.98. found 534 (M+H).

Step 4: 2-((2-chloro-6-fluorobenzyl)thio)-4-(4-fluoro-3-methoxyphenyl)-3-(4-fluorophenyl)-3,4,6,7-tetrahydropyrano[3,4-d]imidazole

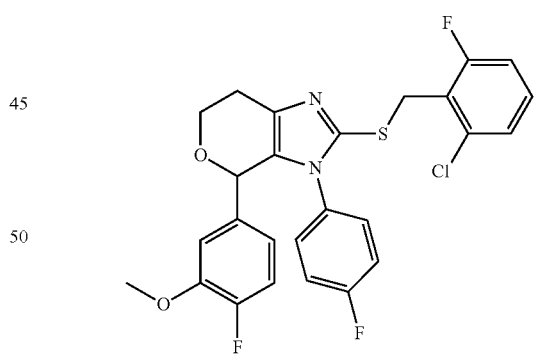

The title compound was prepared according to the procedure as described in Example 131 step 7 reacting 2-(2-((2-chloro-6-fluorobenzyl)thio)-5-((3-methoxy4-fluorophenyl)(hydroxy)methyl)-1-(4-fluorophenyl)-1H-imidazol-4-yl)ethanol in pTSA toluene solution to give an off white solid.

$^1$H NMR (400 MHz, CDCl$_3$) δ 7.25 (t, J=7.2 Hz, 1H), 7.18 (d, J=7.0 Hz, 1H), 6.95 (t, J=7.8 Hz, 1H), 6.85 (m, 2H), 6.80 (t, J=7.8 Hz, 2H), 6.60 (d, J=7.5 Hz, 2H), 6.38 (m, 1H), 5.38 (s, 1H), 4.35 (abq, J=12.5, 7.5 Hz, 2H), 4.24 (m, 1H), 3.92 (m, 1H), 3.75 (s, 3H), 3.20 (m, 1H), 3.01 (m, 1H).

Example 135

2-((2-chloro-6-fluorobenzyl)thio)-3-(4-fluorophenyl)-4-(2-methylbenzo[d]oxazol-6-yl)-3,4,6,7-tetrahydropyrano[3,4-d]imidazole Step 1: (2-((2-chloro-6-fluorobenzyl)thio)-1-(4-fluorophenyl)-4-iodo-1H-imidazol-5-yl)(2-methylbenzo[d]oxazol-6-yl)methanol

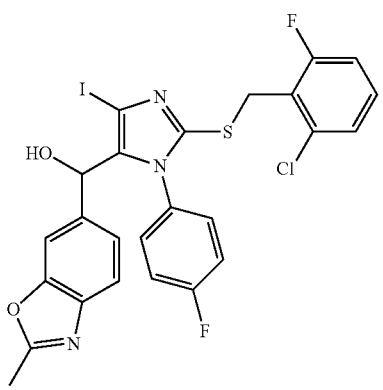 [SMILES: Cc1nc2ccc(C(O)c3c(I)nc(SCc4c(F)cccc4Cl)n3-c3ccc(F)cc3)cc2o1]

The title compound was prepared according to the procedure as described in Example 131 step 4 reacting 2-((2-chloro-6-fluorobenzyl)thio)-1-(4-fluorophenyl)-4,5-diiodo-1H-imidazole (Prepared as described in Example 131, Step 3) with i-Pr—MgBr followed by 2-methylbenzo[d]oxazole-6-carbaldehyde to give an off-white solid.
$^1$H NMR (400 MHz, CDCl$_3$) δ 7.45 (d, J=7.0 Hz, 1H), 7.25 (m, 7H), 6.91 (t, J=6.5 Hz, 2H), 6.11 (m, 1H), 4.35 (abq, 2H), 2.71 (s, 3H).

Step 2: (Z)-(2-((2-chloro-6-fluorobenzyl)thio)-4-(2-ethoxyvinyl)-1-(4-fluorophenyl)-1H-imidazol-5-yl)(2-methylbenzo[d]oxazol-6-yl)methanol

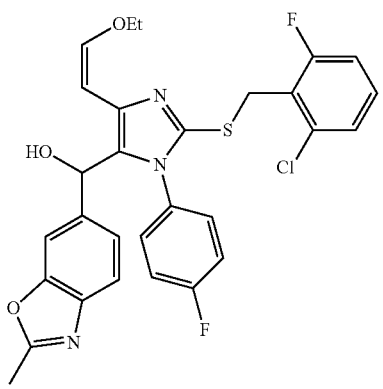 [SMILES: CCO/C=C\c1nc(SCc2c(F)cccc2Cl)n(-c2ccc(F)cc2)c1C(O)c1ccc2nc(C)oc2c1]

The title compound was prepared according to the procedure as described in Example 131 step 5 reacting (2-((2-chloro-6-fluorobenzyl)thio)-1-(4-fluorophenyl)-4-iodo-1H-imidazol-5-yl)(2-methylbenzo[d]oxazol-6-yl)methanol with (Z)-2-(2-ethoxyvinyl)-4,4,5,5-tetramethyl-1,3,2-dioxaborolane with Pd$_2$(dba)$_3$ and BINAP to give a yellow solid. Mass spectrum (ESI, m/z): Calcd. for C$_{29}$H$_{24}$ClF$_2$N$_3$O$_3$S, 568.03. found 564 (M+H).

Step 3: N-(4-((2-((2-chloro-6-fluorobenzyl)thio)-1-(4-fluorophenyl)-4-(2-hydroxyethyl)-1H-imidazol-5-yl)(hydroxy)methyl)-2-hydroxyphenyl)acetamide

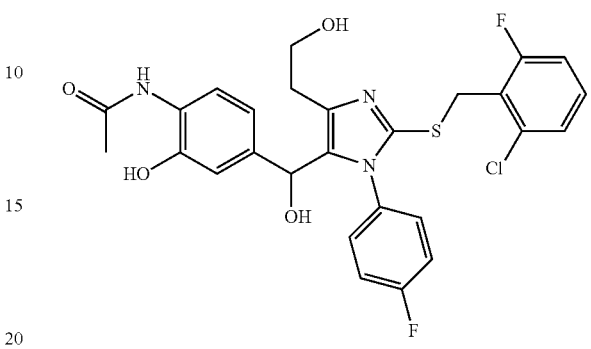

The title compound was prepared according to the procedure as described in Example 131 step 6 reacting (Z)-(2-((2-chloro-6-fluorobenzyl)thio)-4-(2-ethoxyvinyl)-1-(4-fluorophenyl)-1H-imidazol-5-yl)(2-methylbenzo[d]oxazol-6-yl)methanol in aqueous HCl solution followed by NaBH$_4$ reduction of the corresponding aldehyde to give a yellow solid. Mass spectrum (ESI, m/z): Calcd. for C$_{27}$H$_{24}$ClF$_2$N$_3$O$_4$S, 560.01. found 561 (M+H).

Step 4: 2-((2-chloro-6-fluorobenzyl)thio)-3-(4-fluorophenyl)-4-(2-methylbenzo[d]oxazol-6-yl)-3,4,6,7-tetrahydropyrano[3,4-d]imidazole

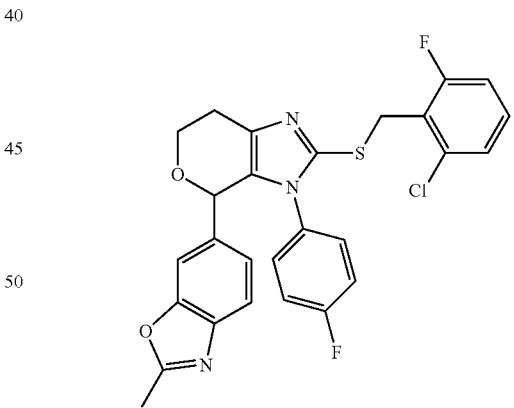

The title compound was prepared according to the procedure as described in Example 131 step 7 reacting N-(4-((2-((2-chloro-6-fluorobenzyl)thio)-1-(4-fluorophenyl)-4-(2-hydroxyethyl)-1H-imidazol-5-yl)(hydroxy)methyl)-2-hydroxyphenyl)acetamide in pTSA toluene solution to give an off white solid.
$^1$H NMR (400 MHz, CDCl$_3$) δ 7.42 (d, J=7.1 Hz, 1H), 7.18 (m, 2H), 7.10 (s, 1H), 6.95 (m, 2H), 6.72 (d, J=7.2 Hz, 2H), 6.51 (m, 2H), 5.61 (s, 1H), 4.30 (abq, J=12.5, 7.5 Hz, 2H), 4.21 (m, 1H), 3.95 (m, 1H), 3.12 (m, 1H), 2.85 (m, 1H), 2.65 (s, 3H).

Example 136

2-((2-chloro-6-fluorobenzyl)thio)-4-(3,4-dimethoxyphenyl)-3-(4-fluorophenyl)-7-methylene-3,4,6,7-tetrahydropyrano[3,4-d]imidazole Step 1: 5-((allyloxy)(3,4-dimethoxyphenyl)methyl)-2-((2-chloro-6-fluorobenzyl)thio)-1-(4-fluorophenyl)-4-iodo-1H-imidazole

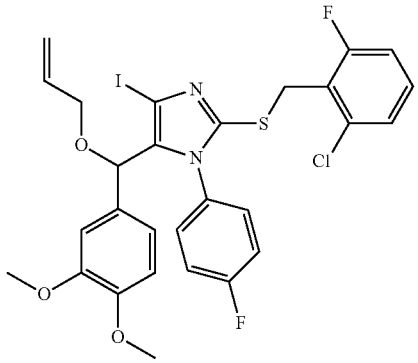 [SMILES: C=CCOC(c1ccc(OC)c(OC)c1)c1c(I)nc(SCc2c(F)cccc2Cl)n1-c1ccc(F)cc1]

A solution of (3,4-dimethoxyphenyl)(2-((2-chloro-6-fluorobenzyl)thio)-1-(4-fluorophenyl)-4-iodo-1H-imidazol-5-yl)methanol (prepared as described in Example 131, Step 4, 50 mg, 0.08 mmol) in THF (1 mL) at 0° C. was treated with NaH (60%, 0.2 mmol, 8 mg) for 10 min and then allyl iodide (34 mg, 0.2 mmol) was added and the reaction was stirred for another 2 hours at 0° C. The reaction was warmed to room temperature and quenched with NH$_4$Cl. The solvent was removed and the residue was partitioned between ethyl acetate and water. The organic layer was washed with water and brine and dried and concentrated to give the title product as a yellow solid (37 mg, 70% yield).

Mass spectrum (ESI, m/z): Calcd. for C$_{28}$H$_{24}$ClF$_2$IN$_2$O$_3$S, 668.92. found 669 (M+H).

Step 2: 2-((2-chloro-6-fluorobenzyl)thio)-4-(3,4-dimethoxyphenyl)-3-(4-fluorophenyl)-7-methylene-3,4,6,7-tetrahydropyrano[3,4-d]imidazole

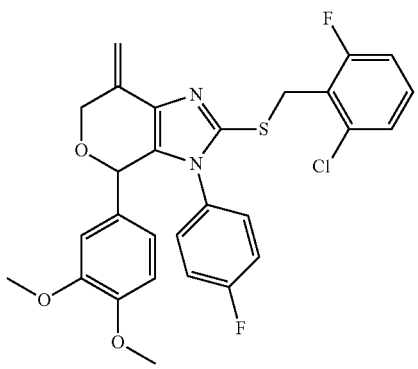 [SMILES: C=C1COC(c2ccc(OC)c(OC)c2)c2c1nc(SCc1c(F)cccc1Cl)n2-c1ccc(F)cc1]

A solution of 5-((allyloxy)(3,4-dimethoxyphenyl)methyl)-2-((2-chloro-6-fluorobenzyl)thio)-1-(4-fluorophenyl)-4-iodo-1H-imidazole (60 mg, 0.09 mmol), Pd$_2$(dba)$_3$ (4 mg, 0.005 mmol), and Ph$_3$P (2 mg, 0.005 mmol) in toluene (2 mL) in a sealed tube were heated at 80° C. for 2 hours. The solvent was removed and the residue was purified by silica gel column chromatography to give the title product as a white solid (12 mg, 24% yield).

$^1$H NMR (400 MHz, CDCl$_3$) δ 7.25 (m, 1H), 7.18 (m, 2H), 6.92 (t, J=7.5 Hz, 1H), 6.85 (m, 1H), 6.81 (t, J=7.1 Hz, 2H), 6.70 (m, 1H), 6.61 (t, J=7.5 Hz, 1H), 6.52 (d, J=7.1 Hz, 1H), 5.71 (s, 1H), 5.52 (s, 1H), 4.92 (s, 1H), 4.42 (abq, J=13.5, 9.1 Hz, 2H), 4.35 (m, 1H), 4.18 (m, 1H), 3.82 (s, 3H), 3.75 (s, 3H).

Example 137

4-(4-chloro-3-methoxyphenyl)-2-((2-chloro-6-fluorobenzyl)thio)-3-(4-fluorophenyl)-7-methylene-3,4,6,7-tetrahydropyrano[3,4-d]imidazole Step 1: (4-chloro-3-methoxyphenyl)(2-((2-chloro-6-fluorobenzyl)thio)-1-(4-fluorophenyl)-4-iodo-1H-imidazol-5-yl)methanol

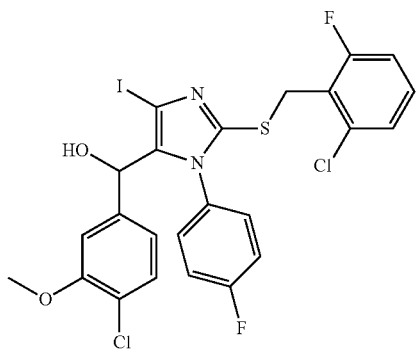 [SMILES: COc1cc(C(O)c2c(I)nc(SCc3c(F)cccc3Cl)n2-c2ccc(F)cc2)ccc1Cl]

The title compound was prepared according to the procedure as described in Example 131 step 4, by reacting 2-((2-chloro-6-fluorobenzyl)thio)-1-(4-fluorophenyl)-4,5-diiodo-1H-imidazole (Derivative prepared as described in Example 131, Step 3) with i-Pr—MgBr followed by 4-chloro-3-methoxybenzaldehyde to give an off-white solid. Mass spectrum (ESI, m/z): Calcd. for C$_{24}$H$_{17}$Cl$_2$F$_2$IN$_2$O$_2$S, 633.28. found 634 (M+H).

Step 2: 5-((allyloxy)(4-chloro-3-methoxyphenyl)methyl)-2-((2-chloro-6-fluorobenzyl)thio)-1-(4-fluorophenyl)-4-iodo-1H-imidazole

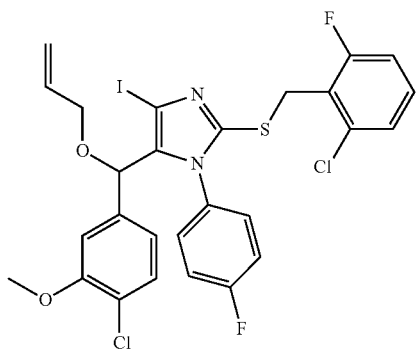 [SMILES: C=CCOC(c1ccc(F)c(OC)c1)c1c(I)nc(SCc2c(F)cccc2Cl)n1-c1ccc(F)cc1]

The title compound was prepared according to the procedure as described in Example 136 step 1 reacting (4-chloro-3-methoxyphenyl)(2-((2-chloro-6-fluorobenzyl)thio)-1-(4-fluorophenyl)-4-iodo-1H-imidazol-5-yl)methanol with allyl iodide in the presence of NaH to give a yellow solid.

Mass spectrum (ESI, m/z): Calcd. for $C_{27}H_{21}Cl_2F_2IN_2O_2S$, 673.34. found 674 (M+H).

Step 3: 4-(4-chloro-3-methoxyphenyl)-2-((2-chloro-6-fluorobenzyl)thio)-3-(4-fluorophenyl)-7-methylene-3,4,6,7-tetrahydropyrano[3,4-d]imidazole

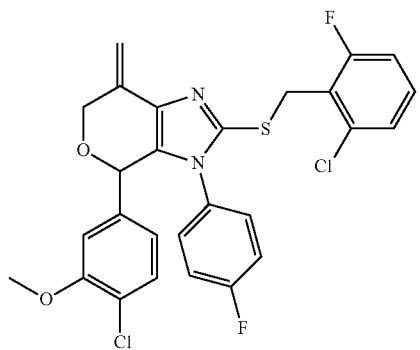 [SMILES: C=C1COC(c2ccc(F)c(OC)c2)c2c1nc(SCc1c(F)cccc1Cl)n2-c1ccc(F)cc1]

The title compound was prepared according to the procedure as described in Example 136 step 2 reacting 5-((allyloxy)(4-chloro-3-methoxyphenyl)methyl)-2-((2-chloro-6-fluorobenzyl)thio)-1-(4-fluorophenyl)-4-iodo-1H-imidazole with $Pd_2(dba)_3$ and $Ph_3P$ to give a yellow solid.

$^1$H NMR (400 MHz, $CDCl_3$) δ 7.32 (s, 1H), 7.21 (m, J=6.5 Hz, 1H), 7.15 (d, J=6.0 Hz, 2H), 6.95 (t, J=7.0 Hz, 1H), 6.84 (m, 2H), 6.58 (m, 2H), 6.42 (d, J=6.5 Hz, 1H), 5.85 (s, 1H), 5.50 (s, 1H), 5.18 (s, 1H), 4.45 (abq, J=12.5, 8.5 Hz, 2H), 4.42 (abq, J=10.5, 7.6 Hz, 2H), 3.78 (s, 3H).

Example 138

4-(4-Fluoro-3-methoxyphenyl)-2-((2-chloro-6-fluorobenzyl)thio)-3-(4-fluorophenyl)-7-methylene-3,4,6,7-tetrahydropyrano[3,4-d]imidazole Step 1: 5-((allyloxy)(4-fluoro-3-methoxyphenyl)methyl)-2-((2-chloro-6-fluorobenzyl)thio)-1-(4-fluorophenyl)-4-iodo-1H-imidazole

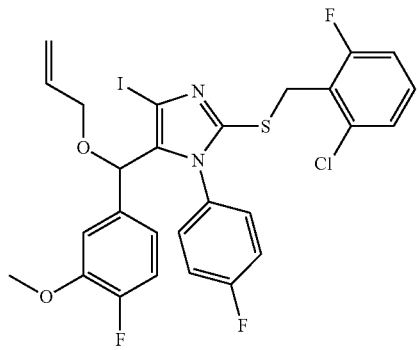

The title compound was prepared according to the procedure as described in Example 136 step 1 reacting (2-((2-chloro-6-fluorobenzyl)thio)-1-(4-fluorophenyl)-4-iodo-1H-imidazol-5-yl)(3-methoxy-4-fluorophenyl)methanol (Prepared as described in Example 134, Step 1) with allyl iodide in the presence of NaH to give a yellow solid.

Mass spectrum (ESI, m/z): Calcd. for $C_{27}H_{21}ClF_3IN_2O_2S$, 656.89. found 657 (M+H).

Step 2: 4-(4-Fluoro-3-methoxyphenyl)-2-((2-chloro-6-fluorobenzyl)thio)-3-(4-fluorophenyl)-7-methylene-3,4,6,7-tetrahydropyrano[3,4-d]imidazole

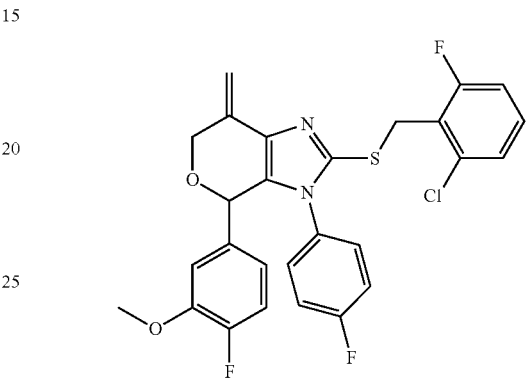

The title compound was prepared according to the procedure as described in Example 136 step 2 reacting 5-((allyloxy)(4-fluoro-3-methoxyphenyl)methyl)-2-((2-chloro-6-fluorobenzyl)thio)-1-(4-fluorophenyl)-4-iodo-1H-imidazole with $Pd_2(dba)_3$ and $Ph_3P$ to give a yellow solid.

$^1$H NMR (400 MHz, $CDCl_3$) δ 7.45 (s, 1H), 7.28 (m, J=7.5 Hz, 1H), 7.30 (d, J=6.5 Hz, 2H), 7.05 (t, J=7.0 Hz, 1H), 6.92 (m, 2H), 6.71 (m, 2H), 6.45 (d, J=6.5 Hz, 1H), 5.87 (s, 1H), 5.60 (s, 1H), 5.15 (s, 1H), 4.51 (abq, J=11.5, 7.5 Hz, 2H), 4.40 (abq, J=11.5, 7.5 Hz, 2H), 3.82 (s, 3H).

In Vitro Biological Data

Example 139

STC1 cAMP Agonist $EC_{50}$ Determination

The STC1 cell line (Cold Spring Harbor Laboratory) was derived from an endocrine tumor that developed in the small intestine of a double transgenic mouse expressing the rat insulin promoters linked to SV40 large T antigen and to the polyomavirus small T antigen. In house expression experiments have shown the presence of the TGR5 mRNA. Cells were cultured in DMEM containing: 10% Horse Serum; 2.5% FBS; 1 μM Sodium Pyruvate; and 1× Penn/Strep. Cell stocks were maintained and grown in a sub-confluent state using standard cell culture procedures. The day before the experiment, the cells were harvested with non-enzymatic cell dissociation buffer and resuspended in complete growth media at 4E5 c/ml. A Greiner PDL coated white 384-plate was then seeded with cells (20 μL per well). The seeded plates were incubated overnight at 37° C.

On the day of the experiment, Assay Buffer containing: HBSS with $Ca^{2+}$ and $Mg^{2+}$; 5 μM HEPES; 0.1% BSA; and, 0.5 μM IBMX was prepared. The growth medium was washed from the cell plates and replaced with 20 μL of Assay Buffer. Test compounds were serially dosed (11 doses at ½ dilution) in DMSO starting at 10 μM. Compound (100 nL) was added to cells using an ECHO. The plate was then incubated at room temperature for 40 min. cAMP standard serial dilution was prepared in Assay Buffer (high concentration 1 M, 12 doses at ½ dilution). 20 μL cAMP standard dilutions were added in duplicate to all plates. The reaction was stopped by the addition of 20 μL 0.1% Formic Acid to all wells. Sixty minutes later 30 μL 3 M deuterated AMP was added to all wells (as a control for volume addition to the mass spec). Plates were mixed on a plate shaker for 1 min and centrifuged (5 min 3000 RPMs no brakes).

Plates were run on a 4000 QTrap triple-quadrapole Mass spectrometer in positive ion mode coupled with a Biocius RapidFire 300is. A C8 cartridge was used, eluting with 80% ACN (250 ms Asp, 4000 ms wash, 3000 ms Elution, 1000 ms $R^e$-equilibration, and pump speed of 1 ml/min). Two ions (cAMP and deuterated AMP were measured using Multiple Reaction Monitoring (MRM) in positive ion mode and the area under the curve (AUC) was determined for each of the ions.

The data from the Mass Spec/Rapid Plate AUC for cAMP and deuterated AMP were imported to an Excel worksheet. A Normalized signal (NS) was generated for each well= (cAMP AUC for the well/deut AMP AUC for the well) *average deut AMP AUC for the plate). nM cAMP was calculated for each well from the cAMP standard curves located on each plate by first calculating the slope and deriving the intercept (b).

$$m = \frac{\Delta NS_{cAMP\_standard\_curve}}{\Delta[standard\_curve]}$$

$$NS_{cAMP\_standard\_cruve} = m(nM\ cAMP\_standard\_curve) + b$$

$$nM\_cAMP = \frac{NS - b}{m}$$

$EC_{50}$ values were determined from a 4-point fit (Hill equation) of a single 11-point compound dosing. A best-fit curve was determined by the minimum sum of squares method plotting cAMP produced vs compound concentration. Net Terminal Value (NTV) was calculated by using the ratio between the size of each dose response curve and the difference of high (p=5 μM standard mTGR5 agonist at a dose that gives a maximal cAMP response) and low (n=vehicle) controls.

size of $CRC$ for compound = nM_cAMP at high[cmpd] − nM cAMP at low[cmpd]

$$\% NTV = \left(1 - \frac{size\ of\ CRC\ for\ compound}{(\mu_P - \mu_N)}\right) * 100$$

% effect was determined at one dose ($2^{nd}$ dose, usually 16 μM) using the nM cAMP of the sample well and the low and high control wells.

$$Percent\ Effect\ (\%_{Eff}) = \left(\frac{S_o - \mu_N}{\mu_p - \mu_n}\right) \times 100$$

Mean ($\mu$) of the positive ($p$) and negative ($n$) controls.

Signal in the compound treated well ($S_o$)

Example 140

NCI-H716 cAMP Agonist $EC_{50}$ Determination

The NCI-H716 cell line (ATCC CCL-251) was derived from cells present in ascites fluid obtained from a patient after treatment with 5-fluorouracil. The cells contain Dopa decarboxylase and, unlike other colorectal lines, contain cytoplasmic dense core granules characteristic of endocrine secretion. In house expression experiments have shown the presence of the TGR5 hRNA. Cells were cultured in suspension using RPM containing: 10% HI FBS, and 1× Penn/Strep and were cryostored (1E7 cells/vial in 5% DMSO).

On the day of the experiment, Assay Buffer containing: HBSS with $Ca^{2+}$ and $Mg^{2+}$; 5 μM HEPES; 0.1% BSA; and, 0.5 μM IBMX was prepared. Cells were thawed, washed in assay buffer, resuspended at 10E5 c/ml, and plated (20 μL) in Corning Non-binding white 384 well plates. Test compounds were serially dosed (11 doses at ½ dilution) in DMSO starting at 10 μM. Compound (100 nL) was added to cells using an ECHO. The plate was then incubated at room temperature for 40 min. cAMP standard serial dilution was prepared in Assay Buffer (high concentration 1 μM, 12 doses at ½ dilution). 20 μL cAMP standard dilutions were added in duplicate to all plates. The reaction was stopped by the addition of 10 μL d2-CAMP in lysis buffer (CisBio cAMP HTRF Dynamic 2 Kit) to all wells. The second component of the detection was immediately added to all wells (10 μL Anti-cAMP in lysis buffer). Plates were mixed on a plate shaker for 1 min and centrifuged (1 min 1000 RPMs) and incubated at room temperature for 1 hour.

The plates were read on an Envision plate reader in HTRF mode (two reads both with Excitation @ 320 nm; Emission Read 1 @ 665 nm; Emission Read 2 @ 615 nm). A Normalized signal (NS) is generated by the Envision for each well ((Read 1/Read 2)×10,000).

The data from the Envision were imported to an Excel worksheet. nM cAMP is calculated for each well from the cAMP standard curves located on each plate by first calculating the slope and deriving the intercept (b).

$$m = \frac{\Delta NS_{cAMP\_standard\_curve}}{\Delta[standard\_curve]}$$

$$NS_{cAMP\_standard\_cruve} = m(nM\ cAMP\_standard\_curve) + b$$

$$nM\_cAMP = \frac{NS - b}{m}$$

$EC_{50}$ values were determined from a 4-point fit (Hill equation) of a single 11-point compound dosing. A best-fit curve was determined by the minimum sum of squares method plotting cAMP produced vs compound concentration. Net Terminal Value (NTV) was calculated by using the ratio between the size of each dose response curve and the difference of high (p=16 μM standard hTGR5 agonist at a dose that gives a maximal cAMP response) and low (n=vehicle) controls.

size of $CRC$ for compound = nM_cAMP at high[cmpd] − nM cAMP at low[cmpd]

-continued $$\% \, NTV = \left(1 - \frac{\text{size of } CRC \text{ for compound}}{(\mu_P - \mu_N)}\right) * 100$$

% effect was determined at one dose ($2^{nd}$ dose, usually 16 µM) using the nM cAMP of the sample well and the low and high control wells.

$$\text{Percent Effect } (\%_{Eff}) = \left(\frac{S_o - \mu_N}{\mu_p - \mu_n}\right) \times 100$$

Mean ($\mu$) of the positive ($p$) and negative ($n$) controls.

Signal in the compound treated well ($S_o$)

In Vitro Biological Data

| Example | STC-1 EC$_{50}$ (µM) | NCI-H716 EC$_{50}$ (µM) |
|---|---|---|
| 1 | 0.89 | >50 |
| 2 | 38.16 | >50 |
| 3 | 0.51 | >50 |
| 4 | 0.31 | 30.51 |
| 5 | 0.49 | >50 |
| 6 | 13.35 | >50 |
| 7 | 0.81 | >50 |
| 8 | 1.34 | >50 |
| 9 | 9.86 | >50 |
| 10 | 0.79 | >50 |
| 11 | 3.71 | >50 |
| 12 | 19.68 | >50 |
| 13 | 8.04 | >50 |
| 14 | 0.53 | >50 |
| 15 | 13.26 | >50 |
| 16 | 4.81 | >50 |
| 17 | 0.62 | >50 |
| 18 | 0.40 | >50 |
| 19 | 7.41 | >50 |
| 20 | 0.51 | >50 |
| 21a | 0.69 | 48.39 |
| 21b | 8.12 | >50 |
| 22 | 32.59 | >50 |
| 23 | 0.66 | >50 |
| 24 | 3.92 | >50 |
| 25 | nt | nt |
| 26 | nt | nt |
| 27 | nt | nt |
| 28 | nt | nt |
| 29 | nt | nt |
| 30 | 0.96 | >50 |
| 31 | 4.10 | 4.44 |
| 32 | 1.38 | 16.90 |
| 33 | 4.90 | >50 |
| 34 | 3.90 | >50 |
| 35 | 3.15 | 9.30 |
| 36 | 1.34 | >50 |
| 37 | 14.89 | >50 |
| 38 | 1.25 | >50 |
| 39a | 0.36 | >50 |
| 39b | 16.27 | >50 |
| 40 | 1.36 | >50 |
| 41 | 0.89 | >50 |
| 42 | 0.53 | >50 |
| 43 | 0.67 | >50 |
| 44 | 1.39 | >50 |
| 45 | 0.35 | >50 |
| 46 | 0.14 | >50 |
| 47 | 0.37 | 47.30 |
| 48 | 0.35 | >50 |
| 49 | 0.94 | >50 |
| 50 | 0.28 | 34.70 |
| 51 | 5.50 | >50 |
| 52 | 0.45 | >50 |
| 53 | nt | nt |
| 54 | 4.41 | >50 |
| 55 | 0.18 | >50 |
| 56 | 0.13 | >50 |
| 57 | 0.65 | >50 |
| 58 | 1.10 | >50 |
| 59 | 2.02 | >50 |
| 60 | 15.49 | >50 |
| 61 | 3.89 | >50 |
| 62 | 0.13 | 12.50 |
| 63a | 9.39 | >50 |
| 63b | 0.07 | 3.41 |
| 64 | 0.15 | 5.34 |
| 65 | 3.75 | >50 |
| 66 | 0.90 | 2.40 |
| 67 | 0.50 | 8.34 |
| 68a | 7.39 | 22.00 |
| 68b | 28.64 | >50 |
| 69 | 0.85 | 7.97 |
| 70 | 2.78 | >50 |
| 71 | 1.91 | >50 |
| 72 | 0.91 | 35.18 |
| 73 | 1.53 | 47.50 |
| 74 | 1.10 | >50 |
| 75 | 2.76 | >50 |
| 76 | 1.51 | >50 |
| 77 | 2.93 | >50 |
| 78 | 0.56 | >50 |
| 79 | 0.46 | 15.8 |
| 80 | 2.94 | 19.22 |
| 81 | 1.75 | >50 |
| 82 | 0.18 | 15.23 |
| 83 | 0.13 | 17.23 |
| 84 | 0.34 | 38.70 |
| 85 | 0.12 | 1.88 |
| 86 | 2.22 | 27.07 |
| 87 | 47.80 | >50 |
| 88 | 4.78 | >50 |
| 89 | 2.08 | >50 |
| 90 | 3.90 | >50 |
| 91 | 0.23 | >50 |
| 92 | 0.12 | 18.10 |
| 93 | 0.25 | >50 |
| 94 | 0.41 | >50 |
| 95 | 0.37 | 12.50 |
| 96 | 13.42 | >50 |
| 97 | 0.68 | 3.73 |
| 98 | 0.16 | 24.27 |
| 99 | 2.39 | 33.13 |
| 100 | 0.01 | 0.44 |
| 101a | >50 | >50 |
| 101b | 0.11 | 0.64 |
| 102 | 0.03 | 1.37 |
| 103 | 0.09 | 3.50 |
| 104 | 0.17 | 0.90 |
| 105 | 0.21 | 0.94 |
| 106 | 0.09 | 0.51 |
| 107 | 0.32 | 1.40 |
| 108 | 0.31 | 0.68 |
| 109 | 0.20 | 3.60 |
| 110 | 0.45 | 1.18 |
| 111 | 0.20 | 1.41 |
| 112 | 0.13 | 0.30 |
| 113 | 0.05 | 0.72 |
| 114 | 1.64 | 25.70 |
| 115 | 0.22 | 2.60 |
| 116 | 0.05 | 0.77 |
| 117 | 0.41 | 2.65 |
| 118 | 0.68 | 4.31 |
| 119 | 0.18 | >50 |
| 120 | 1.18 | >50 |
| 121 | 3.11 | >50 |
| 122 | 0.09 | 18.78 |
| 123 | 0.05 | 17.00 |
| 124 | 0.80 | >50 |
| 125 | 1.09 | 25.10 |
| 126 | 0.30 | 0.68 |

-continued

| Example | STC-1 EC$_{50}$ (μM) | NCI-H716 EC$_{50}$ (μM) |
| --- | --- | --- |
| 127 | >50 | >50 |
| 128 | 7.75 | >50 |
| 129 | 9.74 | >50 |
| 130 | 14.10 | >50 |
| 131 | 0.33 | 20.53 |
| 132 | 0.78 | >50 |
| 133 | 6.07 | >50 |
| 134 | 0.21 | >50 |
| 135 | 3.84 | 10.98 |
| 136 | 1.53 | >50 |
| 137 | 0.88 | >50 |
| 138 | 3.26 | >50 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference in their entireties.

What is claimed is:

1. A compound of Formula (I) wherein:

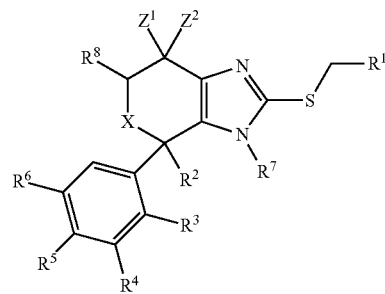

Formula (I)

wherein:

$R^1$ is

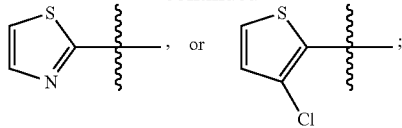

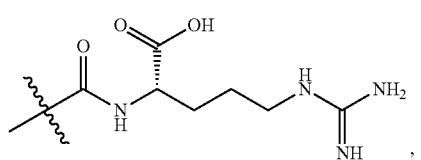, or $R^a$ is H, F, Br, or Cl;
$R^b$ is H, F, Cl, Br, $CF_3$, $OCH_3$, —CN, or $NO_2$;
$R^c$ is H, F, OH, or $(OCH_2CH_2)_nN(CH_3)_2$;
$R^d$ is H, —CN, Br, $SO_2NH_2$, $SO_2NHSO_2CH_3$, $C_{(2-3)}$alkylOH, $C_{(2-3)}$alkylN(CH$_3$)$_2$, $CH_2CH_2$-tetrazolyl, $CH_2CH_2CO_2CH_2CH_3$, $CH_2CH_2CO_2H$, $OCH_2CN$, $OCH_2CO_2H$, $OCH_2$-tetrazolyl, $(OCH_2CH_2)_nN(CH_3)_2$, $(OCH_2CH_2)_n$-pyrrolidinyl, $(OCH_2CH_2)_nCl$, $(OCH_2CH_2)_nOH$, $(OCH_2CH_2)_nOCH_3$, $CO_2H$, $C(O)NH_2$, $C(O)NHCH_3$, $C(O)N(CH_3)_2$, $C(O)NHCH_2CH_2N(CH_3)_3^+(CF_3CO_2)^-$, $SO_2NH(CH_2)_3N(CH_3)_3^+(CF_3CO_2)^-$, $C(O)NHCH_2CH_2(OCH_2CH_2)_nOH$, $C(O)NHCH_2CH_2(OCH_2CH_2)_nOCH_3$, $C(O)$-morpholinyl, $CH_2CH_2$-morpholinyl, $CH_2CH_2CN$, $CH_2CH_2C(O)NH_2$,

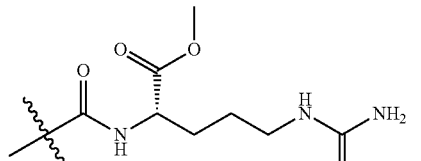

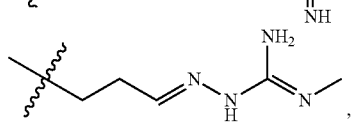

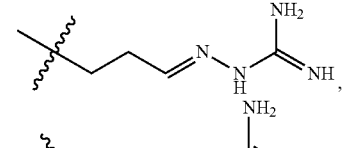

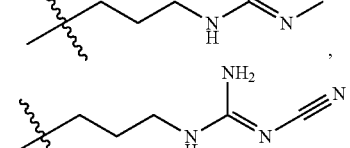

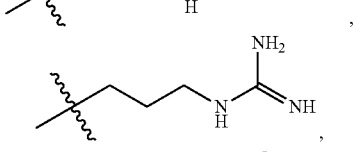

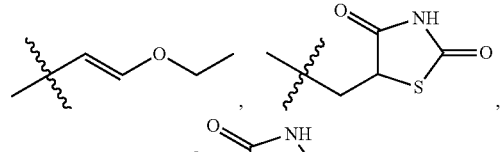

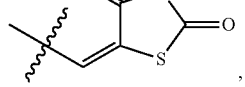

or tetrazolyl;

n is 0, 1, 2, 3, or 4;

$R^2$ is H, $CH_3$, $CH_2CH_3$, $CH_2OH$, $CH_2F$, or CH=O;

$R^3$ is H or Br;

$R^4$ is H or Br;

$R^5$ is Cl, H, F, or $OCH_3$;

$R^6$ is $OCH_3$, or Cl, or $R^6$ and $R^5$ may be taken together with their attached phenyl to form the fused ring system

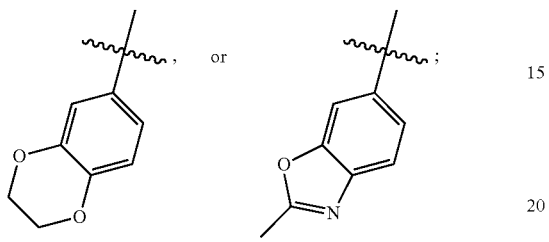

$R^7$ is phenyl, wherein said phenyl is optionally substituted with one substituent selected from the group consisting of F, $CH_3$, Cl, $CF_3$, and $OCH_3$, and further optionally substituted with up to two additional fluorine atoms;

$R^8$ is H or $CH_3$;

X is O or $CH_2$; and $Z^1$ and $Z^2$ are H, or $Z^1$ and $Z^2$ may be taken together with their attached carbon to form a

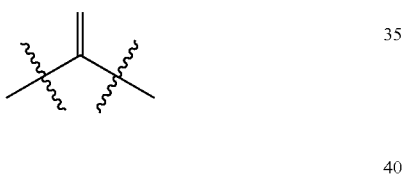

group;

and pharmaceutically acceptable salts thereof.

2. A compound of claim 1, wherein:

X is $CH_2$;

$Z^1$ and $Z^2$ are H;

and pharmaceutically acceptable salts thereof.

3. A compound of claim 2, wherein:

$R^5$ is Cl;

$R^6$ is $OCH_3$;

and pharmaceutically acceptable salts thereof.

4. A compound of claim 3, wherein:

$R^7$ is

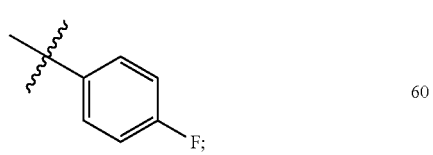

and pharmaceutically acceptable salts thereof.

5. A compound of claim 1 selected from the group consisting of:

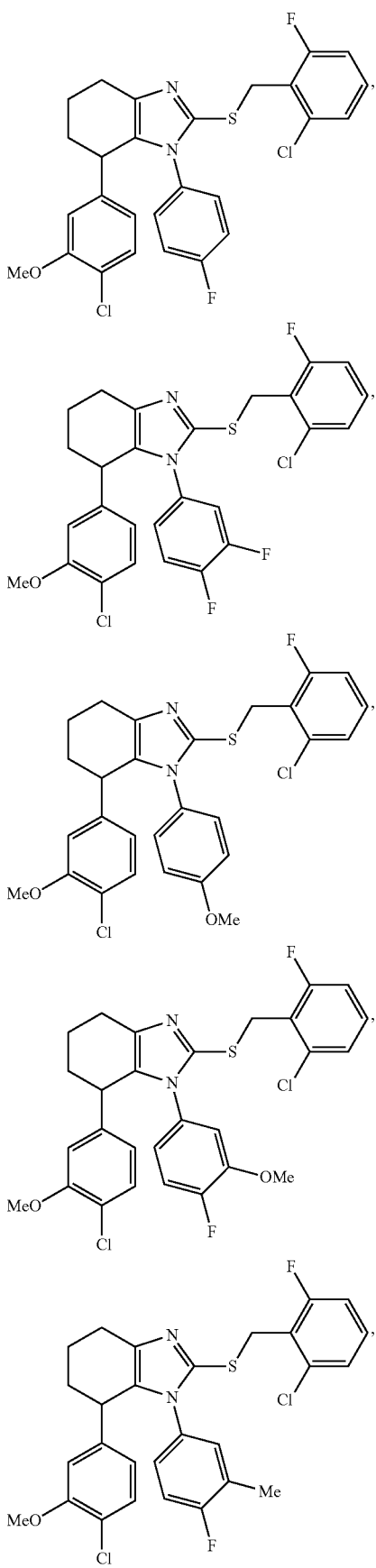

231
-continued
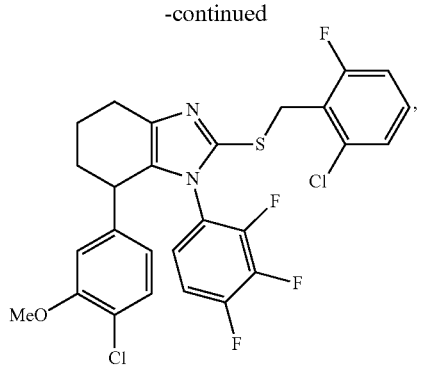
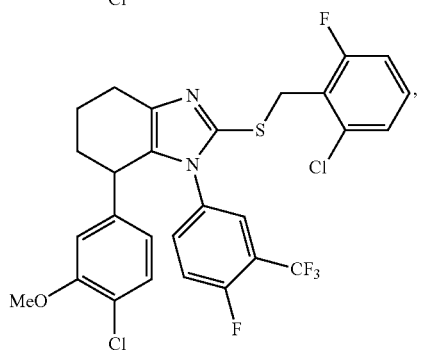
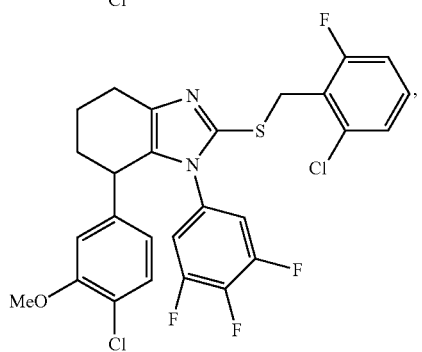
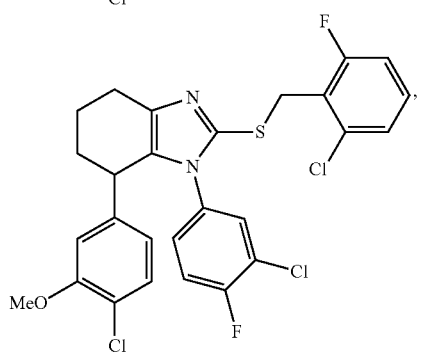
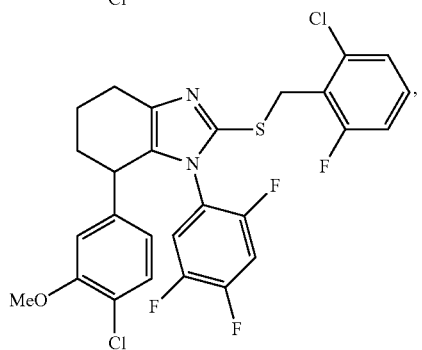
232
-continued
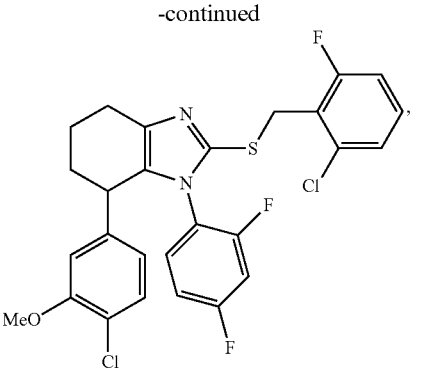
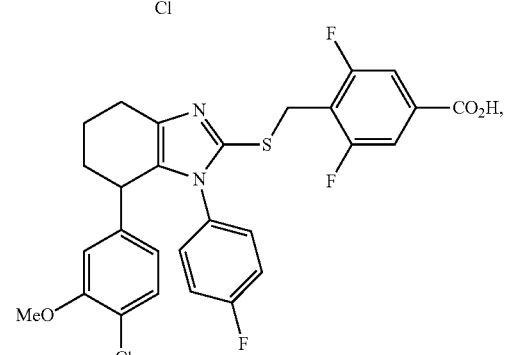
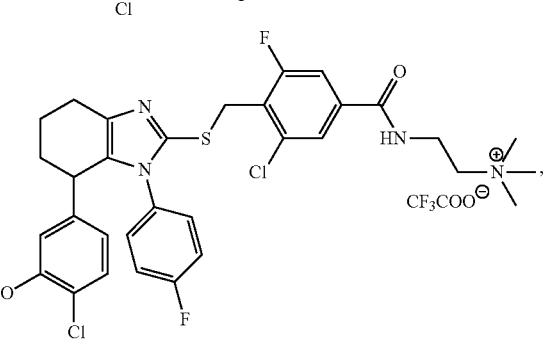
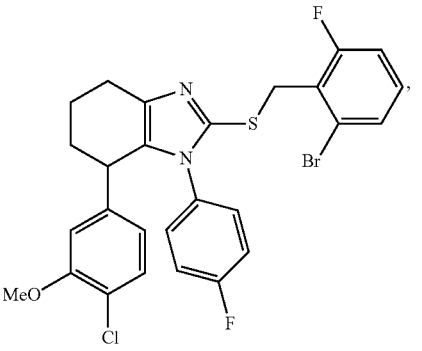
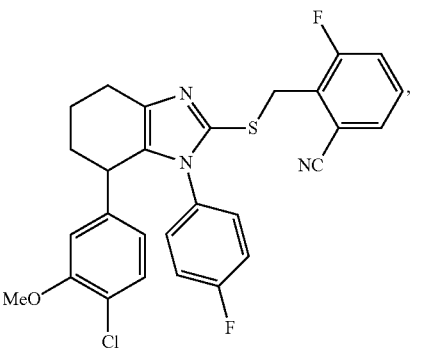

233
-continued
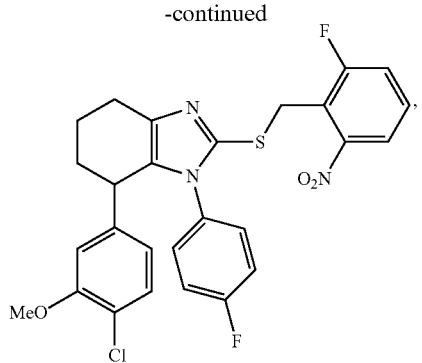
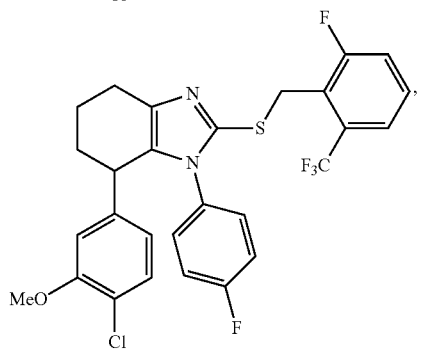
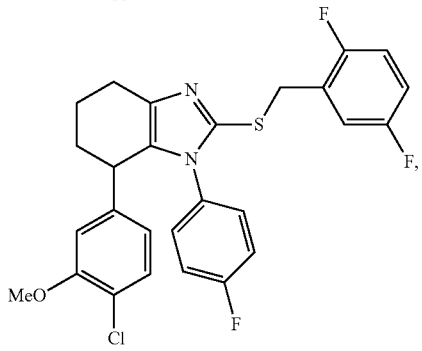
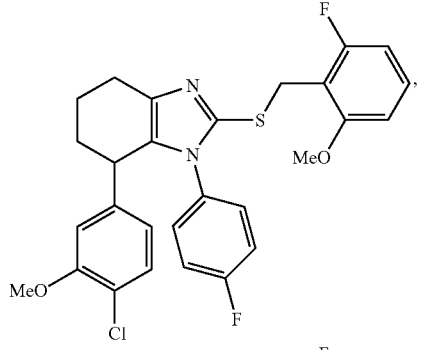
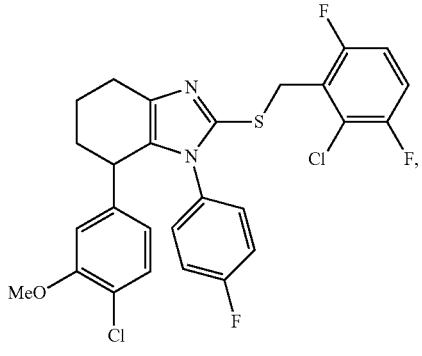
234
-continued
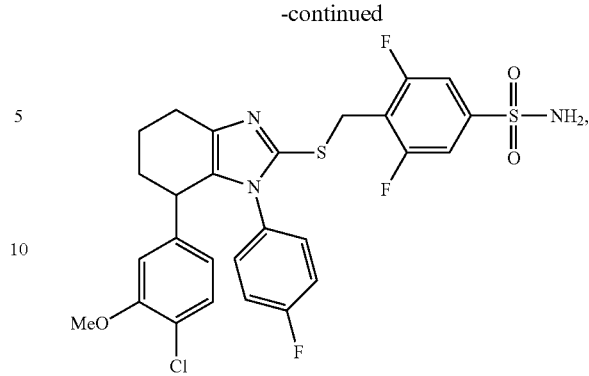
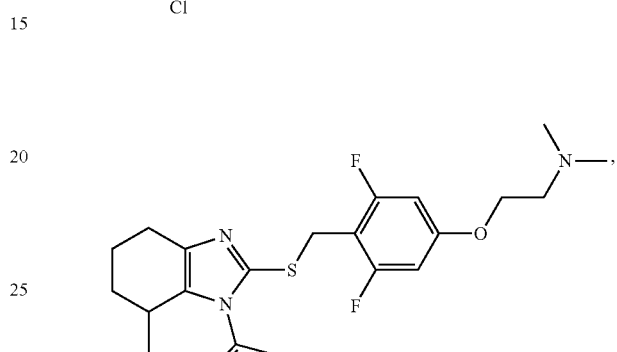
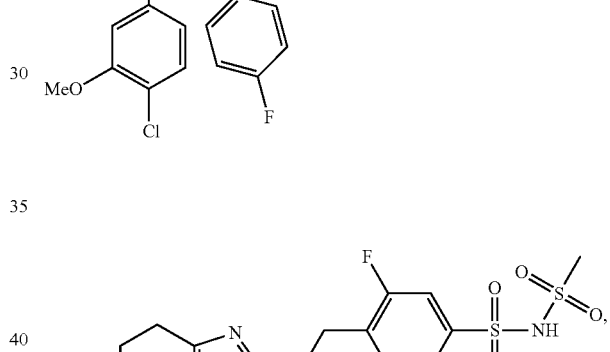
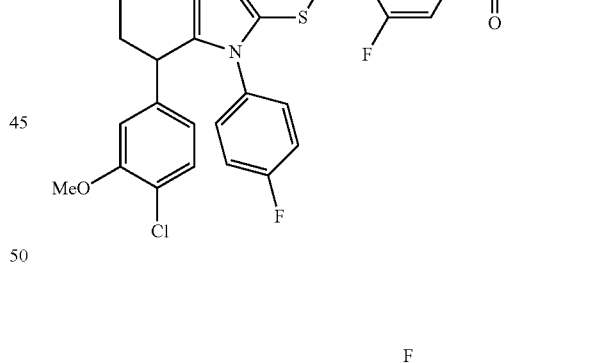
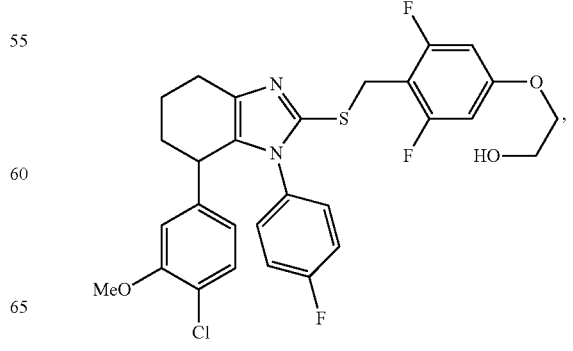

235
-continued
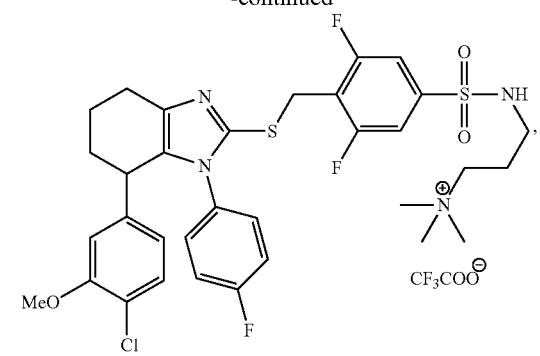
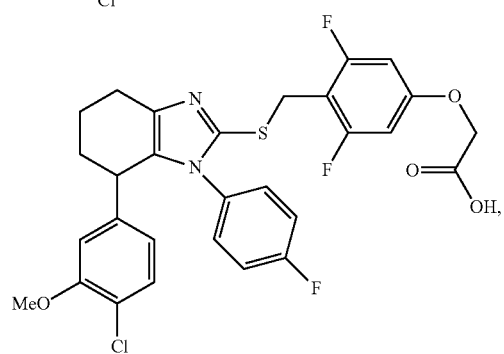
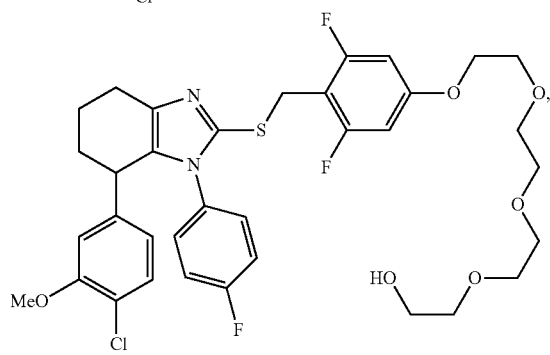
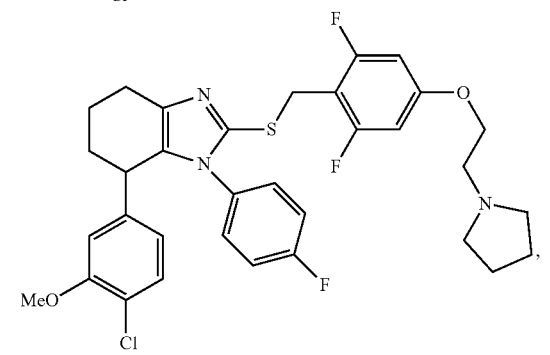
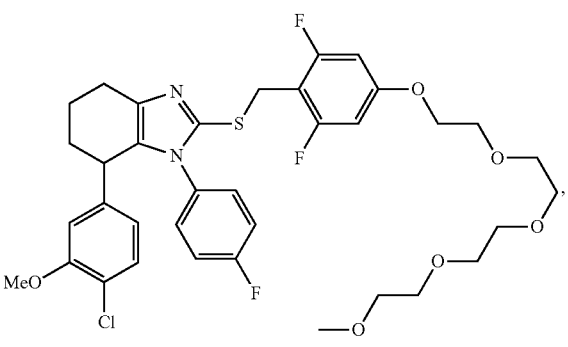
236
-continued
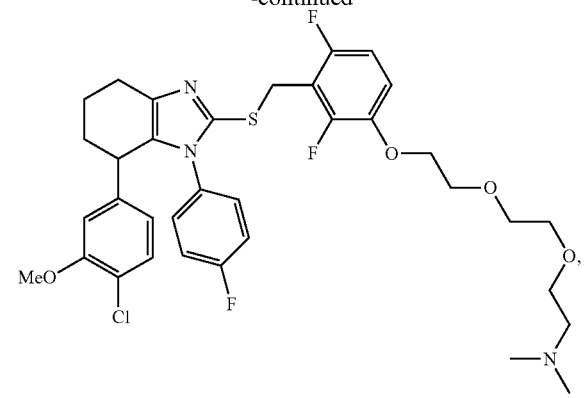
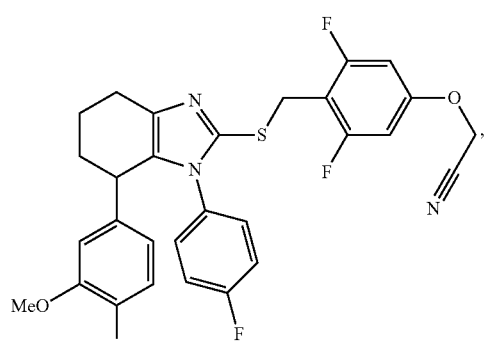
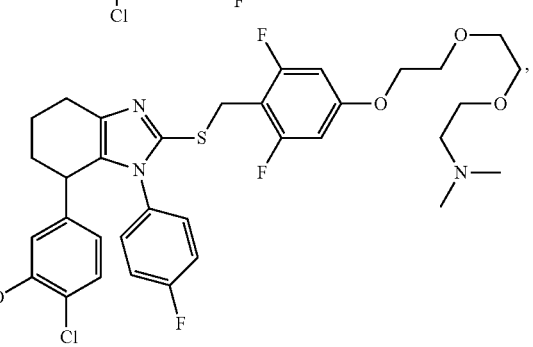
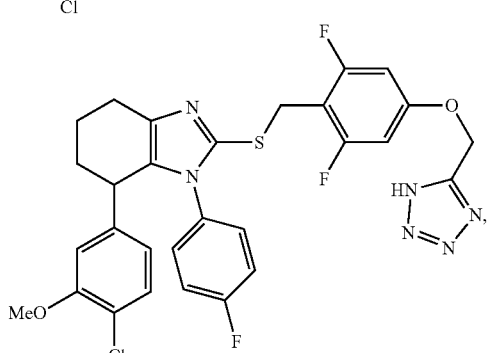
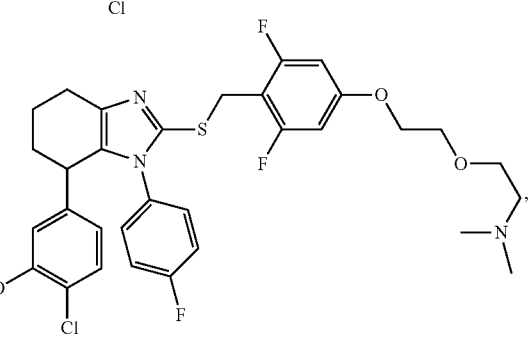

237
-continued
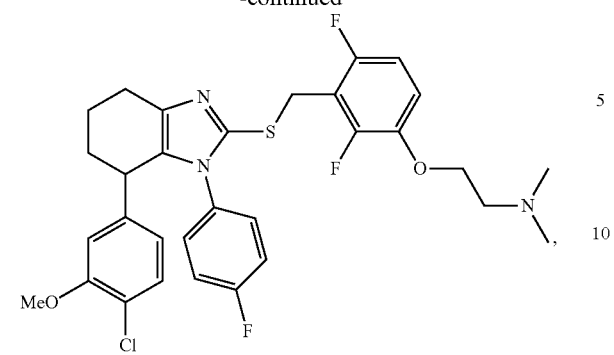
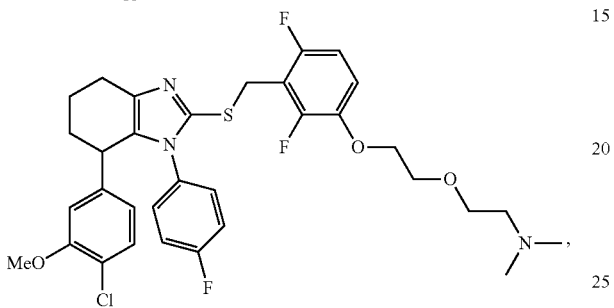
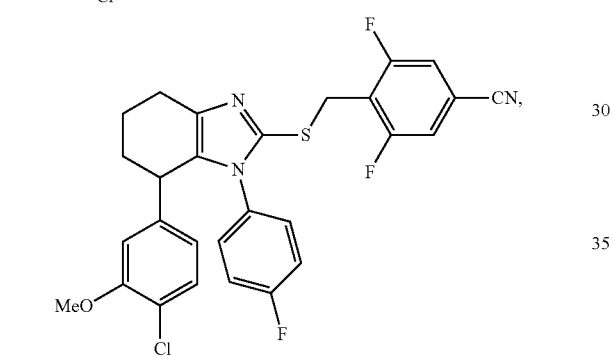
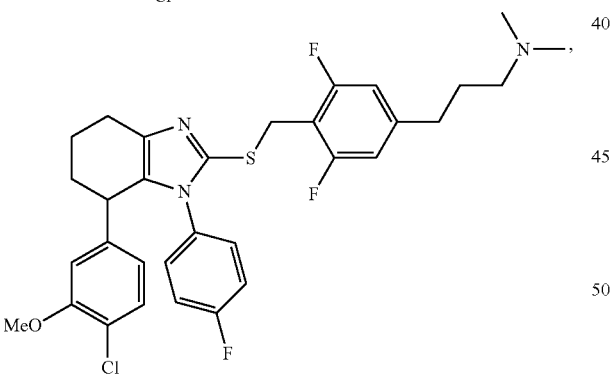
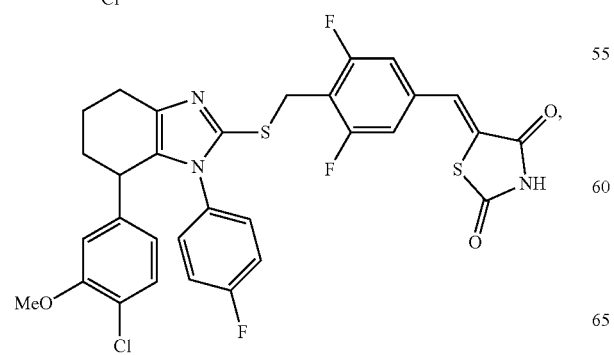
238
-continued
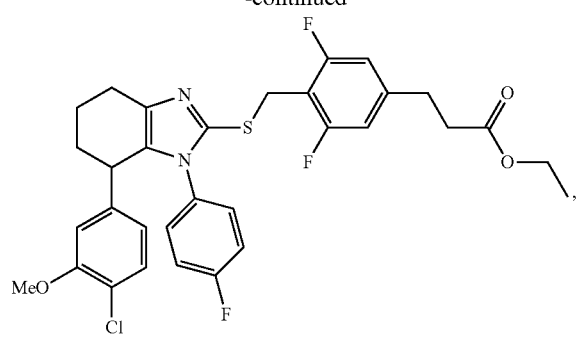
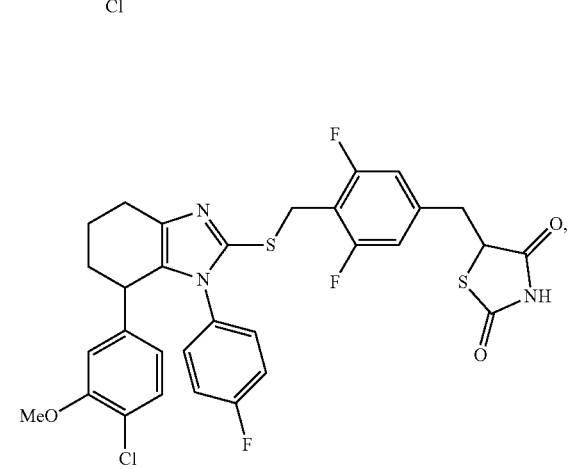
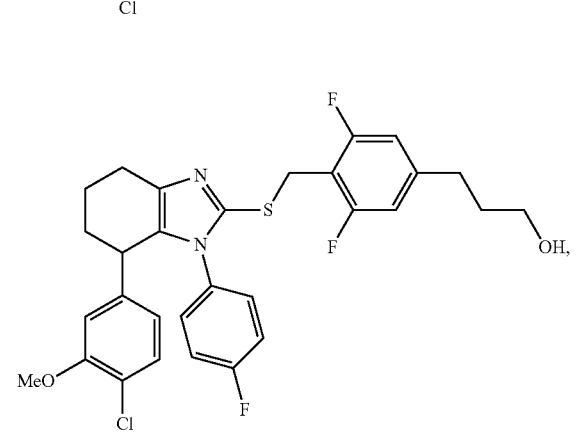
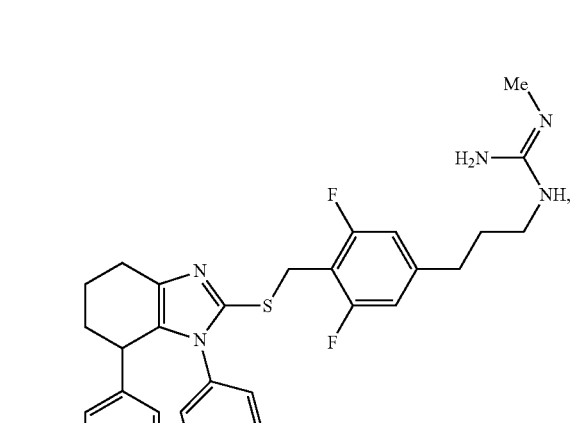
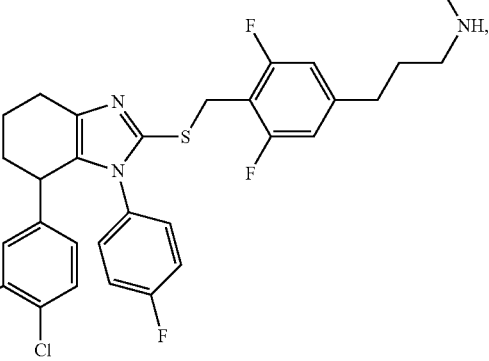

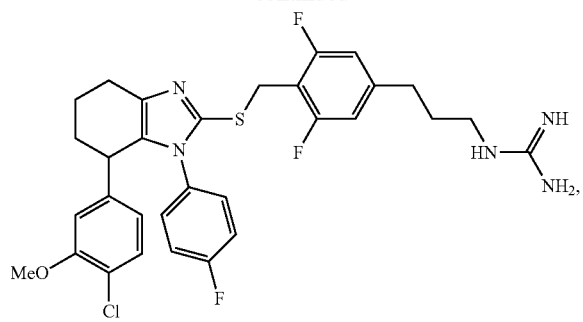
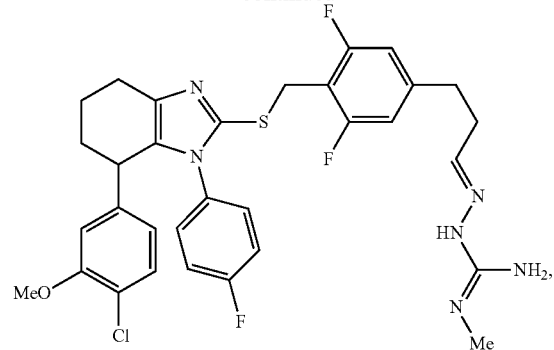

241
-continued
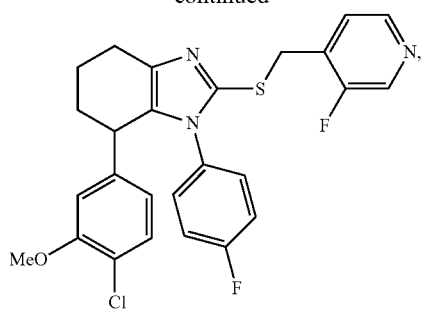
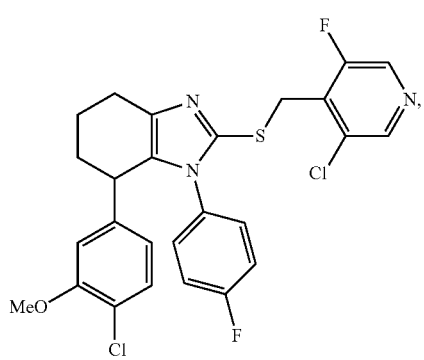
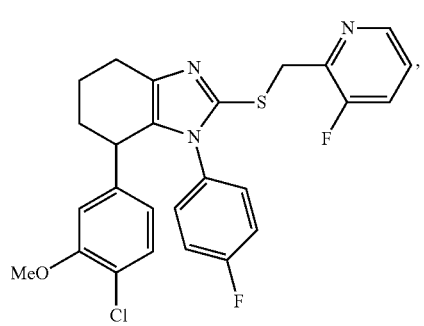
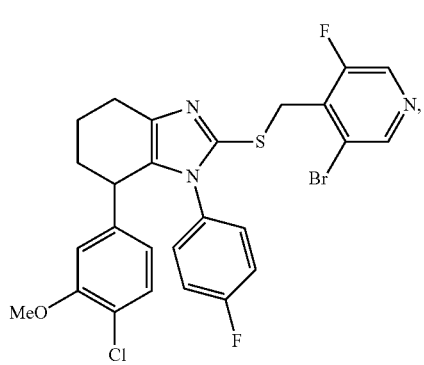
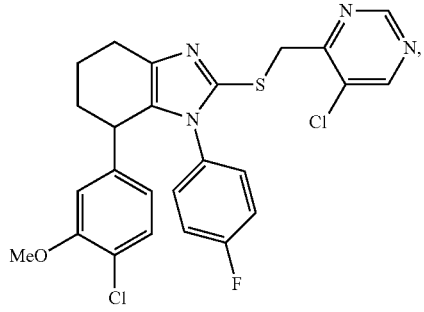
242
-continued
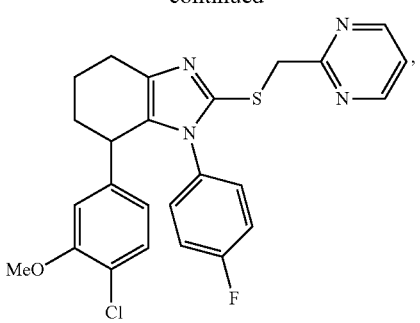
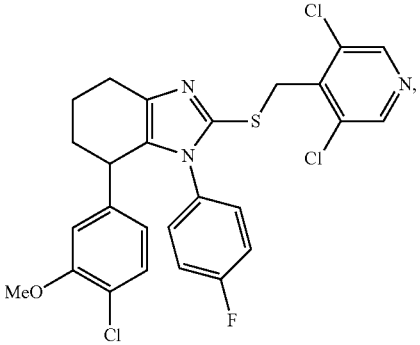
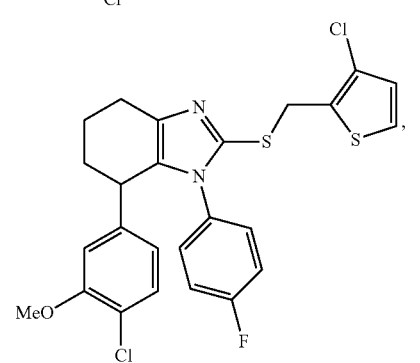
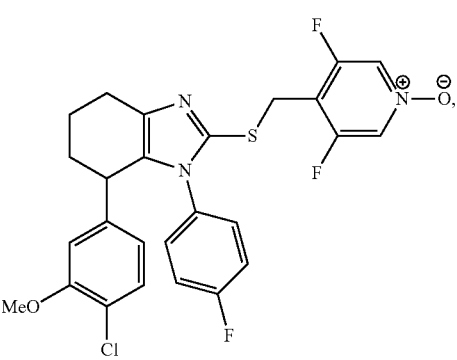
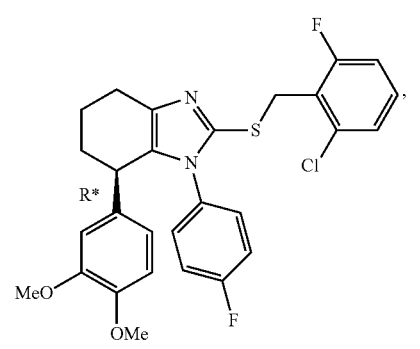

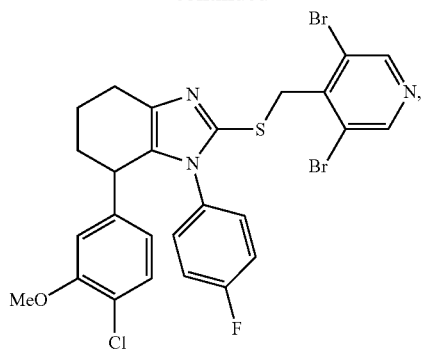
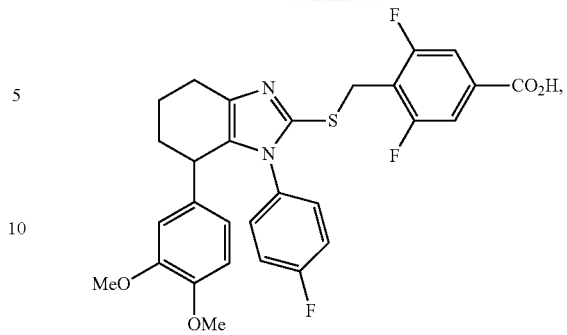
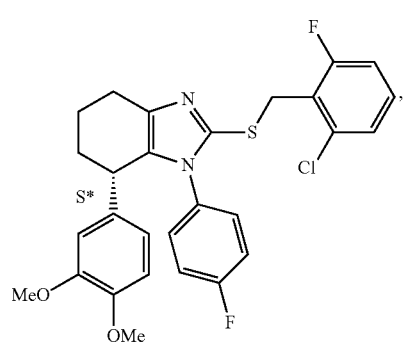
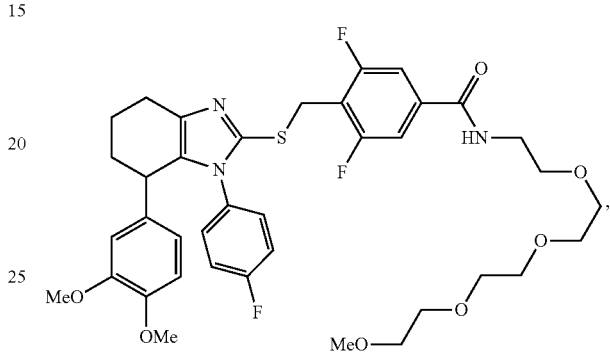
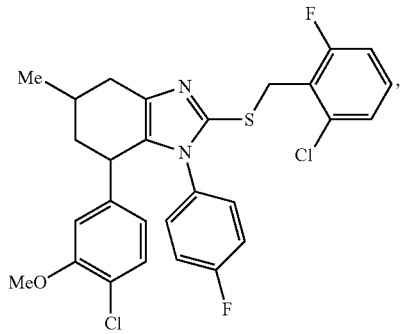
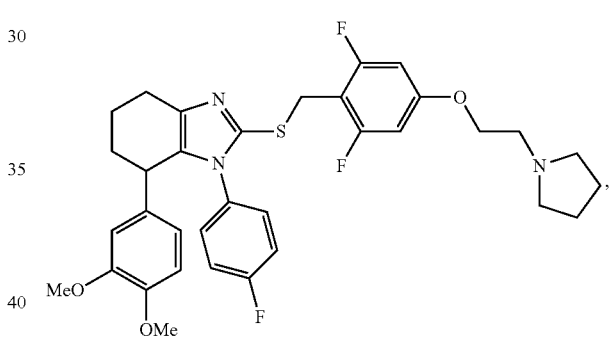
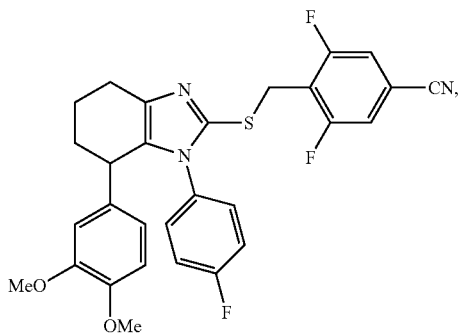
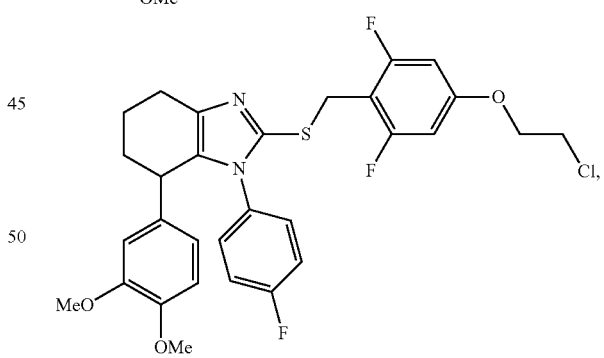
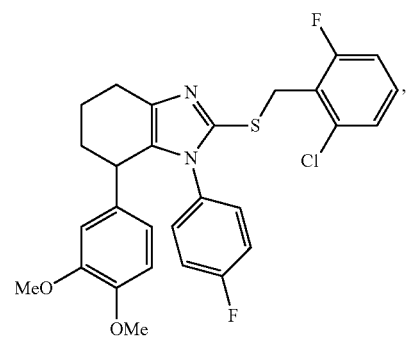
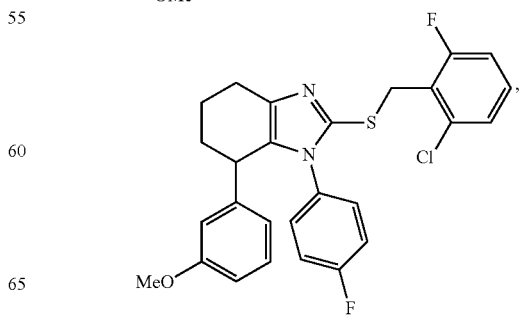

245
-continued
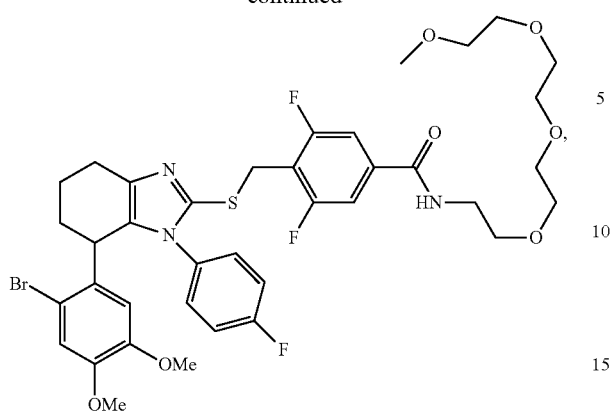
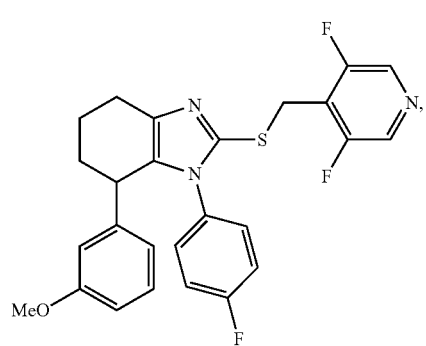
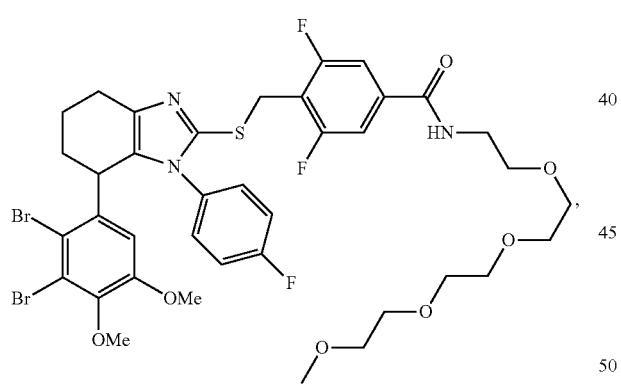
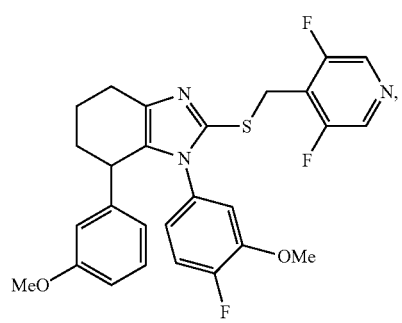
246
-continued
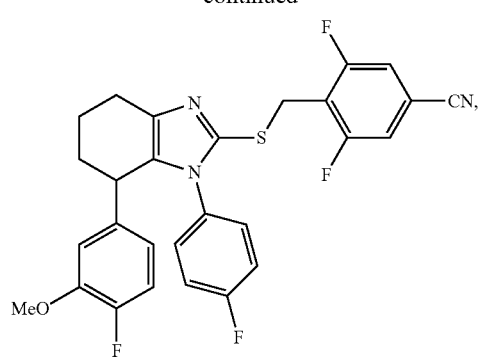
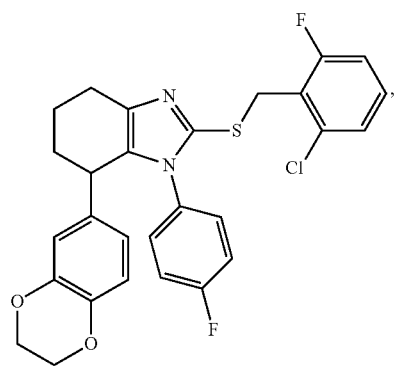
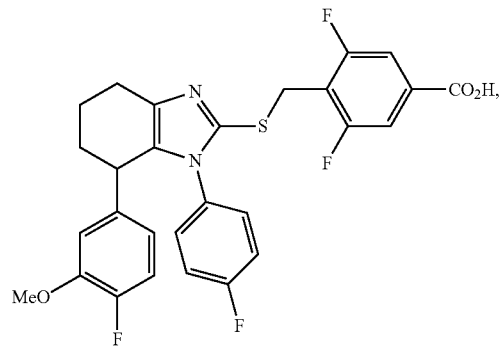
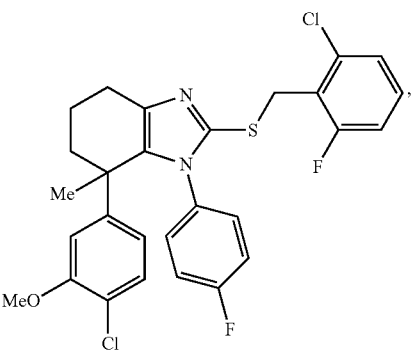

247
-continued
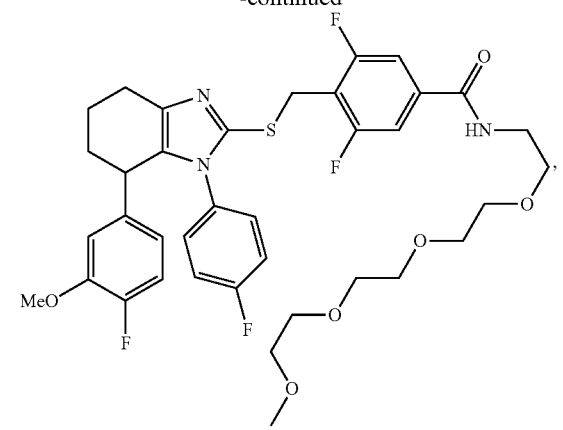
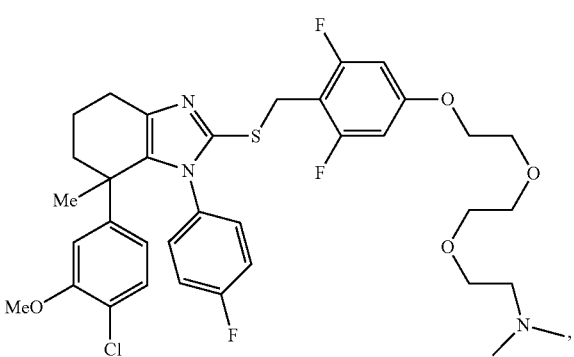
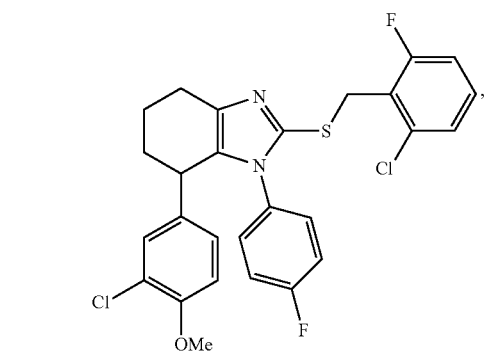
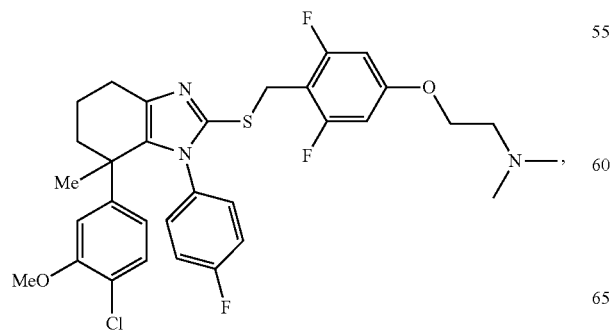
248
-continued
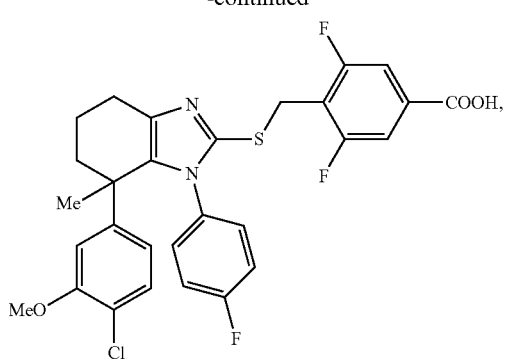
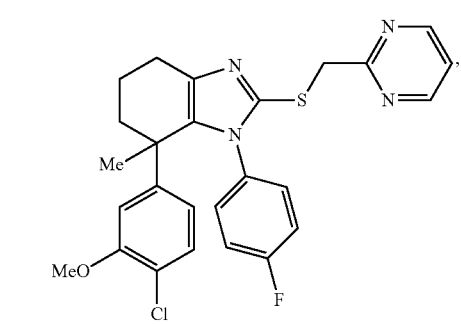
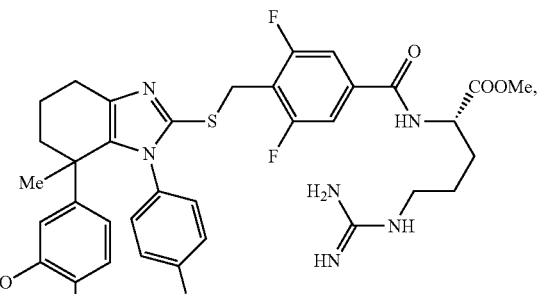
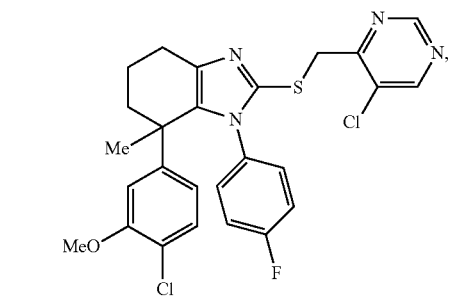
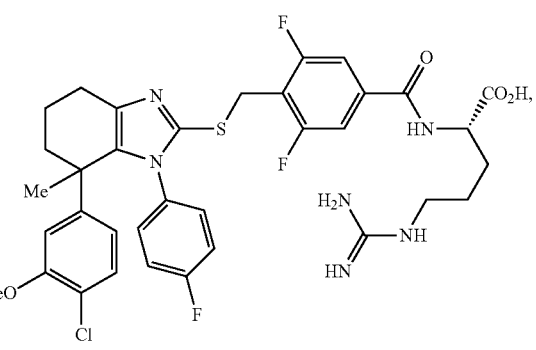

249
-continued
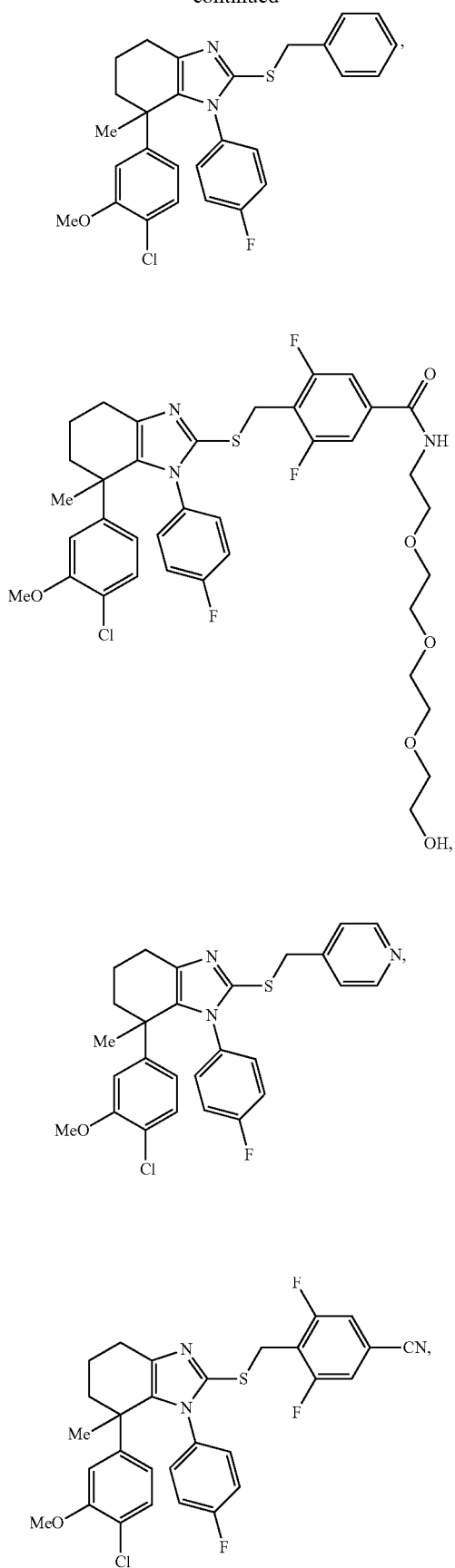
250
-continued
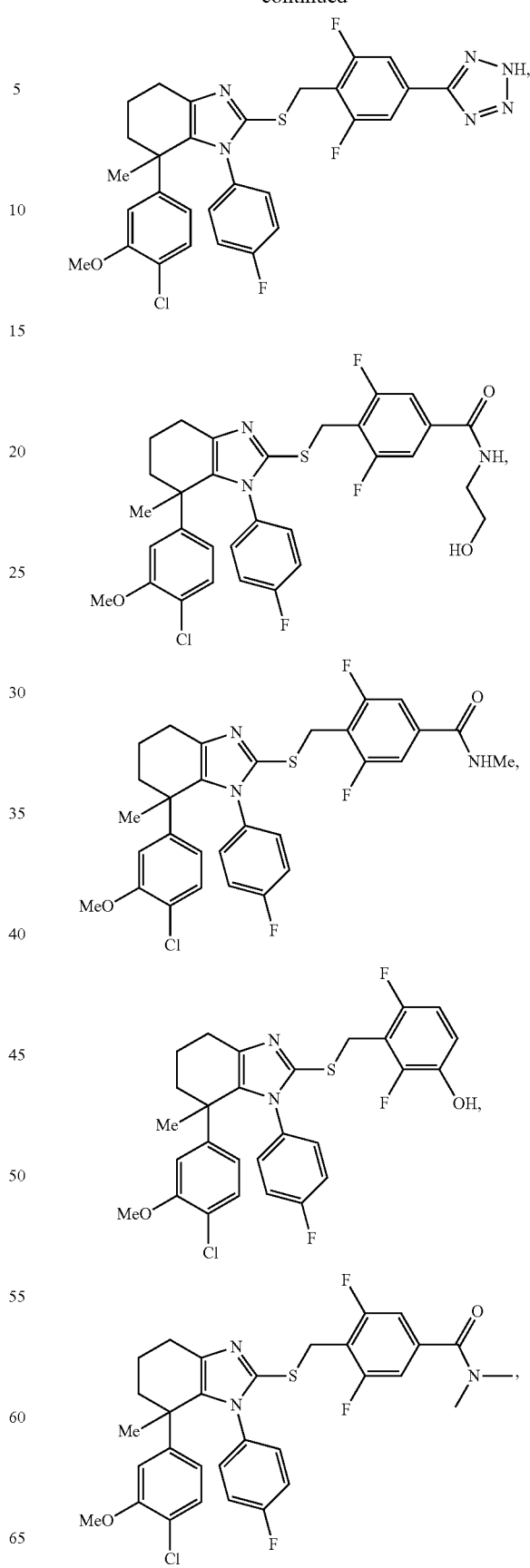

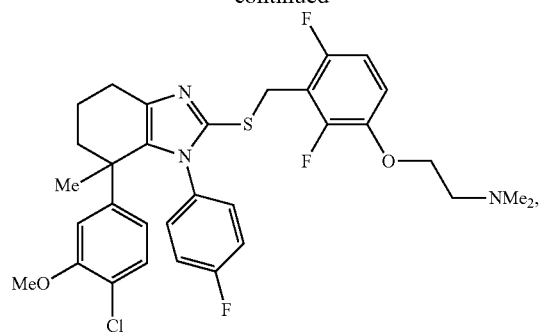
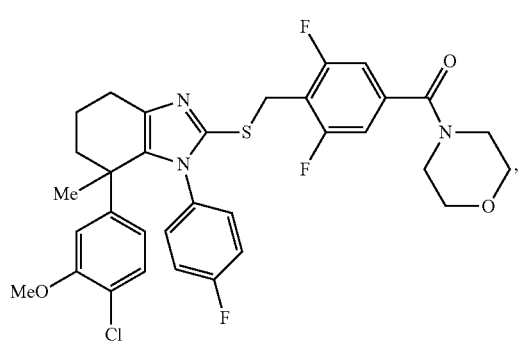
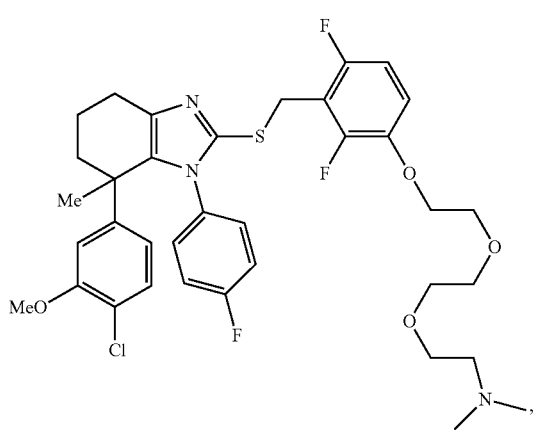
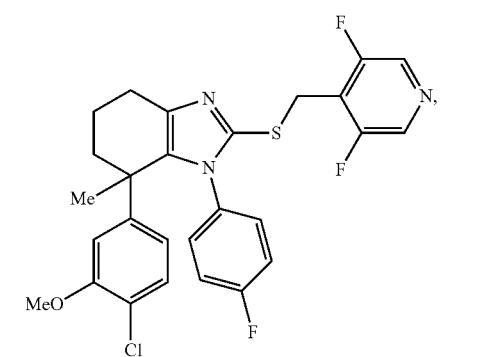
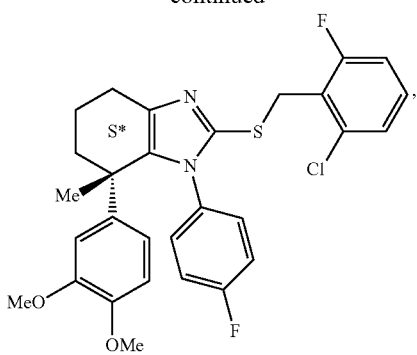
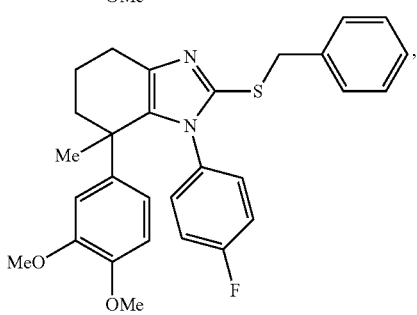
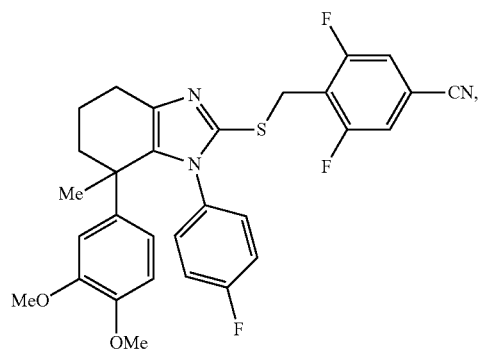
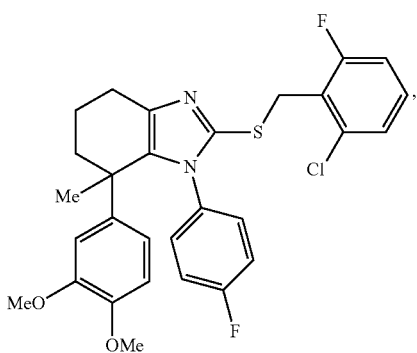
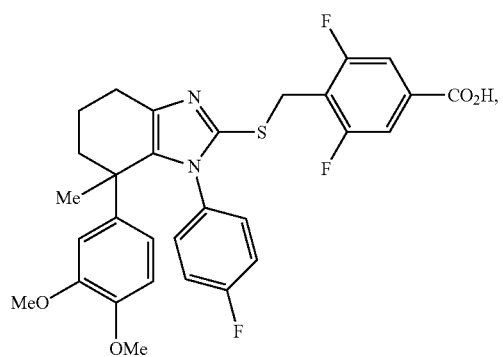

253
-continued
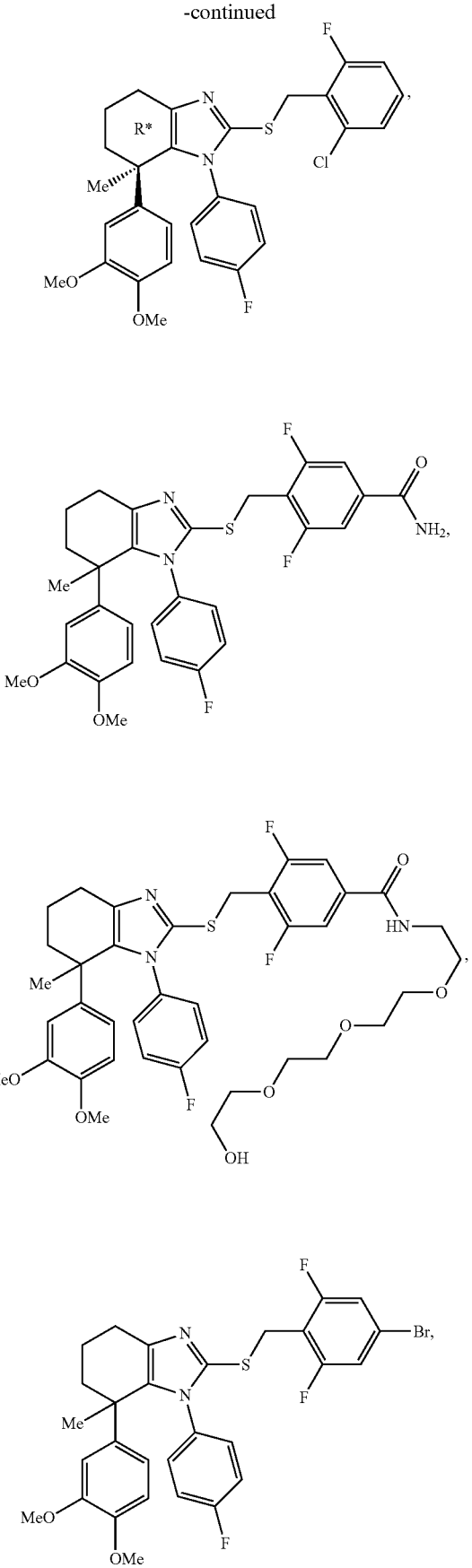
254
-continued
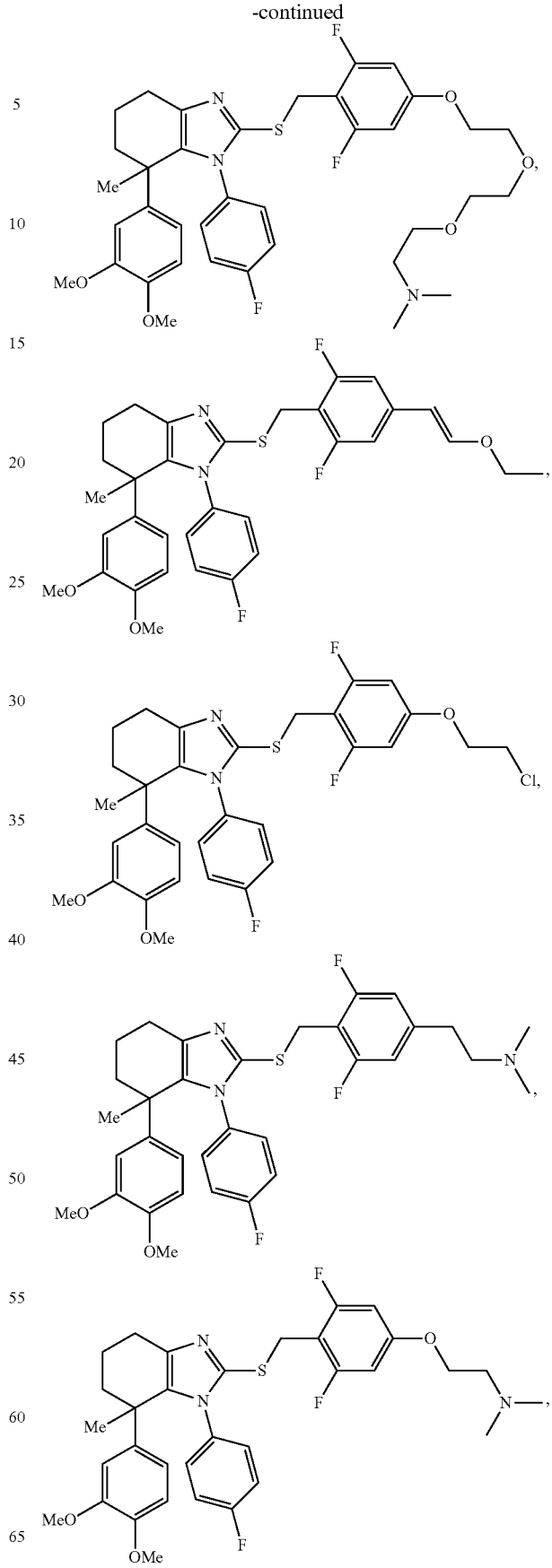

255
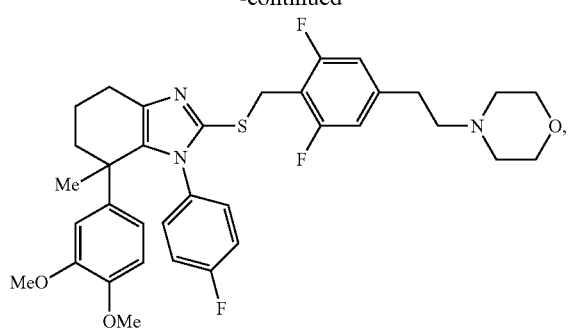
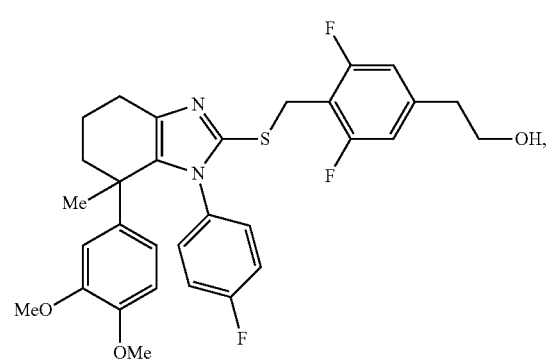
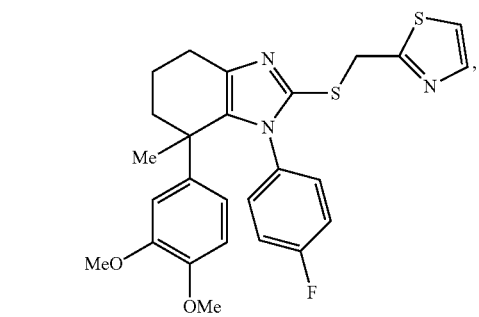
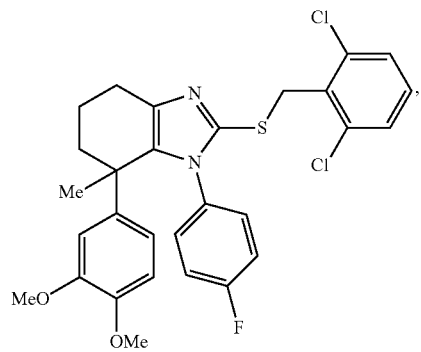
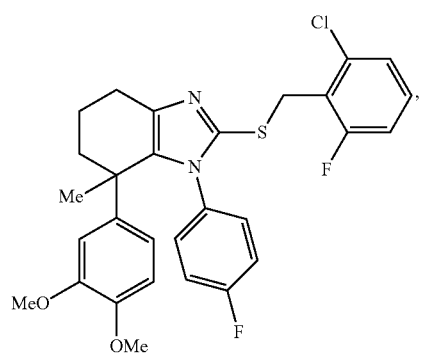
256
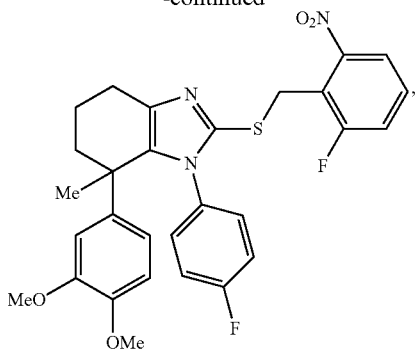
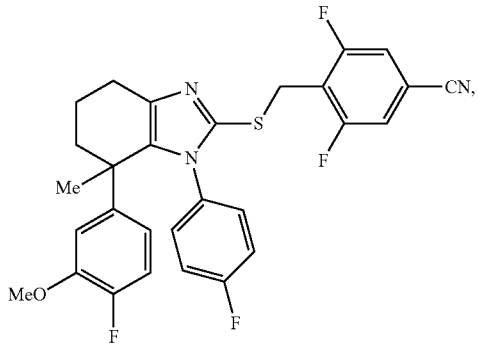
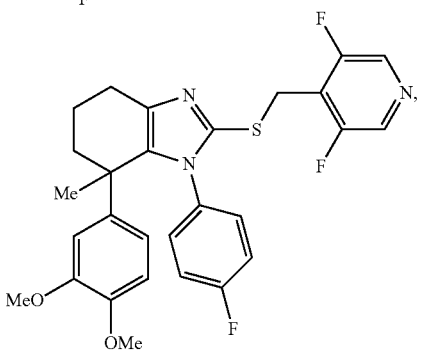
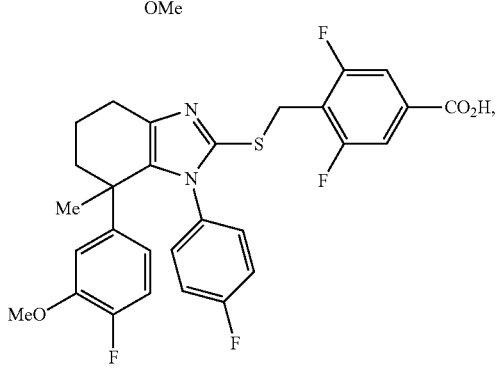
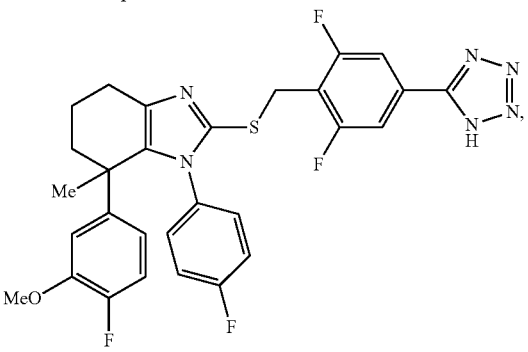

-continued
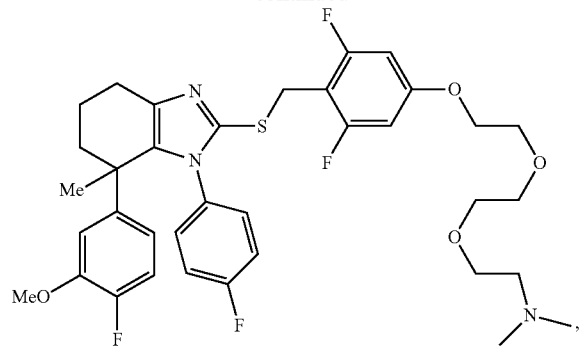
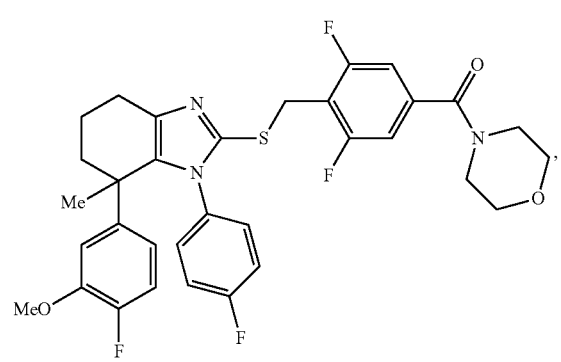
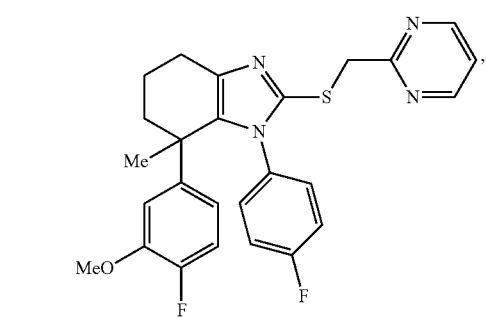
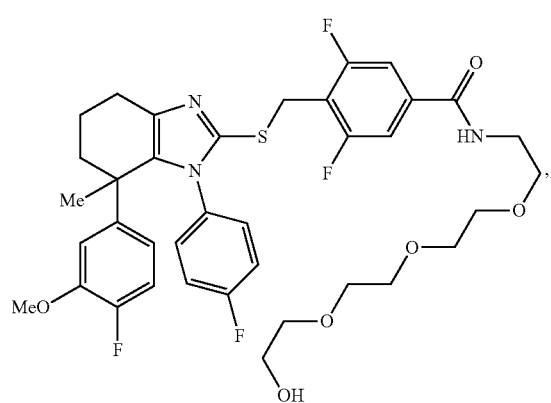
-continued
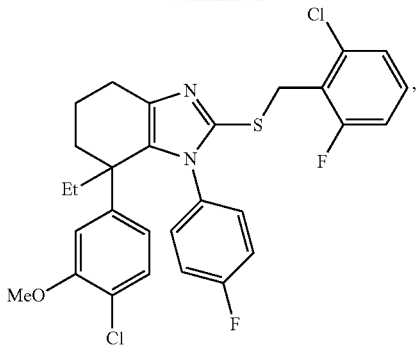
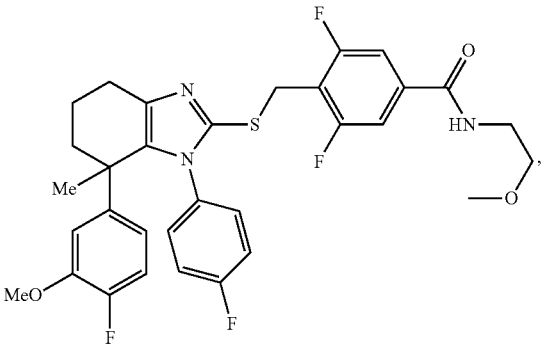
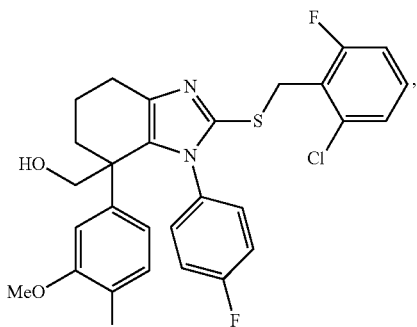
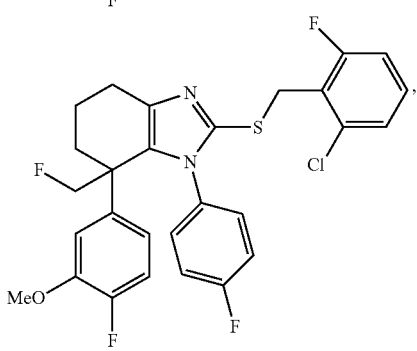
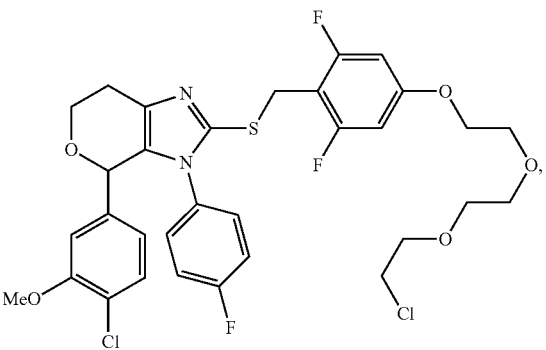

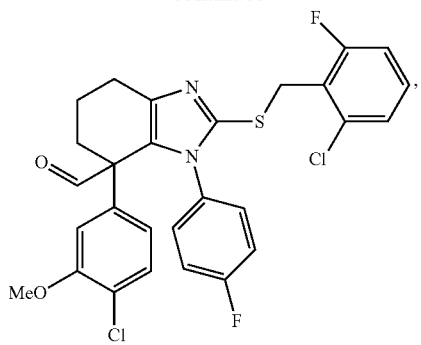

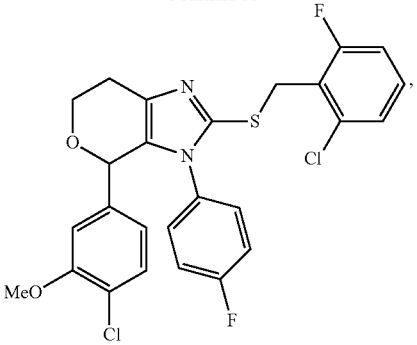

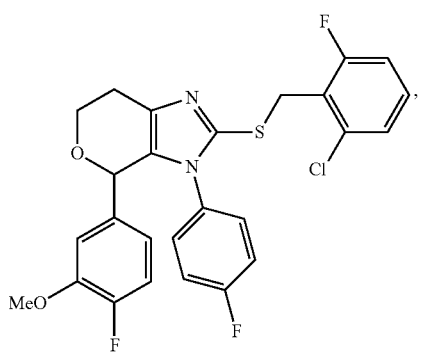

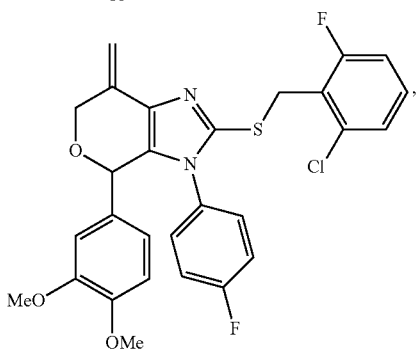

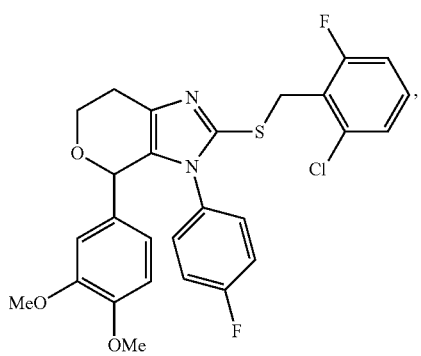

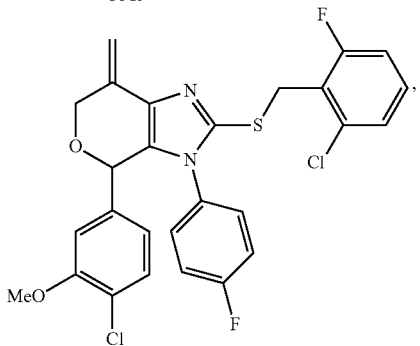

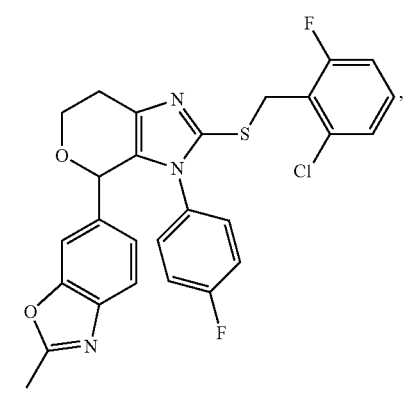

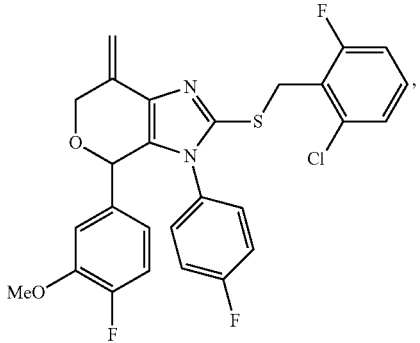

and pharmaceutically acceptable salts thereof.

6. A pharmaceutical composition, comprising a compound of claim 1 and a pharmaceutically acceptable carrier.

7. A pharmaceutical composition made by mixing a compound of claim 1 and a pharmaceutically acceptable carrier.

8. A process for making a pharmaceutical composition comprising mixing a compound of claim 1 and a pharmaceutically acceptable carrier.

9. A method comprising of treating a syndrome, disease or disorder selected from the group consisting of: (a) obesity, (b) type II diabetes, (c) Syndrome X (also known as metabolic syndrome), (d) insulin resistance, (e) inadequate glucose tolerance, (f) impaired glucose metabolism, (g) antherosclerosis, (h) fatty liver disease, and (i) nonalcoholic steatohepatitis, comprising administering to a subject in need thereof an effective amount of a compound of claim 1 or a form, composition or medicament thereof.

10. The method of claim 9, wherein the disease is obesity.

11. The method of claim 9, wherein the disease is type II diabetes.

* * * * *